US012679809B2

(12) United States Patent
DeMorin et al.

(10) Patent No.: US 12,679,809 B2
(45) Date of Patent: *Jul. 14, 2026

(54) CRYSTALLINE FORMS AND SALT FORMS OF A KINASE INHIBITOR

(71) Applicant: Exelixis, Inc., Alameda, CA (US)

(72) Inventors: Frenel DeMorin, Long Beach, CA (US); Khalid Shah, Half Moon Bay, CA (US); Sagar Shakya, San Diego, CA (US); Peter Wong, Brisbane, CA (US); Courtney S. Johnson, West Lafayette, IN (US); Melanie Janelle Bevill, West Lafayette, IN (US); Stephan D. Parent, West Lafayette, IN (US)

(73) Assignee: Exelixis, Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/657,052

(22) Filed: May 7, 2024

(65) Prior Publication Data

US 2024/0300897 A1 Sep. 12, 2024

Related U.S. Application Data

(63) Continuation of application No. 17/312,658, filed as application No. PCT/US2019/065972 on Dec. 12, 2019, now Pat. No. 12,017,995.

(60) Provisional application No. 62/856,469, filed on Jun. 3, 2019, provisional application No. 62/779,430, filed on Dec. 13, 2018.

(51) Int. Cl.

*C07D 215/48* (2006.01)
*A61K 31/47* (2006.01)
*A61P 35/00* (2006.01)

(52) U.S. Cl.

CPC ........ *C07D 215/48* (2013.01); *C07B 2200/13* (2013.01)

(58) Field of Classification Search

CPC .. C07D 215/48; A61K 31/47; C07B 2200/13; A61P 35/00

See application file for complete search history.

(56) References Cited

U.S. PATENT DOCUMENTS

| | | | | |
|---|---|---|---|---|
| 8,877,776 | B2 | 11/2014 | Brown et al. | |
| 12,017,995 | B2 * | 6/2024 | DeMorin | C07D 215/48 |
| 2011/0034439 | A1 | 2/2011 | Suda et al. | |
| 2012/0035212 | A1 | 2/2012 | Brown et al. | |
| 2017/0044106 | A1 | 2/2017 | Aftab et al. | |
| 2021/0261509 | A1 | 8/2021 | Shah | |

FOREIGN PATENT DOCUMENTS

| | | | |
|---|---|---|---|
| CN | 104817497 | B | 3/2017 |
| EP | 2769976 | A1 | 8/2014 |
| WO | 2005030140 | A2 | 4/2005 |
| WO | 2010045095 | | 4/2010 |
| WO | 2019148044 | A1 | 8/2019 |

OTHER PUBLICATIONS

Giron, D. "Monitoring of Polymorphism—From Detection to Quantification" Eng. Life Sci. 3; 2003; pp. 103-112.

International Search Report for PCT/US2019/065972, mailed Apr. 8, 2020.

Berge, S., L. Bighley and D. Monkhouse, "Pharmaceutical Salts", Journal of Pharmaceutical Sciences (1977), 66(1), pp. 1-19 (Year: 1977).

Byjus, "Crystallization", https://byjus.com/chemistry/crystallization/#:-:text=In%20the%2Opharmaceutical%20industry%2C% 20crystallization%20is%20used%20as, published Jul. 17, 2018 [Retrieved on Dec. 22, 2023] (Year: 2018).

* cited by examiner

*Primary Examiner* — Kamal A Saeed
*Assistant Examiner* — Sagar Patel
(74) *Attorney, Agent, or Firm* — Honigman LLP; Heidi Berven; Li Gao

(57) ABSTRACT

The present invention relates to crystalline forms of the free base of the c-Met inhibitor, Compound 1. The invention also relates to crystalline forms of salts of Compound 1. The invention also relates to pharmaceutical compositions comprising the solid polymorphs of the free base and salts of Compound 1. The invention further relates to methods of treating a disease, disorder, or syndrome mediated at least in part by modulating in vivo activity of a protein kinase.

11 Claims, 56 Drawing Sheets

28.6°C 210.0°C, no change 230.0°C, melt with decomp.

231.3°C,
complete melt with decomp.

26.4°C 209.6°C 222.1°C 223.1°C

| | |
|---|---|
| Bravais Type | C-Centered Monoclinic |
| a [Å] | 35.918 |
| b [Å] | 9.256 |
| c [Å] | 17.369 |
| α [deg] | 90 |
| β [deg] | 116.38 |
| γ [deg] | 90 |
| Volume [Å³/cell] | 5,172.6 |
| Chiral Contents? | Not Specified |
| Extinction Symbol | C 1 c 1 |
| Space Group(s) | Cc (9), C2/c (15) |

| | |
|---|---|
| Bravais Type | Primitive Monoclinic |
| a [Å] | 19.400 |
| b [Å] | 9.289 |
| c [Å] | 16.992 |
| α[deg] | 90 |
| β [deg] | 108.17 |
| γ [deg] | 90 |
| Volume [$Å^3$/cell] | 2,909.4 |
| Chiral Contents? | Achiral |
| Extinction Symbol | P 1 $2_1$/c 1 |
| Space Group(s) | P$2_1$/c (14) |

| | |
|---|---|
| Bravais Type | Primitive Monoclinic |
| a [Å] | 5.034 |
| b [Å] | 18.352 |
| c [Å] | 34.622 |
| α[deg] | 90 |
| β [deg] | 92.14 |
| γ [deg] | 90 |
| Volume [$Å^3$/cell] | 3,196.3 |
| Chiral Contents? | Achiral |
| Extinction Symbol | P 1 $2_1$/n 1 |
| Space Group(s) | $P2_1$/n (14) |

| | |
|---|---|
| Bravais Type | Primitive Monoclinic |
| a [Å] | 5.718 |
| b [Å] | 32.737 |
| c [Å] | 15.491 |
| α[deg] | 90 |
| β [deg] | 91.46 |
| γ [deg] | 90 |
| Volume [$Å^3$/cell] | 2,898.8 |
| Chiral Contents? | Achiral |
| Extinction Symbol | P 1 $2_1$/c 1 |
| Space Group(s) | P$2_1$/c (14) |

| | |
|---|---|
| Bravais Type | Triclinic |
| a [Å] | 10.079 |
| b [Å] | 10.592 |
| c [Å] | 14.589 |
| α[deg] | 98.17 |
| β [deg] | 90.51 |
| γ [deg] | 103.21 |
| Volume [Å$^3$/cell] | 1,499.5 |
| Chiral Contents? | Not Specified |
| Extinction Symbol | P - |
| Space Group(s) | P1 (1), P$\bar{1}$ (2) |

| | |
|---|---|
| Bravais Type | Primitive Monoclinic |
| a [Å] | 6.152 |
| b [Å] | 23.805 |
| c [Å] | 18.961 |
| α[deg] | 90 |
| β [deg] | 97.82 |
| γ [deg] | 90 |
| Volume [$Å^3$/cell] | 2,751.0 |
| Chiral Contents? | Achiral |
| Extinction Symbol | P 1 $2_1$/n 1 |
| Space Group(s) | $P2_1$/n (14) |

| | |
|---|---|
| Bravais Type | Triclinic |
| a [Å] | 10.044 |
| b [Å] | 10.691 |
| c [Å] | 14.626 |
| α[deg] | 98.58 |
| β [deg] | 91.18 |
| γ [deg] | 103.65 |
| Volume [Å³/cell] | 1,506.5 |
| Chiral Contents? | Not Specified |
| Extinction Symbol | P - |
| Space Group(s) | P1 (1), P$\bar{1}$ (2) |

| | fumarate |
|---|---|
| Bravais Type | Triclinic |
| a [Å] | 10.711 |
| b [Å] | 11.401 |
| c [Å] | 12.626 |
| α[deg] | 86.78 |
| β [deg] | 67.95 |
| γ [deg] | 77.89 |
| Volume [Å$^3$/cell] | 1,396.8 |
| Chiral Contents? | Not Specified |
| Extinction Symbol | P - |
| Space Group(s) | P1 (1), P$\bar{1}$ (2) |

| | HCl |
|---|---|
| Bravais Type | Primitive Monoclinic |
| a [Å] | 10.809 |
| b [Å] | 9.043 |
| c [Å] | 33.901 |
| α [deg] | 90 |
| β [deg] | 91.90 |
| γ [deg] | 90 |
| Volume [Å³/cell] | 3,310.0 |
| Chiral Contents? | Achiral |
| Extinction Symbol | P 1 $2_1$/c 1 |
| Space Group(s) | $P2_1/c$ (14) |

| | HCl |
|---|---|
| Bravais Type | Primitive Monoclinic |
| a [Å] | 10.754 |
| b [Å] | 9.117 |
| c [Å] | 33.444 |
| α[deg] | 90 |
| β [deg] | 90.66 |
| γ [deg] | 90 |
| Volume [$Å^3$/cell] | 3,278.8 |
| Chiral Contents? | Achiral |
| Extinction Symbol | P 1 $2_1$/c 1 |
| Space Group(s) | $P2_1/c$ (14) |

CRYSTALLINE FORMS AND SALT FORMS OF A KINASE INHIBITOR

CROSS-REFERENCE TO RELATED APPLICATIONS

This application is a continuation application of U.S. application Ser. No. 17/312,658, filed Jun. 10, 2021, which is a United States National Phase filing of PCT/US2019/065972, filed Dec. 12, 2019, which claims the benefit of priority to U.S. Provisional Application No. 62/779,430, filed Dec. 13, 2018, and U.S. Provisional Application No. 62/856,469, filed Jun. 3, 2019, the entire contents of which are incorporated herein by reference.

TECHNICAL FIELD OF THE INVENTION

The present invention relates to crystalline forms of the free base of the c-Met inhibitor, Compound 1. The invention also relates to crystalline forms of salts of Compound 1. The invention also relates to pharmaceutical compositions comprising the solid polymorphs of the free base and salts of Compound 1. The invention further relates to methods of treating a disease, disorder, or syndrome mediated at least in part by modulating in vivo activity of a protein kinase.

BACKGROUND OF THE INVENTION

Human Axl belongs to the Tyro3, Axl, and Mer (TAM) subfamily of receptor tyrosine kinases that includes Mer. TAM kinases are characterized by an extracellular ligand binding domain consisting of two immunoglobulin-like domains and two fibronectin type III domains. Axl is overexpressed in a number of tumor cell types and was initially cloned from patients with chronic myelogenous leukemia. When overexpressed, Axl exhibits transforming potential. Axl signaling is believed to cause tumor growth through activation of proliferative and anti-apoptotic signaling pathways. Axl has been associated with cancers such as lung cancer, myeloid leukemia, uterine cancer, ovarian cancer, gliomas, melanoma, thyroid cancer, renal cell carcinoma, osteosarcoma, gastric cancer, prostate cancer, and breast cancer. The over-expression of Axl results in a poor prognosis for patients with the indicated cancers.

Activation of Mer, like Axl, conveys downstream signaling pathways that cause tumor growth and activation. Mer binds ligands such as the soluble protein Gas-6. Gas-6 binding to Mer induces autophosphorylation of Mer on its intracellular domain, resulting in downstream signal activation. Over-expression of Mer in cancer cells leads to increased metastasis, most likely by generation of soluble Mer extracellular domain protein as a decoy receptor. Tumor cells secrete a soluble form of the extracellular Mer receptor which reduces the ability of soluble Gas-6 ligand to activate Mer on endothelial cells, leading to cancer progression.

A need therefore exists for compounds that inhibit TAM receptor tyrosine kinases such as Axl and Mer for the treatment of selected cancers.

SUMMARY OF THE INVENTION

The present invention provides crystalline forms of the free base and selected salts of Compound 1, N-(4-fluorophenyl)-N-(4-((7-methoxy-6-(methylcarbamoyl)quinolin-4-yl)oxy)phenyl)cyclopropane-1,1-dicarboxamide, which has the structure:

Compound 1

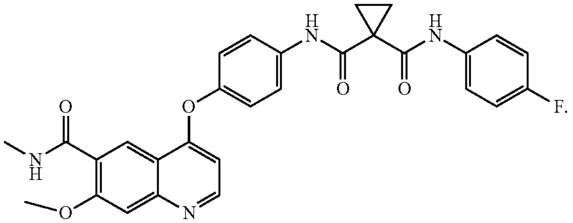

Compound 1 is disclosed in WO 2019/148044, the contents of which is incorporated herein by reference in its entirety.

Specific crystalline forms of an active pharmaceutical ingredient (API), such as Compound 1, can have several advantages over other crystalline or amorphous forms, such as increased stability during storage or processing, more favorable solubility, and increased bioavailability. Reported herein are several stable crystalline forms of Compound 1 and selected salts of Compound 1.

In one aspect, the invention relates to a crystalline solid form of Compound 1 or hydrate or solvate thereof.

In another aspect, the invention relates to a crystalline hydrochloric acid salt form of Compound 1 having the general structure Compound 1

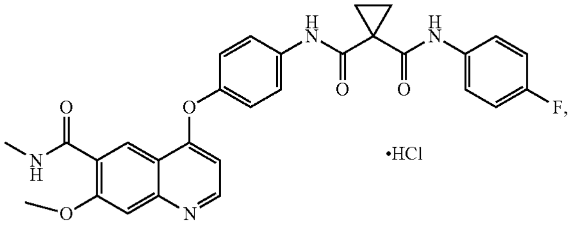

HCl salt or hydrate or solvate thereof.

In one aspect, the invention relates to a crystalline fumaric acid salt form of Compound 1 having the general structure Compound 1

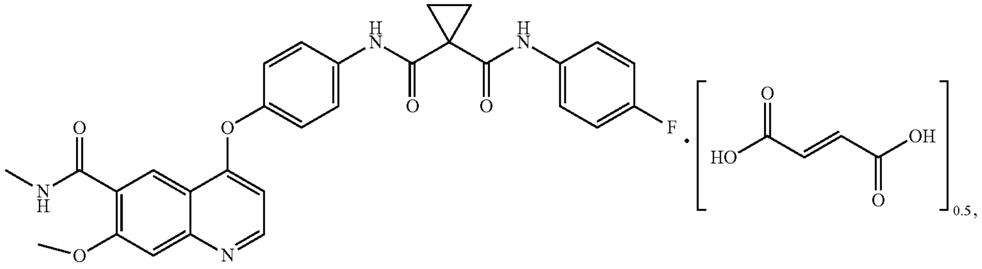

Hemifumarate or hydrate or solvate thereof, wherein the crystalline salt form is the Hemifumarate Compound 1●0.5 Fumaric acid characterized as Compound 1 Hemifumarate Form B.

In another aspect, the invention relates to a crystalline fumaric acid salt form of Compound 1 having the general structure crystalline form, (B) 210.0° C. with no change in crystalline form, (C) 230.0° C. with some melting and decomposition, and (D) 231.3° C. with complete melting and decomposition.

FIG. 6 is an XRPD pattern of Compound 1 Form B.

FIG. 7 is a TGA thermogram of Compound 1 Form B.

Compound 1

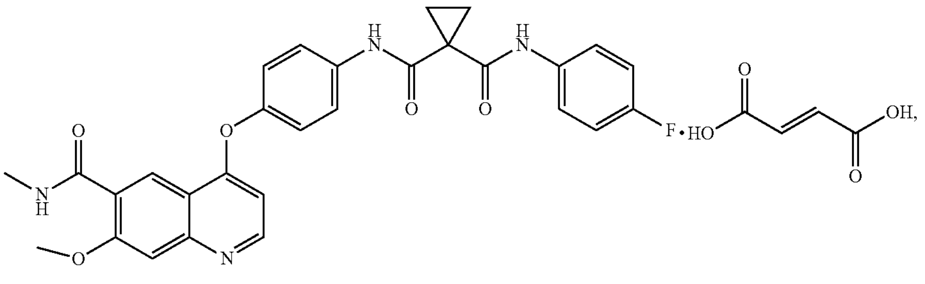

Fumarate or hydrate or solvate thereof, wherein the crystalline salt form is the Fumarate Compound 1●Fumaric acid.

In one aspect, the invention relates to a crystalline phosphoric acid salt form of Compound 1 having the general structure Compound 1

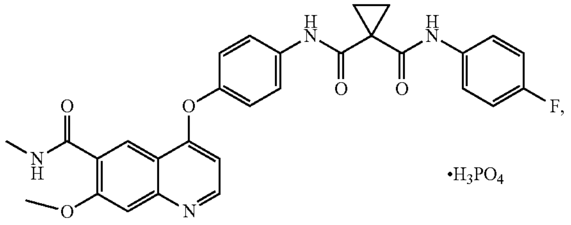

Phosphate Form A or hydrate or solvate thereof, characterized as Compound 1 Phosphate Form A.

In still another aspect, the invention relates to a method of treating a disease, disorder, or syndrome mediated at least in part by modulating in vivo activity of a protein kinase, comprising administering to a subject in need thereof a crystalline form or a crystalline salt form described herein, or a pharmaceutical composition described herein.

In another aspect, the invention relates to a method for inhibiting a protein kinase, the method comprising contacting the protein kinase with a crystalline form or a crystalline salt form described herein.

In yet another aspect, the invention relates to a process of preparing Compound 1 Hemifumarate Form B comprising contacting Compound 1 with fumaric acid in an organic solvent to form a mixture, and stirring the mixture.

DETAILED DESCRIPTION OF THE INVENTION

Definitions, Abbreviations and Acronyms

Analytical Techniques

Figure 1:
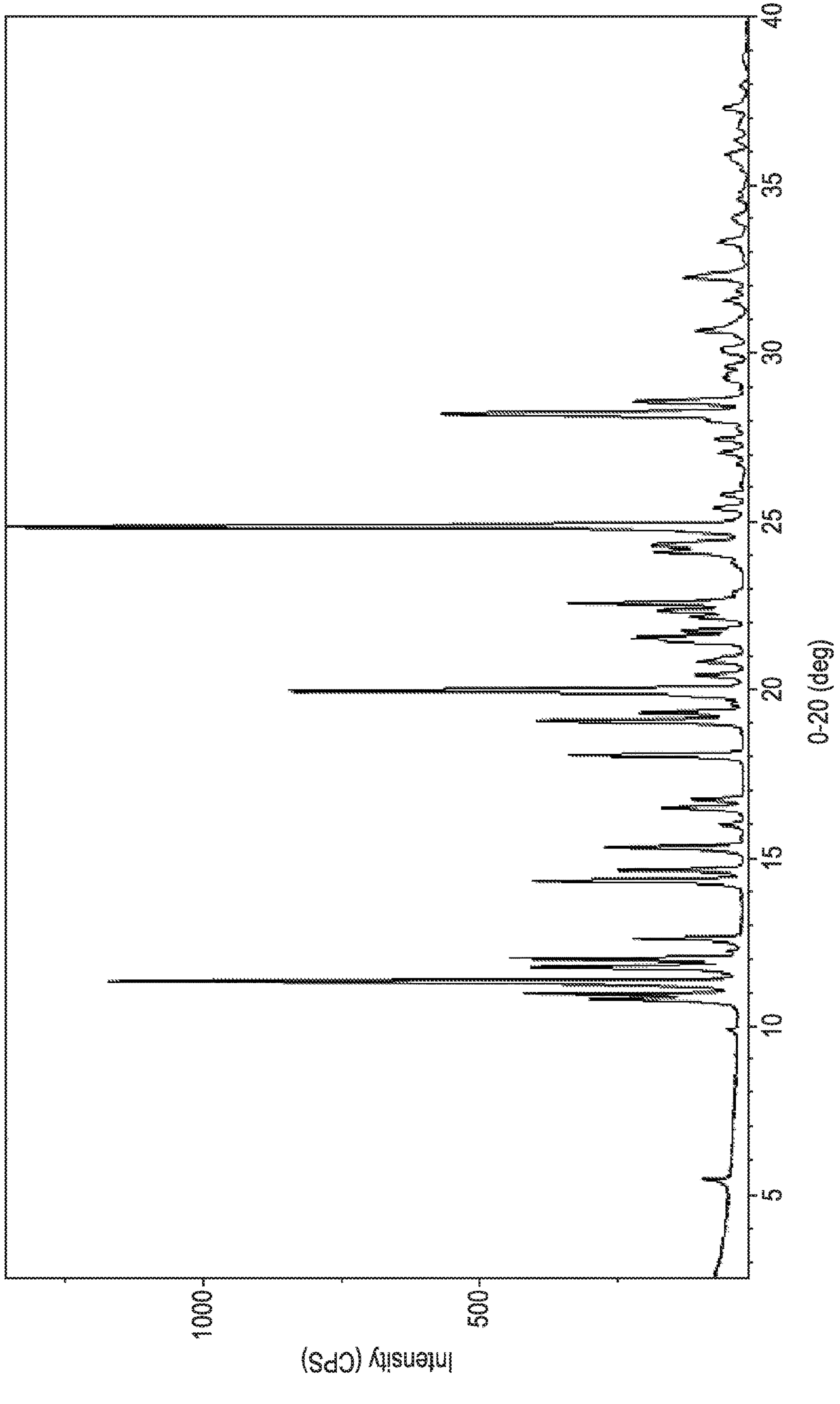
FIG. 1 is an XRPD pattern of Compound 1 Form A.

| Abbreviations/ Acronyms | Full Name/Description |
|---|---|
| DSC | Differential scanning calorimetry |
| DVS | Dynamic (water) vapor sorption |
| HSM | Hot stage microscopy |
| NMR | Nuclear magnetic resonance spectroscopy |
| OM | Optical microscopy |

-continued

| Abbreviations/ Acronyms | Full Name/Description |
|---|---|
| PLM | Polarized light microscopy |
| TGA | Thermogravimetry or Thermogravimetric analysis |
| XRPD | X-ray powder diffraction |

Experimental Techniques

| Abbreviations/ Acronyms | Full Name/Description |
|---|---|
| CC | Crash cooling |
| CP | Crash precipitation |
| FC | Fast cooling |
| FE | Fast evaporation |
| RC | Reaction crystallization |
| SC | Slow cooling |
| SE | Slow evaporation |
| VD | Vapor diffusion |
| VS | Vapor stress |

Miscellaneous

| Abbreviations/ Acronyms | Full Name/Description |
|---|---|
| ~ | About or approximately |
| API | Active pharmaceutical ingredient |
| B/E | Birefringence and extinction |
| Endo/endo | Endotherm or endothermic |
| eq | Equivalent |
| Exo/exo | Exotherm or exothermic |
| FB | Free base |
| FF | Free form |
| frz | Freezer |
| LIMS | Laboratory Information Management System |
| Max/max | Maximum or maxima |
| Obs | Observation |
| PO | Preferred orientation |
| ppt | Precipitate or precipitation |
| ref | Refrigerator |
| RH | Relative humidity |
| RT | Room temperature |
| Soln/soln | Solution |
| vac | Vacuum |
| wt % | Weight percent |

| Abbreviations/ Acronyms | Full Name/Description |
|---|---|
| ACN | Acetonitrile |
| AcOH | Acetic acid |
| DCM | Dichloromethane |
| DMSO | Dimethylsulfoxide |
| EtOAc | Ethyl acetate |
| EtOH | Ethanol |
| HFIPA | Hexafluoroisopropanol |
| IPA | Isopropyl alcohol, 2-propanol |
| MEK | Methyl ethyl ketone |
| MeOH | Methanol |
| MTBE | Methyl-tertiary-butyl ether |
| TFE | 2,2,2-Trifluoroethanol |
| THF | Tetrahydrofuran |

THF Tetrahydrofuran

As used herein, the following definitions shall apply unless otherwise indicated.

For purposes of this invention, the chemical elements are identified in accordance with the Periodic Table of the Elements, CAS version, Handbook of Chemistry and Physics, 95th Ed. Additionally, general principles of organic chemistry are described in "Organic Chemistry," $2^{nd}$ Ed., Thomas Sorrell, University Science Books, Sausalito: 2006, and "March's Advanced Organic Chemistry," 7th Ed., Ed.: Smith, M. B. and March, J., John Wiley & Sons, New York: 2013, the entire contents of which are hereby incorporated by reference.

As used herein, the term "Low/limited/significant hygroscopicity" refers to a material that exhibits <0.5/<2.0/≥2.0 wt % water uptake over a specified RH range.

As used herein, the term "stoichiometric hydrate" refers to crystalline material with a defined water content over an extended RH range. Typical stoichiometric hydrates are hemihydrates, monohydrates, sesquihydrates, dihydrates, etc.

As used herein, the term "variable hydrate" refers to crystalline material with variable water content over an extended RH range, yet with no phase change.

As used herein, a chemical term designated as a "Form" refers to a chemical compound or salt thereof that consists of a single phase.

As used herein, the term "low/limited/intermediate/good/high solubility" refers to a material having a solubility of <1/1-20/20-100/100-200/>200 mg/mL.

As used herein, the term "crystalline" refers to a material that produces an XRPD pattern with sharp peaks (similar to instrumental peak widths) and weak diffuse scattering relative to the peaks.

As used herein, the term "disordered crystalline" refers to a material that produces XRPD pattern with broad peaks (relative to instrumental peak widths) and/or strong diffuse scattering relative to the peaks. Disordered materials may be:

1) microcrystalline,
2) crystalline with large defect density,
3) mixtures of crystalline and X-ray amorphous phases, or
4) a combination of the above.

As used herein, the term "insufficient signal" means that spectrographic analysis of a sample produced a spectrum or pattern (output) having insufficient signal above the expected background noise.

As used herein, the term "single crystalline phase" refers to an XRPD pattern that is judged to contain evidence of a single crystalline form due to the Bragg peaks being indexed with a single unit cell. Indexing is the process of assigning Miller index labels to each peak in a diffraction pattern. Also, the size and shape of the crystal unit cell is determined during the indexing process.

As used herein, the term "slurry" refers to a suspension prepared by adding enough solids to a given solvent at ambient conditions so that undissolved solids are present. A typical slurry includes agitation (typically by stirring or oscillation), an act that is also referred to as "slurrying," in a sealed vial at a given temperature for an extended period of time. Typically, the solids are recovered after a given period of time using a method described herein.

As used herein, the term "X-ray amorphous" or "amorphous" refers to a material having diffuse scatter present, but no evidence for Bragg peaks in the XRPD pattern.

As used herein, the term "crystalline" refers to compounds in a solid state having a periodic and repeating three-dimensional internal arrangement of atoms, ions or molecules characteristic of crystals, for example, arranged in fixed geometric patterns or lattices that have rigid long range order. The term crystalline does not necessarily mean that the compound exists as crystals, but that it has this crystal-like internal structural arrangement.

As used herein, the term "substantially crystalline" refers to a solid material that is predominately arranged in fixed geometric patterns or lattices that have rigid long range order. For example, substantially crystalline materials have more than about 85% crystallinity (e.g., more than about 90% crystallinity, more than about 95% crystallinity, or more than about 99% crystallinity). It is also noted that the term 'substantially crystalline' includes the descriptor 'crystalline,' which is defined in the previous paragraph.

"Patient" for the purposes of the present invention includes humans and any other animals, particularly mammals, and other organisms. Thus, the methods are applicable to both human therapy and veterinary applications. In a preferred embodiment, the patient is a mammal, and in a most preferred embodiment the patient is human. Examples of the preferred mammals include mice, rats, other rodents, rabbits, dogs, cats, swine, cattle, sheep, horses, and primates.

"Kinase-dependent diseases or conditions" refer to pathologic conditions that depend on the activity of one or more kinases. Kinases either directly or indirectly participate in the signal transduction pathways of a variety of cellular activities including proliferation, adhesion, migration, differentiation, and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

"Therapeutically effective amount" is an amount of a crystalline form or crystalline salt form of the present invention that, when administered to a patient, ameliorates a symptom of the disease. The amount of a crystalline form or crystalline salt form of the present invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit risk ratio.

As used herein, the phrase "pharmaceutically acceptable excipient" refers to a pharmaceutically-acceptable material, composition, or vehicle, such as a liquid or solid filler, diluent, solvent, or encapsulating material. Excipients are generally safe, non-toxic and neither biologically nor otherwise undesirable and include excipients that are acceptable for veterinary use as well as human pharmaceutical use. In one embodiment, each component is "pharmaceutically acceptable" as defined herein. See, e.g., Remington: The Science and Practice of Pharmacy, 21st ed.; Lippincott Williams & Wilkins: Philadelphia, Pa., 2005; Handbook of 'Pharmaceutical Excipients, 6th ed.; Rowe et al, Eds.; The Pharmaceutical Press and the American Pharmaceutical Association: 2009; Handbook of Pharmaceutical Additives, 3rd ed.; Ash and Ash Eds. Gower Publishing Company: 2007; Pharmaceutical Pref or mulation and Formulation, 2nd ed; Gibson Ed.; CRC Press LLC: Boca Raton, Fla., 2009.

"Cancer" refers to cellular-proliferative disease states, including, but not limiting to: Cardiac: sarcoma (angiosarcoma, fibrosarcoma, rhabdomyosarcoma, liposarcoma), myxoma, rhabdomyoma, fibroma, lipoma and teratoma; Head and neck: squamous cell carcinomas of the head and neck, laryngeal and hypopharyngeal cancer, nasal cavity and paranasal sinus cancer, nasopharyngeal cancer, salivary gland cancer, oral and orppharyngeal cancer; Lung: bronchogenic carcinoma (squamous cell, undifferentiated small cell, undifferentiated large cell, adenocarcinoma, non-small cell lung cancer), alveolar (bronchiolar) carcinoma, alveolar sarcoma, alveolar soft part sarcoma, bronchial adenoma, sarcoma, lymphoma, chondromatous hamartoma, mesothelioma; Colon: colorectal cancer, adenocarcinoma, gastrointestinal stromal tumors, lymphoma, carcinoids, Turcot Syndrome; Gastrointestinal: gastric cancer, gastroesophageal junction adenocarcinoma, esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Breast: metastatic breast cancer, ductal carcinoma in situ, invasive ductal carcinoma, tubular carcinoma, medullary carcinoma, mucinous carcinoma, lobular carcinoma in situ, triple negative breast cancer; Genitourinary tract: kidney (adenocarcinoma, Wilm's tumor [nephroblastoma], lymphoma, leukemia, renal cell carcinoma, metastatic renal cell carcinoma), bladder and urethra (squamous cell carcinoma, transitional cell carcinoma, adenocarcinoma, urothelial carcinoma), prostate (adenocarcinoma, sarcoma, castrate resistant prostate cancer, bone metastases, bone metastases associated with castrate resistant prostate cancer), testis (seminoma, teratoma, embryonal carcinoma, teratocarcinoma, choriocarcinoma, sarcoma, interstitial cell carcinoma, fibroma, fibroadenoma, adenomatoid tumors, lipoma), clear cell carcinoma, papillary carcinoma, penile cancer, penile squamous cell carrcinoma; Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma, and giant cell tumors; Thyroid: medullary thyroid cancer, differentiated thyroid cancer, papillary thyroid cancer, follicular thyroid cancer, hurthle cell cancer, and anaplastic thyroid cancer; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma), NF1, neurofibromatosis, plexiform neurofibromas; Gynecological: uterus (endometrial cancer), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematoloic: blood (myeloid leukemia [acute and chronic], acute lymphoblastic leukemia, chronic lymphocytic leukemia, myeloproliferative diseases, multiple myeloma, myelodysplastic syndrome), myelofibrosis, polycythemia vera, essential thrombocythemia, Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In some embodiments, a compound or combination as disclosed herein can be used for the treatment of diseases including HIV, sickle cell disease, graft-versus-host disease, acute graft-versus-host disease, chronic graft-versus-host disease, and sickle cell anemia.

In general, the nomenclature used in this application is based on naming conventions adopted by the international union of pure and applied chemistry (IUPAC). Chemical structures shown herein were prepared using CHEMDRAW®. Any open valency appearing on a carbon, oxygen, or nitrogen atom in the structures herein indicates the presence of a hydrogen atom.

EMBODIMENTS

In one aspect, the invention relates to a crystalline solid form of Compound 1

Compound 1

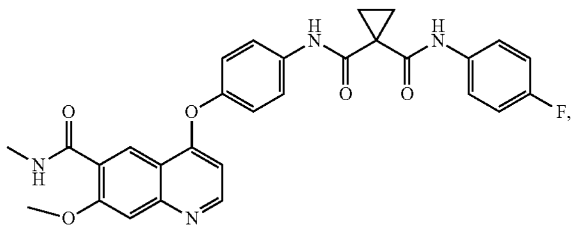

which is 1-N'-(4-Fluorophenyl)-1-N-[4-[7-methoxy-6-(methylcarbamoyl)quinolin-4-yl]oxyphenyl]cyclopropane-1,1-dicarboxamide, or N'-(4-Fluorophenyl)-N-[4-[7-methoxy-6-(methylcarbamoyl)quinolin-4-yl]oxyphenyl] cyclopropane-1,1-dicarboxamide, or a salt, solvate, or hydrate thereof.

In some embodiments of this aspect, the salt is an inorganic salt, an organic salt, a pharmaceutically acceptable salt, or a chiral salt.

In one aspect, the invention relates to a crystalline solid form of Compound 1

Compound 1

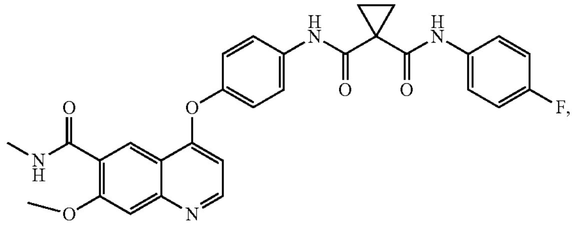

which is 1-N'-(4-Fluorophenyl)-1-N-[4-[7-methoxy-6-(methylcarbamoyl)quinolin-4-yl]oxyphenyl]cyclopropane-1,1-dicarboxamide, or N'-(4-Fluorophenyl)-N-[4-[7-methoxy-6-(methylcarbamoyl)quinolin-4-yl]oxyphenyl]cyclopropane-1,1-dicarboxamide, or hydrate or solvate thereof.

In one embodiment of this aspect, the crystalline solid form of Compound 1 is characterized as Form A, Form B, Form C, Form D, Form E, Form F, Form G, Form H, Form K, Form O, or Form Q In one embodiment, the crystalline solid is characterized as Compound 1 Form A.

In still a further embodiment, the Compound 1 Form A is characterized by one or more of the following peaks in an XRPD pattern on a 2 Theta scale ±0.20, wherein the one or more peaks is selected from 5.48, 9.93, 10.83, 10.98, 11.36, 11.79, 12.04, 12.25, 12.62, 14.33, 14.67, 15.33, 16.02, 16.51, 16.77, 18.07, 19.09, 19.34, 19.60, 20.00, 20.46, 20.85, 21.45, 21.55, 21.76, 22.16, 22.35, 22.58, 22.87, 23.79, 24.11, 24.29, 24.35, 24.87, 25.42, 25.81, 26.09, 26.72, 27.04, 27.44, 27.77, 27.98, 28.19, and 28.56.

In another embodiment, the Compound 1 Form A is characterized by one or more peaks in an XRPD pattern on a 2 Theta scale, ±0.20, wherein the one or more peaks is selected from 5.48, 9.93, 11.36, 11.79, 12.04, 12.62, 14.33, 14.67, 15.33, 16.51, 18.07, 19.09, 20.00, 21.55, 22.35, 22.58, 24.29, 24.35, 24.87, 28.19, and 28.56.

In another embodiment, the Compound 1 Form A is characterized by one or more peaks in an XRPD pattern on a 2 Theta scale, ±0.20, wherein the one or more peaks is selected from 10.83, 10.98, 11.36, 11.79, 12.04, 14.33, 18.07, 19.09, 20.00, 22.58, 24.87, and 28.19.

In a further embodiment, the Compound 1 Form A is characterized by all of the following peaks in an XRPD pattern on a 2 Theta scale ±0.20, wherein the peaks are 10.83, 10.98, 11.36, 11.79, 12.04, 14.33, 18.07, 19.09, 20.00, 22.58, 24.87, and 28.19.

In still a further embodiment, the Compound 1 Form A is characterized by all of the following peaks in an XRPD pattern on a 2 Theta scale ±0.20, wherein the peaks are 5.48, 9.93, 11.36, 11.79, 12.04, 12.62, 14.33, 14.67, 15.33, 16.51, 18.07, 19.09, 20.00, 21.55, 22.35, 22.58, 24.29, 24.35, 24.87, 28.19, and 28.56.

In still a further embodiment, the Compound 1 Form A is characterized by all of the following peaks in an XRPD pattern on a 2 Theta scale ±0.20, wherein the peaks are 5.48, 9.93, 10.83, 10.98, 11.36, 11.79, 12.04, 12.25, 12.62, 14.33, 14.67, 15.33, 16.02, 16.51, 16.77, 18.07, 19.09, 19.34, 19.60, 20.00, 20.46, 20.85, 21.45, 21.55, 21.76, 22.16, 22.35, 22.58, 22.87, 23.79, 24.11, 24.29, 24.35, 24.87, 25.42, 25.81, 26.09, 26.72, 27.04, 27.44, 27.77, 27.98, 28.19, and 28.56.

In still a further embodiment, the Compound 1 Form A is characterized by an XRPD pattern substantially identical to FIG. 1.

In one embodiment, the Compound 1 Form A is characterized by an endotherm at a temperature greater than 200° C. in a DSC thermogram. In one embodiment, the Compound 1 Form A is characterized by an endotherm with on an onset temperature at greater than 200° C. in a DSC thermogram.

In another embodiment, the Compound 1 Form A is characterized by a weight loss at a temperature greater than 200° C. in a TGA thermogram.

In another embodiment, the Compound 1 Form A is characterized by a weight gain of from about 0.8 to about 1.0 wt %, as determined by DVS analysis, when taken from an environment of 5% relative humidity to an environment of 95% relative humidity.

In one embodiment, the crystalline solid is characterized as Compound 1 Form B.

In one embodiment, the Compound 1 Form B is characterized by one or more peaks in an XRPD pattern on a 2 Theta scale, ±0.2, wherein the one or more peaks is selected from 4.76, 9.58, 10.49, 10.97, 11.27, 12.10, 13.26, 13.52, 14.52, 15.15, 15.42, 16.69, 17.29, 17.92, 18.34, 19.05, 19.25, 19.48, 20.04, 20.59, 20.90, 21.39, 21.84, 22.25, 22.68, 22.84, 23.12, 23.32, 23.60, 24.03, 24.79, 25.32, 25.65, 25.88, 26.50, 26.79, 27.25, 28.55, and 29.49.

In one embodiment, the Compound 1 Form B is characterized by one or more peaks in an XRPD pattern on a 2 Theta scale, ±0.2, wherein the one or more peaks is selected from 9.58, 10.49, 11.27, 12.10, 13.26, 13.52, 15.15, and 16.69.

In another embodiment, the Compound 1 Form B is characterized by one or more peaks in an XRPD pattern on a 2 Theta scale, ±0.2, wherein the one or more peaks is selected from 10.49, 12.10, 13.26, and 13.52.

In a further embodiment, the Compound 1 Form B is characterized by all of the following peaks in an XRPD pattern on a 2 Theta scale, ±0.2, wherein the peaks are 10.49, 12.10, 13.26, and 13.52.

In still a further embodiment, the Compound 1 Form B is characterized by all of the following peaks in an XRPD pattern on a 2 Theta scale, ±0.2, wherein the peaks are 9.58, 10.49, 11.27, 12.10, 13.26, 13.52, 15.15, and 16.69.

In still a further embodiment, the Compound 1 Form B is characterized by all of the following peaks in an XRPD pattern on a 2 Theta scale, ±0.2, wherein the peaks are 4.76, 9.58, 10.49, 10.97, 11.27, 12.10, 13.26, 13.52, 14.52, 15.15, 15.42, 16.69, 17.29, 17.92, 18.34, 19.05, 19.25, 19.48, 20.04, 20.59, 20.90, 21.39, 21.84, 22.25, 22.68, 22.84, 23.12, 23.32, 23.60, 24.03, 24.79, 25.32, 25.65, 25.88, 26.50, 26.79, 27.25, 28.55, and 29.49.

Figure 6:
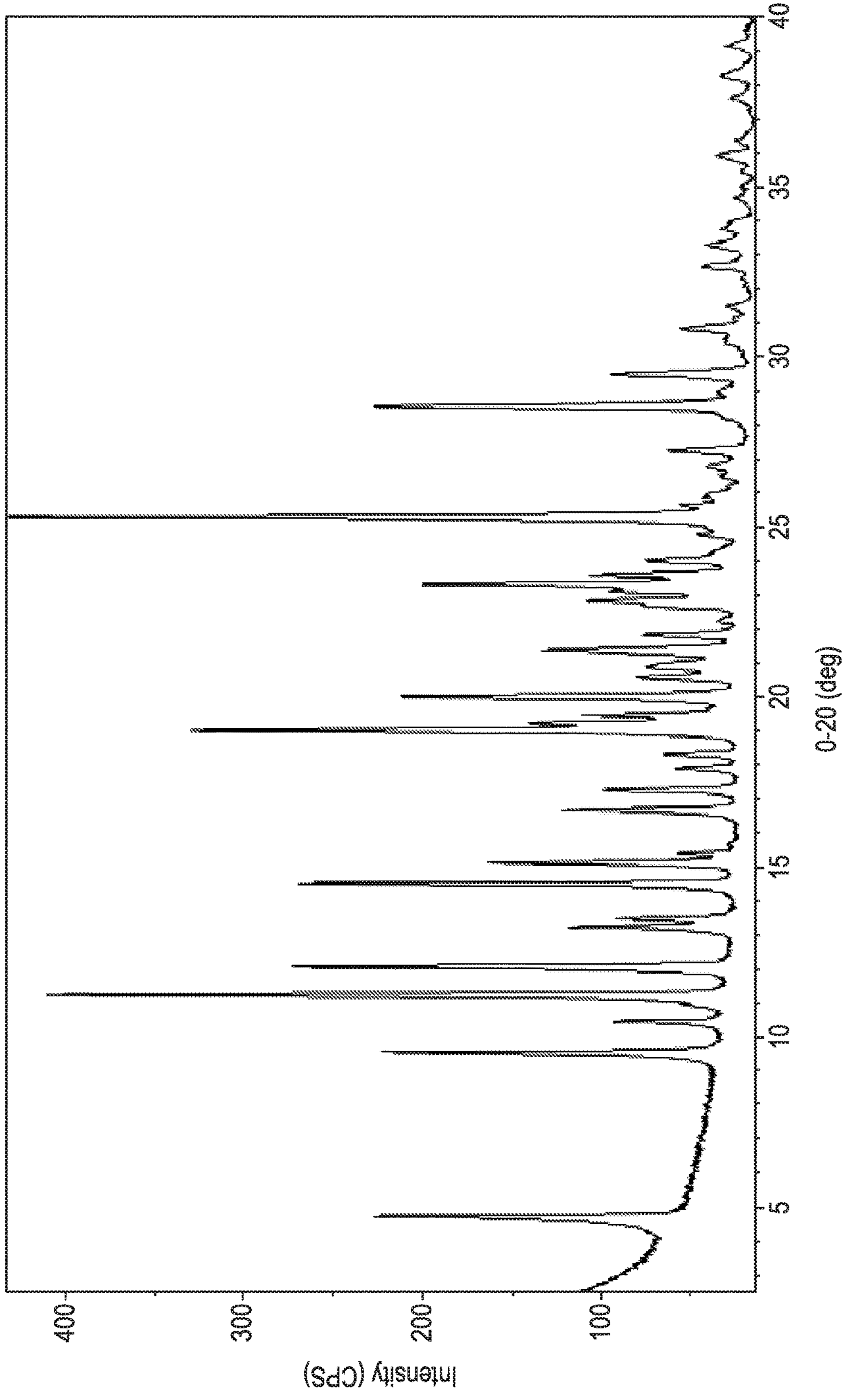

In still a further embodiment, the Compound 1 Form B is characterized by an XRPD pattern substantially identical to FIG. 6.

In one embodiment, the Compound 1 Form B is characterized by a first weight loss of ~0.3 wt % between the temperatures of 38-92° C., and a second weight loss of ~11.2 wt % between the temperatures of 92-188° C. in a TGA thermogram.

In one embodiment, the crystalline solid is characterized as Compound 1 Form C.

In one embodiment, the Compound 1 Form C is characterized by one or more peaks in an XRPD pattern on a 2 Theta scale, ±0.2, wherein the one or more peaks is selected from 3.89, 4.63, 7.95, 9.31, 10.54, 10.87, 11.14, 11.31, 11.49, 11.75, 12.22, 12.96, 13.59, 13.84, 14.01, 14.62, 14.79, 15.46, 15.86, 16.07, 16.61, 16.73, 16.88, 17.64, 18.13, 18.73, 19.10, 19.42, 19.75, 20.09, 20.47, 21.00, 21.65, 21.95, 22.47, 23.11, 23.46, 23.77, 24.84, 25.17, 26.14, 26.48, 26.88, 27.72, 28.35, 28.70, and 28.96.

In one embodiment, the Compound 1 Form C is characterized by one or more peaks in an XRPD pattern on a 2 Theta scale, ±0.2, wherein the one or more peaks is selected from 3.89, 7.95, 9.31, 10.54, 12.96, 16.61, 17.64, and 20.47.

In another embodiment, the Compound 1 Form C is characterized by one or more peaks in an XRPD pattern on a 2 Theta scale, ±0.2, wherein the one or more peaks is selected from 3.89, 7.95, 9.31, and 17.64.

In a further embodiment, the Compound 1 Form C is characterized by all of the following peaks in an XRPD pattern on a 2 Theta scale, ±0.2, wherein the peaks are 3.89, 7.95, 9.31, and 17.64.

In still a further embodiment, the Compound 1 Form C is characterized by all of the following peaks in an XRPD pattern on a 2 Theta scale, ±0.2, wherein the peaks are 3.89, 7.95, 9.31, 10.54, 12.96, 16.61, 17.64, and 20.47.

In still a further embodiment, the Compound 1 Form C is characterized by all of the following peaks in an XRPD pattern on a 2 Theta scale, ±0.2, wherein the peaks are 3.89, 4.63, 7.95, 9.31, 10.54, 10.87, 11.14, 11.31, 11.49, 11.75, 12.22, 12.96, 13.59, 13.84, 14.01, 14.62, 14.79, 15.46, 15.86, 16.07, 16.61, 16.73, 16.88, 17.64, 18.13, 18.73, 19.10, 19.42, 19.75, 20.09, 20.47, 21.00, 21.65, 21.95, 22.47, 23.11, 23.46, 23.77, 24.84, 25.17, 26.14, 26.48, 26.88, 27.72, 28.35, 28.70, and 28.96.

Figure 8:
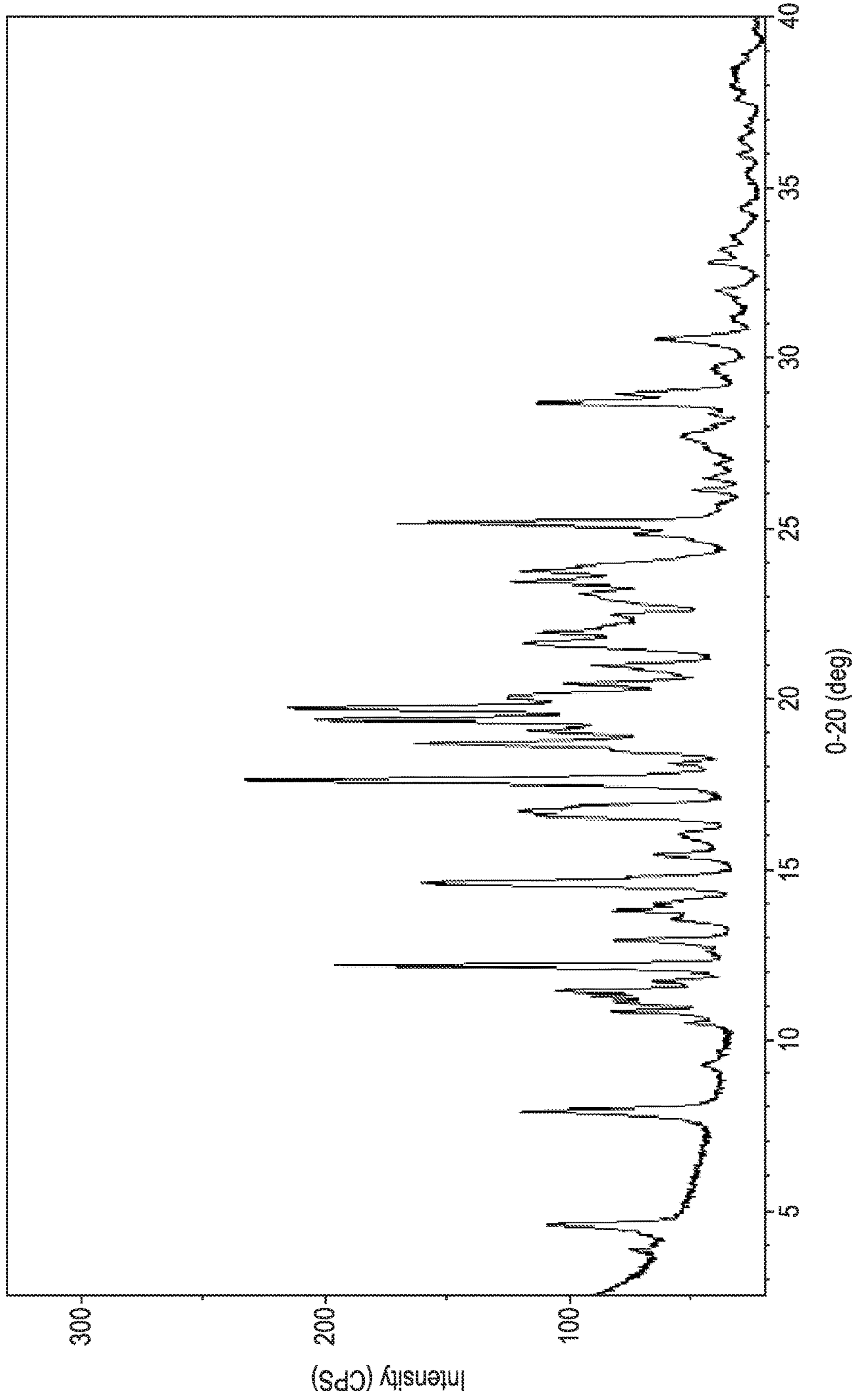

In still a further embodiment, the Compound 1 Form C is characterized by an XRPD pattern substantially identical to FIG. 8.

In one embodiment, the Compound 1 Form C is characterized by a first weight loss of ~0.4 wt % between the temperatures of 40-75° C., a second weight loss of ~13.8 wt % between the temperatures of 75-154° C., and a third weight loss of ~1.9 wt % between the temperatures of 190-220° C. in a TGA thermogram.

In one embodiment, the crystalline solid is characterized as Compound 1 Form D.

In one embodiment, the Compound 1 Form D is characterized by one or more peaks in an XRPD pattern on a 2 Theta scale, ±0.2, wherein the one or more peaks is selected from 5.08, 5.43, 7.00, 9.62, 10.21, 10.90, 12.31, 13.66, 14.06, 14.70, 15.35, 16.06, 16.39, 17.89, 18.17, 18.35, 18.53, 18.80, 18.96, 19.15, 19.50, 20.09, 20.37, 20.58, 20.93, 21.31, 21.79, 21.97, 22.30, 22.91, 23.12, 23.26, 23.62, 23.93, 24.37, 24.77, 24.99, 25.39, 25.96, 26.62, 27.10, 27.53, 28.05, 28.38, 28.78, 29.09, 29.38, and 29.64.

In one embodiment, the Compound 1 Form D is characterized by one or more peaks in an XRPD pattern on a 2 Theta scale, ±0.2, wherein the one or more peaks is selected from 5.43, 7.00, 10.21, 18.96, 23.62, 24.99, 26.62, 27.10, and 29.64.

In another embodiment, the Compound 1 Form D is characterized by one or more peaks in an XRPD pattern on a 2 Theta scale, ±0.2, wherein the one or more peaks is selected from 5.43, 7.00, 10.21, and 29.64.

In a further embodiment, the Compound 1 Form D is characterized by all of the following peaks in an XRPD pattern on a 2 Theta scale, ±0.2, wherein the peaks are 5.43, 7.00, 10.21, and 29.64.

In still a further embodiment, the Compound 1 Form D is characterized by all of the following peaks in an XRPD pattern on a 2 Theta scale, ±0.2, wherein the peaks are 5.43, 7.00, 10.21, 18.96, 23.62, 24.99, 26.62, 27.10, and 29.64.

In still a further embodiment, the Compound 1 Form D is characterized by all of the following peaks in an XRPD pattern on a 2 Theta scale, ±0.2, wherein the peaks are 5.08, 5.43, 7.00, 9.62, 10.21, 10.90, 12.31, 13.66, 14.06, 14.70, 15.35, 16.06, 16.39, 17.89, 18.17, 18.35, 18.53, 18.80, 18.96, 19.15, 19.50, 20.09, 20.37, 20.58, 20.93, 21.31, 21.79, 21.97, 22.30, 22.91, 23.12, 23.26, 23.62, 23.93, 24.37, 24.77, 24.99, 25.39, 25.96, 26.62, 27.10, 27.53, 28.05, 28.38, 28.78, 29.09, 29.38, and 29.64.

Figure 10:
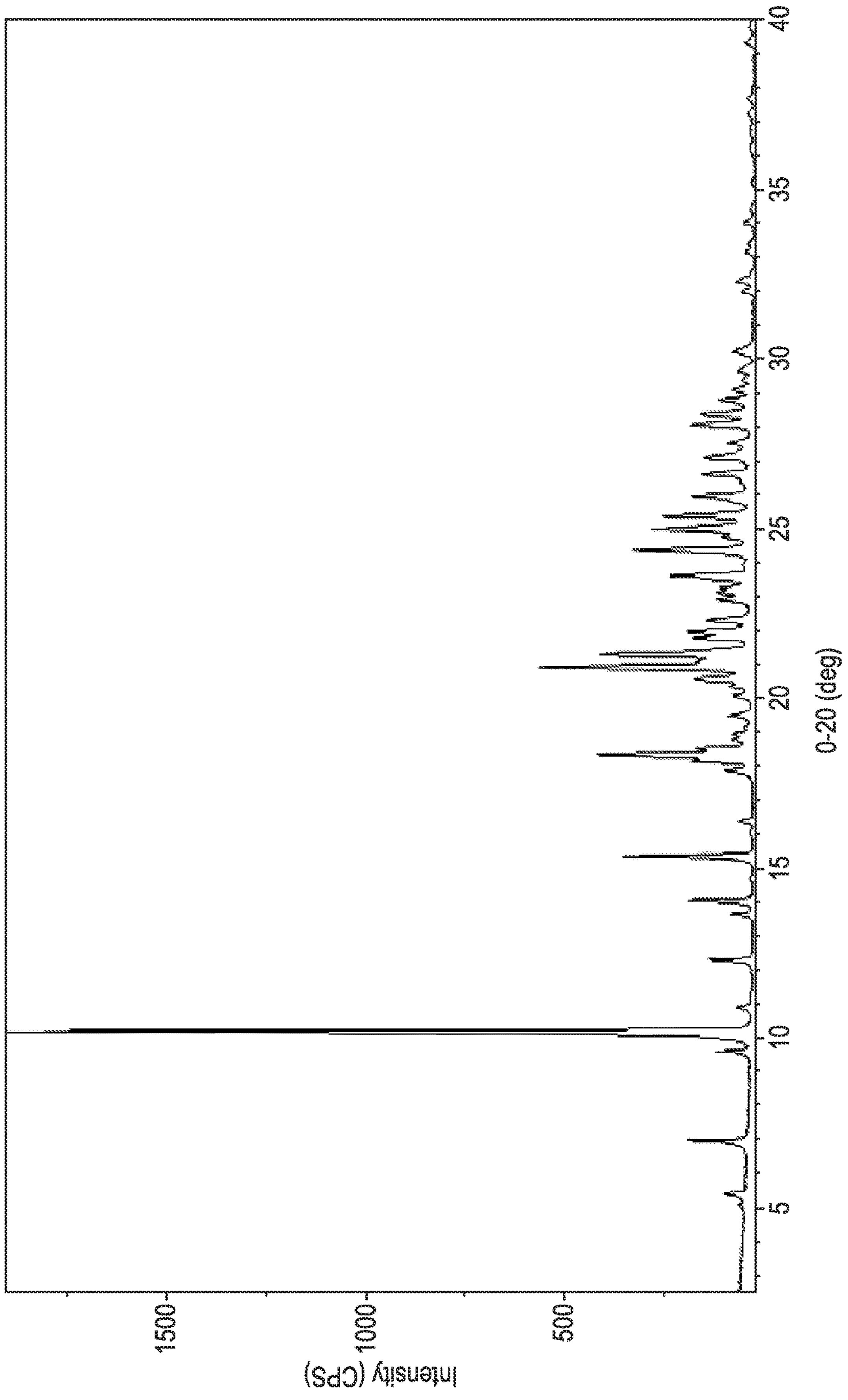
FIG. 10 is an XRPD pattern of Compound 1 Form D.

In still a further embodiment, the Compound 1 Form D is characterized by an XRPD pattern substantially identical to FIG. 10.

In another embodiment, the Compound 1 Form D is characterized by a weight loss of ~13.5 wt % between the temperatures of 38-130° C. in a TGA thermogram.

In one embodiment, the crystalline solid is characterized as Compound 1 Form E.

In one embodiment, the Compound 1 Form E is characterized by one or more peaks in an XRPD pattern on a 2 Theta scale, ±0.2, wherein the one or more peaks is selected from 5.16, 6.13, 9.77, 10.37, 10.82, 11.69, 13.73, 14.34, 14.79, 15.47, 15.79, 16.33, 16.64, 16.82, 17.60, 17.89, 18.16, 18.72, 19.09, 19.59, 20.65, 21.73, 22.10, 22.72, 23.23, 23.54, 23.79, 24.78, 25.13, 26.37, 26.91, 29.12, and 29.95.

In one embodiment, the Compound 1 Form E is characterized by one or more peaks in an XRPD pattern on a 2 Theta scale, ±0.2, wherein the one or more peaks is selected from 6.13, 9.77, 10.37, 13.73, 14.79, 26.37, 29.12, and 29.95.

In another embodiment, the Compound 1 Form E is characterized by one or more peaks in an XRPD pattern on a 2 Theta scale, ±0.2, wherein the one or more peaks is selected from 10.37, 14.79, 26.37, and 29.95.

In a further embodiment, the Compound 1 Form E is characterized by all of the following peaks in an XRPD pattern on a 2 Theta scale, ±0.2, wherein the peaks are 10.37, 14.79, 26.37, and 29.95.

In still a further embodiment, the Compound 1 Form E is characterized by all of the following peaks in an XRPD pattern on a 2 Theta scale, ±0.2, wherein the peaks are 6.13, 9.77, 10.37, 13.73, 14.79, 26.37, 29.12, and 29.95.

In still a further embodiment, the Compound 1 Form E is characterized by all of the following peaks in an XRPD pattern on a 2 Theta scale, ±0.2, wherein the peaks are 5.16, 6.13, 9.77, 10.37, 10.82, 11.69, 13.73, 14.34, 14.79, 15.47, 15.79, 16.33, 16.64, 16.82, 17.60, 17.89, 18.16, 18.72, 19.09, 19.59, 20.65, 21.73, 22.10, 22.72, 23.23, 23.54, 23.79, 24.78, 25.13, 26.37, 26.91, 29.12, and 29.95.

Figure 12:
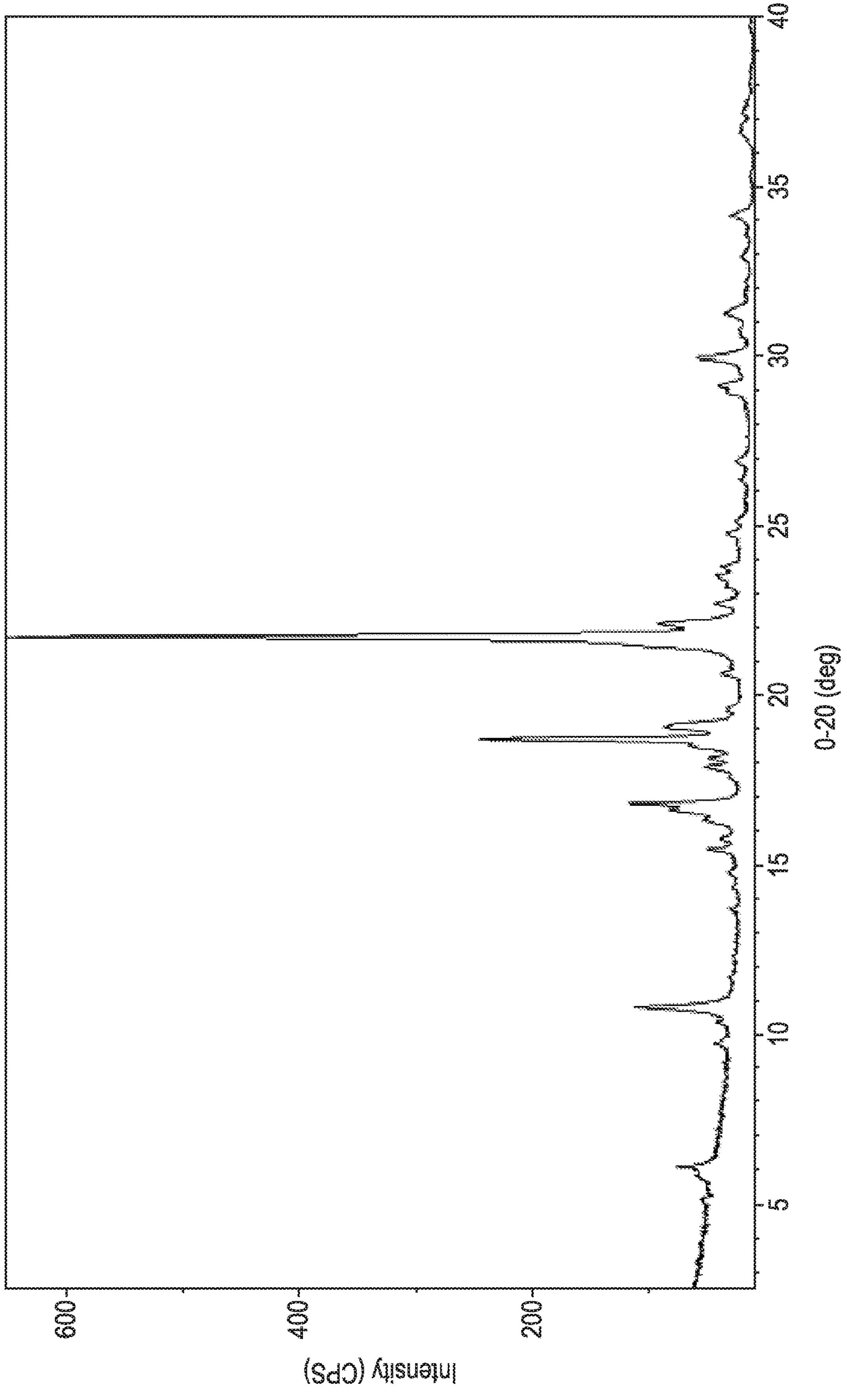
FIG. 12 is an XRPD pattern of Compound 1 Form E.

In still a further embodiment, the Compound 1 Form E is characterized by an XRPD pattern substantially identical to FIG. 12.

In another embodiment, the Compound 1 Form E is characterized by a weight loss of ~8.2 wt % between the temperatures of 60-130° C. in a TGA thermogram.

In one embodiment, the crystalline solid is characterized as Compound 1 Form F.

In one embodiment, the Compound 1 Form F is characterized by one or more peaks in an XRPD pattern on a 2 Theta scale, ±0.2, wherein the one or more peaks is selected from 5.85, 7.44, 8.56, 10.95, 11.75, 12.28, 13.65, 14.48, 14.94, 15.61, 16.27, 16.68, 17.84, 18.39, 19.25, 19.52, 20.30, 21.62, 22.07, 22.83, 23.58, 24.33, 25.93, 26.20, 26.48, 27.79, 29.2 and 29.9.

In one embodiment, the Compound 1 Form F is characterized by one or more peaks in an XRPD pattern on a 2 Theta scale, ±0.2, wherein the one or more peaks is selected from 7.44, 8.56, 13.65, 16.27, 19.25, 25.93, 29.2 and 29.9.

In another embodiment, the Compound 1 Form F is characterized by one or more peaks in an XRPD pattern on a 2 Theta scale, ±0.2, wherein the one or more peaks is selected from 7.44, 8.56, 13.65, and 29.9.

In a further embodiment, the Compound 1 Form F is characterized by all of the following peaks in an XRPD pattern on a 2 Theta scale, ±0.2, wherein the peaks are 7.44, 8.56, 13.65, and 29.9.

In still a further embodiment, the Compound 1 Form F is characterized by all of the following peaks in an XRPD pattern on a 2 Theta scale, ±0.2, wherein the peaks are 7.44, 8.56, 13.65, 16.27, 19.25, 25.93, 29.2 and 29.9.

In still a further embodiment, the Compound 1 Form F is characterized by all of the following peaks in an XRPD pattern on a 2 Theta scale, ±0.2, wherein the peaks are 5.85, 7.44, 8.56, 10.95, 11.75, 12.28, 13.65, 14.48, 14.94, 15.61, 16.27, 16.68, 17.84, 18.39, 19.25, 19.52, 20.30, 21.62, 22.07, 22.83, 23.58, 24.33, 25.93, 26.20, 26.48, 27.79, 29.2 and 29.9.

In one embodiment, the Compound 1 Form F is characterized by one or more peaks in an XRPD pattern on a 2 Theta scale, ±0.2, wherein the one or more peaks is selected from 5.85, 7.44, 8.56, 10.95, 11.75, 12.28, 13.65, 14.48, 14.94, 15.61, 16.27, 16.68, 17.84, 18.39, 19.25, 19.52, 20.30, 21.62, 22.07, 22.83, 23.58, 24.33, 25.93, 26.20, 26.48, and 27.79.

In one embodiment, the Compound 1 Form F is characterized by one or more peaks in an XRPD pattern on a 2 Theta scale, ±0.2, wherein the one or more peaks is selected from 7.44, 8.56, 13.65, 16.27, 19.25, and 25.93.

In another embodiment, the Compound 1 Form F is characterized by one or more peaks in an XRPD pattern on a 2 Theta scale, ±0.2, wherein the one or more peaks is selected from 7.44, 8.56, and 13.65.

In a further embodiment, the Compound 1 Form F is characterized by all of the following peaks in an XRPD pattern on a 2 Theta scale, ±0.2, wherein the peaks are 7.44, 8.56, and 13.65.

In still a further embodiment, the Compound 1 Form F is characterized by all of the following peaks in an XRPD pattern on a 2 Theta scale, ±0.2, wherein the peaks are 7.44, 8.56, 13.65, 16.27, 19.25, and 25.93.

In still a further embodiment, the Compound 1 Form F is characterized by all of the following peaks in an XRPD pattern on a 2 Theta scale, ±0.2, wherein the peaks are 5.85, 7.44, 8.56, 10.95, 11.75, 12.28, 13.65, 14.48, 14.94, 15.61, 16.27, 16.68, 17.84, 18.39, 19.25, 19.52, 20.30, 21.62, 22.07, 22.83, 23.58, 24.33, 25.93, 26.20, 26.48, and 27.79.

Figure 14:
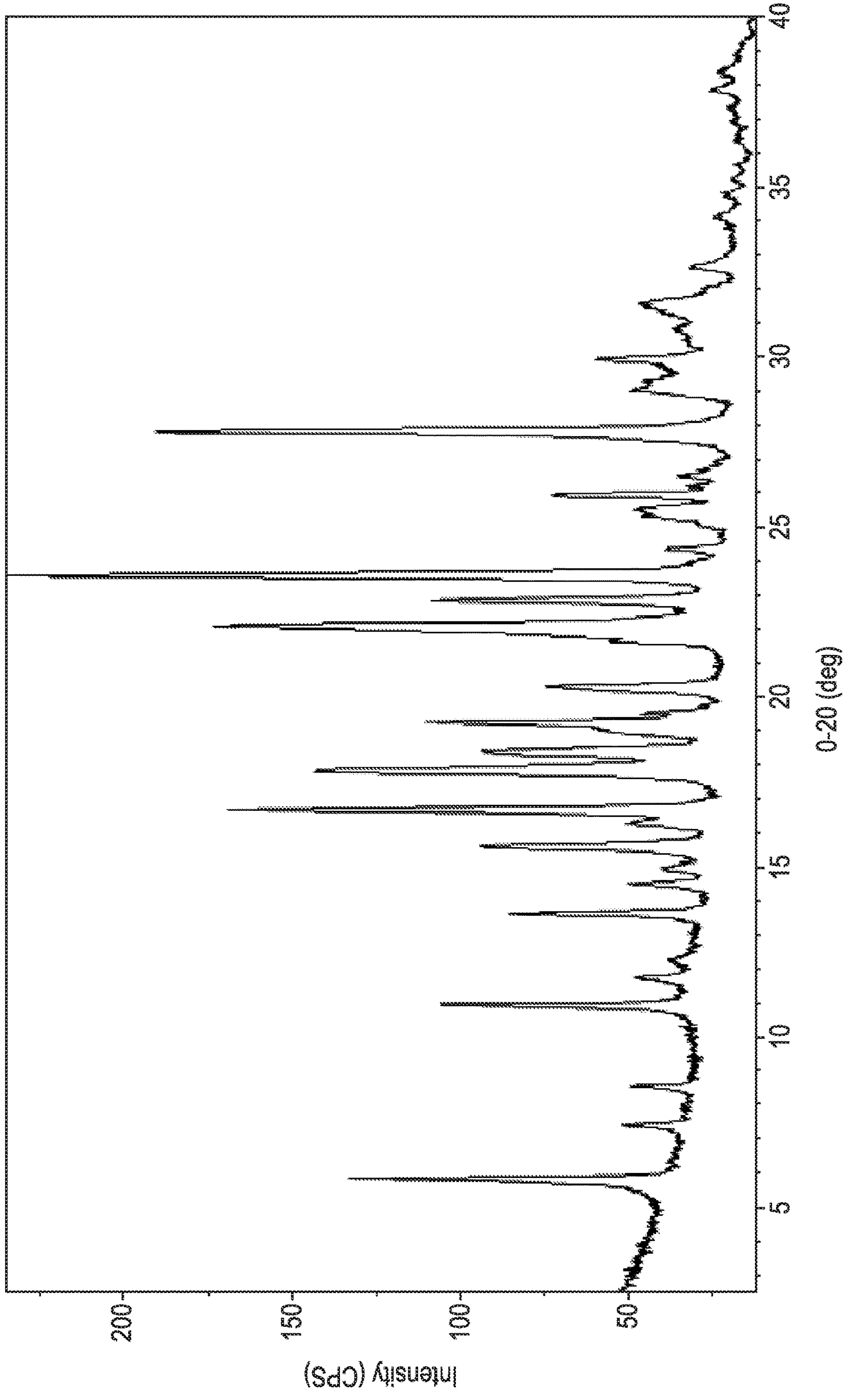
FIG. 14 is an XRPD pattern of Compound 1 Form F.

In still a further embodiment, the Compound 1 Form F is characterized by an XRPD pattern substantially identical to FIG. 14.

In another embodiment, the Compound 1 Form F is characterized by a first weight loss of ~0.1 wt % between the temperatures of 38-77° C., and a second weight loss of ~14.4 wt % between the temperatures of 77-178° C. in a TGA thermogram.

In one embodiment, the crystalline solid is characterized as Compound 1 Form G.

In one embodiment, the Compound 1 Form G is characterized by one or more peaks in an XRPD pattern on a 2 Theta scale, ±0.2, wherein the one or more peaks is selected from 4.72, 6.71, 9.47, 11.51, 11.84, 13.04, 14.40, 15.12, 16.03, 16.28, 16.51, 17.04, 17.85, 18.04, 18.73, 19.29, 19.49, 19.73, 20.72, 21.10, 22.61, 23.16, 24.10, 25.49, 26.47, 27.25, 27.84, 30.3, and 30.7.

In one embodiment, the Compound 1 Form G is characterized by one or more peaks in an XRPD pattern on a 2 Theta scale, ±0.2, wherein the one or more peaks is selected from 6.71, 9.47, 14.40, 17.04, 17.85, 21.10, 30.3, and 30.7.

In another embodiment, the Compound 1 Form G is characterized by one or more peaks in an XRPD pattern on a 2 Theta scale, ±0.2, wherein the one or more peaks is selected from 6.71, 9.47, 30.3, and 30.7.

In a further embodiment, the Compound 1 Form G is characterized by all of the following peaks in an XRPD pattern on a 2 Theta scale, ±0.2, wherein the peaks are 6.71, 9.47, 30.3, and 30.7.

In still a further embodiment, the Compound 1 Form G is characterized by all of the following peaks in an XRPD pattern on a 2 Theta scale, ±0.2, wherein the peaks are 6.71, 9.47, 14.40, 17.04, 17.85, 21.10, 30.3, and 30.7.

In still a further embodiment, the Compound 1 Form G is characterized by all of the following peaks in an XRPD pattern on a 2 Theta scale, ±0.2, wherein the peaks are 4.72, 6.71, 9.47, 11.51, 11.84, 13.04, 14.40, 15.12, 16.03, 16.28, 16.51, 17.04, 17.85, 18.04, 18.73, 19.29, 19.49, 19.73, 20.72, 21.10, 22.61, 23.16, 24.10, 25.49, 26.47, 27.25, 27.84, 30.3, and 30.7.

In one embodiment, the Compound 1 Form G is characterized by one or more peaks in an XRPD pattern on a 2 Theta scale, ±0.2, wherein the one or more peaks is selected from 4.72, 6.71, 9.47, 11.51, 11.84, 13.04, 14.40, 15.12, 16.03, 16.28, 16.51, 17.04, 17.85, 18.04, 18.73, 19.29, 19.49, 19.73, 20.72, 21.10, 22.61, 23.16, 24.10, 25.49, 26.47, 27.25, and 27.84.

In one embodiment, the Compound 1 Form G is characterized by one or more peaks in an XRPD pattern on a 2 Theta scale, ±0.2, wherein the one or more peaks is selected from 6.71, 9.47, 14.40, 17.04, 17.85, and 21.10.

In another embodiment, the Compound 1 Form G is characterized by one or more peaks in an XRPD pattern on a 2 Theta scale, ±0.2, wherein the one or more peaks is selected from 6.71 and 9.47.

In a further embodiment, the Compound 1 Form G is characterized by all of the following peaks in an XRPD pattern on a 2 Theta scale, ±0.2, wherein the peaks are 6.71 and 9.47.

In still a further embodiment, the Compound 1 Form G is characterized by all of the following peaks in an XRPD pattern on a 2 Theta scale, ±0.2, wherein the peaks are 6.71, 9.47, 14.40, 17.04, 17.85, and 21.10.

In still a further embodiment, the Compound 1 Form G is characterized by all of the following peaks in an XRPD pattern on a 2 Theta scale, ±0.2, wherein the peaks are 4.72, 6.71, 9.47, 11.51, 11.84, 13.04, 14.40, 15.12, 16.03, 16.28, 16.51, 17.04, 17.85, 18.04, 18.73, 19.29, 19.49, 19.73, 20.72, 21.10, 22.61, 23.16, 24.10, 25.49, 26.47, 27.25, and 27.84.

Figure 16:
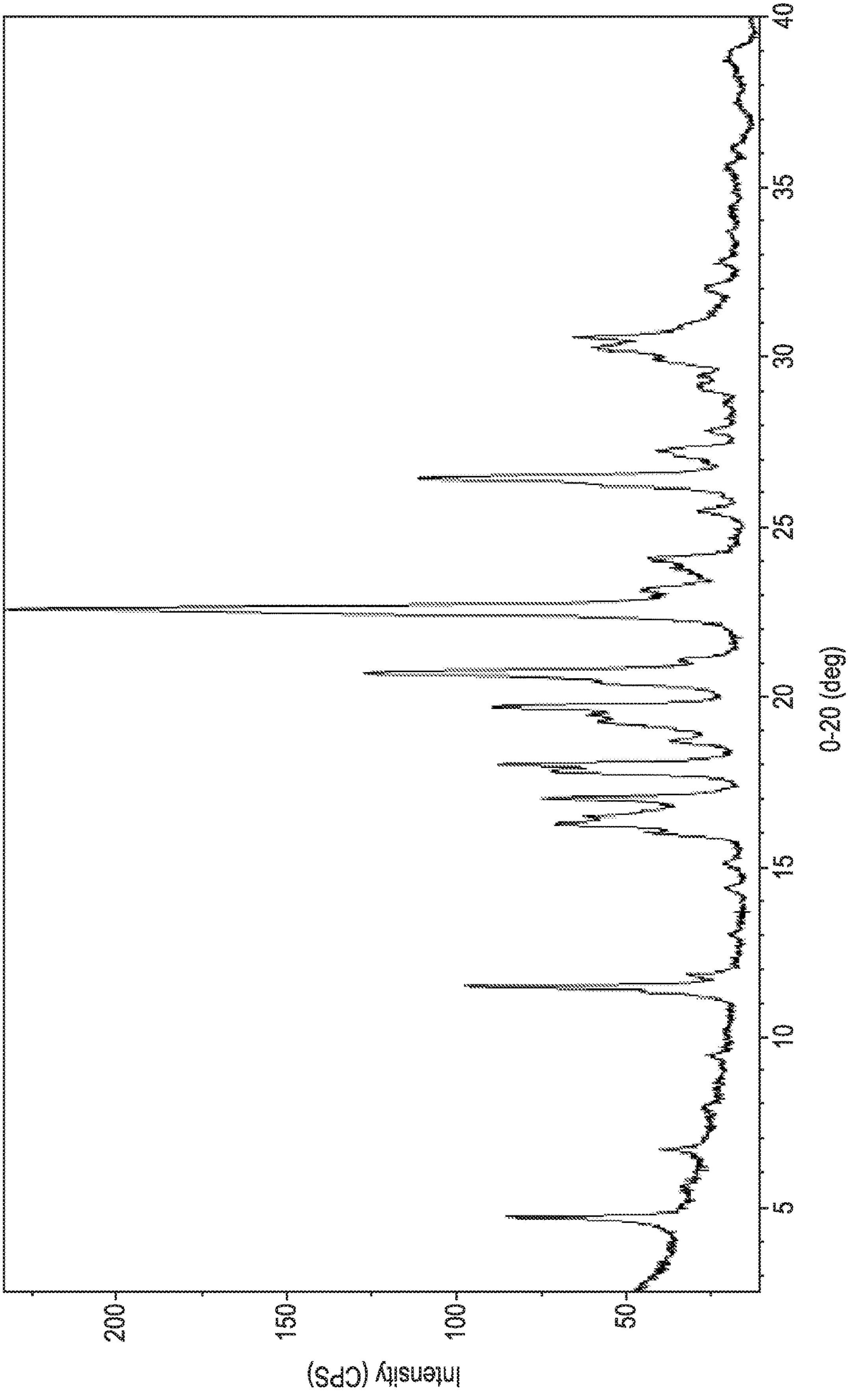
FIG. 16 is an XRPD pattern of Compound 1 Form G.

In still a further embodiment, the Compound 1 Form G is characterized by an XRPD pattern substantially identical to FIG. 16.

In one embodiment, the Compound 1 Form G is characterized by a weight loss of ~20.8 wt % between the temperatures of 40-165° C. in a TGA thermogram.

In one embodiment, the crystalline solid is characterized as Compound 1 Form H.

In another embodiment, the Compound 1 Form H is characterized by one or more peaks in an XRPD pattern on a 2 Theta scale, ±0.2, wherein the one or more peaks is selected from 6.30, 10.79, 11.42, 11.73, 12.63, 14.01, 14.29, 14.67, 15.74, 16.41, 17.23, 17.52, 18.01, 18.31, 18.56, 19.04, 19.67, 19.80, 20.32, 20.72, 21.53, 21.69, 21.95, 22.47, 23.14, 23.53, 24.33, 24.84, 25.13, 25.38, 25.69, 26.75, 27.48, 28.19, 28.70, 29.09, and 29.60.

In another embodiment, the Compound 1 Form H is characterized by one or more peaks in an XRPD pattern on a 2 Theta scale, ±0.2, wherein the one or more peaks is selected from 6.30, 11.42, 11.73, 17.52, 18.01, 18.56, 21.95, and 25.69.

In another embodiment, the Compound 1 Form H is characterized by one or more peaks in an XRPD pattern on a 2 Theta scale, ±0.2, wherein the one or more peaks is selected from 6.30, 17.52, 18.56, and 25.69.

In a further embodiment, the Compound 1 Form H is characterized by all of the following peaks in an XRPD pattern on a 2 Theta scale, ±0.2, wherein the peaks are 6.30, 17.52, 18.56, and 25.69.

In still a further embodiment, the Compound 1 Form H is characterized by all of the following peaks in an XRPD pattern on a 2 Theta scale, ±0.2, wherein the peaks are 6.30, 11.42, 11.73, 17.52, 18.01, 18.56, 21.95, and 25.69.

In still a further embodiment, the Compound 1 Form H is characterized by all of the following peaks in an XRPD pattern on a 2 Theta scale, ±0.2, wherein the peaks are 6.30, 10.79, 11.42, 11.73, 12.63, 14.01, 14.29, 14.67, 15.74, 16.41, 17.23, 17.52, 18.01, 18.31, 18.56, 19.04, 19.67, 19.80, 20.32, 20.72, 21.53, 21.69, 21.95, 22.47, 23.14, 23.53, 24.33, 24.84, 25.13, 25.38, 25.69, 26.75, 27.48, 28.19, 28.70, 29.09, and 29.60.

Figure 18:
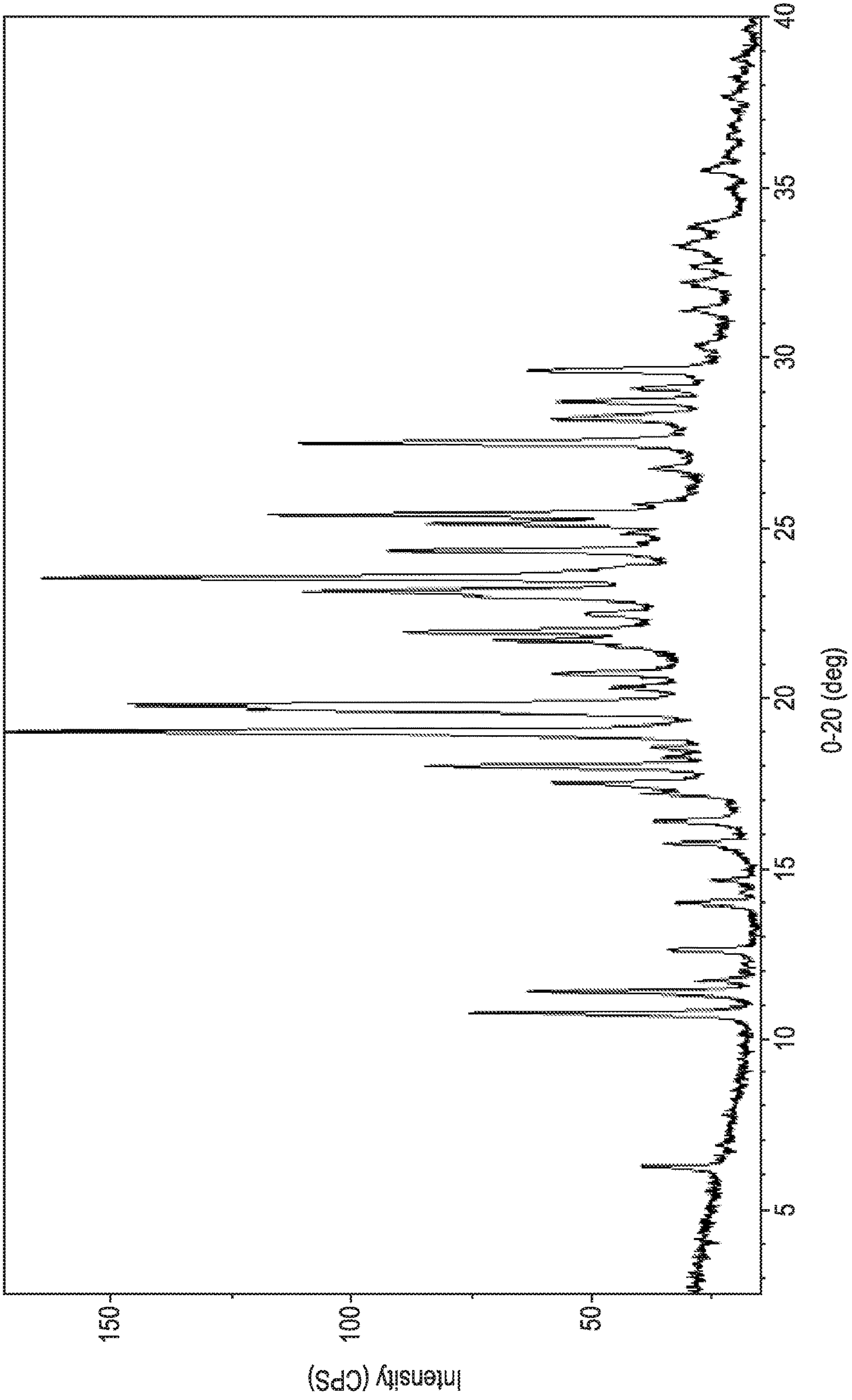
FIG. 18 is an XRPD pattern of Compound 1 Form H.

In still a further embodiment, the Compound 1 Form H is characterized by an XRPD pattern substantially identical to FIG. 18.

In one embodiment, the crystalline solid is characterized as Compound 1 Form I.

Figure 49:
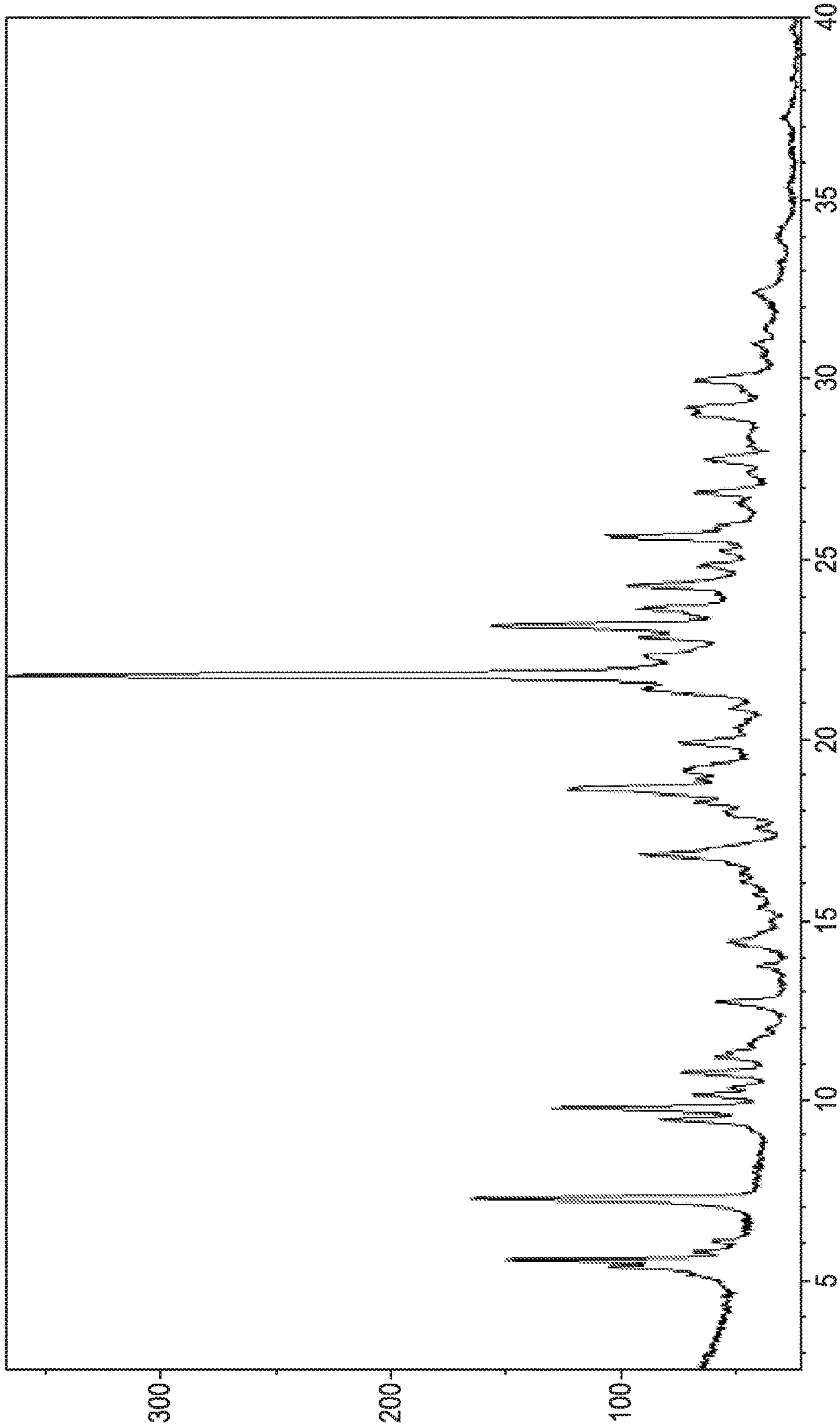
FIG. 49 is an XRPD pattern of Compound 1 Form I.

In a further embodiment, the Compound 1 Form I is characterized by an XRPD pattern substantially identical to FIG. 49.

In one embodiment, the crystalline solid is characterized as Compound 1 Form J.

Figure 50:
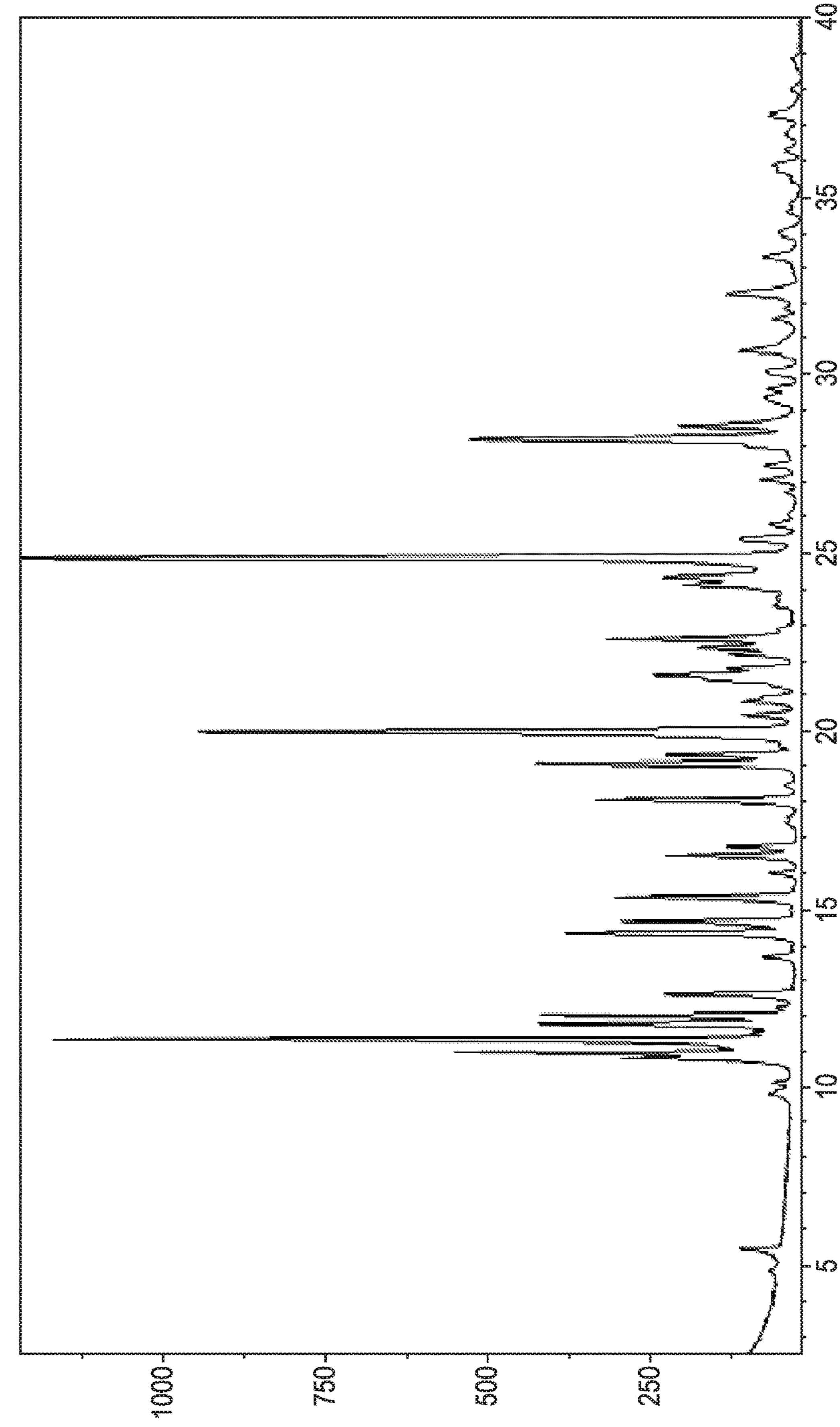
FIG. 50 is an XRPD pattern of Compound 1 Form J.

In a further embodiment, the Compound 1 Form J is characterized by an XRPD pattern substantially identical to FIG. 50.

In one embodiment, the crystalline solid is characterized as Compound 1 Form K.

In one embodiment, the Compound 1 Form K is characterized by one or more peaks in an XRPD pattern on a 2 Theta scale, ±0.2, wherein the one or more peaks is selected from 5.73, 6.39, 8.10, 11.53, 11.78, 12.83, 14.36, 15.56, 16.25, 17.42, 18.17, 19.07, 19.70, 19.89, 20.53, 21.11, 21.55, 22.34, 22.50, 23.24, 23.76, 24.50, 25.94, 26.42, 27.76, and 28.28.

In one embodiment, the Compound 1 Form K is characterized by one or more peaks in an XRPD pattern on a 2 Theta scale, ±0.2, wherein the one or more peaks is selected from 6.39, 8.10, 11.53, 19.89, 21.11, 22.34, 24.50, and 26.42.

In another embodiment, the Compound 1 Form K is characterized by one or more peaks in an XRPD pattern on a 2 Theta scale, ±0.2, wherein the one or more peaks is selected from 6.39, 8.10, 22.34, and 24.50.

In a further embodiment, the Compound 1 Form K is characterized by all of the following peaks in an XRPD pattern on a 2 Theta scale, ±0.2, wherein the peaks are 6.39, 8.10, 22.34, and 24.50.

In still a further embodiment, the Compound 1 Form K is characterized by all of the following peaks in an XRPD pattern on a 2 Theta scale, ±0.2, wherein the peaks are 6.39, 8.10, 11.53, 19.89, 21.11, 22.34, 24.50, and 26.42.

In still a further embodiment, the Compound 1 Form K is characterized by all of the following peaks in an XRPD pattern on a 2 Theta scale, ±0.2, wherein the peaks are 5.73, 6.39, 8.10, 11.53, 11.78, 12.83, 14.36, 15.56, 16.25, 17.42, 18.17, 19.07, 19.70, 19.89, 20.53, 21.11, 21.55, 22.34, 22.50, 23.24, 23.76, 24.50, 25.94, 26.42, 27.76, and 28.28.

Figure 19:
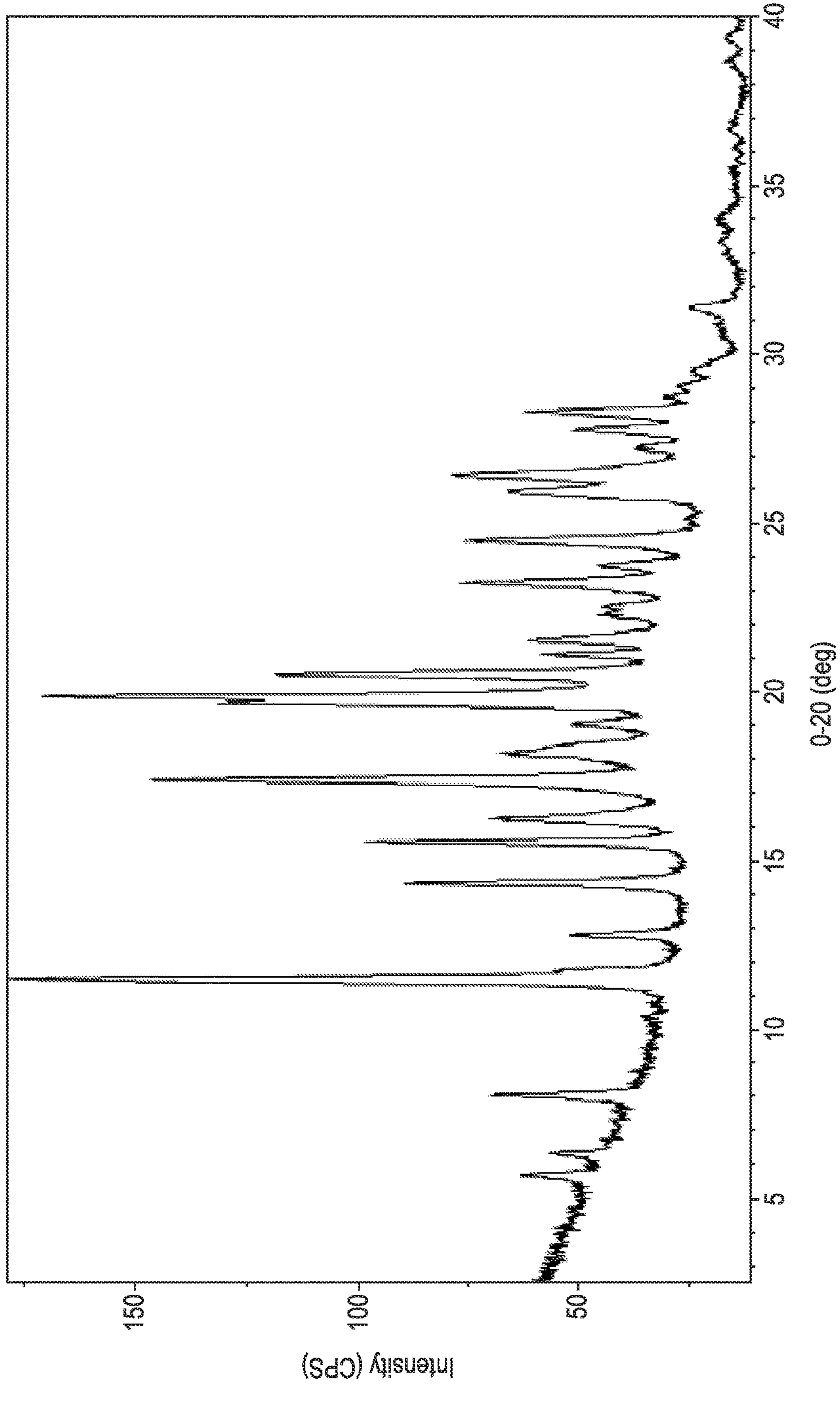
FIG. 19 is an XRPD pattern of Compound 1 Form K.

In still a further embodiment, the Compound 1 Form K is characterized by an XRPD pattern substantially identical to FIG. 19.

In another embodiment, the Compound 1 Form K is characterized by an endotherm at a temperature of about 226° C. in a DSC thermogram.

In another embodiment, the Compound 1 Form K is characterized by a weight loss of ~0.2 wt % between the temperatures of 40-180° C. in a TGA thermogram.

In one embodiment, the crystalline solid is characterized as Compound 1 Form L.

Figure 51:
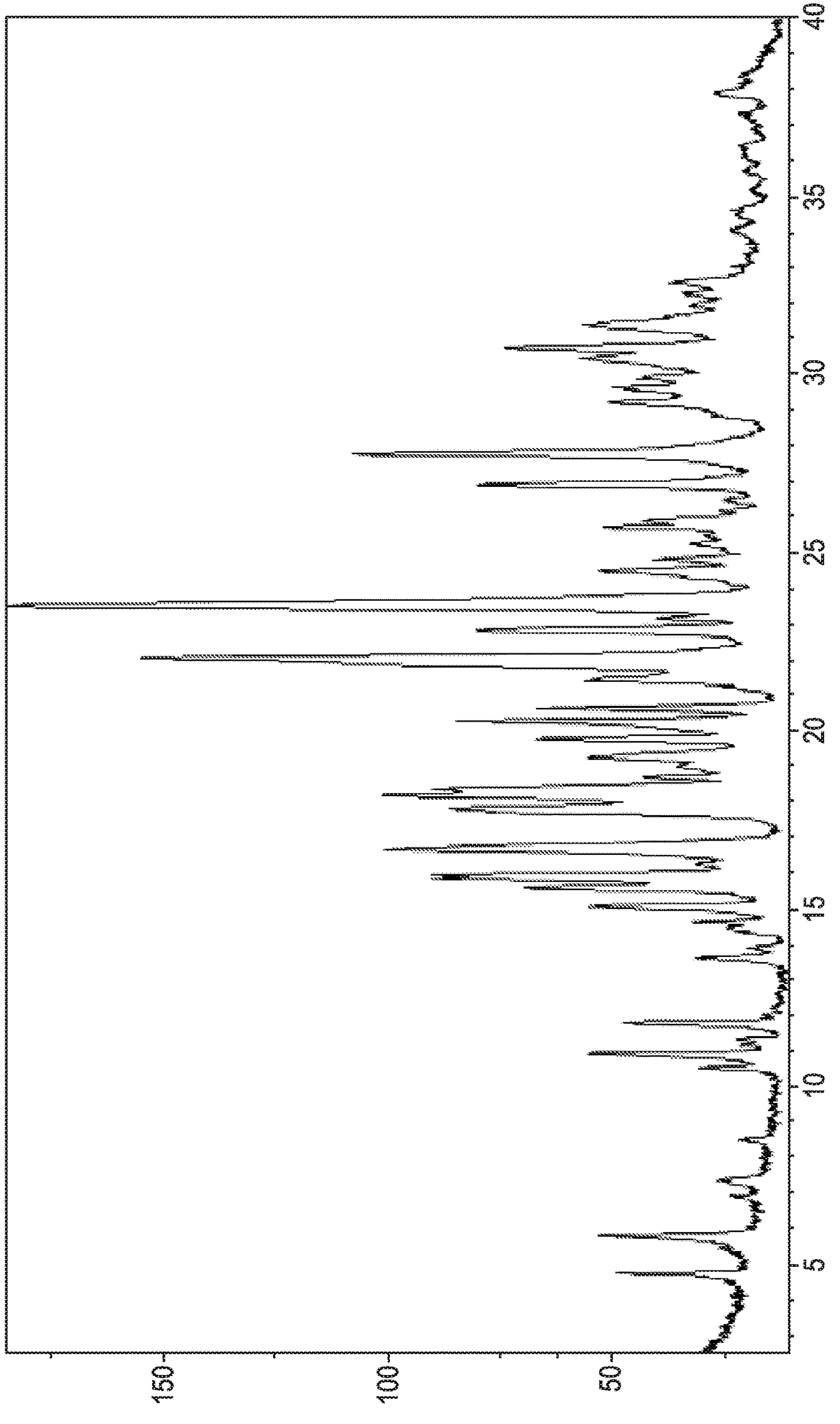
FIG. 51 is an XRPD pattern of Compound 1 Form L.

In a further embodiment, the Compound 1 Form L is characterized by an XRPD pattern substantially identical to FIG. 51.

In one embodiment, the crystalline solid is characterized as Compound 1 Form M.

Figure 52:
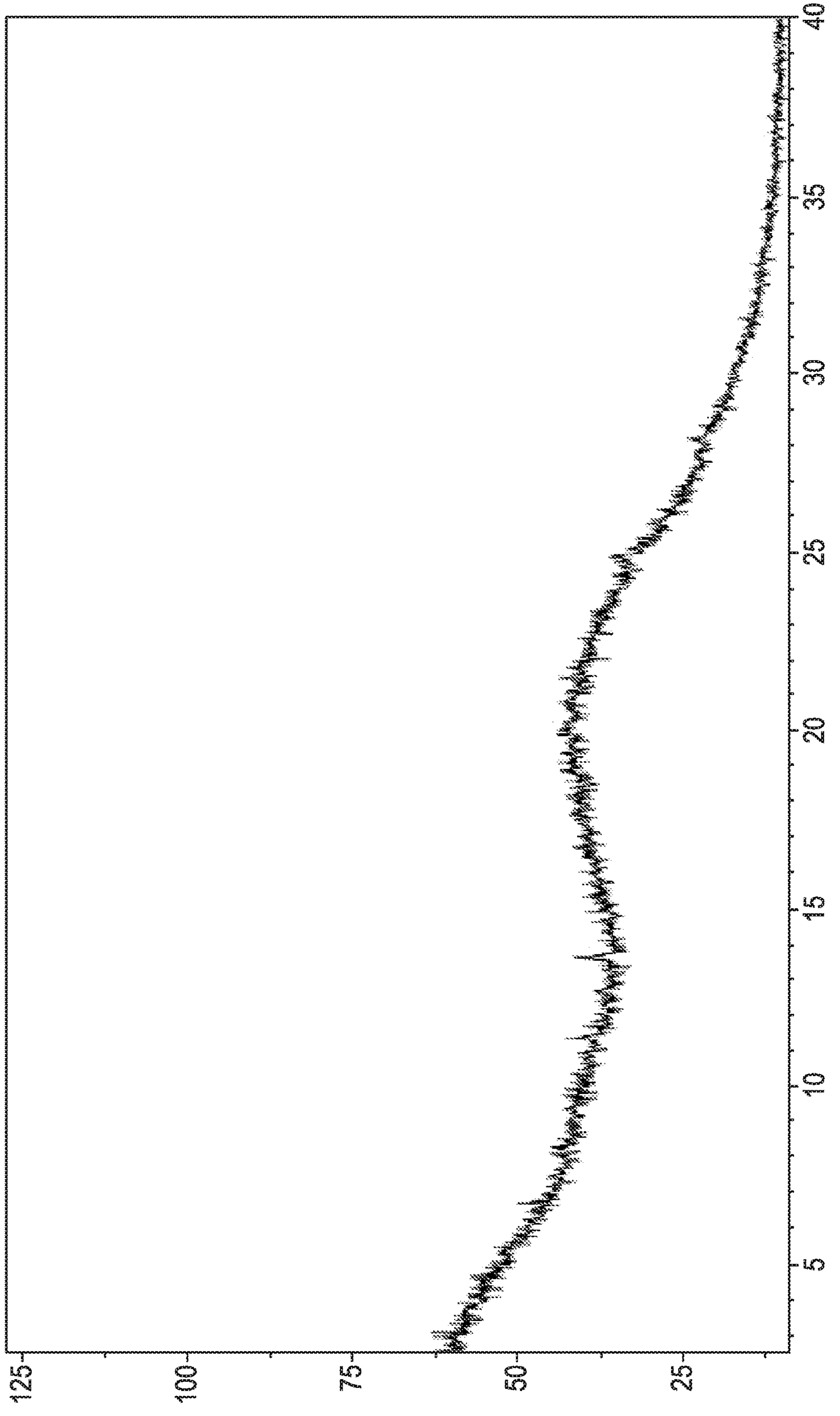
FIG. 52 is an XRPD pattern of Compound 1 Form M.

In a further embodiment, the Compound 1 Form M is characterized by an XRPD pattern substantially identical to FIG. 52.

In one embodiment, the crystalline solid is characterized as Compound 1 Form N.

Figure 53:
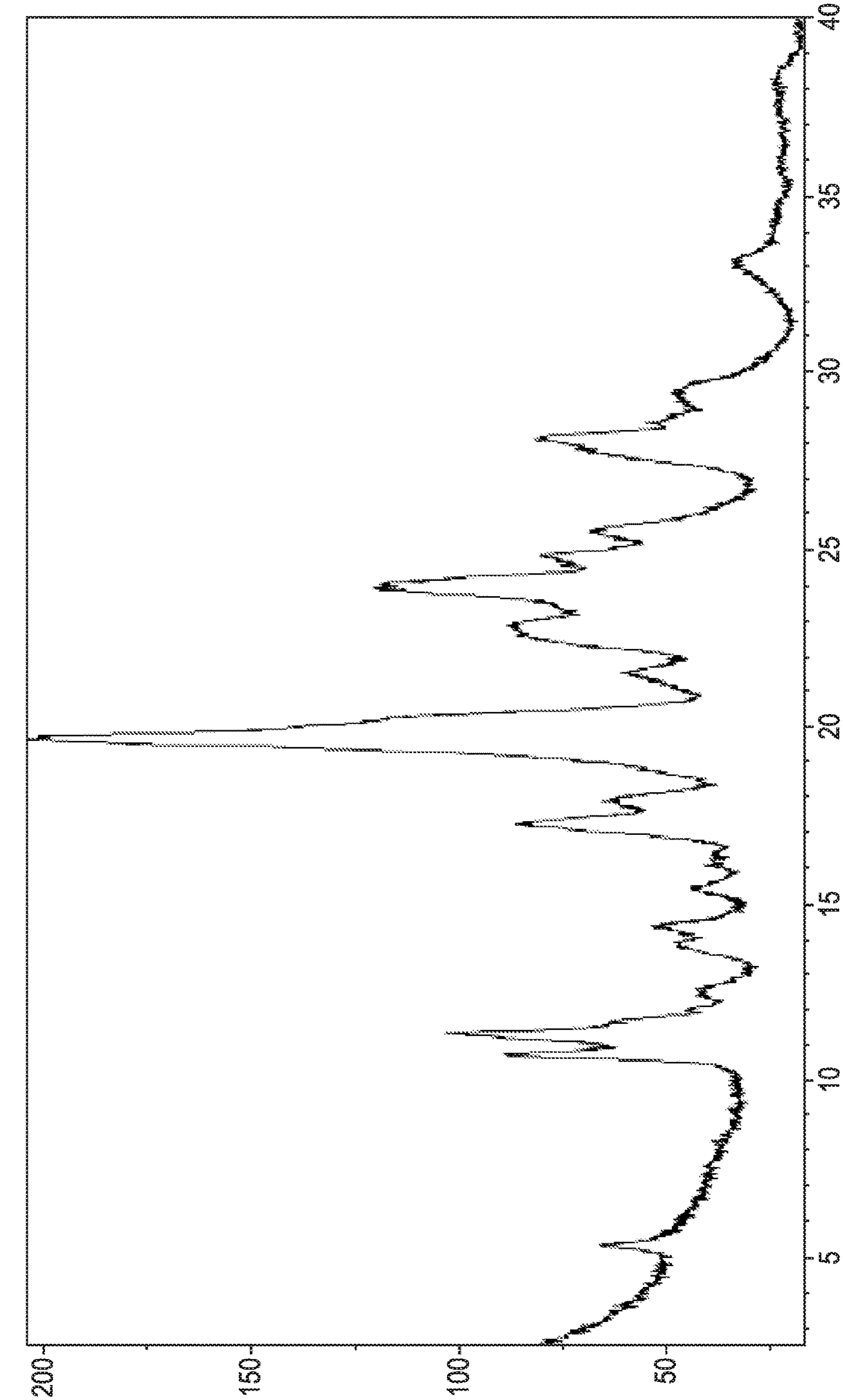
FIG. 53 is an XRPD pattern of Compound 1 Form N.

In a further embodiment, the Compound 1 Form N is characterized by an XRPD pattern substantially identical to FIG. 53.

In one embodiment, the crystalline solid is characterized as Compound 1 Form O.

In one embodiment, the Compound 1 Form O is characterized by one or more peaks in an XRPD pattern on a 2 Theta scale, ±0.2, wherein the one or more peaks is selected from 6.10, 9.01, 9.83, 10.68, 11.12, 11.33, 12.25, 12.99, 13.93, 14.51, 14.92, 15.55, 15.79, 17.14, 17.43, 17.58, 18.15, 18.42, 19.35, 19.77, 20.24, 20.71, 20.90, 21.49, 21.68, 22.04, 22.36, 22.78, 23.37, 23.96, 24.39, 24.92, 25.62, 26.20, 26.64, 26.93, 27.32, 27.68, 27.96, 28.26, 28.60, and 28.81.

In one embodiment, the Compound 1 Form O is characterized by one or more peaks in an XRPD pattern on a 2 Theta scale, ±0.2, wherein the one or more peaks is selected from 6.10, 9.01, 14.92, 17.14, 17.58, 23.96, 25.62, and 27.96.

In another embodiment, the Compound 1 Form O is characterized by one or more peaks in an XRPD pattern on a 2 Theta scale, ±0.2, wherein the one or more peaks is selected from 6.10, 14.92, 17.14, and 23.96.

In a further embodiment, the Compound 1 Form O is characterized by all of the following peaks in an XRPD pattern on a 2 Theta scale, ±0.2, wherein the peaks are 6.10, 14.92, 17.14, and 23.96.

In still a further embodiment, the Compound 1 Form O is characterized by all of the following peaks in an XRPD pattern on a 2 Theta scale, ±0.2, wherein the peaks are 6.10, 9.01, 14.92, 17.14, 17.58, 23.96, 25.62, and 27.96.

In still a further embodiment, the Compound 1 Form O is characterized by all of the following peaks in an XRPD pattern on a 2 Theta scale, ±0.2, wherein the peaks are 6.10, 9.01, 9.83, 10.68, 11.12, 11.33, 12.25, 12.99, 13.93, 14.51, 14.92, 15.55, 15.79, 17.14, 17.43, 17.58, 18.15, 18.42, 19.35, 19.77, 20.24, 20.71, 20.90, 21.49, 21.68, 22.04, 22.36, 22.78, 23.37, 23.96, 24.39, 24.92, 25.62, 26.20, 26.64, 26.93, 27.32, 27.68, 27.96, 28.26, 28.60, and 28.81.

Figure 22:
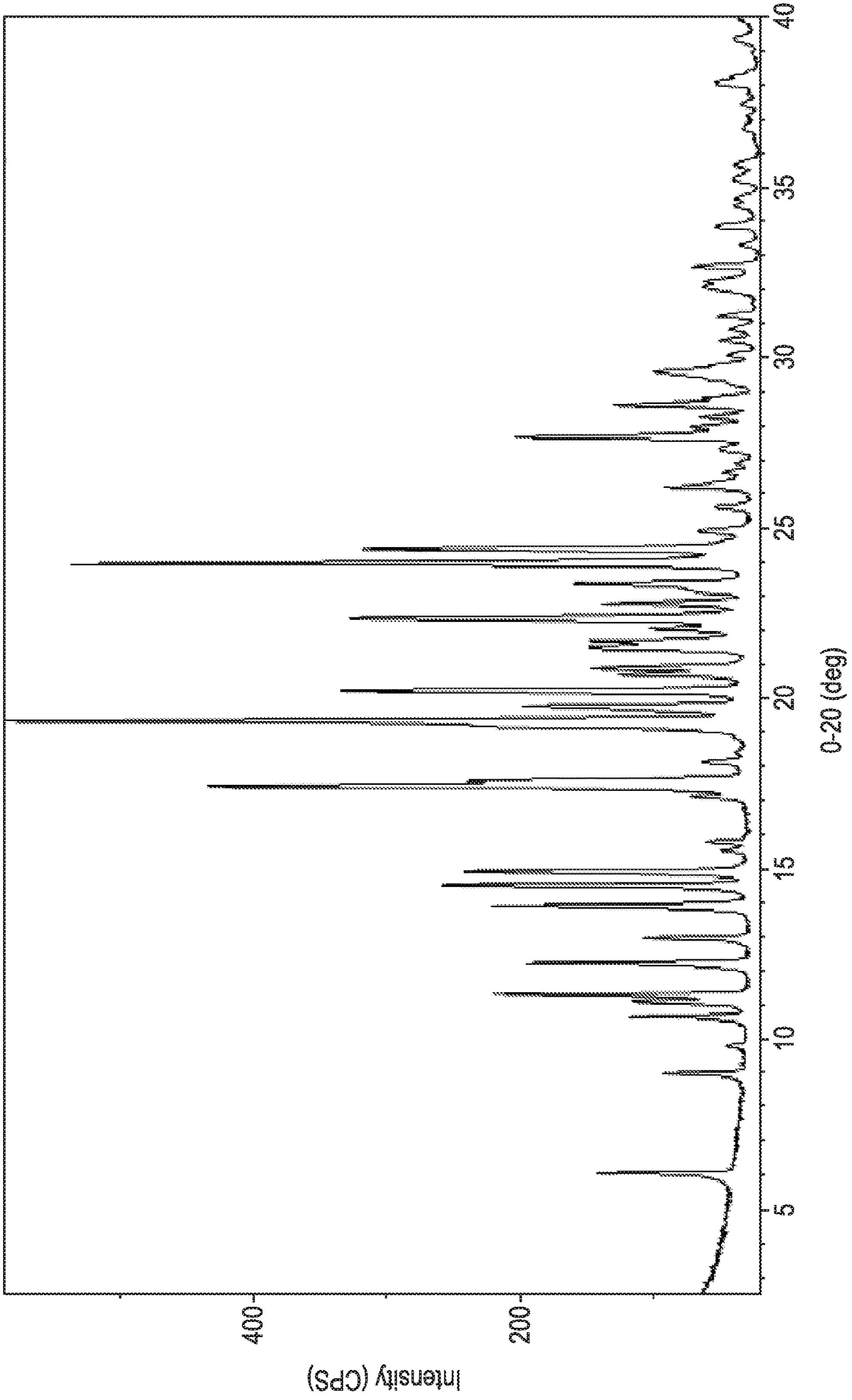
FIG. 22 is an XRPD pattern of Compound 1 Form O.

In still a further embodiment, the Compound 1 Form O is characterized by an XRPD pattern substantially identical to FIG. 22.

In one embodiment, the crystalline solid is characterized as Compound 1 Form P.

In one embodiment, the Compound 1 Form P is characterized by one or more peaks in an XRPD pattern on a 2 Theta scale, ±0.2, wherein the one or more peaks is selected from 5.99, 8.78, 9.40, 10.12, 11.99, 14.61, 14.87, 15.61, 15.98, 16.32, 16.62, 17.56, 17.62, 17.84, 18.05, 18.43, 18.88, 19.22, 19.72, 19.85, 20.32, 20.91, 21.67, 22.04, 22.39, 22.93, 23.46, 23.71, 23.98, 24.11, 24.43, 24.84, 25.74, 26.39, 26.64, 26.85, 27.77, 28.74, 29.26, 29.55, and 30.07.

In one embodiment, the Compound 1 Form P is characterized by one or more peaks in an XRPD pattern on a 2 Theta scale, ±0.2, wherein the one or more peaks is selected from 11.99, 14.61, 14.87, 20.91, 21.67, 22.04, 22.93, and 26.85.

In still a further embodiment, the Compound 1 Form P is characterized by all of the following peaks in an XRPD pattern on a 2 Theta scale, ±0.2, wherein the peaks are 11.99, 14.61, 14.87, 20.91, 21.67, 22.04, 22.93, and 26.85.

In still a further embodiment, the Compound 1 Form P is characterized by all of the following peaks in an XRPD pattern on a 2 Theta scale, ±0.2, wherein the peaks are 5.99, 8.78, 9.40, 10.12, 11.99, 14.61, 14.87, 15.61, 15.98, 16.32, 16.62, 17.56, 17.62, 17.84, 18.05, 18.43, 18.88, 19.22, 19.72, 19.85, 20.32, 20.91, 21.67, 22.04, 22.39, 22.93, 23.46, 23.71, 23.98, 24.11, 24.43, 24.84, 25.74, 26.39, 26.64, 26.85, 27.77, 28.74, 29.26, 29.55, and 30.07.

Figure 23:
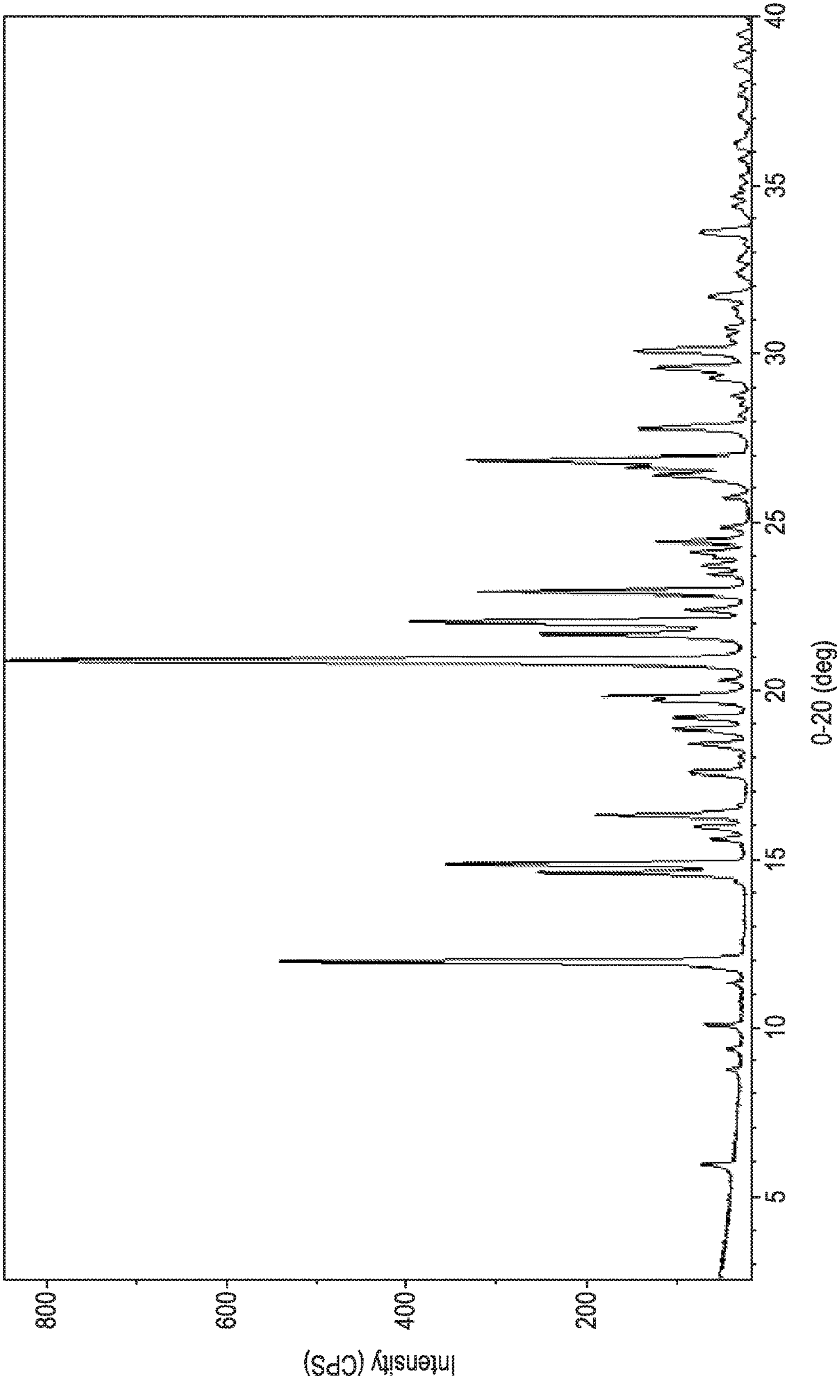
FIG. 23 is an XRPD pattern of Compound 1 Form P.

In a further embodiment, the Compound 1 Form P is characterized by an XRPD pattern substantially identical to FIG. 23.

In one embodiment, the crystalline solid is characterized as Compound 1 Form Q.

In one embodiment, the Compound 1 Form Q is characterized by one or more peaks in an XRPD pattern on a 2 Theta scale, ±0.2, wherein the one or more peaks is selected from 6.11, 8.61, 9.06, 9.74, 10.64, 10.89, 11.24, 11.33, 12.06, 12.24, 12.91, 13.82, 14.46, 14.83, 15.69, 15.76, 16.07, 17.05, 17.31, 17.40, 17.78, 18.16, 18.42, 18.88, 19.08, 19.28, 19.56, 19.84, 20.07, 20.70, 21.04, 21.38, 21.59, 21.91, 22.18, 22.30, 22.58, 22.78, 23.04, 23.23, 23.50, 23.81, 24.01, 24.32, 24.86, 25.43, 25.80, 26.05, 26.20, 26.69, 27.02, 27.44, 27.63, 27.99, 28.48, 28.75, 29.17, and 29.36.

In one embodiment, the Compound 1 Form Q is characterized by one or more peaks in an XRPD pattern on a 2 Theta scale, ±0.2, wherein the one or more peaks is selected from 6.11, 8.61, 9.06, 9.74, 15.69, 16.07, 20.04, and 24.01.

In another embodiment, the Compound 1 Form Q is characterized by one or more peaks in an XRPD pattern on a 2 Theta scale, ±0.2, wherein the one or more peaks is selected from 8.61, 9.74, 16.07, and 20.04.

In a further embodiment, the Compound 1 Form Q is characterized by all of the following peaks in an XRPD pattern on a 2 Theta scale, ±0.2, wherein the peaks are 8.61, 9.74, 16.07, and 20.04.

In still a further embodiment, the Compound 1 Form Q is characterized by all of the following peaks in an XRPD pattern on a 2 Theta scale, +0.2, wherein the peaks are 6.11, 8.61, 9.06, 9.74, 15.69, 16.07, 20.04, and 24.01.

In still a further embodiment, the Compound 1 Form Q is characterized by all of the following peaks in an XRPD pattern on a 2 Theta scale, +0.2, wherein the peaks are 6.11, 8.61, 9.06, 9.74, 10.64, 10.89, 11.24, 11.33, 12.06, 12.24, 12.91, 13.82, 14.46, 14.83, 15.69, 15.76, 16.07, 17.05, 17.31, 17.40, 17.78, 18.16, 18.42, 18.88, 19.08, 19.28, 19.56, 19.84, 20.07, 20.70, 21.04, 21.38, 21.59, 21.91, 22.18, 22.30, 22.58, 22.78, 23.04, 23.23, 23.50, 23.81, 24.01, 24.32, 24.86, 25.43, 25.80, 26.05, 26.20, 26.69, 27.02, 27.44, 27.63, 27.99, 28.48, 28.75, 29.17, and 29.36.

Figure 25:
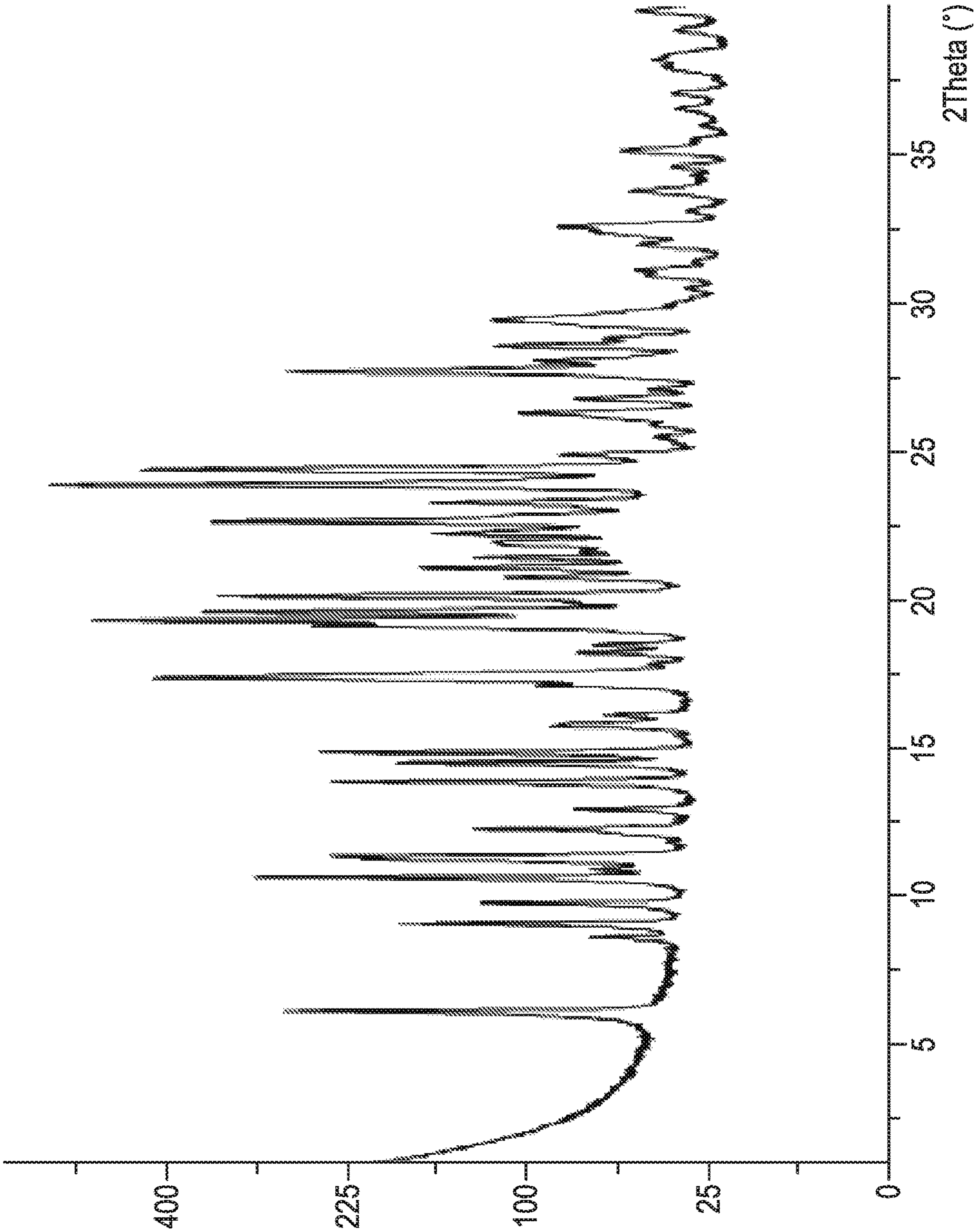
FIG. 25 is an XRPD pattern of Compound 1 Form Q.

In still a further embodiment, the Compound 1 Form Q is characterized by an XRPD pattern substantially identical to FIG. 25.

In another embodiment, the Compound 1 Form Q is characterized by an endotherm at a temperature of 194-195° C. in a DSC thermogram. In another embodiment, the Compound 1 Form Q is characterized by an endotherm with an onset temperature at about 194-195° C. in a DSC thermogram.

In another embodiment, the Compound 1 Form Q is characterized by a weight loss of ~11-12 wt % between the temperatures of 120-160° C. in a TGA thermogram.

In another aspect, the invention relates to a crystalline hydrochloric acid salt form of Compound 1 having the general structure Compound 1

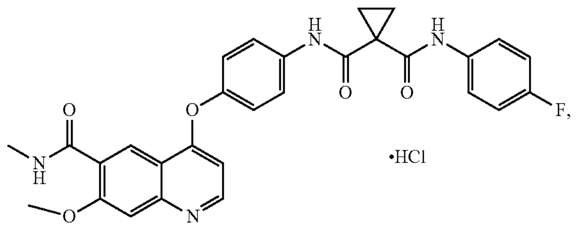

HCl salt or hydrate or solvate thereof.

In one embodiment, the crystalline solid is characterized as characterized as Compound 1 HCl Form A, Compound 1 HCl Form B, Compound 1 HCl Form C, or Compound 1 HCl Form D. In one embodiment, the crystalline solid is characterized as Compound 1 HCl Form A.

In one embodiment, the Compound 1 HCl Form A is characterized by one or more peaks in an XRPD pattern on a 2 Theta scale, +0.2, wherein the one or more peaks is selected from 5.19, 8.17, 9.84, 10.10, 10.42, 11.07, 12.52, 12.76, 12.98, 13.49, 13.69, 13.89, 14.31, 14.84, 15.12, 15.68, 16.34, 16.68, 17.08, 17.47, 17.96, 18.49, 19.23, 19.78, 20.31, 20.91, 21.16, 21.42, 22.10, 22.81, 23.18, 23.89, 24.39, 25.20, 25.87, 26.34, 27.06, 27.59, 28.07, 28.4, and 30.0.

In one embodiment, the Compound 1 HCl Form A is characterized by one or more peaks in an XRPD pattern on a 2 Theta scale, ±0.2, wherein the one or more peaks is selected from 5.19, 13.49, 13.69, 13.89, 14.84, 15.12, 16.34, 16.68, 17.47, 18.49, 20.31, 23.18, 24.39, 25.87, 26.34, 27.06, 28.07, 28.4, and 30.0.

In another embodiment, the Compound 1 HCl Form A is characterized by one or more peaks in an XRPD pattern on a 2 Theta scale, ±0.2, wherein the one or more peaks is selected from 13.49, 17.47, 18.49, and 30.0.

In a further embodiment, the Compound 1 HCl Form A is characterized by all of the following peaks in an XRPD pattern on a 2 Theta scale, ±0.2, wherein the peaks are 13.49, 17.47, 18.49, and 30.0.

In still a further embodiment, the Compound 1 HCl Form A is characterized by all of the following peaks in an XRPD pattern on a 2 Theta scale, ±0.2, wherein the peaks are 5.19, 13.49, 13.69, 13.89, 14.84, 15.12, 16.34, 16.68, 17.47, 18.49, 20.31, 23.18, 24.39, 25.87, 26.34, 27.06, 28.07, 28.4, and 30.0.

In still a further embodiment, the Compound 1 HCl Form A is characterized by all of the following peaks in an XRPD pattern on a 2 Theta scale, ±0.2, wherein the peaks are 5.19, 8.17, 9.84, 10.10, 10.42, 11.07, 12.52, 12.76, 12.98, 13.49, 13.69, 13.89, 14.31, 14.84, 15.12, 15.68, 16.34, 16.68, 17.08, 17.47, 17.96, 18.49, 19.23, 19.78, 20.31, 20.91, 21.16, 21.42, 22.10, 22.81, 23.18, 23.89, 24.39, 25.20, 25.87, 26.34, 27.06, 27.59, 28.07, 28.4, and 30.0.

In one embodiment, the Compound 1 HCl Form A is characterized by one or more peaks in an XRPD pattern on a 2 Theta scale, ±0.2, wherein the one or more peaks is selected from 5.19, 8.17, 9.84, 10.10, 10.42, 11.07, 12.52, 12.76, 12.98, 13.49, 13.69, 13.89, 14.31, 14.84, 15.12, 15.68, 16.34, 16.68, 17.08, 17.47, 17.96, 18.49, 19.23, 19.78, 20.31, 20.91, 21.16, 21.42, 22.10, 22.81, 23.18, 23.89, 24.39, 25.20, 25.87, 26.34, 27.06, 27.59, and 28.07.

In one embodiment, the Compound 1 HCl Form A is characterized by one or more peaks in an XRPD pattern on a 2 Theta scale, ±0.2, wherein the one or more peaks is selected from 5.19, 13.49, 13.69, 13.89, 14.84, 15.12, 16.34, 16.68, 17.47, 18.49, 20.31, 23.18, 24.39, 25.87, 26.34, 27.06, and 28.07.

In another embodiment, the Compound 1 HCl Form A is characterized by one or more peaks in an XRPD pattern on a 2 Theta scale, ±0.2, wherein the one or more peaks is selected from 13.49, 17.47, and 18.49.

In a further embodiment, the Compound 1 HCl Form A is characterized by all of the following peaks in an XRPD pattern on a 2 Theta scale, ±0.2, wherein the peaks are 13.49, 17.47, and 18.49.

In still a further embodiment, the Compound 1 HCl Form A is characterized by all of the following peaks in an XRPD pattern on a 2 Theta scale, ±0.2, wherein the peaks are 5.19, 13.49, 13.69, 13.89, 14.84, 15.12, 16.34, 16.68, 17.47, 18.49, 20.31, 23.18, 24.39, 25.87, 26.34, 27.06, and 28.07.

In still a further embodiment, the Compound 1 HCl Form A is characterized by all of the following peaks in an XRPD pattern on a 2 Theta scale, ±0.2, wherein the peaks are 5.19, 8.17, 9.84, 10.10, 10.42, 11.07, 12.52, 12.76, 12.98, 13.49, 13.69, 13.89, 14.31, 14.84, 15.12, 15.68, 16.34, 16.68, 17.08, 17.47, 17.96, 18.49, 19.23, 19.78, 20.31, 20.91, 21.16, 21.42, 22.10, 22.81, 23.18, 23.89, 24.39, 25.20, 25.87, 26.34, 27.06, 27.59, and 28.07.

Figure 34:
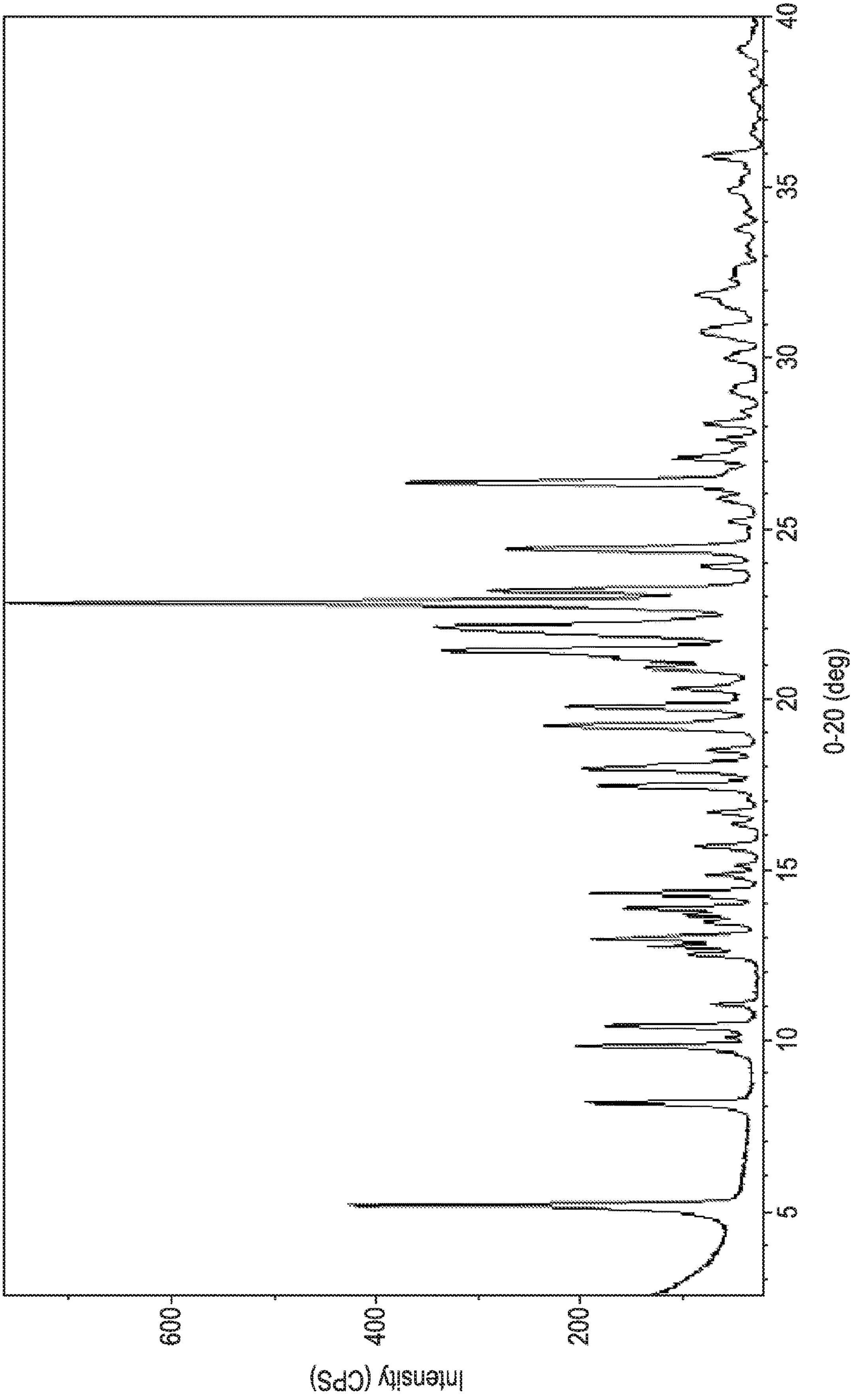
FIG. 34 is an XRPD pattern of Compound 1 HCl Form A.

In still a further embodiment, the Compound 1 HCl Form A is characterized by an XRPD pattern substantially identical to FIG. 34.

In one embodiment, the crystalline solid is characterized as Compound 1 HCl Form B.

In one embodiment, the Compound 1 HCl Form B is characterized by one or more peaks in an XRPD pattern on a 2 Theta scale, ±0.2, wherein the one or more peaks is selected from 8.20, 9.72, 9.81, 10.04, 10.56, 12.52, 12.97, 13.32, 13.48, 13.81, 14.35, 14.95, 15.89, 16.63, 17.37, 17.83, 17.99, 18.32, 19.15, 19.31, 19.51, 19.72, 20.17, 20.84, 21.04, 21.15, 21.30, 21.81, 22.02, 22.65, 23.11, 23.40, 23.75, 24.76, 25.34, 25.74, 26.20, 26.90, 27.71, 27.98, 28.34, and 28.98.

In one embodiment, the Compound 1 HCl Form B is characterized by one or more peaks in an XRPD pattern on a 2 Theta scale, ±0.2, wherein the one or more peaks is selected from 9.72, 15.89, 16.63, 17.37, 18.32, 19.51, 21.04, 21.30, 21.81, 23.40, 24.76, 26.20, and 27.71.

In another embodiment, the Compound 1 HCl Form B is characterized by one or more peaks in an XRPD pattern on a 2 Theta scale, ±0.2, wherein the one or more peaks is selected from 9.72, 17.37, 18.32, and 19.51.

In a further embodiment, the Compound 1 HCl Form B is characterized by all of the following peaks in an XRPD pattern on a 2 Theta scale, ±0.2, wherein the peaks are 9.72, 17.37, 18.32, and 19.51.

In still a further embodiment, the Compound 1 HCl Form B is characterized by all of the following peaks in an XRPD pattern on a 2 Theta scale, ±0.2, wherein the peaks are 9.72, 15.89, 16.63, 17.37, 18.32, 19.51, 21.04, 21.30, 21.81, 23.40, 24.76, 26.20, and 27.71.

In still a further embodiment, the Compound 1 HCl Form B is characterized by all of the following peaks in an XRPD pattern on a 2 Theta scale, ±0.2, wherein the peaks are 8.20, 9.72, 9.81, 10.04, 10.56, 12.52, 12.97, 13.32, 13.48, 13.81, 14.35, 14.95, 15.89, 16.63, 17.37, 17.83, 17.99, 18.32, 19.15, 19.31, 19.51, 19.72, 20.17, 20.84, 21.04, 21.15, 21.30, 21.81, 22.02, 22.65, 23.11, 23.40, 23.75, 24.76, 25.34, 25.74, 26.20, 26.90, 27.71, 27.98, 28.34, and 28.98.

Figure 35:
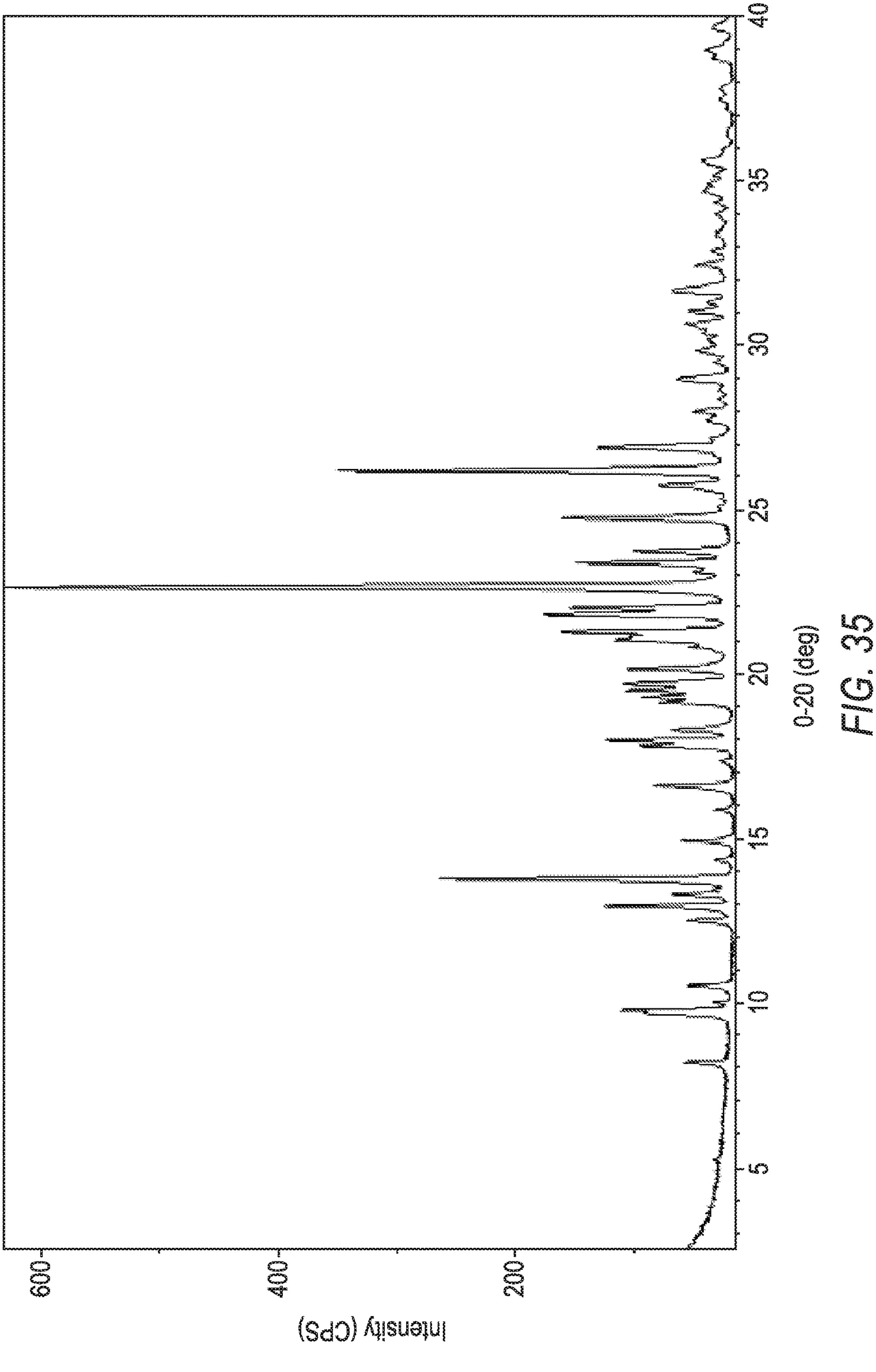
FIG. 35 is an XRPD pattern of Compound 1 HCl Form B.

In still a further embodiment, the Compound 1 HCl Form B is characterized by an XRPD pattern substantially identical to FIG. 35.

In one embodiment, the crystalline solid is characterized as Compound 1 HCl Form C.

In still a further embodiment, the Compound 1 HCl Form C is characterized by one or more of the following peaks in an XRPD pattern on a 2 Theta scale, ±0.2, wherein the peaks are 2.5, 3.0, 4.3, 5.1, 6.2, 6.8, 7.3, 7.8, 8.8, 10.6, 11.6, 12.5, 13.3, 13.8, 15.3, 15.7, 17.1, 17.8, 19.0, 19.4, 20.0, 20.5, 20.8, 21.5, 22.2, 22.6, 23.0, 23.5, 23.9, 25.2, 26.2, 26.8, 27.2, 28.0, 28.9, and 29.5.

In one embodiment, the Compound 1 HCl Form C is characterized by one or more peaks in an XRPD pattern on a 2 Theta scale, ±0.2, wherein the one or more peaks is selected from 2.5, 3.0, 4.3, 6.2, 7.3, 7.8, and 29.5.

In another embodiment, the Compound 1 HCl Form C is characterized by one or more peaks in an XRPD pattern on a 2 Theta scale, ±0.2, wherein the one or more peaks is selected from 2.5, 3.0, 4.3, 11.6, 17.1, 19.0, 20.5, 26.8, and 29.5.

In one embodiment, the Compound 1 HCl Form C is characterized by all of the following peaks in an XRPD pattern on a 2 Theta scale, ±0.2, wherein the peaks are 2.5, 3.0, 4.3, 6.2, 7.3, 7.8, and 29.5.

In still a further embodiment, the Compound 1 HCl Form C is characterized by all of the following peaks in an XRPD pattern on a 2 Theta scale, ±0.2, wherein the peaks are 2.5, 3.0, 4.3, 6.2, 7.3, 7.8, 8.8, 11.6, 17.1, 19.0, 20.5, 26.8, and 29.5.

In still a further embodiment, the Compound 1 HCl Form C is characterized by all of the following peaks in an XRPD pattern on a 2 Theta scale, ±0.2, wherein the peaks are 2.5, 3.0, 4.3, 5.1, 6.2, 6.8, 7.3, 7.8, 8.8, 10.6, 11.6, 12.5, 13.3, 13.8, 15.3, 15.7, 17.1, 17.8, 19.0, 19.4, 20.0, 20.5, 20.8, 21.5, 22.2, 22.6, 23.0, 23.5, 23.9, 25.2, 26.2, 26.8, 27.2, 28.0, 28.9, and 29.5.

Figure 36:
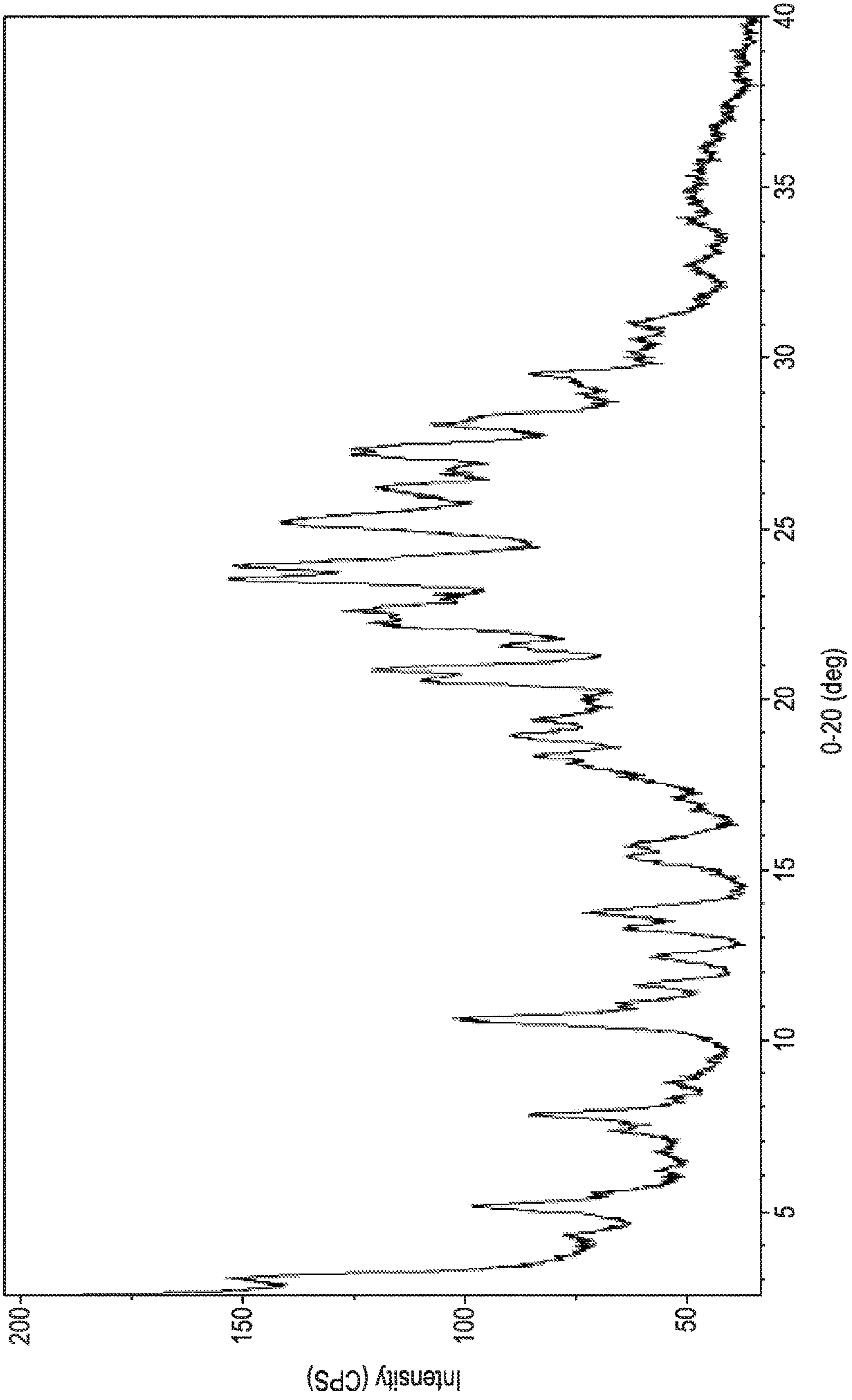
FIG. 36 is an XRPD pattern of Compound 1 HCl Form C.

In still a further embodiment, the Compound 1 HCl Form C is characterized by an XRPD pattern substantially identical to FIG. 36.

In one embodiment, the crystalline solid is characterized as Compound 1 HCl Form D.

In still a further embodiment, the Compound 1 HCl Form D is characterized by one or more of the following peaks in an XRPD pattern on a 2 Theta scale, ±0.2, wherein the peaks are 3.47, 5.27, 6.93, 8.21, 8.97, 9.86, 10.16, 10.44, 10.69, 11.28, 12.26, 12.75, 13.27, 13.92, 14.23, 14.54, 14.95, 15.44, 15.58, 15.80, 16.08, 16.25, 17.84, 18.44, 18.65, 19.34, 19.75, 20.13, 20.93, 21.29, 22.05, 22.69, 22.90, 23.69, 24.15, 24.39, 24.60, 24.91, 25.16, 26.27, 27.03, 27.61, and 28.37.

In one embodiment, the Compound 1 HCl Form D is characterized by one or more peaks in an XRPD pattern on a 2 Theta scale, ±0.2, wherein the one or more peaks is selected from 3.47, 5.27, 10.16, 10.69, 12.26, 14.54, 14.95, 17.84, 20.93, 21.29, 22.05, 22.69, 22.90, 23.69, 24.91, and 25.16.

In a further embodiment, the Compound 1 HCl Form D is characterized by all of the following peaks in an XRPD pattern on a 2 Theta scale, ±0.2, wherein the peaks are 3.47, 5.27, 10.16, 10.69, 12.26, 14.54, 14.95, 17.84, 20.93, 21.29, 22.05, 22.69, 22.90, 23.69, 24.91, and 25.16.

In still a further embodiment, the Compound 1 HCl Form D is characterized by all of the following peaks in an XRPD pattern on a 2 Theta scale, ±0.2, wherein the peaks are 3.47, 5.27, 6.93, 8.21, 8.97, 9.86, 10.16, 10.44, 10.69, 11.28, 12.26, 12.75, 13.27, 13.92, 14.23, 14.54, 14.95, 15.44, 15.58, 15.80, 16.08, 16.25, 17.84, 18.44, 18.65, 19.34, 19.75, 20.13, 20.93, 21.29, 22.05, 22.69, 22.90, 23.69, 24.15, 24.39, 24.60, 24.91, 25.16, 26.27, 27.03, 27.61, and 28.37.

Figure 37:
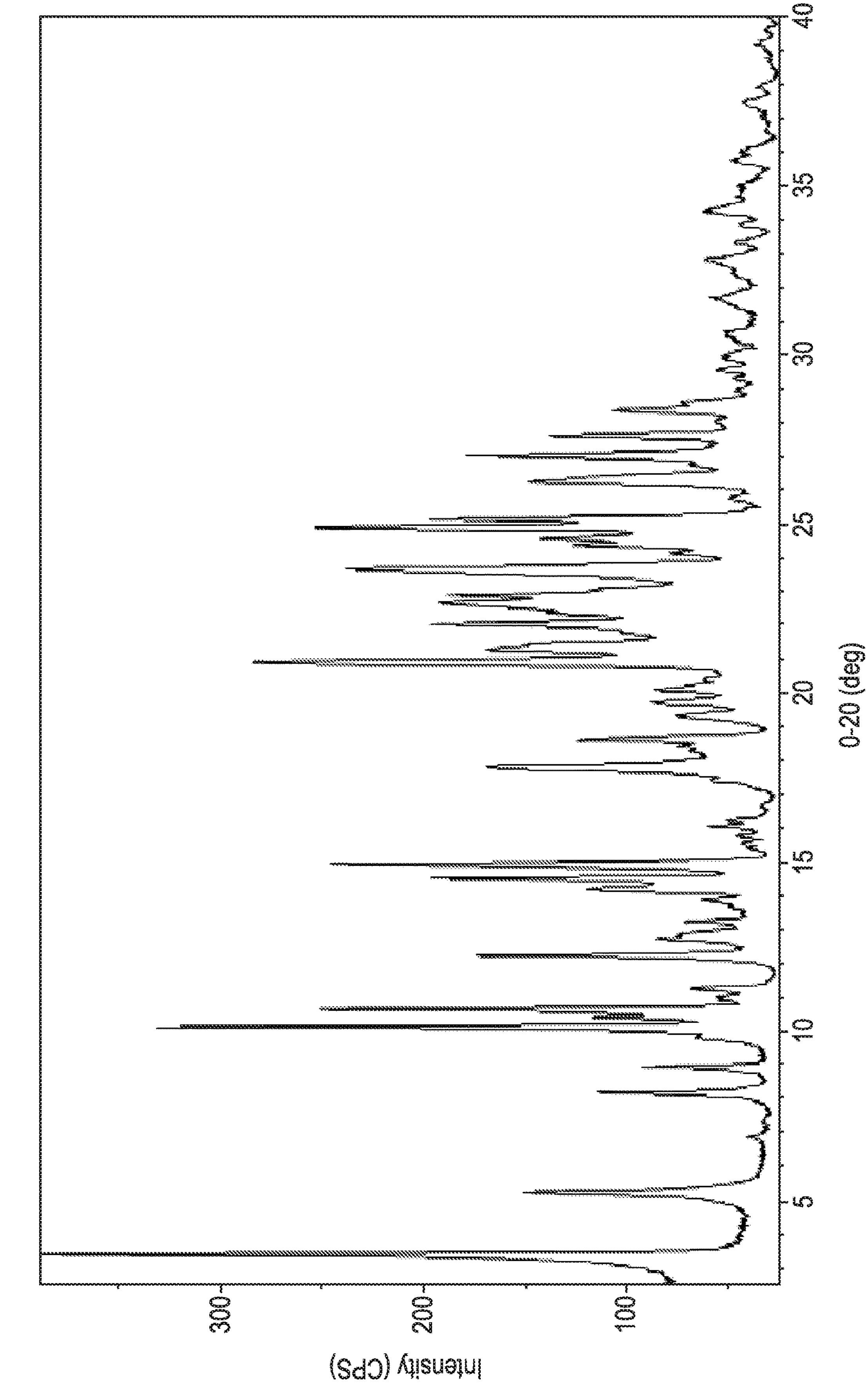
FIG. 37 is an XRPD pattern of Compound 1 HCl Form D.
Figure 38:
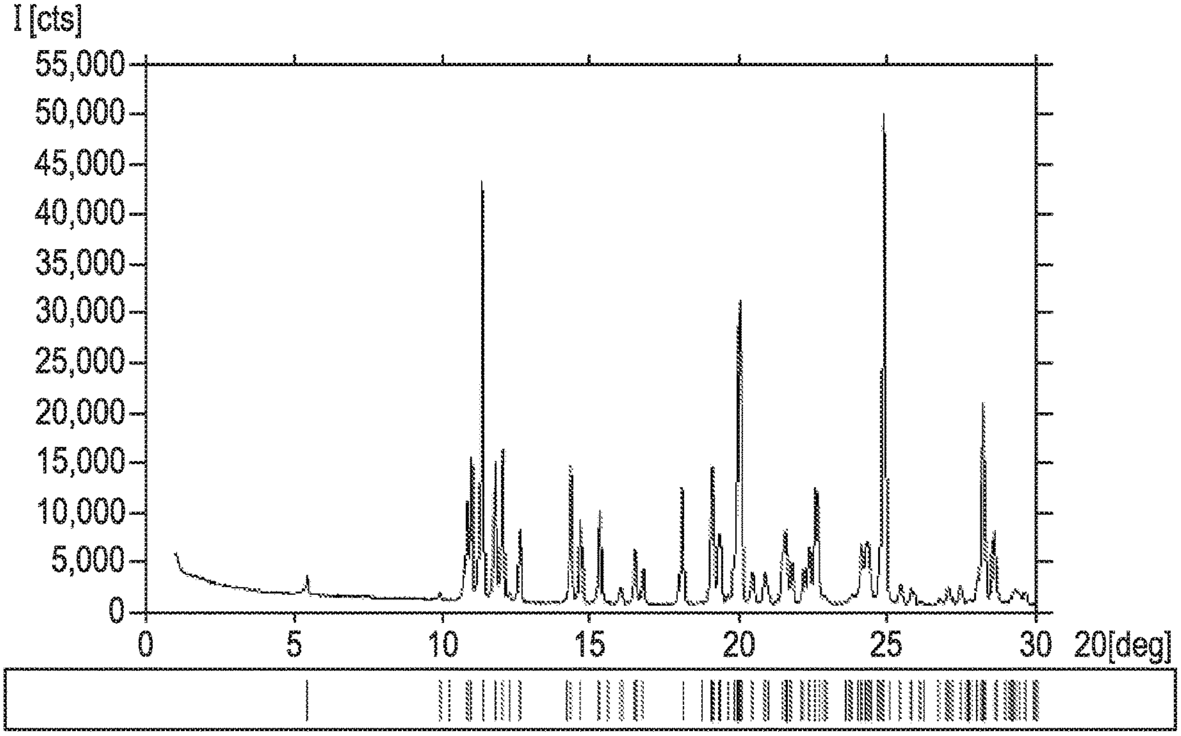
FIG. 38 is the indexing results for Compound 1 Form A, including the tabulated space group consistent with the assigned extinction symbol, unit cell parameters, and derived quantities.
Figure 39:
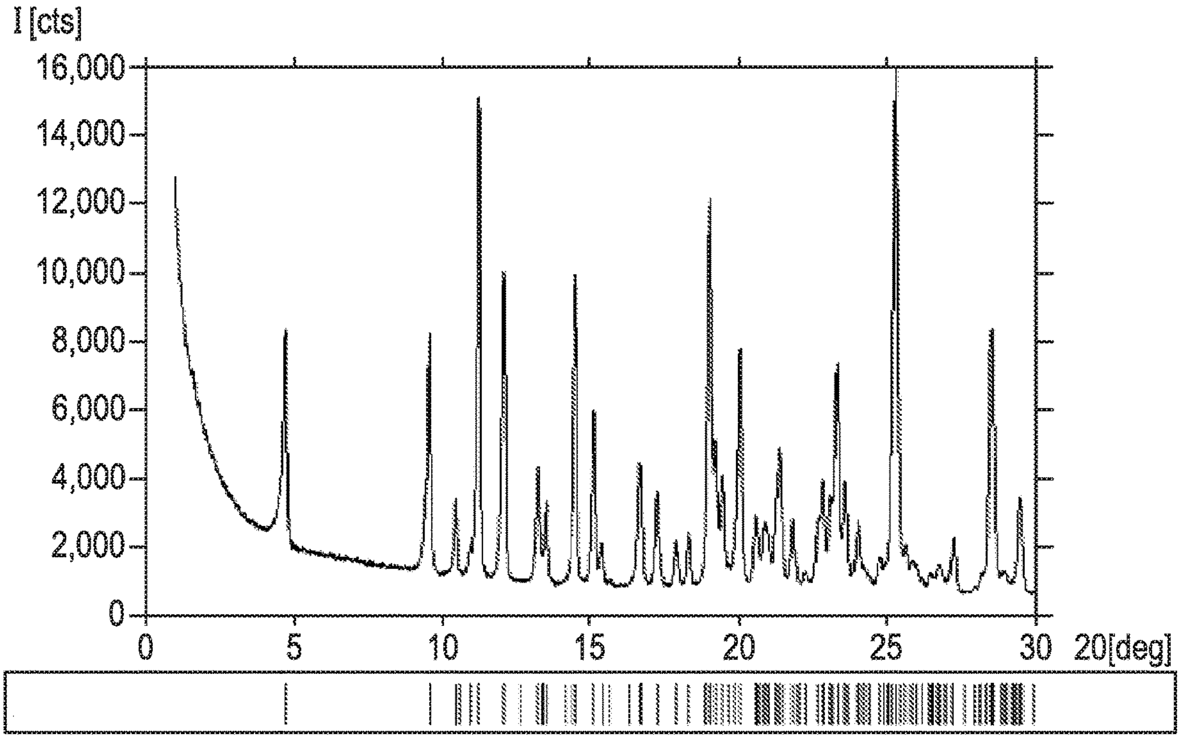
FIG. 39 is the indexing results for Compound 1 Form B, including the tabulated space group consistent with the assigned extinction symbol, unit cell parameters, and derived quantities.
Figure 40:
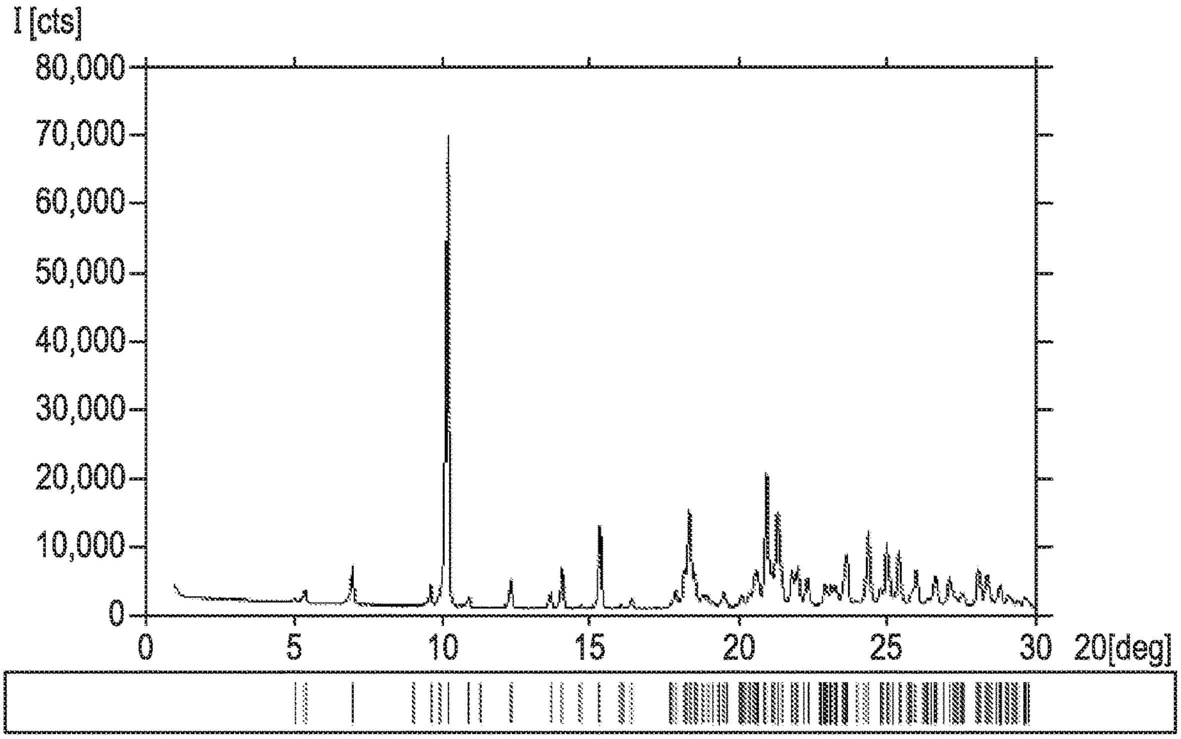
FIG. 40 is the indexing results for Compound 1 Form D, including the tabulated space group consistent with the assigned extinction symbol, unit cell parameters, and derived quantities.
Figure 41:
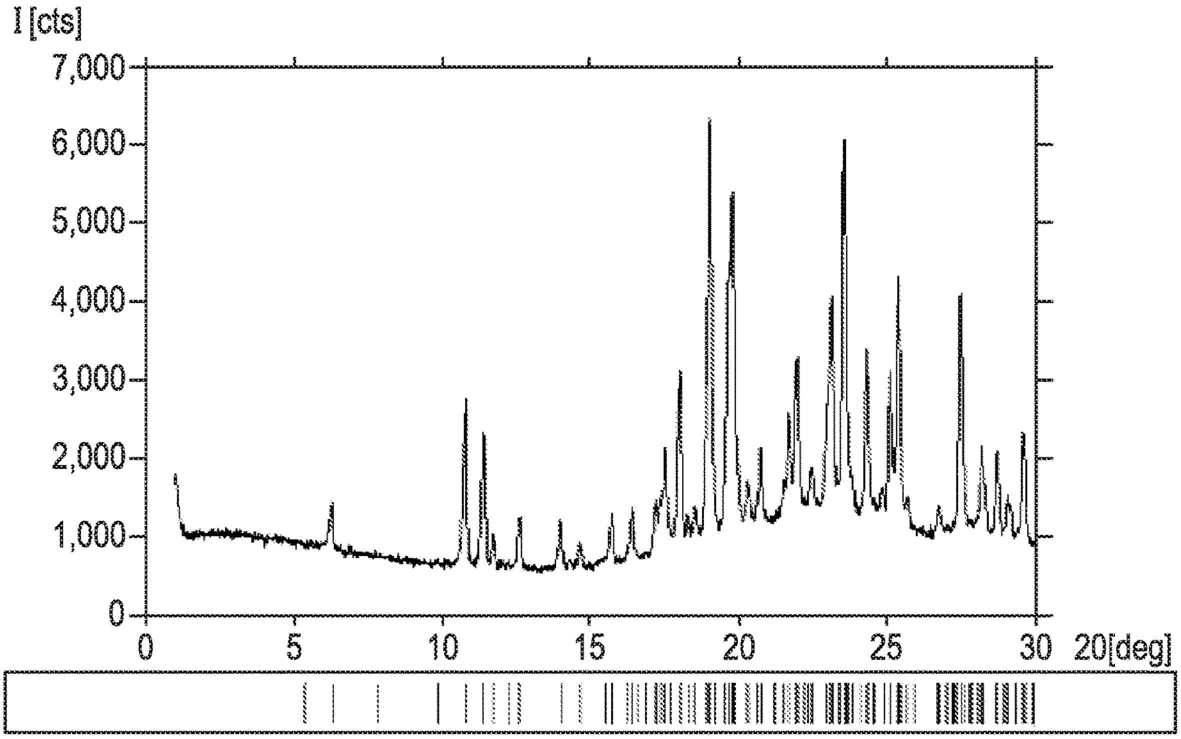
FIG. 41 is the indexing results for Compound 1 Form H, including the tabulated space group consistent with the assigned extinction symbol, unit cell parameters, and derived quantities.
Figure 42:
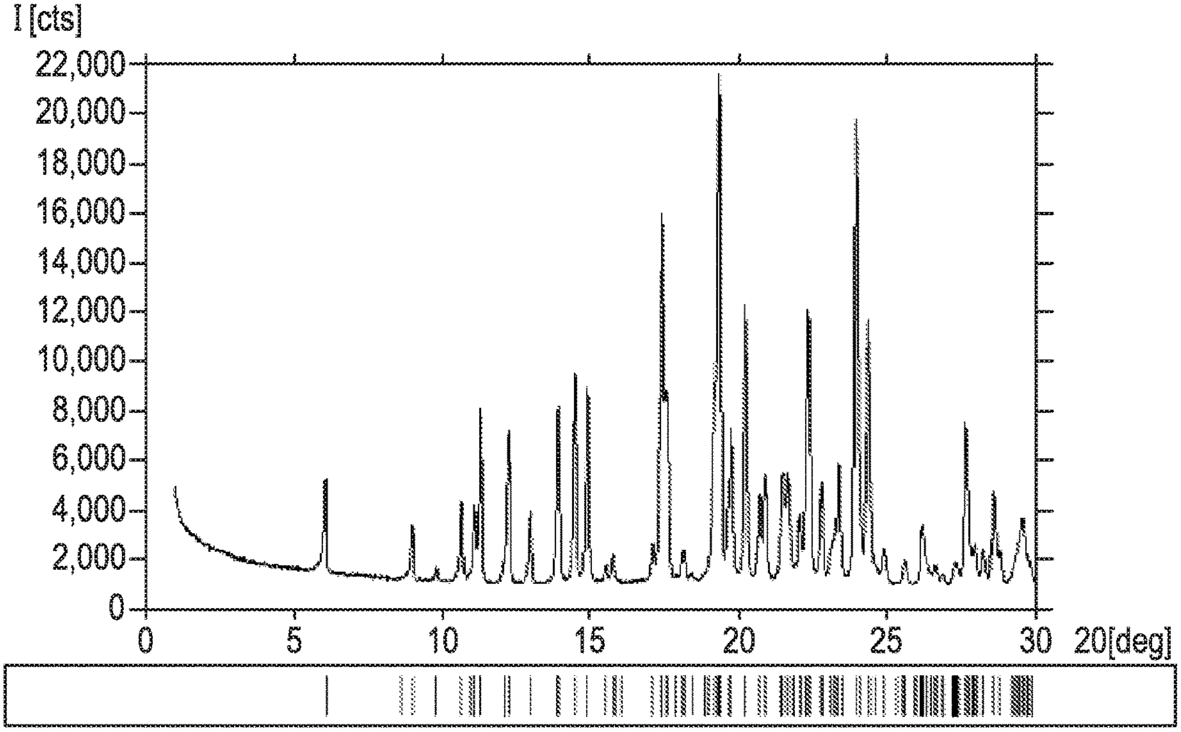
FIG. 42 is the indexing results for Compound 1 Form O, including the tabulated space group consistent with the assigned extinction symbol, unit cell parameters, and derived quantities.
Figure 43:
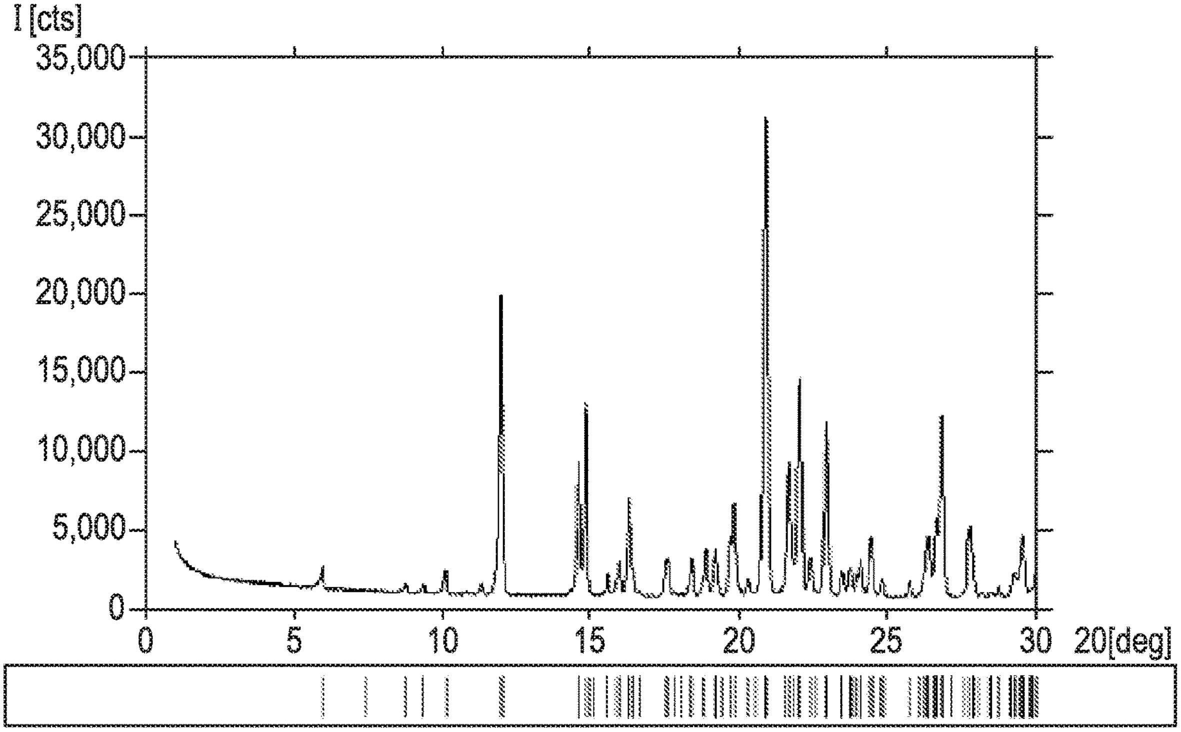
FIG. 43 is the indexing results for Compound 1 Form P, including the tabulated space group consistent with the assigned extinction symbol, unit cell parameters, and derived quantities.
Figure 44:
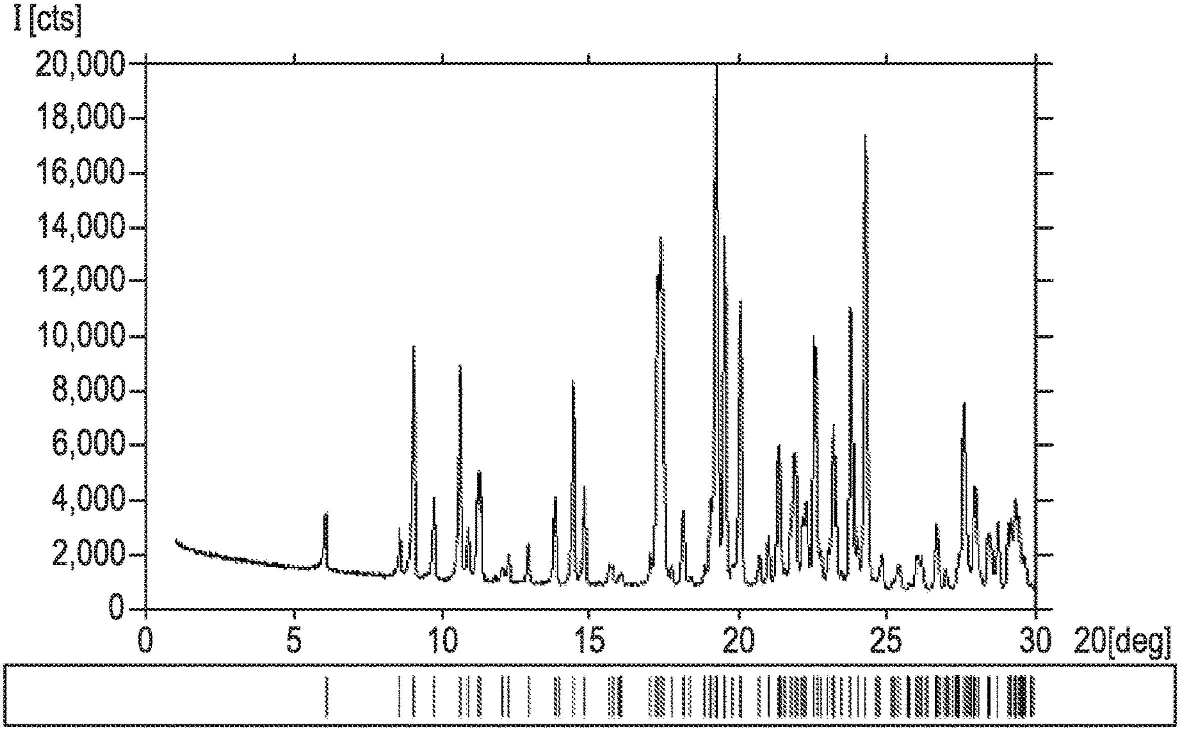
FIG. 44 is the indexing results for Compound 1 Form Q, including the tabulated space group consistent with the assigned extinction symbol, unit cell parameters, and derived quantities.
Figure 45:
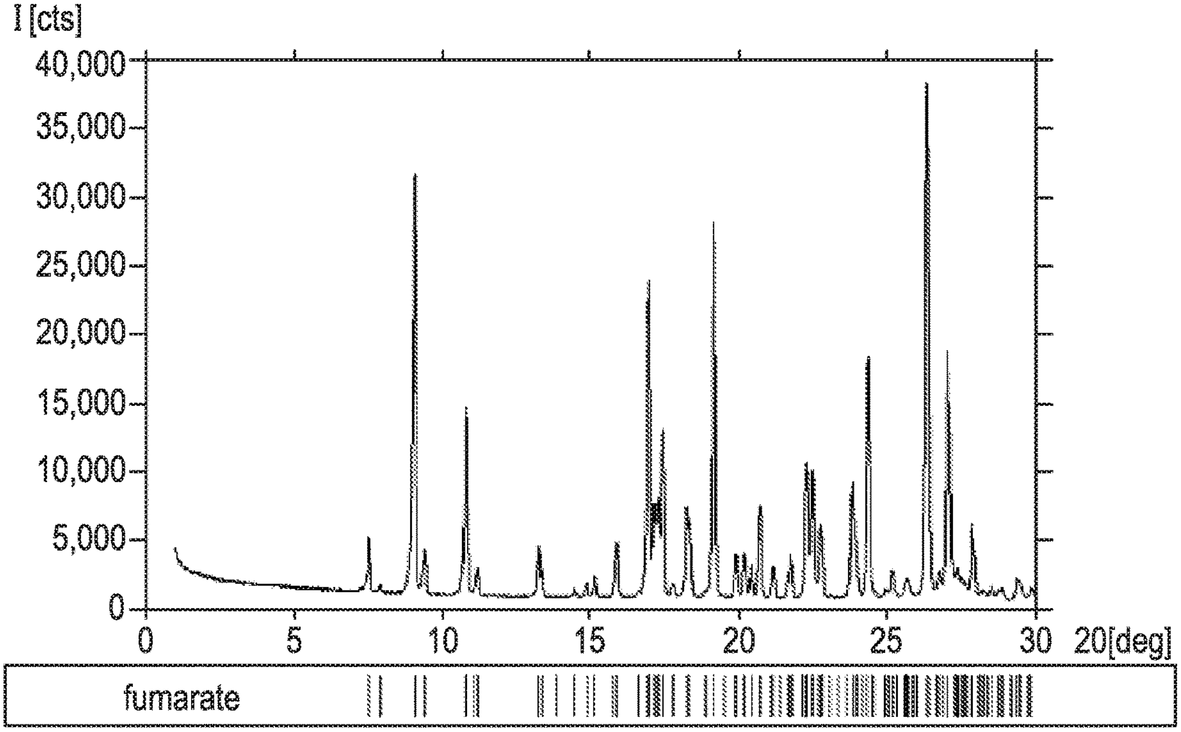
FIG. 45 is the indexing results for Compound 1 Hemifumarate Form B, including the tabulated space group consistent with the assigned extinction symbol, unit cell parameters, and derived quantities.
Figure 46:
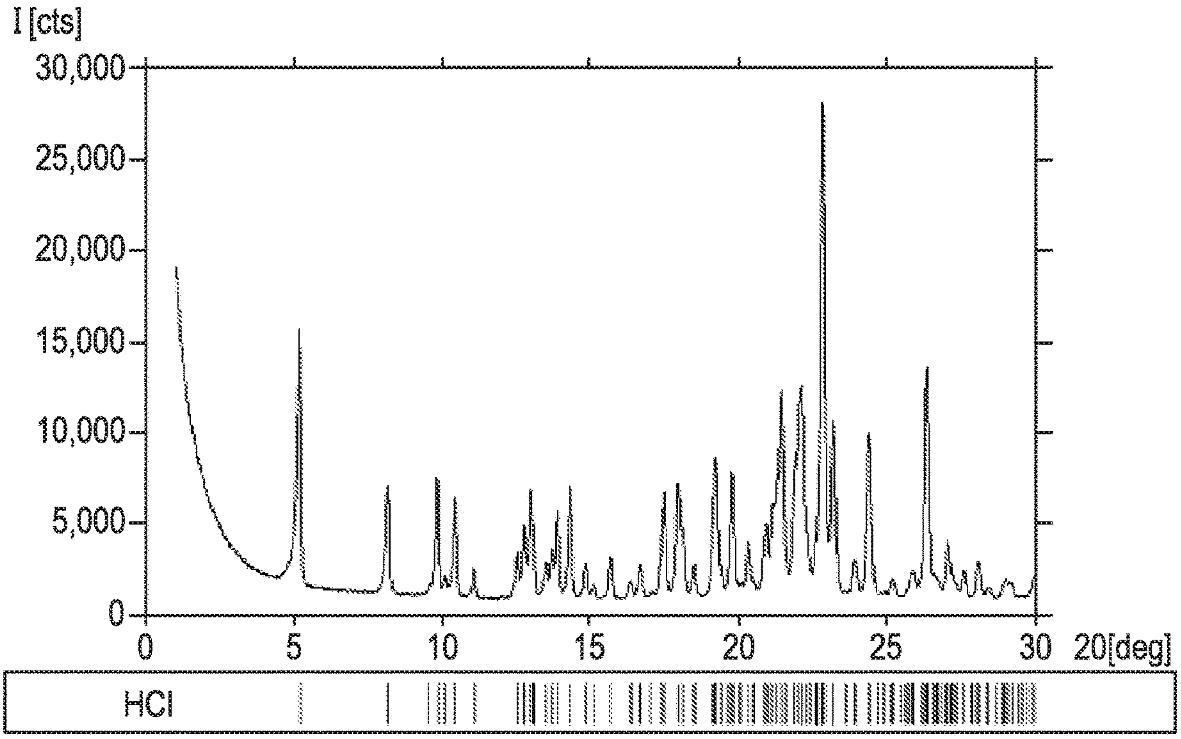
FIG. 46 is the indexing results for Compound 1 HCl Form A, including the tabulated space group consistent with the assigned extinction symbol, unit cell parameters, and derived quantities.
Figure 47:
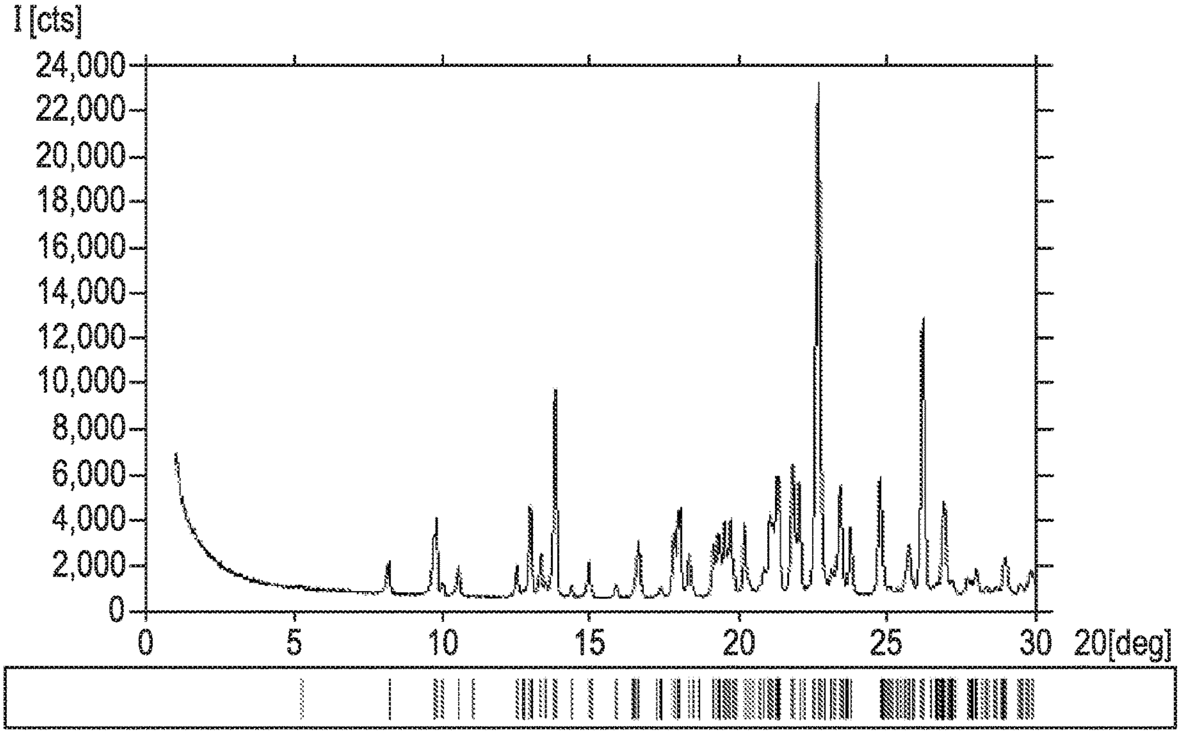
FIG. 47 is the indexing results for Compound 1 HCl Form B, including the tabulated space group consistent with the assigned extinction symbol, unit cell parameters, and derived quantities.

In a further embodiment, the Compound 1 HCl Form D is characterized by an XRPD pattern substantially identical to FIG. 37.

In one aspect, the invention relates to a crystalline fumaric acid salt form of Compound 1 having the general structure Compound 1

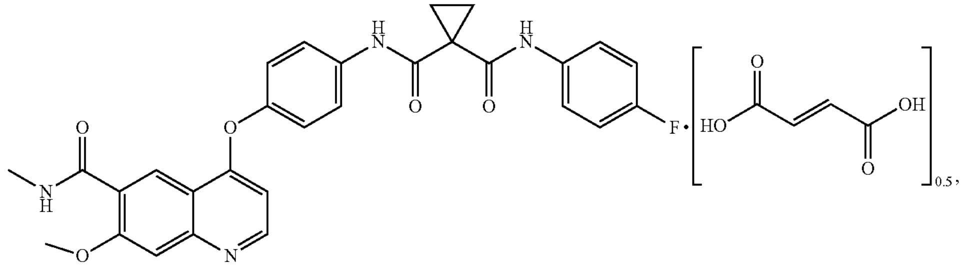

Hemifumarate or hydrate or solvate thereof, wherein the crystalline salt form is the Hemifumarate Compound 1●0.5 Fumaric acid.

In another aspect, the invention relates to a crystalline fumaric acid salt form of Compound 1 having the general structure Compound 1

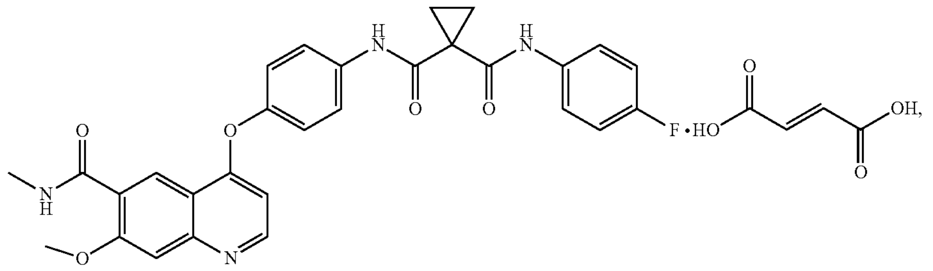

Fumarate or hydrate or solvate thereof, wherein the crystalline salt form is the Fumarate Compound 1●Fumaric acid.

In one embodiment, the crystalline solid is characterized as Compound 1 Fumarate Form A.

Figure 28:
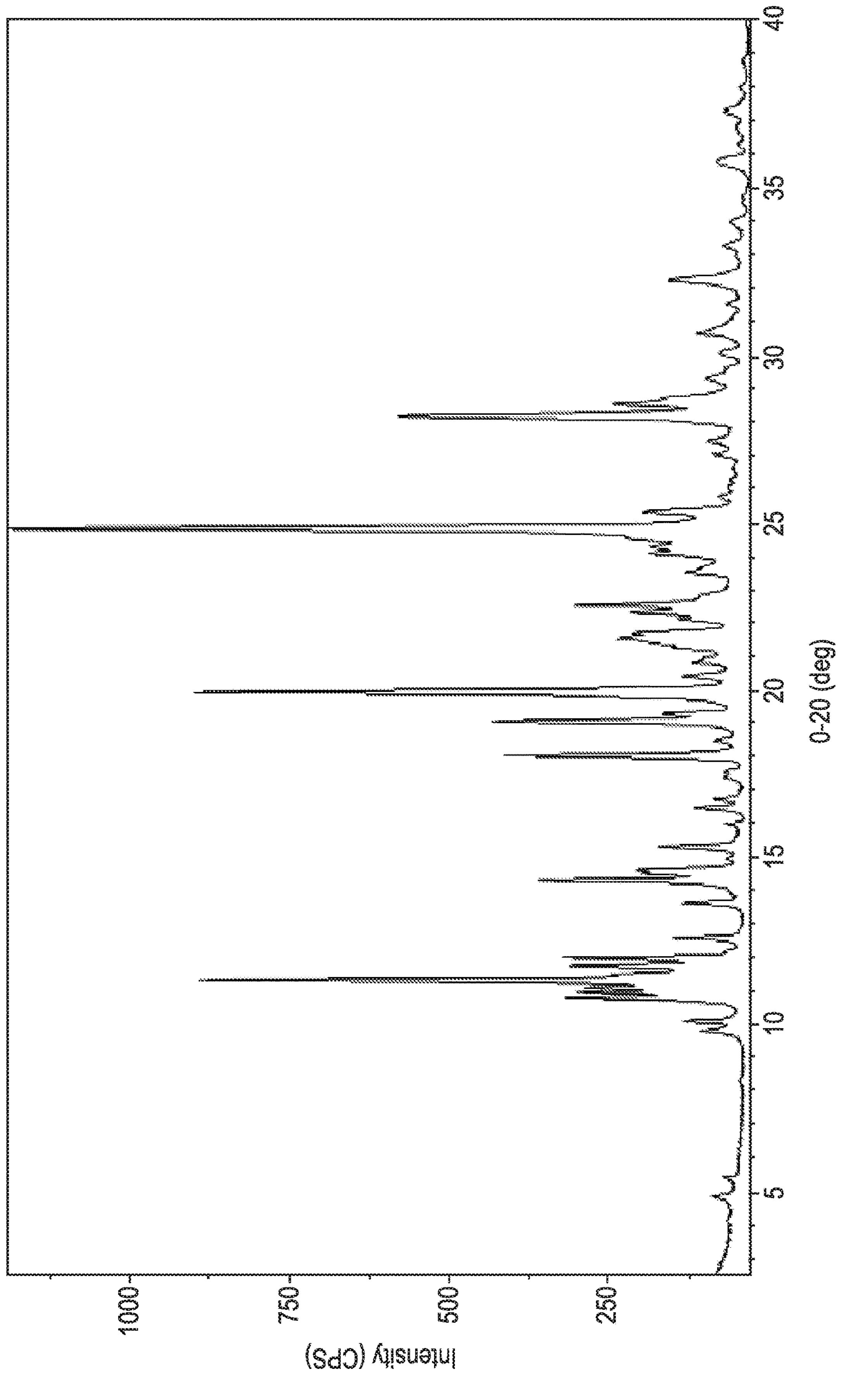
FIG. 28 is an XRPD pattern of Compound 1 Fumarate Form A+Compound 1 Form A (free base form).

In a further embodiment, the Compound 1 Fumarate Form A is characterized by an XRPD pattern substantially identical to FIG. 28.

In one aspect, the invention includes a crystalline fumaric acid salt of Compound 1 having the structure Compound 1

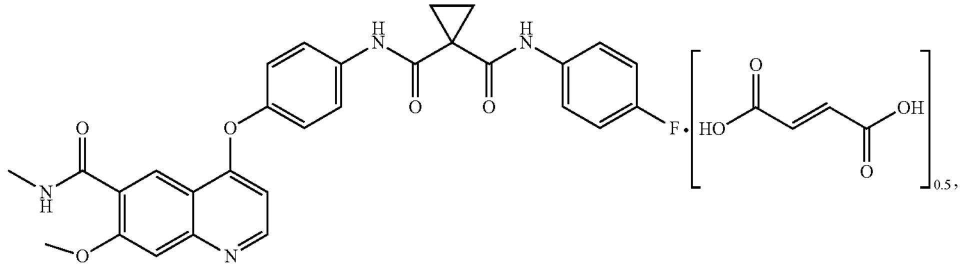

Hemifumarate or hydrate or solvate thereof.

In one embodiment of this aspect, the crystalline fumaric acid salt is characterized as Compound 1 hemifumarate Form B.

In one embodiment, the crystalline solid is characterized as Compound 1 Hemifumarate Form B.

In one embodiment, the Compound 1 Hemifumarate Form B is characterized by one or more of the following peaks in an XRPD pattern on a 2 Theta scale, ±0.2, wherein the one or more peaks is selected from 7.55, 7.92, 9.08, 9.40, 10.81, 11.18, 13.24, 13.35, 14.47, 14.90, 15.14, 15.89, 16.64, 16.95, 17.14, 17.29, 17.44, 17.79, 18.24, 18.34, 19.16, 19.91, 20.19, 20.42, 20.70, 21.16, 21.74, 22.29, 22.48, 22.75, 23.82, 24.37, 24.97, 25.17, 25.69, 26.34, 26.75, 27.05, 27.35, 27.50, and 27.88.

In one embodiment, the Compound 1 Hemifumarate Form B is characterized by one or more peaks in an XRPD pattern on a 2 Theta scale, ±0.2, wherein the one or more peaks is selected from 7.55, 9.08, 10.81, 13.24, 15.89, 16.95, 17.14, 17.29, 17.44, 18.24, 19.16, 19.91, 20.19, 20.42, 20.70, 21.16, 21.74, 22.29, 22.48, 22.75, 23.82, 24.37, 26.34, 27.05, and 27.88.

In one embodiment, the Compound 1 Hemifumarate Form B is characterized by one or more peaks in an XRPD pattern on a 2 Theta scale, ±0.2, wherein the one or more peaks is selected from 9.08, 10.81, 16.95, 17.44, 22.29, 22.48, 23.82, 24.37, 26.34, and 27.05.

In one embodiment, the Compound 1 Hemifumarate Form B is characterized by all of the following peaks in an XRPD pattern on a 2 Theta scale, ±0.2, wherein the peaks are 9.08, 10.81, 16.95, 17.44, 22.29, 22.48, 23.82, 24.37, 26.34, and 27.05.

In one embodiment, the Compound 1 Hemifumarate Form B is characterized by all of the following peaks in an XRPD pattern on a 2 Theta scale, ±0.2, wherein the peaks are 7.55, 9.08, 10.81, 13.24, 15.89, 16.95, 17.14, 17.29, 17.44, 18.24, 19.16, 19.91, 20.19, 20.42, 20.70, 21.16, 21.74, 22.29, 22.48, 22.75, 23.82, 24.37, 26.34, 27.05, and 27.88.

In one embodiment, the Compound 1 Hemifumarate Form B is characterized by all of the following peaks in an XRPD pattern on a 2 Theta scale, ±0.2, wherein the peaks are 7.55, 7.92, 9.08, 9.40, 10.81, 11.18, 13.24, 13.35, 14.47, 14.90, 15.14, 15.89, 16.64, 16.95, 17.14, 17.29, 17.44, 17.79, 18.24, 18.34, 19.16, 19.91, 20.19, 20.42, 20.70, 21.16, 21.74, 22.29, 22.48, 22.75, 23.82, 24.37, 24.97, 25.17, 25.69, 26.34, 26.75, 27.05, 27.35, 27.50, and 27.88.

Figure 29:
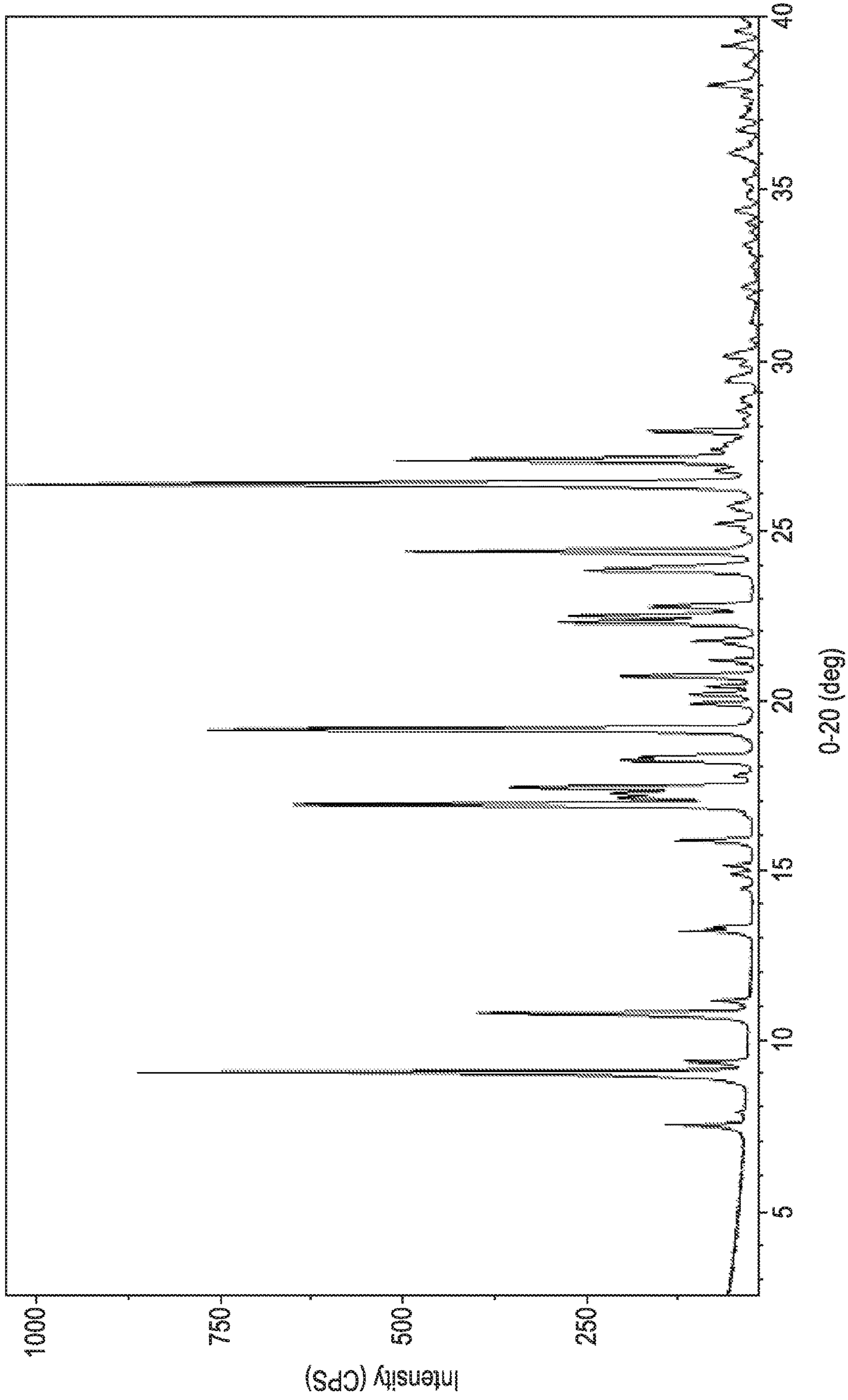
FIG. 29 is an XRPD pattern of Compound 1 Hemifumarate Form B.

In still a further embodiment, the Compound 1 Hemifumarate Form B is characterized by an XRPD pattern substantially identical to FIG. 29.

In one embodiment, the Compound 1 Hemifumarate Form B is characterized by an endotherm at about 226° C. in a DSC thermogram. In one embodiment, the Compound 1 Hemifumarate Form B is characterized by an endotherm with an onset temperature at about 226° C. in a DSC thermogram.

In one embodiment, the Compound 1 Hemifumarate Form B is characterized by negligible weight loss under a temperature of about 220° C. in a TGA thermogram.

In one embodiment, the Compound 1 Hemifumarate Form B is characterized by an increase in weight of about 0.2 wt %, as measured by DVS, in an environment that is taken from 5% relative humidity to 95% relative humidity.

In one aspect, the invention relates to a crystalline phosphoric acid salt form of Compound 1 having the general structure Compound 1

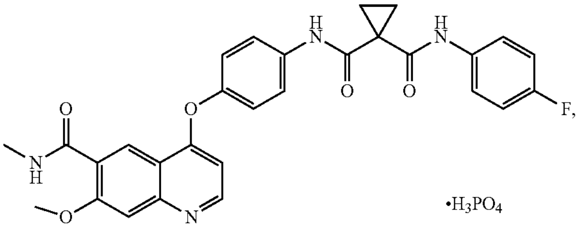

Phosphate Form A or hydrate or solvate thereof, characterized as Compound 1 Phosphate Form A.

In one embodiment, the Compound 1 Phosphate Form A is characterized by one or more of the following peaks in an XRPD pattern on a 2 Theta scale, ±0.2, wherein the one or more peaks is selected from 6.3, 6.8, 10.3, 10.5, 11.4, 12.7, 13.8, 14.7, 15.7, 16.1, 17.3, 17.5, 18.1, 18.8, 19.4, 20.3, 20.9, 21.2, 22.1, 22.7, 23.2, 23.6, 24.7, 25.5, 27.4, 27.8, 28.5, 29.1, and 29.3.

In one embodiment, the Compound 1 Phosphate Form A is characterized by one or more peaks in an XRPD pattern on a 2 Theta scale, ±0.2, wherein the one or more peaks is selected from 6.3, 6.8, 10.5, 12.7, 13.8, 16.1, 17.3, 18.1, 18.8, 19.4, 20.3, 20.9, 21.2, 22.1, 23.2, 24.7, 27.4, 27.8, and 28.5.

In another embodiment, the Compound 1 Phosphate Form A is characterized by one or more peaks in an XRPD pattern on a 2 Theta scale, ±0.2, wherein the one or more peaks is selected from 6.3, 6.8, 13.8, 16.1, 19.4, 20.3, 23.2, and 24.7.

In a further embodiment, the Compound 1 Phosphate Form A is characterized by all of the following peaks in an XRPD pattern on a 2 Theta scale, ±0.2, wherein the peaks are 6.3, 6.8, 13.8, 16.1, 19.4, 20.3, 23.2, and 24.7.

In still a further embodiment, the Compound 1 Phosphate Form A is characterized by all of the following peaks in an XRPD pattern on a 2 Theta scale, ±0.2, wherein the peaks are 6.3, 6.8, 10.5, 12.7, 13.8, 16.1, 17.3, 18.1, 18.8, 19.4, 20.3, 20.9, 21.2, 22.1, 23.2, 24.7, 27.4, 27.8, and 28.5.

In still a further embodiment, the Compound 1 Phosphate Form A is characterized by all of the following peaks in an XRPD pattern on a 2 Theta scale, ±0.2, wherein the peaks are 6.3, 6.8, 10.3, 10.5, 11.4, 12.7, 13.8, 14.7, 15.7, 16.1, 17.3, 17.5, 18.1, 18.8, 19.4, 20.3, 20.9, 21.2, 22.1, 22.7, 23.2, 23.6, 24.7, 25.5, 27.4, 27.8, 28.5, 29.1, and 29.3.

Figure 48:
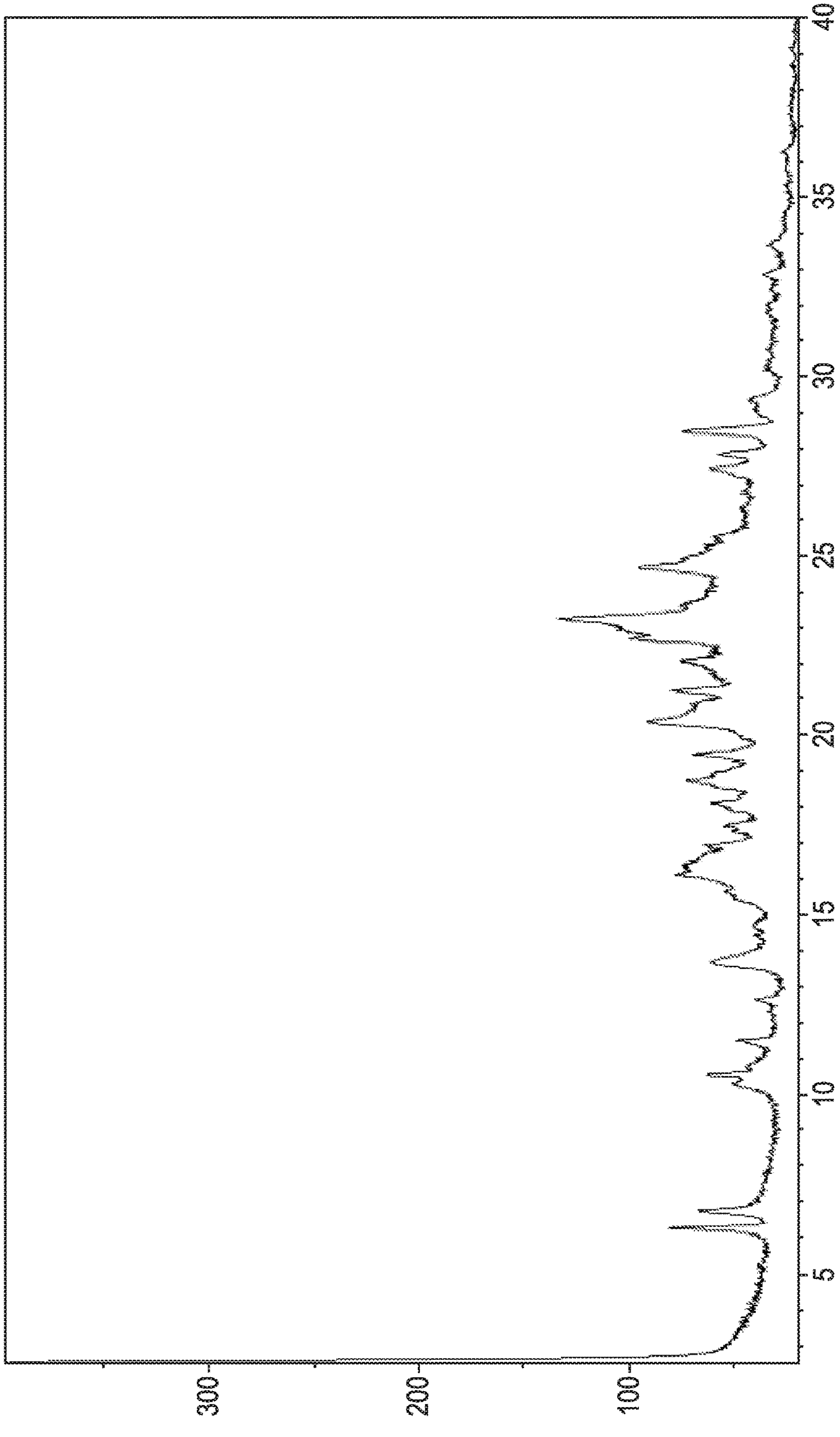
FIG. 48 is an XRPD pattern of Compound 1 Phosphate Form A.

In still a further embodiment, the Compound 1 Phosphate Form A is characterized by an XRPD pattern substantially identical to FIG. 48.

In one aspect, the invention includes a crystalline solid form of Compound 1

Compound 1

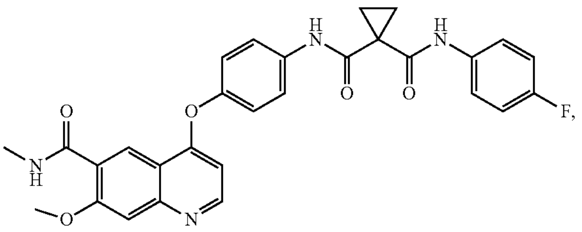

or hydrate or solvate thereof, characterized as Compound 1 Form A by at least one of the following:

(i) one or more peaks in an XRPD pattern on a 2 Theta scale, ±0.20, wherein the one or more peaks is selected from 5.48, 9.93, 10.83, 10.98, 11.36, 11.79, 12.04, 12.25, 12.62, 14.33, 14.67, 15.33, 16.02, 16.51, 16.77, 18.07, 19.09, 19.34, 19.60, 20.00, 20.46, 20.85, 21.45, 21.55, 21.76, 22.16, 22.35, 22.58, 22.87, 23.79, 24.11, 24.29, 24.35, 24.87, 25.42, 25.81, 26.09, 26.72, 27.04, 27.44, 27.77, 27.98, 28.19, and 28.56;

(ii) an endotherm with an onset temperature at greater than 200° C. in a DSC thermogram;

(iii) a weight loss at a temperature greater than 200° C. in a TGA thermogram; (iv) a weight gain of from about 0.8 to about 1.0 wt %, as determined by DVS analysis, when taken from an environment of 5% relative humidity to an environment of 95% relative humidity; and (v) an $^{1}H$ NMR spectrum substantially identical to FIG. 55.

In one aspect, the invention includes a crystalline solid form of Compound 1

Compound 1

Figure 55:
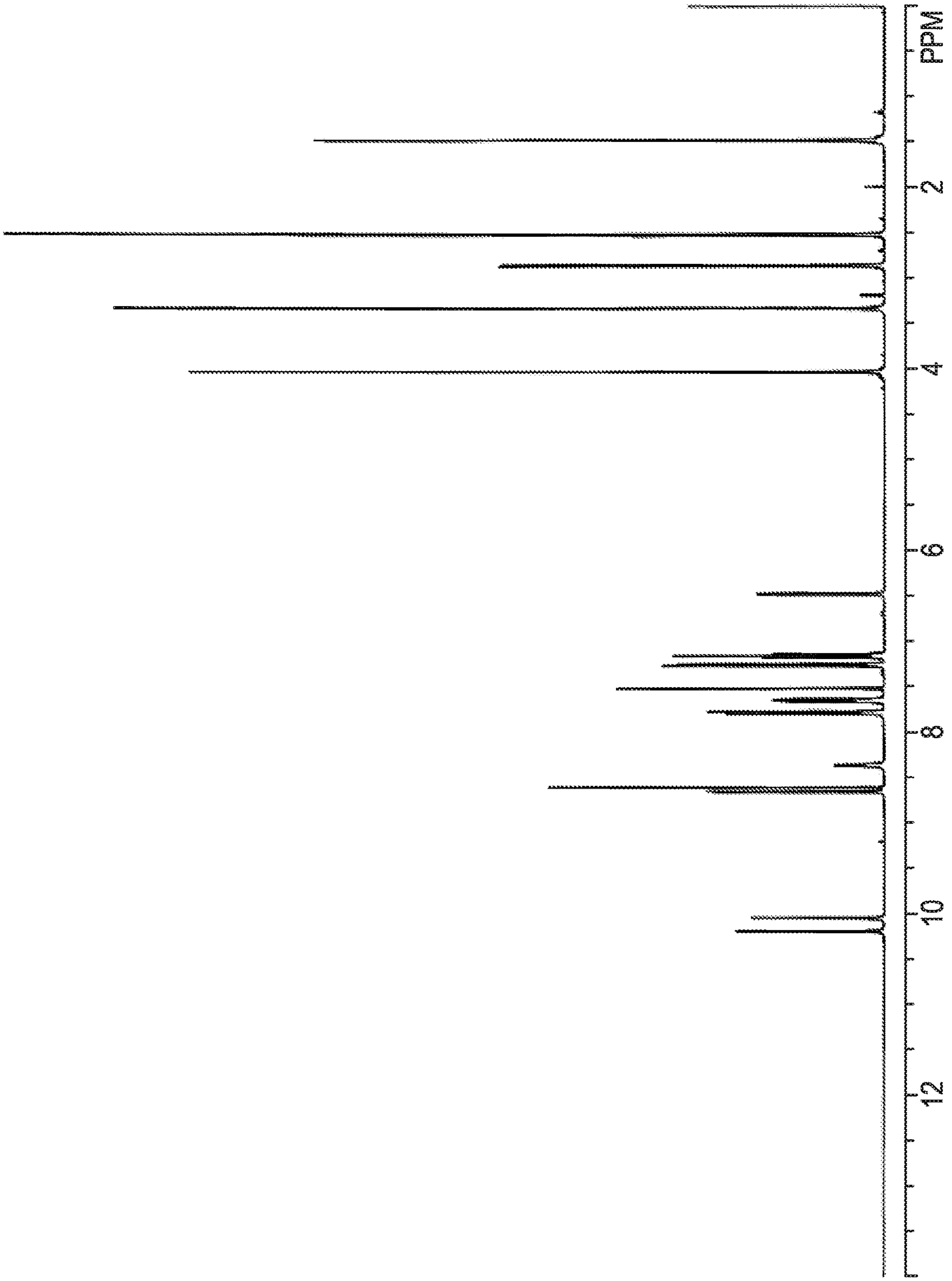
FIG. 55 is an $^1H$ NMR spectrum of Compound 1 Form A in DMSO-$d_6$.

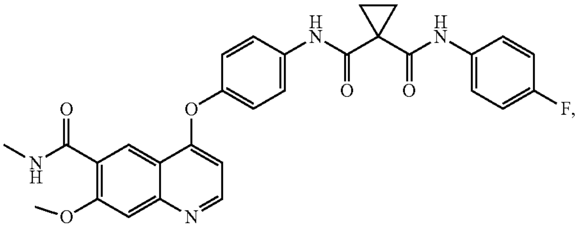

or hydrate or solvate thereof, characterized by at least one of the following:

(i) one or more peaks in an XRPD pattern on a 2 Theta scale, ±0.20, wherein the one or more peaks is selected from 5.48, 9.93, 10.83, 10.98, 11.36, 11.79, 12.04, 12.25, 12.62, 14.33, 14.67, 15.33, 16.02, 16.51, 16.77, 18.07, 19.09, 19.34, 19.60, 20.00, 20.46, 20.85, 21.45, 21.55, 21.76, 22.16, 22.35, 22.58, 22.87, 23.79, 24.11, 24.29, 24.35, 24.87, 25.42, 25.81, 26.09, 26.72, 27.04, 27.44, 27.77, 27.98, 28.19, and 28.56;

(ii) an endotherm with an onset temperature at greater than 200° C. in a DSC thermogram;

(iii) a weight loss at a temperature greater than 200° C. in a TGA thermogram;

(iv) a weight gain of from about 0.8 to about 1.0 wt %, as determined by DVS analysis, when taken from an environment of 5% relative humidity to an environment of 95% relative humidity; and (v) an $^{1}H$ NMR spectrum substantially identical to FIG. 55.

In one embodiment of this aspect, the crystalline solid form of Compound 1 is characterized as Form A.

In one embodiment, the Compound 1 Form A is characterized by one or more peaks in an XRPD pattern on a 2 Theta scale, ±0.20, wherein the one or more peaks is selected from 10.83, 10.98, 11.36, 11.79, 12.04, 14.33, 18.07, 19.09, 20.00, 22.58, 24.87, and 28.19.

In another embodiment, the Compound 1 Form A is characterized by all of the following peaks in an XRPD pattern on a 2 Theta scale ±0.20, wherein the peaks are 10.83, 10.98, 11.36, 11.79, 12.04, 14.33, 18.07, 19.09, 20.00, 22.58, 24.87, and 28.19.

In one embodiment, the Compound 1 Form A is characterized by all of the following peaks in an XRPD pattern on a 2 Theta scale ±0.20, wherein the peaks are 5.48, 9.93, 10.83, 10.98, 11.36, 11.79, 12.04, 12.25, 12.62, 14.33, 14.67, 15.33, 16.02, 16.51, 16.77, 18.07, 19.09, 19.34, 19.60, 20.00, 20.46, 20.85, 21.45, 21.55, 21.76, 22.16, 22.35, 22.58, 22.87, 23.79, 24.11, 24.29, 24.35, 24.87, 25.42, 25.81, 26.09, 26.72, 27.04, 27.44, 27.77, 27.98, 28.19, and 28.56.

In one embodiment, the Compound 1 Form A is characterized as Compound 1 Form A by at least two of (i), (ii), (iii), and (iv).

In a further embodiment, the Compound 1 Form A is characterized as Compound 1 Form A by at least three of (i), (ii), (iii), and (iv).

In still a further embodiment, the Compound 1 Form A is characterized as Compound 1 Form A by all of (i), (ii), (iii), and (iv).

In another aspect, the invention includes a crystalline solid form of Compound 1

Compound 1

Figure 56:
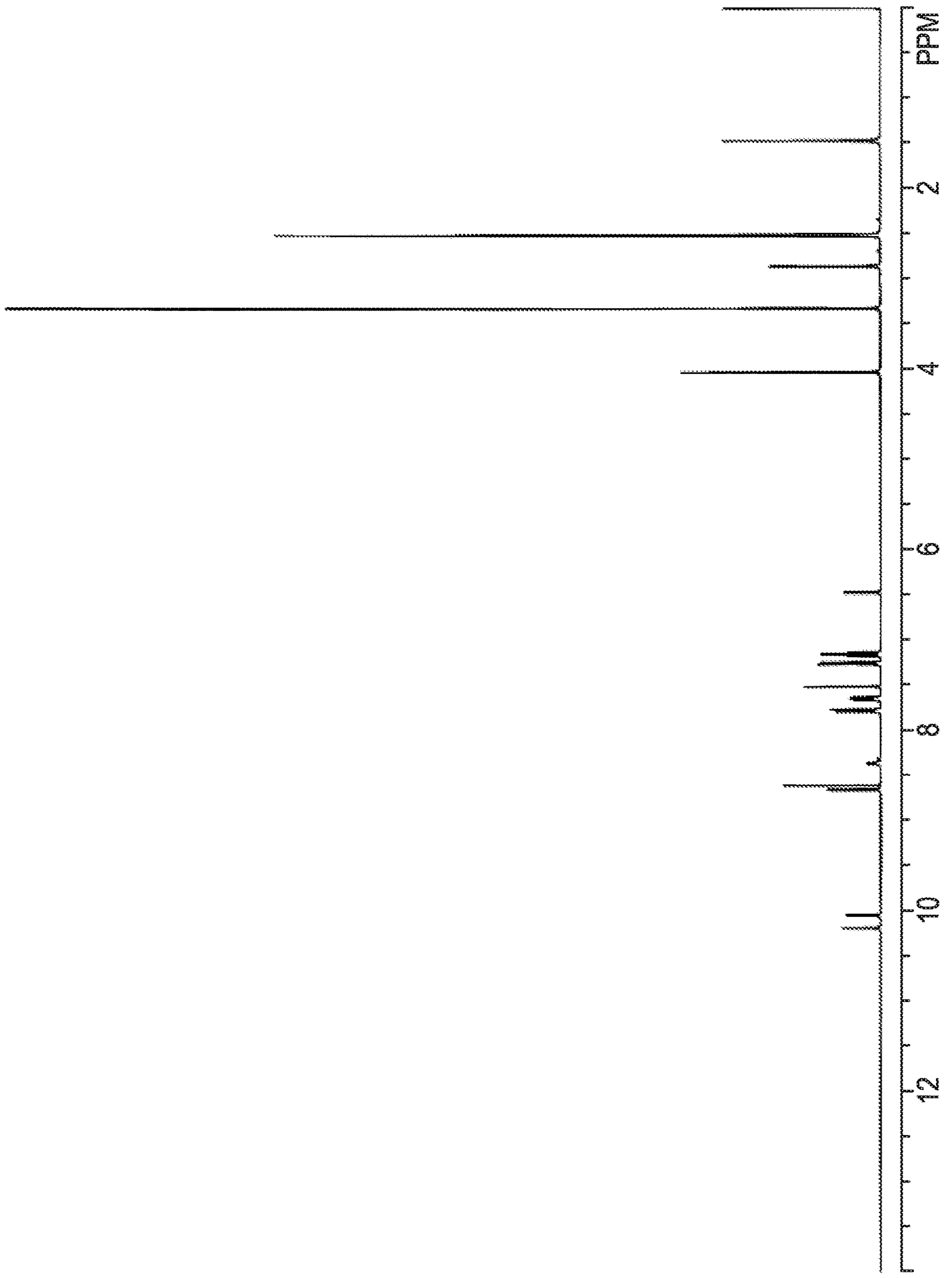
FIG. 56 is an $^1H$ NMR spectrum of Compound 1 Form K in DMSO-$d_6$.

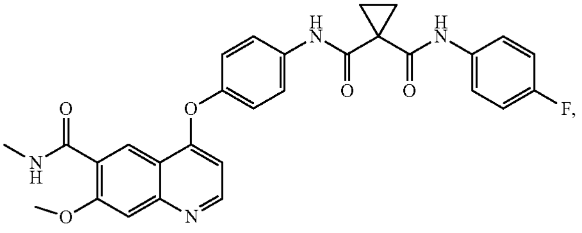

or hydrate or solvate thereof, characterized as Compound 1 Form K by at least one of the following:

(i) one or more peaks in an XRPD pattern on a 2 Theta scale, ±0.20, wherein the one or more peaks is selected from 6.39, 8.10, 11.53, 19.89, 21.11, 22.34, 24.50, and 26.42;

(ii) an endotherm with an onset at a temperature of about 226° C. in a DSC thermogram;

(iii) a weight loss of ~0.2 wt % between the temperatures of 40-180° C. in a TGA thermogram; and (v) an $^{1}$H NMR spectrum substantially identical to FIG. 56.

In another aspect, the invention includes a crystalline solid form of Compound 1

Compound 1

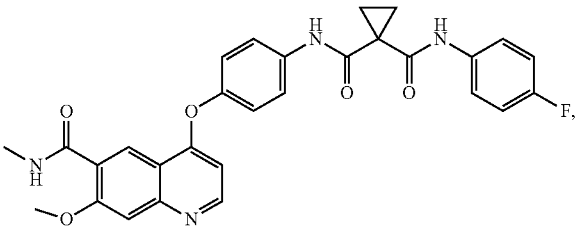

or hydrate or solvate thereof, characterized by at least one of the following:

(i) one or more peaks in an XRPD pattern on a 2 Theta scale, ±0.20, wherein the one or more peaks is selected from 6.39, 8.10, 11.53, 19.89, 21.11, 22.34, 24.50, and 26.42;

(ii) an endotherm with an onset at a temperature of about 226° C. in a DSC thermogram;

(iii) a weight loss of ~0.2 wt % between the temperatures of 40-180° C. in a TGA thermogram; and (v) an $^{1}$H NMR spectrum substantially identical to FIG. 56.

In one embodiment of this aspect, the crystalline solid form of Compound 1 is characterized as Form K.

In one embodiment, the Compound 1 Form K is characterized by one or more peaks in an XRPD pattern on a 2 Theta scale, +0.2, wherein the one or more peaks is selected from 6.39, 8.10, 22.34, and 24.50.

In another embodiment, the Compound 1 Form K is characterized by all of the following peaks in an XRPD pattern on a 2 Theta scale, +0.2, wherein the peaks are 6.39, 8.10, 22.34, and 24.50.

In another embodiment, the Compound 1 Form K is characterized by all of the following peaks in an XRPD pattern on a 2 Theta scale, +0.2, wherein the peaks are 6.39, 8.10, 11.53, 19.89, 21.11, 22.34, 24.50, and 26.42.

In another embodiment, the Compound 1 Form K is characterized as Compound 1 Form K by at least two of (i), (ii), and (iii).

In a further embodiment, the Compound 1 Form K is characterized as Compound 1 Form K by all of (i), (ii), and (iii).

In another aspect, the invention includes a crystalline solid form of Compound 1

Compound 1

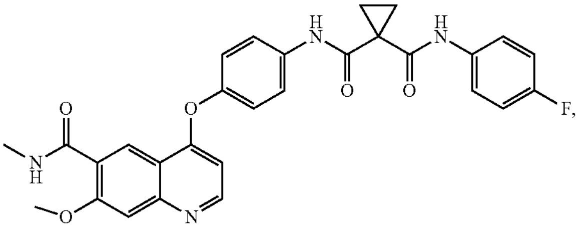

or hydrate or solvate thereof, characterized as Compound 1 Form Q by at least one of the following:

(i) one or more peaks in an XRPD pattern on a 2 Theta scale, +0.20, wherein the one or more peaks is selected from 6.11, 8.61, 9.06, 9.74, 15.69, 16.07, 20.04, and 24.01;

(ii) an endotherm with an onset at a temperature of about 194-195° C. in a DSC thermogram; and (iii) a weight loss of ~11-12 wt % between the temperatures of 120-160° C. in a TGA thermogram.

In another aspect, the invention includes a crystalline solid form of Compound 1

Compound 1

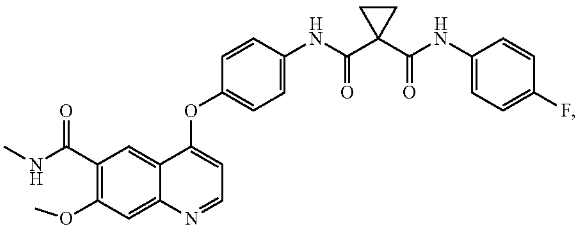

or hydrate or solvate thereof, characterized by at least one of the following:

(i) one or more peaks in an XRPD pattern on a 2 Theta scale, ±0.20, wherein the one or more peaks is selected from 6.11, 8.61, 9.06, 9.74, 15.69, 16.07, 20.04, and 24.01;

(ii) an endotherm with an onset at a temperature of about 194-195° C. in a DSC thermogram; and (iii) a weight loss of ~11-12 wt % between the temperatures of 120-160° C. in a TGA thermogram.

In one embodiment of this aspect, the crystalline solid form of Compound 1 is characterized as Form K.

In one embodiment, the Compound 1 Form Q is characterized by one or more peaks in an XRPD pattern on a 2 Theta scale, ±0.2, wherein the one or more peaks is selected from 8.61, 9.74, 16.07, and 20.04.

In another embodiment, the Compound 1 Form Q is characterized by all of the following peaks in an XRPD pattern on a 2 Theta scale, ±0.2, wherein the peaks are 8.61, 9.74, 16.07, and 20.04.

In another embodiment, the Compound 1 Form Q characterized by all of the following peaks in an XRPD pattern on a 2 Theta scale, ±0.2, wherein the peaks are 6.11, 8.61, 9.06, 9.74, 15.69, 16.07, 20.04, and 24.01.

In one embodiment, the Compound 1 Form Q characterized as Compound 1 Form Q by at least two of (i), (ii), and (iii).

In a further embodiment, the Compound 1 Form Q characterized as Compound 1 Form Q by all of (i), (ii), and (iii).

In one aspect, the invention includes a crystalline solid form of Compound 1

Compound 1

Figure 54:
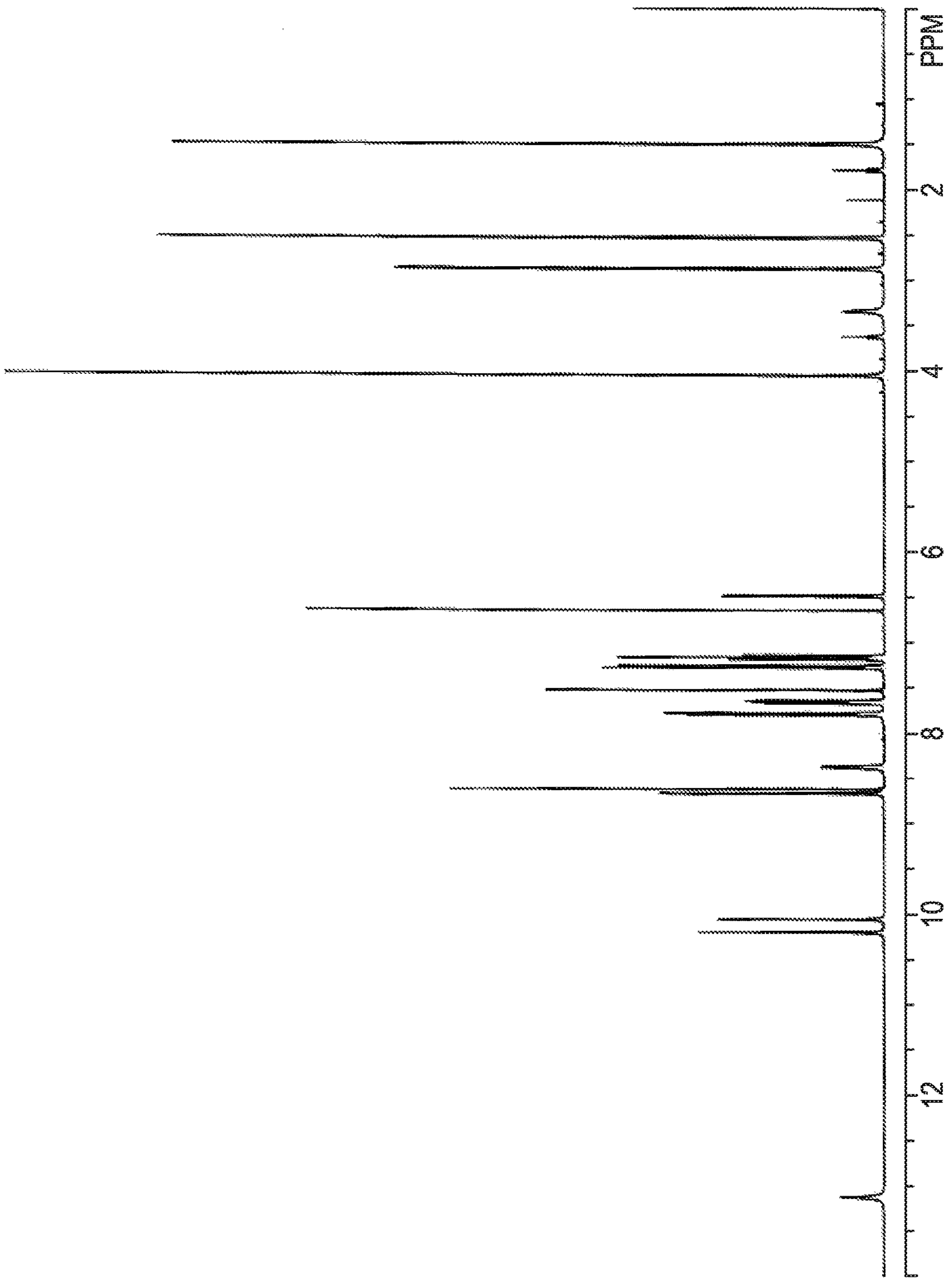
FIG. 54 is an $^1H$ NMR spectrum of Compound 1 Hemifumarate Form B in DMSO-$d_6$.

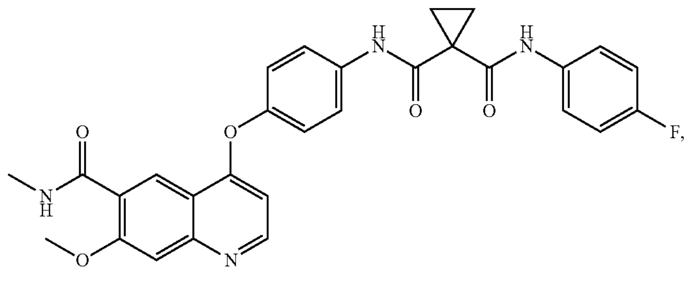

or hydrate or solvate thereof, characterized as Compound 1 Hemifumarate Form B by at least one of the following:

(i) one or more peaks in an XRPD pattern on a 2 Theta scale, ±0.2, wherein the one or more peaks is selected from 7.55, 9.08, 10.81, 13.24, 15.89, 16.95, 17.14, 17.29, 17.44, 18.24, 19.16, 19.91, 20.19, 20.42, 20.70, 21.16, 21.74, 22.29, 22.48, 22.75, 23.82, 24.37, 26.34, 27.05, and 27.88;

(ii) an endotherm with an onset temperature of about 226° C. in a DSC thermogram;

(iii) negligible weight loss under a temperature of about 220° C. in a TGA thermogram;

(iv) an increase in weight of about 0.2 wt %, as measured by DVS, in an environment that is taken from 5% relative humidity to 95% relative humidity; and (v) an $^1$H NMR spectrum substantially identical to FIG. 54.

In one aspect the invention includes a crystalline solid form of Compound 1

Compound 1

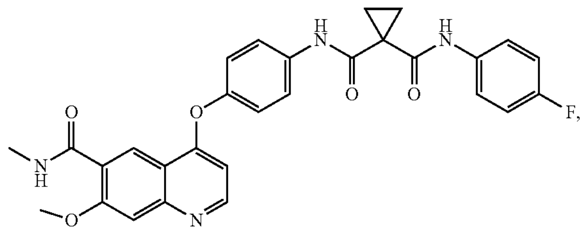

or hydrate or solvate thereof, characterized by at least one of the following:

(i) one or more peaks in an XRPD pattern on a 2 Theta scale, ±0.2, wherein the one or more peaks is selected from 7.55, 9.08, 10.81, 13.24, 15.89, 16.95, 17.14, 17.29, 17.44, 18.24, 19.16, 19.91, 20.19, 20.42, 20.70, 21.16, 21.74, 22.29, 22.48, 22.75, 23.82, 24.37, 26.34, 27.05, and 27.88;

(ii) an endotherm with an onset temperature of about 226° C. in a DSC thermogram;

(iii) negligible weight loss under a temperature of about 220° C. in a TGA thermogram;

(iv) an increase in weight of about 0.2 wt %, as measured by DVS, in an environment that is taken from 5% relative humidity to 95% relative humidity; and (v) an $^1$H NMR spectrum substantially identical to FIG. 54.

In one embodiment of this aspect, the crystalline solid form of Compound 1 is characterized as Hemifumarate Form B.

In one embodiment, the Compound 1 Hemifumarate Form B is characterized by one or more peaks in an XRPD pattern on a 2 Theta scale, ±0.2, wherein the one or more peaks is selected from 9.08, 10.81, 16.95, 17.44, 22.29, 22.48, 23.82, 24.37, 26.34, and 27.05.

In one embodiment, the Compound 1 Hemifumarate Form B is characterized by all of the following peaks in an XRPD pattern on a 2 Theta scale, ±0.2, wherein the peaks are 9.08, 10.81, 16.95, 17.44, 22.29, 22.48, 23.82, 24.37, 26.34, and 27.05.

In another embodiment, the Compound 1 Hemifumarate Form B is characterized by all of the following peaks in an XRPD pattern on a 2 Theta scale, ±0.2, wherein the peaks are 7.55, 9.08, 10.81, 13.24, 15.89, 16.95, 17.14, 17.29, 17.44, 18.24, 19.16, 19.91, 20.19, 20.42, 20.70, 21.16, 21.74, 22.29, 22.48, 22.75, 23.82, 24.37, 26.34, 27.05, and 27.88.

In one embodiment, the Compound 1 Hemifumarate Form B is characterized as Compound 1 Hemifumarate Form B by at least two of (i), (ii), (iii), and (iv).

In a further embodiment, the Compound 1 Hemifumarate Form B is characterized as Compound 1 Hemifumarate Form B by at least three of (i), (ii), (iii), and (iv).

In still a further embodiment, the Compound 1 Hemifumarate Form B is characterized as Compound 1 Hemifumarate Form B by all of (i), (ii), (iii), and (iv).

In another aspect, the invention relates to a pharmaceutical composition comprising a crystalline form or a crystalline salt form described herein and a pharmaceutically acceptable excipient.

In still another aspect, the invention relates to a method of treating a disease, disorder, or syndrome mediated at least in part by modulating in vivo activity of a protein kinase, comprising administering to a subject in need thereof a crystalline form or a crystalline salt form described herein, or a pharmaceutical composition described herein.

In one embodiment of this aspect, the disease, disorder, or syndrome mediated at least in part by modulating in vivo activity of a protein kinase is cancer.

In one aspect, the invention relates to a method for inhibiting a protein kinase, the method comprising contacting the protein kinase with a crystalline form or a crystalline salt form described herein.

In one embodiment of this aspect, the protein kinase is Axl, Mer, c-Met, KDR, or a combination thereof.

In yet another aspect, the invention relates to a process of preparing Compound 1 Hemifumarate Form B comprising contacting Compound 1 with fumaric acid in an organic solvent to form a mixture, and stirring the mixture.

In one embodiment of this aspect, the organic solvent is acetone.

In another embodiment, the mixture is stirred at a temperature of about 50° C.

In another embodiment, the mixture is stirred for about 6 days.

Crystalline Forms of the Invention

Compound 1 Form A

Compound 1 Form A is the likely thermodynamically stable anhydrous/non-solvated form of Compound 1 at RT. Characterization for Compound 1 Form A is provided herein by XRPD, DSC, TGA, DVS, and hot stage microscopy.

The XRPD pattern for Compound 1 Form A is provided in FIG. 1, and a list of peaks from the pattern is provided in Table 1 below.

TABLE 1

XRPD peaks of Compound 1 Form A

| 2θ (°) | d-spacing (Å) | Intensity (%) |
|---|---|---|
| 5.48 ± 0.20 | 16.106 ± 0.587 | 7 |
| 9.93 ± 0.20 | 8.901 ± 0.179 | 4 |
| 10.83 ± 0.20 | 8.165 ± 0.150 | 22 |
| 10.98 ± 0.20 | 8.052 ± 0.146 | 31 |
| 11.36 ± 0.20 | 7.785 ± 0.137 | 85 |
| 11.79 ± 0.20 | 7.502 ± 0.127 | 30 |
| 12.04 ± 0.20 | 7.346 ± 0.122 | 33 |
| 12.25 ± 0.20 | 7.222 ± 0.118 | 4 |
| 12.62 ± 0.20 | 7.009 ± 0.111 | 17 |
| 14.33 ± 0.20 | 6.175 ± 0.086 | 29 |
| 14.67 ± 0.20 | 6.035 ± 0.082 | 18 |
| 15.33 ± 0.20 | 5.777 ± 0.075 | 20 |
| 16.02 ± 0.20 | 5.529 ± 0.069 | 5 |
| 16.51 ± 0.20 | 5.365 ± 0.065 | 13 |
| 16.77 ± 0.20 | 5.283 ± 0.063 | 9 |
| 18.07 ± 0.20 | 4.904 ± 0.054 | 25 |
| 19.09 ± 0.20 | 4.645 ± 0.048 | 29 |
| 19.34 ± 0.20 | 4.586 ± 0.047 | 16 |
| 19.60 ± 0.20 | 4.525 ± 0.046 | 3 |
| 20.00 ± 0.20 | 4.436 ± 0.044 | 62 |
| 20.46 ± 0.20 | 4.338 ± 0.042 | 8 |
| 20.85 ± 0.20 | 4.257 ± 0.040 | 8 |
| 21.45 ± 0.20 | 4.139 ± 0.038 | 12 |
| 21.55 ± 0.20 | 4.120 ± 0.038 | 17 |
| 21.76 ± 0.20 | 4.080 ± 0.037 | 10 |
| 22.16 ± 0.20 | 4.008 ± 0.036 | 9 |
| 22.35 ± 0.20 | 3.974 ± 0.035 | 13 |
| 22.58 ± 0.20 | 3.935 ± 0.034 | 25 |
| 22.87 ± 0.20 | 3.885 ± 0.034 | 3 |
| 23.79 ± 0.20 | 3.737 ± 0.031 | 4 |
| 24.11 ± 0.20 | 3.689 ± 0.030 | 14 |
| 24.29 ± 0.20 | 3.662 ± 0.030 | 14 |
| 24.35 ± 0.20 | 3.653 ± 0.030 | 14 |
| 24.87 ± 0.20 | 3.577 ± 0.028 | 100 |
| 25.42 ± 0.20 | 3.501 ± 0.027 | 6 |
| 25.81 ± 0.20 | 3.449 ± 0.026 | 5 |
| 26.09 ± 0.20 | 3.413 ± 0.026 | 2 |
| 26.72 ± 0.20 | 3.334 ± 0.024 | 3 |
| 27.04 ± 0.20 | 3.294 ± 0.024 | 5 |
| 27.44 ± 0.20 | 3.248 ± 0.023 | 5 |
| 27.77 ± 0.20 | 3.210 ± 0.023 | 3 |
| 27.98 ± 0.20 | 3.187 ± 0.022 | 7 |
| 28.19 ± 0.20 | 3.163 ± 0.022 | 42 |
| 28.56 ± 0.20 | 3.123 ± 0.021 | 16 |

The XRPD pattern for Compound 1 Form A was successfully indexed, suggesting the material consists primarily or exclusively of a single crystalline phase. The unit cell volume is consistent with anhydrous/non-solvated Compound 1.

Unit Cell Data for Compound 1 Form A:

| Bravais Type | C-Centered Monoclinic |
|---|---|
| a [Å] | 35.918 |
| b [Å] | 9.256 |
| c [Å] | 17.368 |
| α [deg] | 90 |
| β [deg] | 116.38 |
| γ [deg] | 90 |
| Volume [Å$^3$/cell] | 5,172.6 |
| Chiral Contents? | Not Specified |
| Extinction Symbol | C 1 c 1 |
| Space Group(s) | Cc (9), C2/c (15) |

Figure 2:
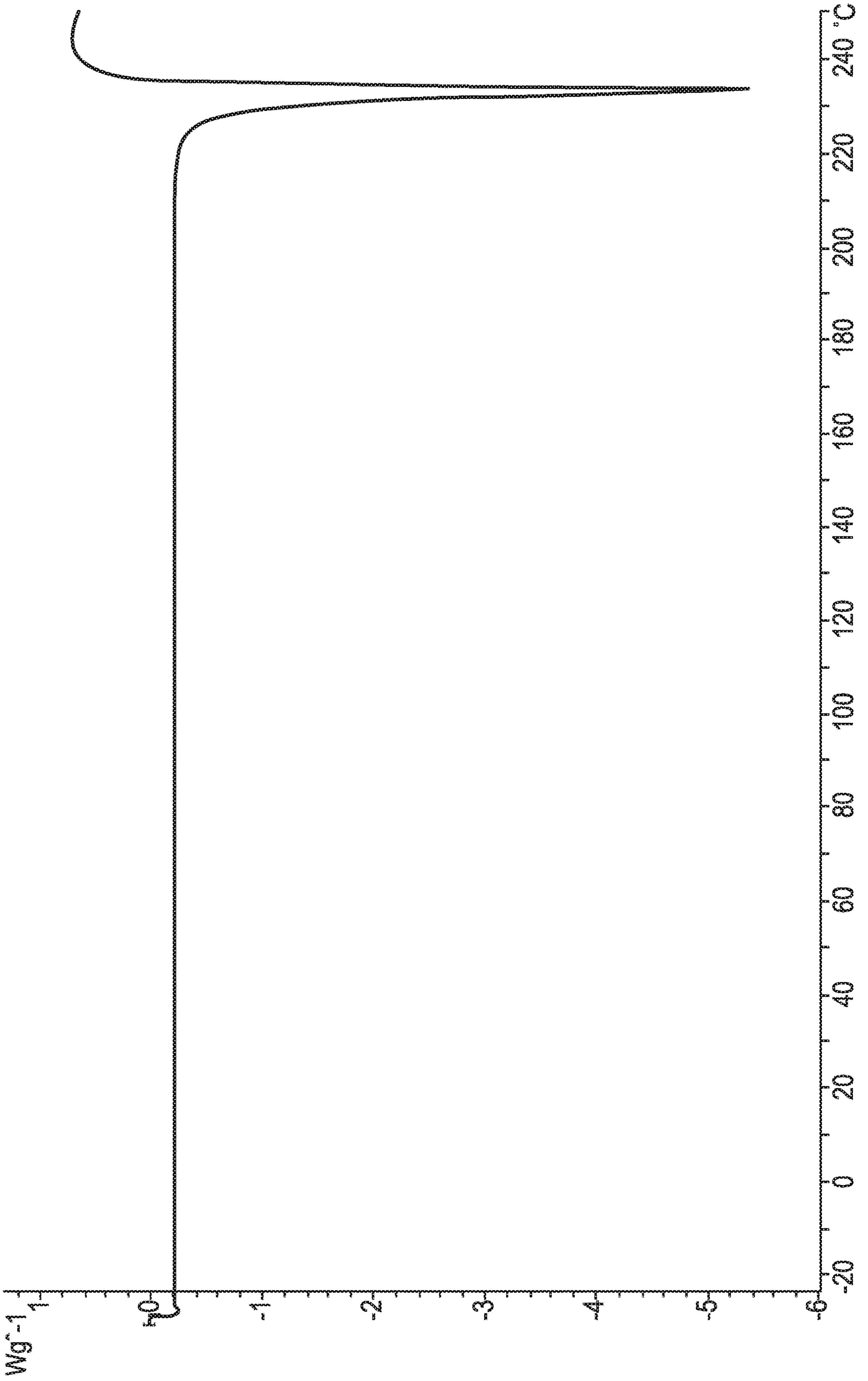
FIG. 2 is a DSC thermogram of Compound 1 Form A.
Figure 3:
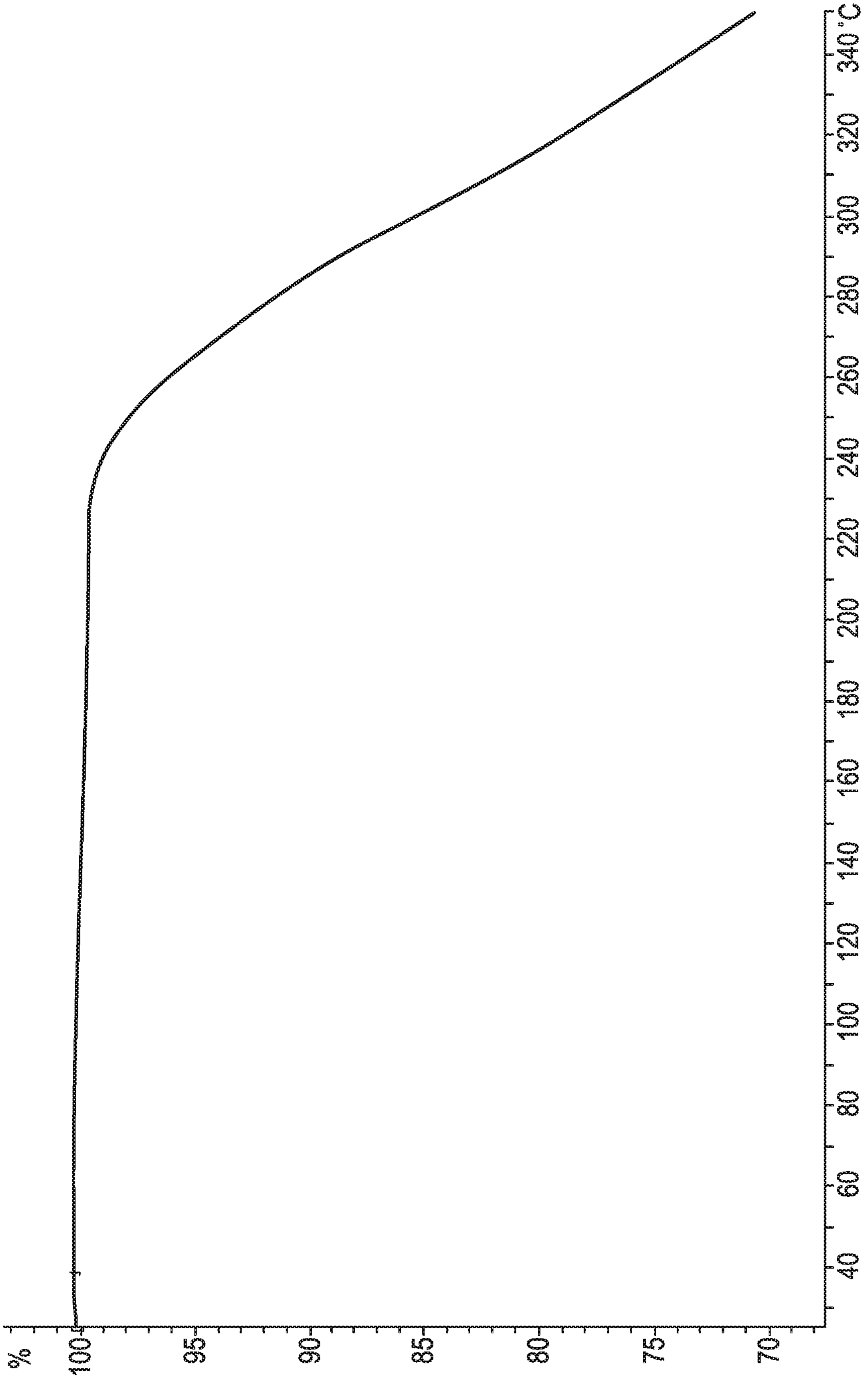
FIG. 3 is a TGA thermogram of Compound 1 Form A.

DSC and TGA thermograms for Compound 1 Form A are provided in FIGS. 2 and 3, respectively. Negligible weight loss is noted by TGA up to 220° C., consistent with an anhydrous/non-solvated material. A sharp endotherm at ~230° C. (onset) in the DSC thermogram likely corresponds with simultaneous melting and decomposition. DSC thermograms for various samples of Compound 1 Form A exhibit inconsistency in the onset temperature of the endotherm. The variability in the endotherm onset temperatures is likely due to the accompanying decomposition. Due to the interference by decomposition, these endotherm onset temperatures do not represent true melting points.

Compound 1 Form A was additionally analyzed by hot stage microscopy (FIGS. 5A-5D). The observations upon heating are consistent with the DSC and TGA data described herein. An onset of melting with accompanying decomposition was noted at ~230° C., with discoloration observed at ~231° C.

Figure 4:
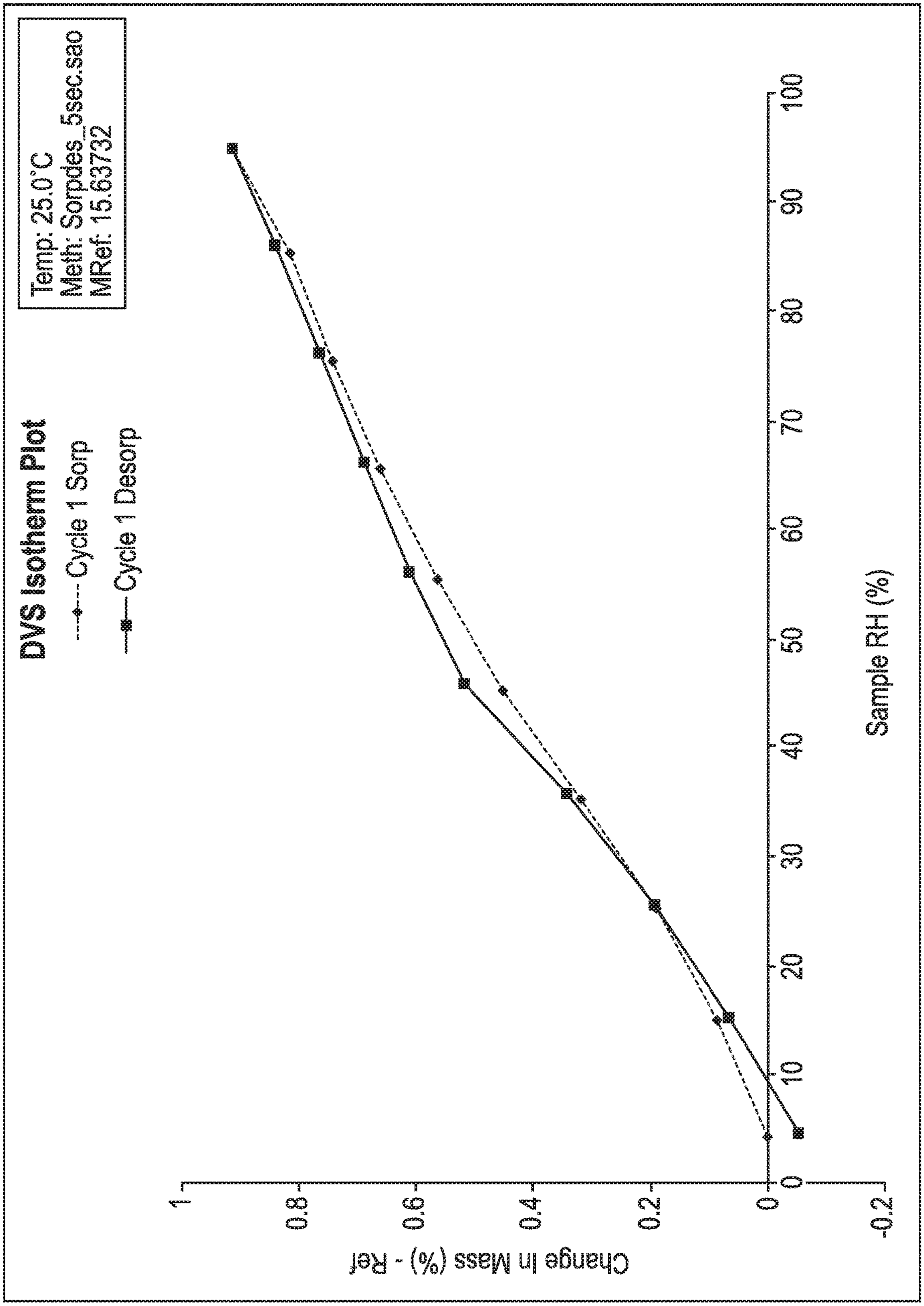
FIG. 4 is a DVS isotherm plot of Compound 1 Form A from 5% relative humidity to 95% relative humidity.
Figure 5A:
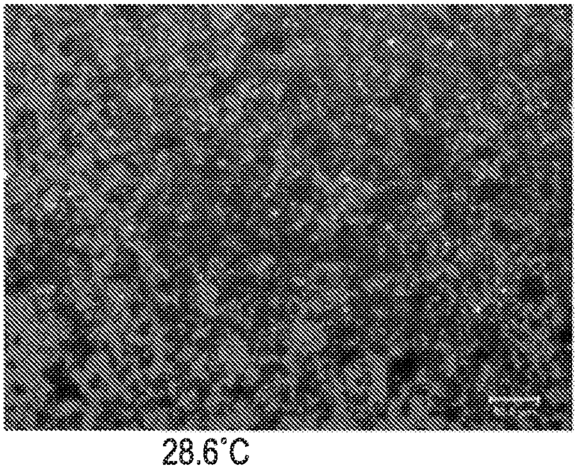
FIG. 5A-FIG. 5D are hot stage photomicrographs showing Compound 1 Form A at (A) 28.6° C. with no change in FIG. 8 is an XRPD pattern of Compound 1 Form C.
Figure 5B:
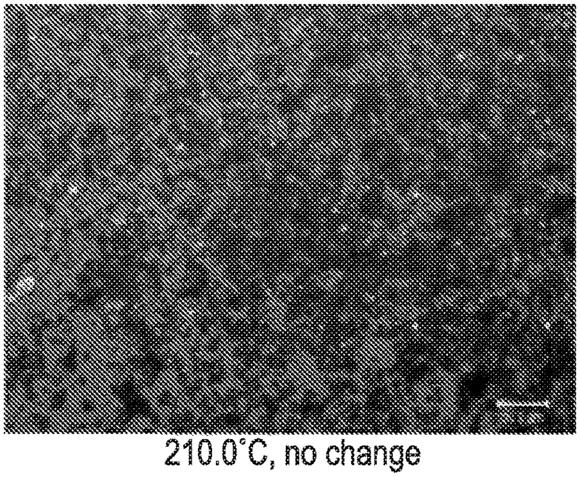
Figure 5C:
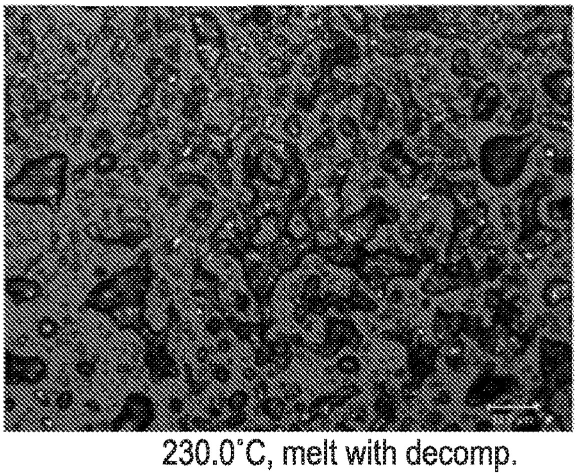
Figure 5D:
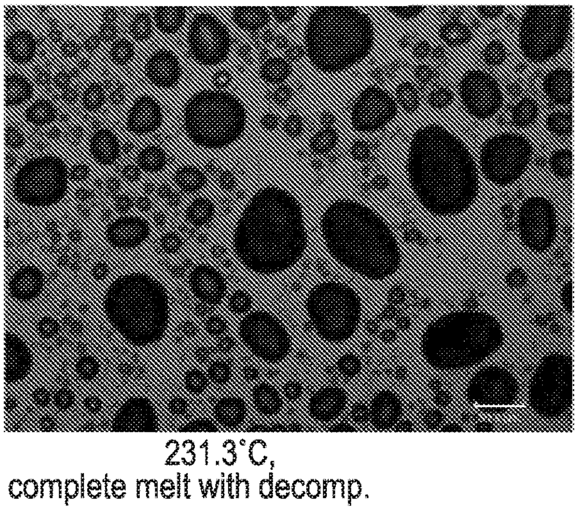

Limited hygroscopicity of Compound 1 Form A was observed by DVS (FIG. 4). The material took up ~0.91 wt % water vapor steadily between 5% and 95% RH. All of this weight was lost on desorption, with very little hysteresis noted. XRPD of the post-DVS sample indicates no change in crystalline form.

Determination of pKa and log P values for Compound 1 Form A were conducted by Pion Inc./Sirius Analytical Instruments Ltd. Accordingly, it was determined that Compound 1 Form A has a pKa of 5.43±0.4, neutral log P of 4.50±0.5, and a cationic log P of 1.79±0.8.

Compound 1 Form B

Compound 1 Form B is an acetic acid solvate that resulted from a vapor diffusion experiment in acetic acid with diethyl ether.

The XRPD pattern for Compound 1 Form B is provided in FIG. 6, and a list of peaks from the pattern is provided in Table 2 below.

TABLE 2

XRPD peaks of Compound 1 Form B

| 2θ (°) | d-spacing (Å) | Intensity (%) |
|---|---|---|
| 4.76 ± 0.20 | 18.536 ± 0.778 | 52 |
| 9.58 ± 0.20 | 9.227 ± 0.192 | 51 |
| 10.49 ± 0.20 | 8.430 ± 0.160 | 21 |
| 10.97 ± 0.20 | 8.060 ± 0.147 | 13 |
| 11.27 ± 0.20 | 7.847 ± 0.139 | 94 |
| 12.10 ± 0.20 | 7.308 ± 0.120 | 63 |
| 13.26 ± 0.20 | 6.671 ± 0.100 | 27 |
| 13.52 ± 0.20 | 6.546 ± 0.096 | 21 |
| 14.52 ± 0.20 | 6.096 ± 0.084 | 61 |
| 15.15 ± 0.20 | 5.845 ± 0.077 | 37 |
| 15.42 ± 0.20 | 5.743 ± 0.074 | 13 |

TABLE 2-continued

XRPD peaks of Compound 1 Form B

| 2θ (°) | d-spacing (Å) | Intensity (%) |
|---|---|---|
| 16.69 ± 0.20 | 5.306 ± 0.063 | 28 |
| 17.29 ± 0.20 | 5.124 ± 0.059 | 23 |
| 17.92 ± 0.20 | 4.946 ± 0.055 | 13 |
| 18.34 ± 0.20 | 4.834 ± 0.052 | 15 |
| 19.05 ± 0.20 | 4.654 ± 0.048 | 76 |
| 19.25 ± 0.20 | 4.608 ± 0.047 | 32 |
| 19.48 ± 0.20 | 4.554 ± 0.046 | 25 |
| 20.04 ± 0.20 | 4.426 ± 0.044 | 49 |
| 20.59 ± 0.20 | 4.309 ± 0.041 | 18 |
| 20.90 ± 0.20 | 4.247 ± 0.040 | 17 |
| 21.39 ± 0.20 | 4.151 ± 0.038 | 31 |
| 21.84 ± 0.20 | 4.066 ± 0.037 | 18 |
| 22.25 ± 0.20 | 3.991 ± 0.035 | 8 |
| 22.68 ± 0.20 | 3.917 ± 0.034 | 17 |
| 22.84 ± 0.20 | 3.890 ± 0.034 | 25 |
| 23.12 ± 0.20 | 3.844 ± 0.033 | 22 |
| 23.32 ± 0.20 | 3.811 ± 0.032 | 46 |
| 23.60 ± 0.20 | 3.767 ± 0.031 | 24 |
| 24.03 ± 0.20 | 3.701 ± 0.030 | 17 |
| 24.79 ± 0.20 | 3.589 ± 0.029 | 11 |
| 25.32 ± 0.20 | 3.515 ± 0.027 | 100 |
| 25.65 ± 0.20 | 3.471 ± 0.027 | 13 |
| 25.88 ± 0.20 | 3.441 ± 0.026 | 10 |
| 26.50 ± 0.20 | 3.361 ± 0.025 | 7 |
| 26.79 ± 0.20 | 3.326 ± 0.024 | 10 |
| 27.25 ± 0.20 | 3.270 ± 0.024 | 14 |
| 28.55 ± 0.20 | 3.124 ± 0.021 | 52 |
| 29.49 ± 0.20 | 3.026 ± 0.020 | 22 |

The XRPD pattern was successfully indexed, and the unit cell volume is large enough to accommodate solvated Compound 1.

Unit Cell Data for Compound 1 Form B

| Bravais Type | Primitive Monoclinic |
|---|---|
| a [Å] | 19.400 |
| b [Å] | 9.289 |
| c [Å] | 16.992 |
| α [deg] | 90 |
| β [deg] | 108.17 |
| γ [deg] | 90 |
| Volume [$Å^3$/cell] | 2,909.4 |
| Chiral Contents? | Achiral |
| Extinction Symbol | P 1 $2_1$/c 1 |
| Space Group(s) | P$2_1$/c (14) |

A proton NMR spectrum for Compound 1 Form B is consistent with the chemical structure of Compound 1 with 1 mole of acetic acid per mole of API present.

Figure 7:
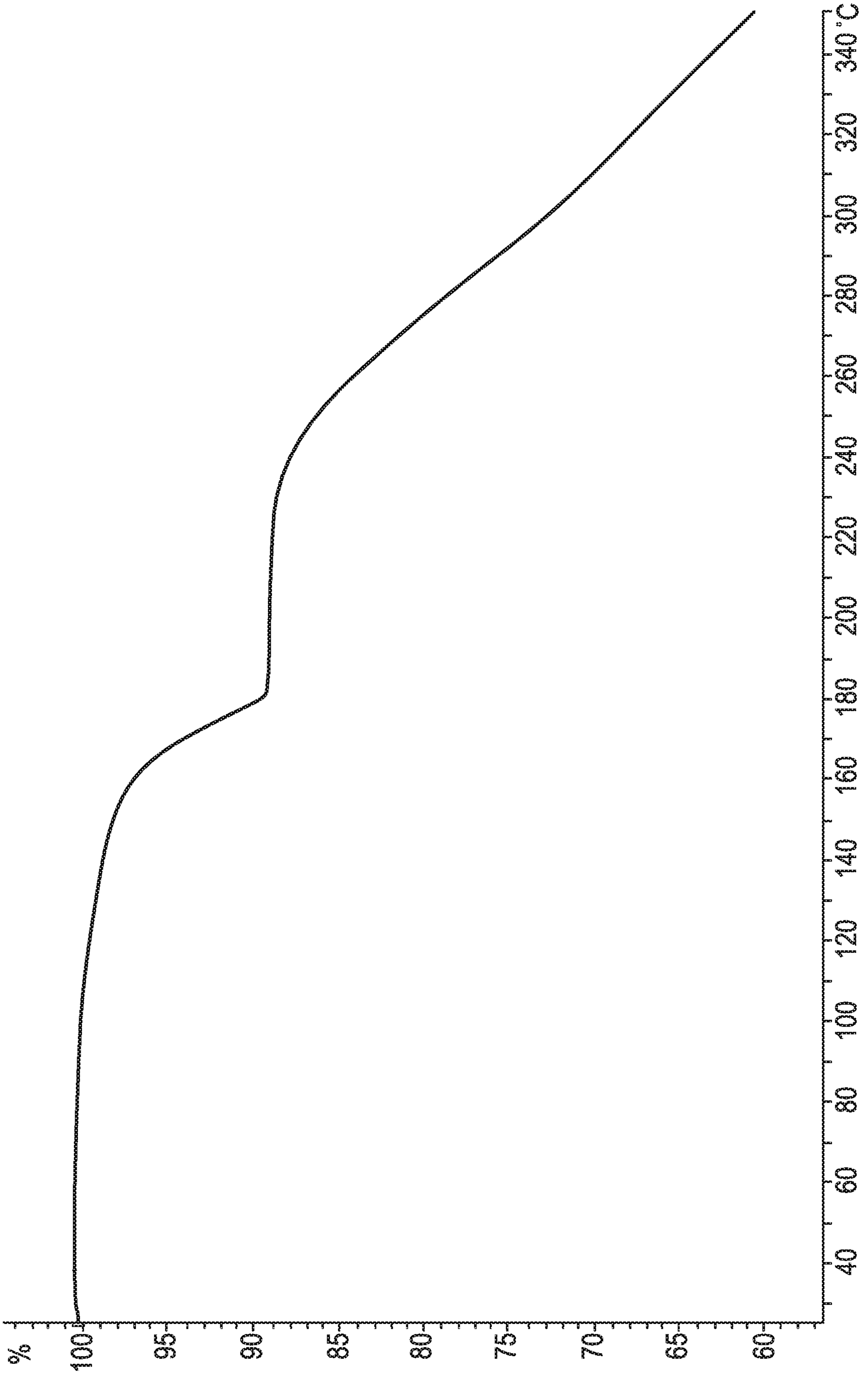

A TGA thermogram for Compound 1 Form B indicates ~11.2% weight loss between 92° C. and 188° C. (FIG. 7). Assuming the weight loss corresponds exclusively to the loss of acetic acid, it would equate to approximately 1.1 mol/mol.

Based on the TGA data, a drying experiment for Compound 1 Form B was set up by heating the material at ~200° C. for ~5 minutes. The solids were observed to turn black, indicating decomposition at those conditions.

Compound 1 Form C

Compound 1 Form C is an HFIPA solvate that resulted by anti-solvent precipitation from HFIPA with MTBE.

The XRPD pattern for Compound 1 Form C is provided in FIG. 8, and a list of peaks from the pattern is provided in Table 3 below.

TABLE 3

XRPD peaks of Compound 1 Form C

| 2θ (°) | d-spacing (Å) | Intensity (%) |
|---|---|---|
| 3.89 ± 0.20 | 22.667 ± 1.164 | 32 |
| 4.63 ± 0.20 | 19.085 ± 0.825 | 47 |
| 7.95 ± 0.20 | 11.115 ± 0.279 | 51 |
| 9.31 ± 0.20 | 9.495 ± 0.204 | 20 |
| 10.54 ± 0.20 | 8.386 ± 0.159 | 23 |
| 10.87 ± 0.20 | 8.131 ± 0.149 | 36 |
| 11.14 ± 0.20 | 7.934 ± 0.142 | 35 |
| 11.31 ± 0.20 | 7.820 ± 0.138 | 39 |
| 11.49 ± 0.20 | 7.698 ± 0.134 | 45 |
| 11.75 ± 0.20 | 7.528 ± 0.128 | 28 |
| 12.22 ± 0.20 | 7.239 ± 0.118 | 84 |
| 12.96 ± 0.20 | 6.826 ± 0.105 | 35 |
| 13.59 ± 0.20 | 6.512 ± 0.095 | 25 |
| 13.84 ± 0.20 | 6.392 ± 0.092 | 35 |
| 14.01 ± 0.20 | 6.315 ± 0.090 | 28 |
| 14.62 ± 0.20 | 6.054 ± 0.082 | 65 |
| 14.79 ± 0.20 | 5.984 ± 0.080 | 32 |
| 15.46 ± 0.20 | 5.727 ± 0.074 | 27 |
| 15.86 ± 0.20 | 5.583 ± 0.070 | 21 |
| 16.07 ± 0.20 | 5.512 ± 0.068 | 24 |
| 16.61 ± 0.20 | 5.333 ± 0.064 | 49 |
| 16.73 ± 0.20 | 5.294 ± 0.063 | 52 |
| 16.88 ± 0.20 | 5.248 ± 0.062 | 44 |
| 17.64 ± 0.20 | 5.024 ± 0.057 | 100 |
| 18.13 ± 0.20 | 4.889 ± 0.053 | 24 |
| 18.73 ± 0.20 | 4.734 ± 0.050 | 69 |
| 19.10 ± 0.20 | 4.642 ± 0.048 | 51 |
| 19.42 ± 0.20 | 4.567 ± 0.047 | 88 |
| 19.75 ± 0.20 | 4.490 ± 0.045 | 93 |
| 20.09 ± 0.20 | 4.417 ± 0.044 | 54 |
| 20.47 ± 0.20 | 4.335 ± 0.042 | 44 |
| 21.00 ± 0.20 | 4.227 ± 0.040 | 38 |
| 21.65 ± 0.20 | 4.102 ± 0.037 | 51 |
| 21.95 ± 0.20 | 4.045 ± 0.036 | 48 |
| 22.47 ± 0.20 | 3.953 ± 0.035 | 36 |
| 23.11 ± 0.20 | 3.846 ± 0.033 | 41 |
| 23.46 ± 0.20 | 3.789 ± 0.032 | 53 |
| 23.77 ± 0.20 | 3.740 ± 0.031 | 52 |
| 24.84 ± 0.20 | 3.581 ± 0.028 | 31 |
| 25.17 ± 0.20 | 3.535 ± 0.028 | 73 |
| 26.14 ± 0.20 | 3.406 ± 0.026 | 21 |
| 26.48 ± 0.20 | 3.364 ± 0.025 | 19 |
| 26.88 ± 0.20 | 3.314 ± 0.024 | 17 |
| 27.72 ± 0.20 | 3.216 ± 0.023 | 23 |
| 28.35 ± 0.20 | 3.145 ± 0.022 | 18 |
| 28.70 ± 0.20 | 3.108 ± 0.021 | 49 |
| 28.96 ± 0.20 | 3.081 ± 0.021 | 34 |

A proton NMR spectrum of Compound 1 Form C is consistent with the chemical structure of Compound 1 and indicates the presence of 0.6 mole HFIPA and 0.05 mole MTBE per mole of API.

Figure 9:
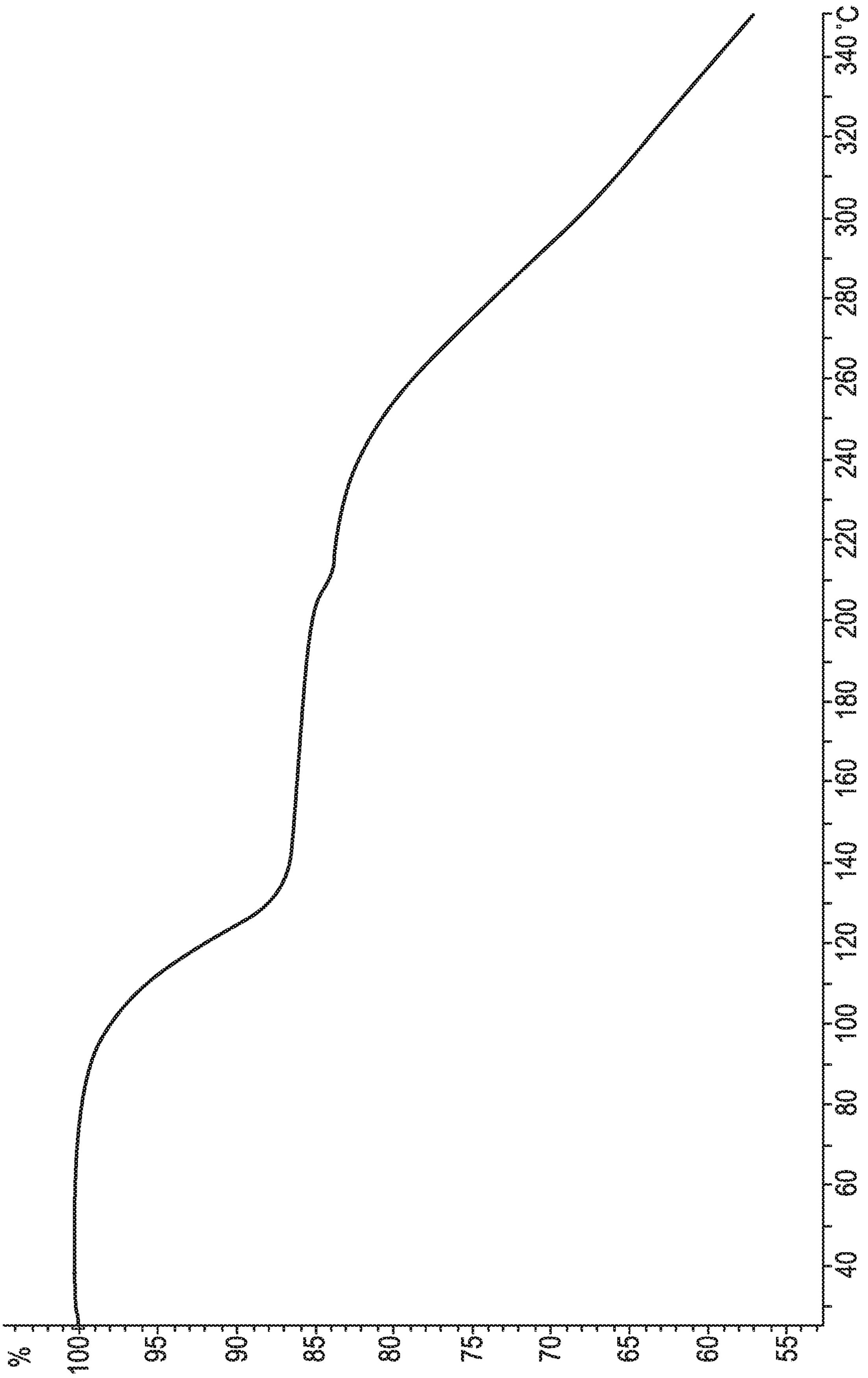
FIG. 9 is a TGA thermogram of Compound 1 Form C.

TGA analysis of Compound 1 Form C exhibits ~13.8% weight loss between 75° C. and 154° C. (FIG. 9). Assuming the weight loss corresponds with the loss of HFIPA, this is equivalent to approximately 0.5 mol/mol. An additional weight loss step of ~1.9% is noted between 190° C. and 220° C., possibly due to the start of decomposition.

Compound 1 Form D

Compound 1 Form D is a MeOH solvate that resulted from a crash cooling experiment in MeOH and as a minor component of a mixture with Compound 1 Form A from a sub-ambient slurry in MeOH.

The XRPD pattern for Compound 1 Form D is provided in FIG. 10, and a list of peaks from the pattern is provided in Table 4 below.

TABLE 4

| XRPD peaks of Compound 1 Form D | | |
|---|---|---|
| 2θ (°) | d-spacing (Å) | Intensity (%) |
| 5.08 ± 0.20 | 17.369 ± 0.683 | 4 |
| 5.43 ± 0.20 | 16.269 ± 0.599 | 5 |
| 7.00 ± 0.20 | 12.617 ± 0.360 | 10 |
| 9.62 ± 0.20 | 9.183 ± 0.190 | 7 |
| 10.21 ± 0.20 | 8.659 ± 0.169 | 100 |
| 10.90 ± 0.20 | 8.111 ± 0.148 | 4 |
| 12.31 ± 0.20 | 7.183 ± 0.116 | 7 |
| 13.66 ± 0.20 | 6.478 ± 0.094 | 5 |
| 14.06 ± 0.20 | 6.295 ± 0.089 | 10 |
| 14.70 ± 0.20 | 6.022 ± 0.082 | 2 |
| 15.35 ± 0.20 | 5.768 ± 0.075 | 19 |
| 16.06 ± 0.20 | 5.514 ± 0.068 | 2 |
| 16.39 ± 0.20 | 5.403 ± 0.065 | 4 |
| 17.89 ± 0.20 | 4.954 ± 0.055 | 5 |
| 18.17 ± 0.20 | 4.878 ± 0.053 | 10 |
| 18.35 ± 0.20 | 4.831 ± 0.052 | 23 |
| 18.53 ± 0.20 | 4.785 ± 0.051 | 9 |
| 18.80 ± 0.20 | 4.716 ± 0.050 | 5 |
| 18.96 ± 0.20 | 4.678 ± 0.049 | 4 |
| 19.15 ± 0.20 | 4.631 ± 0.048 | 3 |
| 19.50 ± 0.20 | 4.549 ± 0.046 | 5 |
| 20.09 ± 0.20 | 4.416 ± 0.044 | 4 |
| 20.37 ± 0.20 | 4.357 ± 0.042 | 5 |
| 20.58 ± 0.20 | 4.312 ± 0.041 | 9 |
| 20.93 ± 0.20 | 4.241 ± 0.040 | 30 |
| 21.31 ± 0.20 | 4.166 ± 0.039 | 22 |
| 21.79 ± 0.20 | 4.075 ± 0.037 | 10 |
| 21.97 ± 0.20 | 4.043 ± 0.036 | 11 |
| 22.30 ± 0.20 | 3.983 ± 0.035 | 8 |
| 22.91 ± 0.20 | 3.878 ± 0.033 | 7 |
| 23.12 ± 0.20 | 3.844 ± 0.033 | 6 |
| 23.26 ± 0.20 | 3.822 ± 0.032 | 6 |
| 23.62 ± 0.20 | 3.763 ± 0.031 | 13 |
| 23.93 ± 0.20 | 3.716 ± 0.031 | 3 |
| 24.37 ± 0.20 | 3.649 ± 0.029 | 18 |
| 24.77 ± 0.20 | 3.592 ± 0.029 | 6 |
| 24.99 ± 0.20 | 3.560 ± 0.028 | 15 |
| 25.39 ± 0.20 | 3.506 ± 0.027 | 14 |
| 25.96 ± 0.20 | 3.430 ± 0.026 | 10 |
| 26.62 ± 0.20 | 3.346 ± 0.025 | 9 |
| 27.10 ± 0.20 | 3.287 ± 0.024 | 8 |
| 27.53 ± 0.20 | 3.238 ± 0.023 | 5 |
| 28.05 ± 0.20 | 3.178 ± 0.022 | 10 |
| 28.38 ± 0.20 | 3.143 ± 0.022 | 9 |
| 28.78 ± 0.20 | 3.100 ± 0.021 | 6 |
| 29.09 ± 0.20 | 3.068 ± 0.021 | 4 |
| 29.38 ± 0.20 | 3.038 ± 0.020 | 3 |
| 29.64 ± 0.20 | 3.011 ± 0.020 | 4 |

The XRPD pattern was successfully indexed, and the unit cell volume can PU-QT, accommodate solvated Compound 1 with up to 3 moles of MeOH.

Unit Cell Data for Compound 1 Form D

| Bravais Type | Primitive Monoclinic |
|---|---|
| a [Å] | 5.034 |
| b [Å] | 18.352 |
| c [Å] | 34.622 |
| α [deg] | 90 |
| β [deg] | 92.14 |
| γ [deg] | 90 |
| Volume [$Å^3$/cell] | 3,196.3 |
| Chiral Contents? | Achiral |
| Extinction Symbol | P 1 $2_1$/n 1 |
| Space Group(s) | $P2_1$/n (14) |

A proton NMR spectrum for Compound 1 Form D is consistent with the chemical structure of Compound 1 with 2 moles of MeOH present per mole of API.

Figure 11:
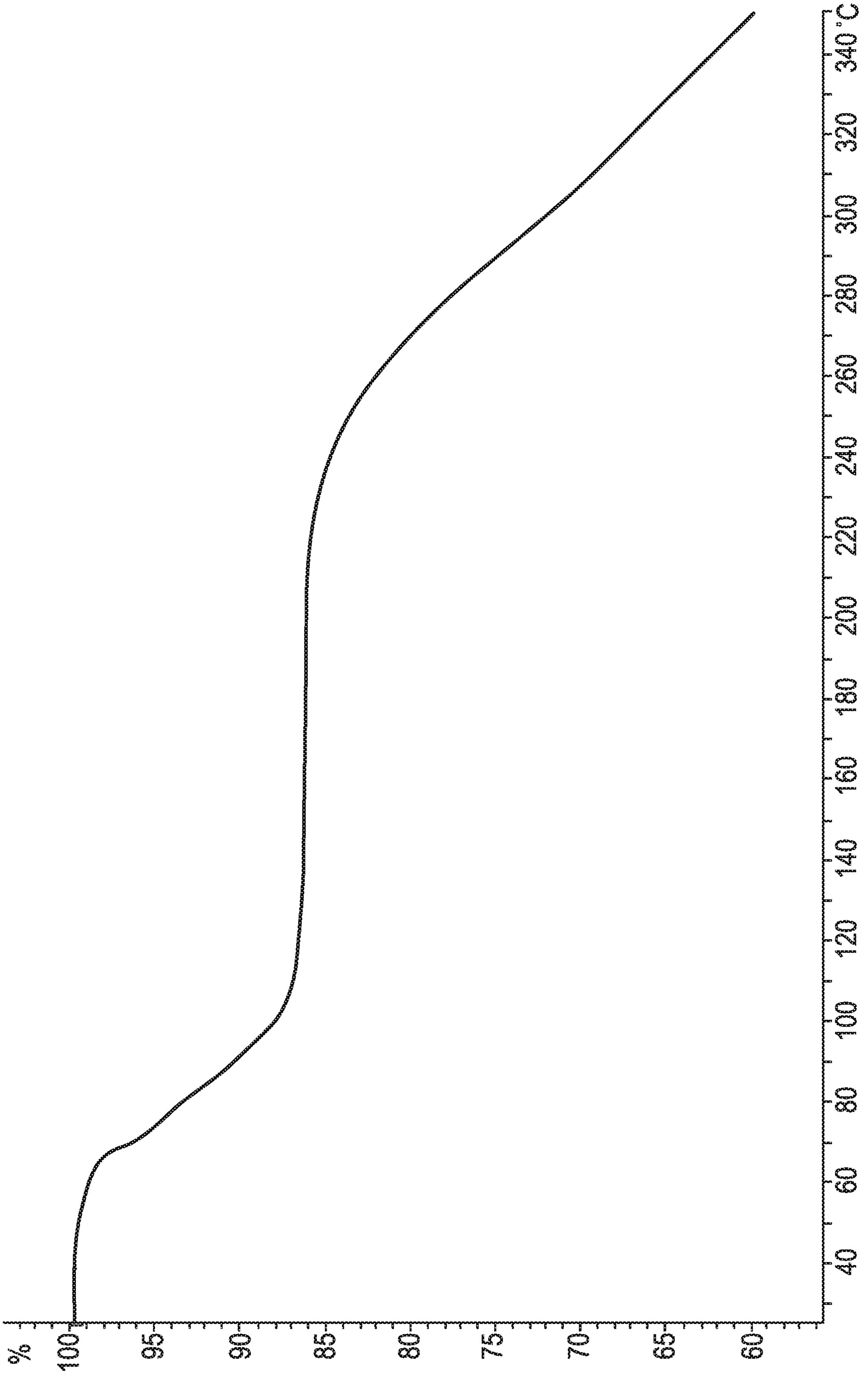
FIG. 11 is a TGA thermogram of Compound 1 Form D.

TGA analysis of Compound 1 Form D indicates that the material readily desolvates upon heating, losing ~13.5 wt % between 38° C. and 130° C. (FIG. 11). This weight loss would be equivalent to ~2.6 moles of MeOH, a larger amount than the 2 moles detected by proton NMR. Therefore, the weight loss by TGA may be attributed to the loss of MeOH and an additional volatile such as water.

Compound 1 Form D was dried under vacuum at ~80-81° C. for 1 day, resulting in conversion to amorphous material with a few small peaks by XRPD.

Compound 1 Form E

Compound 1 Form E is a THF solvate that resulted from a crash cooling experiment in THF and from a crash precipitation experiment from THF/water with heptane. To be noted, the solids collected from the crash cooling experiment were white, while nearly all other Compound 1 forms exhibited a color such as tan, brown, or rust.

The XRPD pattern for Compound 1 Form E is provided in FIG. 12, and a list of peaks from the pattern is provided in Table 5 below.

TABLE 5

| XRPD peaks of Compound 1 Form E | | |
|---|---|---|
| 2θ (°) | d-spacing (Å) | Intensity (%) |
| 5.16 ± 0.20 | 17.123 ± 0.664 | 9 |
| 6.13 ± 0.20 | 14.403 ± 0.469 | 12 |
| 9.77 ± 0.20 | 9.043 ± 0.185 | 7 |
| 10.37 ± 0.20 | 8.520 ± 0.164 | 6 |
| 10.82 ± 0.20 | 8.172 ± 0.151 | 17 |
| 11.69 ± 0.20 | 7.564 ± 0.129 | 5 |
| 13.73 ± 0.20 | 6.443 ± 0.093 | 5 |
| 14.34 ± 0.20 | 6.173 ± 0.086 | 4 |
| 14.79 ± 0.20 | 5.986 ± 0.081 | 5 |
| 15.47 ± 0.20 | 5.725 ± 0.074 | 8 |
| 15.79 ± 0.20 | 5.607 ± 0.071 | 6 |
| 16.33 ± 0.20 | 5.423 ± 0.066 | 8 |
| 16.64 ± 0.20 | 5.322 ± 0.064 | 13 |
| 16.82 ± 0.20 | 5.265 ± 0.062 | 18 |
| 17.60 ± 0.20 | 5.034 ± 0.057 | 5 |
| 17.89 ± 0.20 | 4.955 ± 0.055 | 8 |
| 18.16 ± 0.20 | 4.882 ± 0.053 | 7 |
| 18.72 ± 0.20 | 4.736 ± 0.050 | 37 |
| 19.09 ± 0.20 | 4.645 ± 0.048 | 13 |
| 19.59 ± 0.20 | 4.529 ± 0.046 | 5 |
| 20.65 ± 0.20 | 4.298 ± 0.041 | 6 |
| 21.73 ± 0.20 | 4.087 ± 0.037 | 100 |
| 22.10 ± 0.20 | 4.019 ± 0.036 | 14 |
| 22.72 ± 0.20 | 3.910 ± 0.034 | 7 |
| 23.23 ± 0.20 | 3.825 ± 0.032 | 5 |
| 23.54 ± 0.20 | 3.777 ± 0.032 | 6 |
| 23.79 ± 0.20 | 3.737 ± 0.031 | 6 |
| 24.78 ± 0.20 | 3.591 ± 0.029 | 5 |
| 25.13 ± 0.20 | 3.541 ± 0.028 | 4 |
| 26.37 ± 0.20 | 3.377 ± 0.025 | 3 |
| 26.91 ± 0.20 | 3.310 ± 0.024 | 4 |
| 29.12 ± 0.20 | 3.064 ± 0.021 | 6 |
| 29.95 ± 0.20 | 2.981 ± 0.019 | 9 |

The proton NMR spectrum is consistent with the chemical structure of Compound 1 with 0.7 mole of THF present per mole of API.

Figure 13:
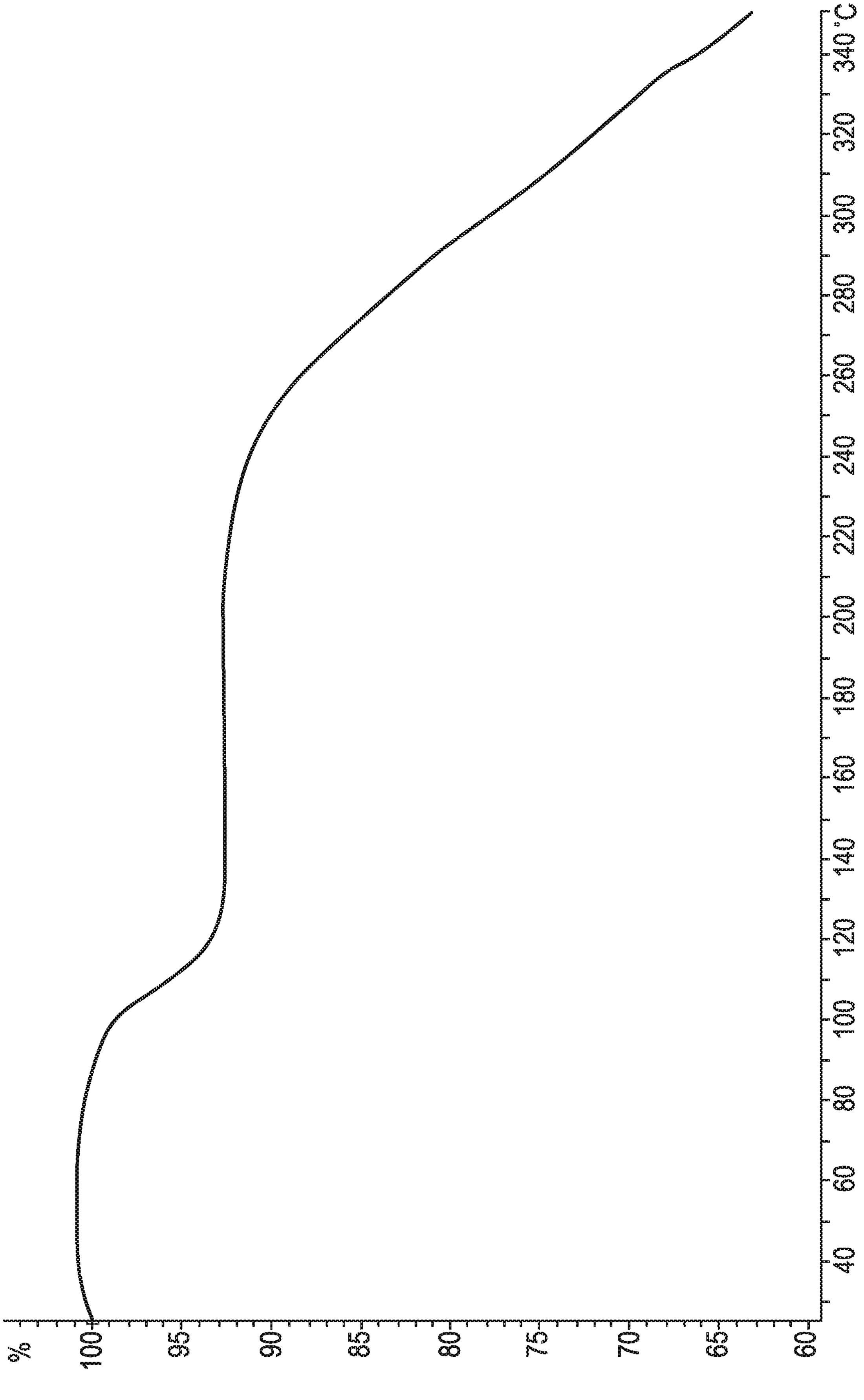
FIG. 13 is a TGA thermogram of Compound 1 Form E.

The TGA thermogram exhibits ~8.2% weight loss between 60 and 130° C. (FIG. 13). If THF is assumed to be the only volatile, this weight loss corresponds with ~0.7 mol/mol, consistent with the proton NMR spectrum.

Based on this data, Compound 1 Form E was dried under vacuum at ~77° C. for 1 day, resulting in conversion to a new disordered material, designated as Compound 1 Form M.

Compound 1 Form F

Compound 1 Form F is a chloroform solvate (~0.7 mole chloroform) that resulted by slow evaporation from chloroform and from a RT slurry in chloroform (mixture with Compound 1 Form L).

The XRPD pattern for Compound 1 Form F is provided in FIG. 14, and a list of peaks from the pattern is provided in Table 6 below.

TABLE 6

XRPD peaks of Compound 1 Form F

| 2θ (°) | d-spacing (Å) | Intensity (%) |
|---|---|---|
| 5.85 ± 0.20 | 15.090 ± 0.515 | 57 |
| 7.44 ± 0.20 | 11.876 ± 0.319 | 22 |
| 8.56 ± 0.20 | 10.326 ± 0.241 | 21 |
| 10.95 ± 0.20 | 8.071 ± 0.147 | 45 |
| 11.75 ± 0.20 | 7.524 ± 0.128 | 20 |
| 12.28 ± 0.20 | 7.202 ± 0.117 | 16 |
| 13.65 ± 0.20 | 6.480 ± 0.094 | 36 |
| 14.48 ± 0.20 | 6.112 ± 0.084 | 21 |
| 14.94 ± 0.20 | 5.924 ± 0.079 | 17 |
| 15.61 ± 0.20 | 5.673 ± 0.072 | 40 |
| 16.27 ± 0.20 | 5.443 ± 0.066 | 21 |
| 16.68 ± 0.20 | 5.310 ± 0.063 | 72 |
| 17.84 ± 0.20 | 4.968 ± 0.055 | 61 |
| 18.39 ± 0.20 | 4.820 ± 0.052 | 39 |
| 19.25 ± 0.20 | 4.606 ± 0.047 | 45 |
| 19.52 ± 0.20 | 4.544 ± 0.046 | 19 |
| 20.30 ± 0.20 | 4.371 ± 0.043 | 31 |
| 21.62 ± 0.20 | 4.106 ± 0.038 | 24 |
| 22.07 ± 0.20 | 4.024 ± 0.036 | 72 |
| 22.83 ± 0.20 | 3.892 ± 0.034 | 46 |
| 23.58 ± 0.20 | 3.770 ± 0.032 | 100 |
| 24.33 ± 0.20 | 3.655 ± 0.030 | 16 |
| 25.93 ± 0.20 | 3.434 ± 0.026 | 31 |
| 26.20 ± 0.20 | 3.399 ± 0.025 | 14 |
| 26.48 ± 0.20 | 3.364 ± 0.025 | 15 |
| 27.79 ± 0.20 | 3.208 ± 0.023 | 81 |

The proton NMR spectrum for Compound 1 Form F is consistent with the chemical structure of Compound 1 with 0.7 mole chloroform per mole of API present.

Figure 15:
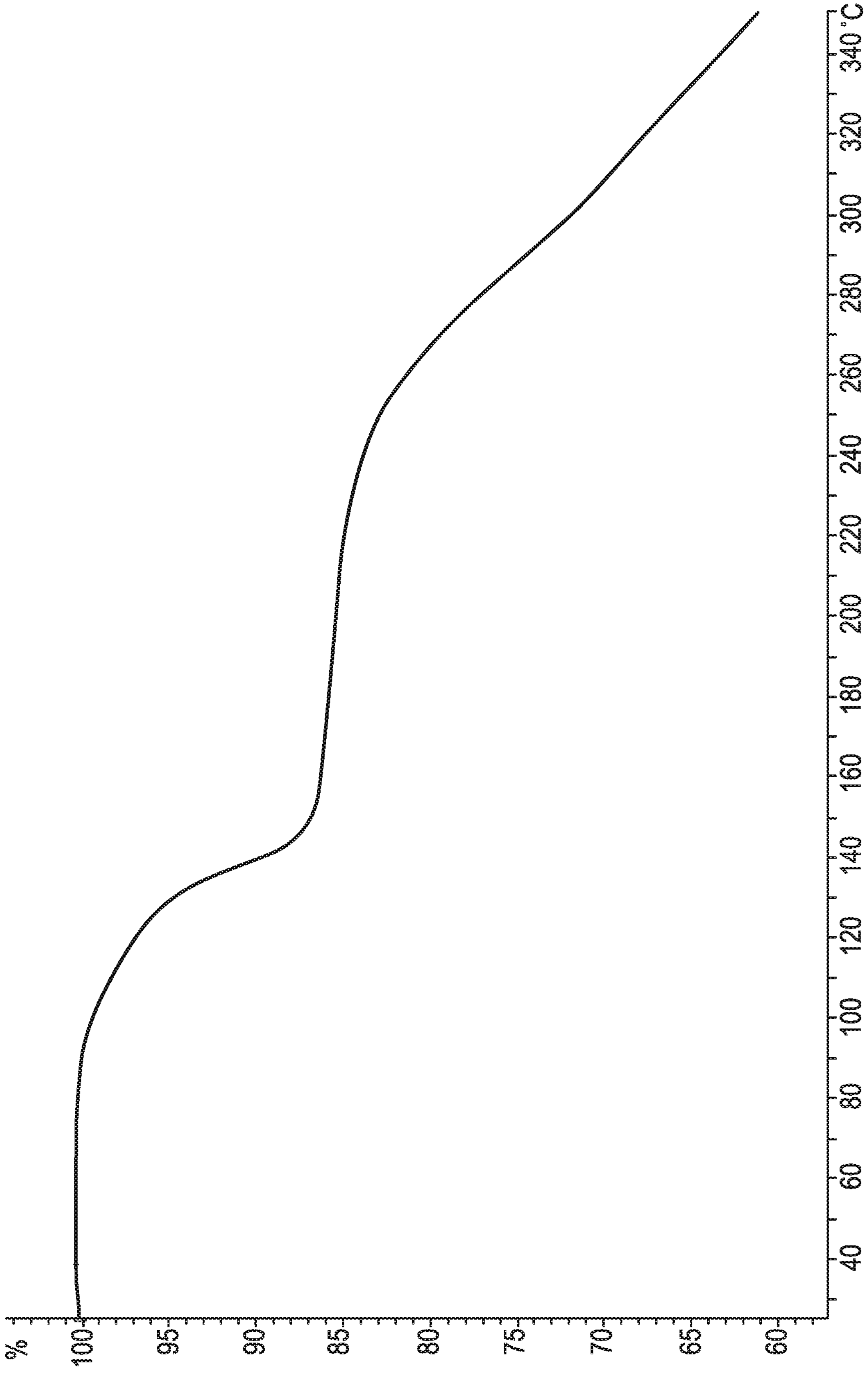
FIG. 15 is a TGA thermogram of Compound 1 Form F.

The TGA thermogram for Compound 1 Form F exhibits ~14.4% weight loss between 77° C. and 178° C., equivalent to the loss of 0.7 mol/mol chloroform if that is the only volatile (FIG. 15).

Based on the TGA data, a drying experiment was set up in which Compound 1 Form F was heated at −175° C. for ~13 minutes. The material fully converted to a new material, designated as Compound 1 Form K. To be noted, discoloration to yellow and brown was observed during the heating experiment.

Compound 1 Form G

Similar to Compound 1 Form F, Compound 1 Form G is also a chloroform solvate (~1 mole chloroform) that resulted by precipitation from chloroform at sub-ambient temperature.

The XRPD pattern for Compound 1 Form G is provided in FIG. 16, and a list of peaks from the pattern is provided in Table 7 below.

TABLE 7

XRPD peaks of Compound 1 Form G

| 2θ (°) | d-spacing (Å) | Intensity (%) |
|---|---|---|
| 4.72 ± 0.20 | 18.724 ± 0.794 | 37 |
| 6.71 ± 0.20 | 13.153 ± 0.391 | 17 |
| 9.47 ± 0.20 | 9.330 ± 0.197 | 11 |
| 11.51 ± 0.20 | 7.684 ± 0.133 | 42 |
| 11.84 ± 0.20 | 7.468 ± 0.126 | 14 |
| 13.04 ± 0.20 | 6.782 ± 0.104 | 8 |
| 14.40 ± 0.20 | 6.148 ± 0.085 | 9 |
| 15.12 ± 0.20 | 5.853 ± 0.077 | 9 |
| 16.03 ± 0.20 | 5.526 ± 0.069 | 19 |

TABLE 7-continued

XRPD peaks of Compound 1 Form G

| 2θ (°) | d-spacing (Å) | Intensity (%) |
|---|---|---|
| 16.28 ± 0.20 | 5.439 ± 0.066 | 31 |
| 16.51 ± 0.20 | 5.365 ± 0.065 | 27 |
| 17.04 ± 0.20 | 5.199 ± 0.061 | 32 |
| 17.85 ± 0.20 | 4.966 ± 0.055 | 31 |
| 18.04 ± 0.20 | 4.914 ± 0.054 | 38 |
| 18.73 ± 0.20 | 4.733 ± 0.050 | 15 |
| 19.29 ± 0.20 | 4.598 ± 0.047 | 25 |
| 19.49 ± 0.20 | 4.551 ± 0.046 | 26 |
| 19.73 ± 0.20 | 4.495 ± 0.045 | 38 |
| 20.72 ± 0.20 | 4.284 ± 0.041 | 55 |
| 21.10 ± 0.20 | 4.207 ± 0.039 | 15 |
| 22.61 ± 0.20 | 3.930 ± 0.034 | 100 |
| 23.16 ± 0.20 | 3.838 ± 0.033 | 20 |
| 24.10 ± 0.20 | 3.689 ± 0.030 | 19 |
| 25.49 ± 0.20 | 3.492 ± 0.027 | 13 |
| 26.47 ± 0.20 | 3.365 ± 0.025 | 48 |
| 27.25 ± 0.20 | 3.270 ± 0.024 | 18 |
| 27.84 ± 0.20 | 3.202 ± 0.023 | 12 |

The proton NMR spectrum for Compound 1 Form G is consistent with the chemical structure of Compound 1 with 0.9 mol/mol chloroform present.

Figure 17:
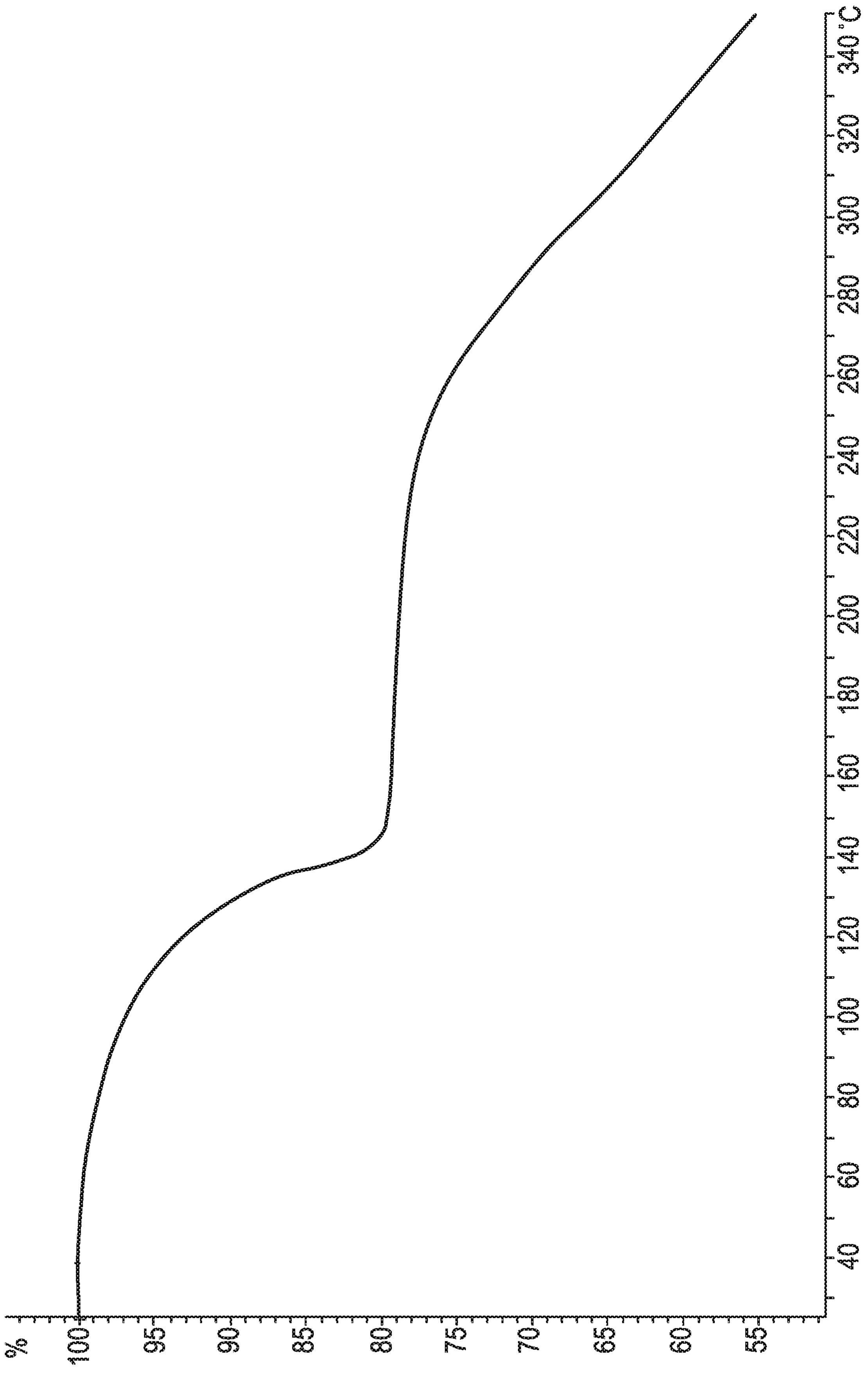
FIG. 17 is a TGA thermogram of Compound 1 Form G.

The TGA thermogram for Compound 1 Form G, shown in FIG. 17, exhibits ~20.8% weight loss between 40° C. and 165° C. Assuming chloroform is the only volatile, this is equivalent to ~1.2 mole, slightly higher than the 0.9 mole detected by proton NMR. This may indicate a small amount of an additional volatile such as water or partial drying of the material prior to NMR analysis. To be noted, the TGA weight loss for Compound 1 Form G begins at a lower temperature than that for Compound 1 Form F (40° C. versus 77° C.), indicating that partial drying at ambient conditions could be possible.

The sample of Compound 1 Form G was heated at −175° C. for ~10 minutes, similar to the drying conditions for Compound 1 Form F. This experiment resulted in conversion to the same form, Compound 1 Form K.

Compound 1 Form H

Compound 1 Form H is a likely DCM solvate that resulted by vapor stressing amorphous Compound 1 with DCM.

The XRPD pattern for Compound 1 Form H is provided in FIG. 18, and a list of peaks from the pattern is provided in Table 8 below.

TABLE 8

XRPD peaks of Compound 1 Form H

| 2θ (°) | d-spacing (Å) | Intensity (%) |
|---|---|---|
| 6.30 ± 0.20 | 14.027 ± 0.445 | 23 |
| 10.79 ± 0.20 | 8.196 ± 0.152 | 44 |
| 11.42 ± 0.20 | 7.743 ± 0.135 | 37 |
| 11.73 ± 0.20 | 7.536 ± 0.128 | 15 |
| 12.63 ± 0.20 | 7.005 ± 0.110 | 19 |
| 14.01 ± 0.20 | 6.316 ± 0.090 | 18 |
| 14.29 ± 0.20 | 6.193 ± 0.086 | 11 |
| 14.67 ± 0.20 | 6.034 ± 0.082 | 14 |
| 15.74 ± 0.20 | 5.625 ± 0.071 | 20 |
| 16.41 ± 0.20 | 5.396 ± 0.065 | 22 |
| 17.23 ± 0.20 | 5.143 ± 0.059 | 23 |
| 17.52 ± 0.20 | 5.057 ± 0.057 | 34 |
| 18.01 ± 0.20 | 4.921 ± 0.054 | 49 |
| 18.31 ± 0.20 | 4.841 ± 0.052 | 20 |
| 18.56 ± 0.20 | 4.777 ± 0.051 | 22 |
| 19.04 ± 0.20 | 4.658 ± 0.048 | 100 |
| 19.67 ± 0.20 | 4.510 ± 0.045 | 71 |
| 19.80 ± 0.20 | 4.480 ± 0.045 | 85 |

TABLE 8-continued

| XRPD peaks of Compound 1 Form H | | |
|---|---|---|
| 2θ (°) | d-spacing (Å) | Intensity (%) |
| 20.32 ± 0.20 | 4.367 ± 0.043 | 26 |
| 20.72 ± 0.20 | 4.283 ± 0.041 | 34 |
| 21.53 ± 0.20 | 4.123 ± 0.038 | 27 |
| 21.69 ± 0.20 | 4.095 ± 0.037 | 41 |
| 21.95 ± 0.20 | 4.047 ± 0.036 | 52 |
| 22.47 ± 0.20 | 3.954 ± 0.035 | 30 |
| 23.14 ± 0.20 | 3.841 ± 0.033 | 64 |
| 23.53 ± 0.20 | 3.777 ± 0.032 | 96 |
| 24.33 ± 0.20 | 3.656 ± 0.030 | 53 |
| 24.84 ± 0.20 | 3.581 ± 0.028 | 25 |
| 25.13 ± 0.20 | 3.541 ± 0.028 | 48 |
| 25.38 ± 0.20 | 3.506 ± 0.027 | 68 |
| 25.69 ± 0.20 | 3.464 ± 0.027 | 24 |
| 26.75 ± 0.20 | 3.330 ± 0.024 | 22 |
| 27.48 ± 0.20 | 3.243 ± 0.023 | 65 |
| 28.19 ± 0.20 | 3.163 ± 0.022 | 34 |
| 28.70 ± 0.20 | 3.108 ± 0.021 | 33 |
| 29.09 ± 0.20 | 3.068 ± 0.021 | 23 |
| 29.60 ± 0.20 | 3.015 ± 0.020 | 36 |

The XRPD pattern was successfully indexed, and the unit cell volume can accommodate Compound 1 with up to 1 mole of DCM.

Unit Cell Data for Compound 1 Form H

| Bravais Type | Primitive Monoclinic |
|---|---|
| a [Å] | 5.718 |
| b [Å] | 32.737 |
| c [Å] | 15.491 |
| α [deg] | 90 |
| β [deg] | 91.46 |
| γ [deg] | 90 |
| Volume [$Å^3$/cell] | 2,898.8 |
| Chiral Contents? | Achiral |
| Extinction Symbol | P 1 $2_1$/c 1 |
| Space Group(s) | $P2_1$/c (14) |

The sample was initially analyzed by XRPD while damp with solvent. The solids were air dried at ambient conditions for ~2 hours to remove the residual solvent that would interfere with characterization; however, the material partially desolvated, converting to disordered material with peaks similar to a mixture of Compound 1 Form H and Compound 1 Form A. Therefore, Compound 1 Form H exhibits poor physical stability at ambient conditions and was not further characterized.

Compound 1 Form K

Compound 1 Form K consists of anhydrous/non-solvated Compound 1 and resulted by drying two different chloroform solvates, Compound 1 Forms F and G, at ~175° C.

The XRPD pattern for Compound 1 Form K is provided in FIG. 19, and a list of peaks from the pattern is provided in Table 9 below.

TABLE 9

| XRPD peaks of Compound 1 Form K | | |
|---|---|---|
| 2θ (°) | d-spacing (Å) | Intensity (%) |
| 5.73 ± 0.20 | 15.398 ± 0.537 | 35 |
| 6.39 ± 0.20 | 13.811 ± 0.431 | 32 |
| 8.10 ± 0.20 | 10.912 ± 0.269 | 38 |
| 11.53 ± 0.20 | 7.668 ± 0.133 | 100 |
| 11.78 ± 0.20 | 7.506 ± 0.127 | 31 |

TABLE 9-continued

| XRPD peaks of Compound 1 Form K | | |
|---|---|---|
| 2θ (°) | d-spacing (Å) | Intensity (%) |
| 12.83 ± 0.20 | 6.896 ± 0.107 | 28 |
| 14.36 ± 0.20 | 6.164 ± 0.085 | 50 |
| 15.56 ± 0.20 | 5.689 ± 0.073 | 53 |
| 16.25 ± 0.20 | 5.449 ± 0.067 | 38 |
| 17.42 ± 0.20 | 5.086 ± 0.058 | 82 |
| 18.17 ± 0.20 | 4.878 ± 0.053 | 36 |
| 19.07 ± 0.20 | 4.649 ± 0.048 | 28 |
| 19.70 ± 0.20 | 4.502 ± 0.045 | 71 |
| 19.89 ± 0.20 | 4.460 ± 0.044 | 95 |
| 20.53 ± 0.20 | 4.322 ± 0.042 | 66 |
| 21.11 ± 0.20 | 4.205 ± 0.039 | 32 |
| 21.55 ± 0.20 | 4.121 ± 0.038 | 34 |
| 22.34 ± 0.20 | 3.977 ± 0.035 | 24 |
| 22.50 ± 0.20 | 3.948 ± 0.035 | 24 |
| 23.24 ± 0.20 | 3.825 ± 0.032 | 42 |
| 23.76 ± 0.20 | 3.742 ± 0.031 | 24 |
| 24.50 ± 0.20 | 3.630 ± 0.029 | 42 |
| 25.94 ± 0.20 | 3.432 ± 0.026 | 37 |
| 26.42 ± 0.20 | 3.371 ± 0.025 | 43 |
| 27.76 ± 0.20 | 3.211 ± 0.023 | 29 |
| 28.28 ± 0.20 | 3.153 ± 0.022 | 34 |

The proton NMR spectrum for Compound 1 Form K, is consistent with the chemical structure of Compound 1 and shows no signs of decomposition (negligible chloroform is detected).

Figure 20:
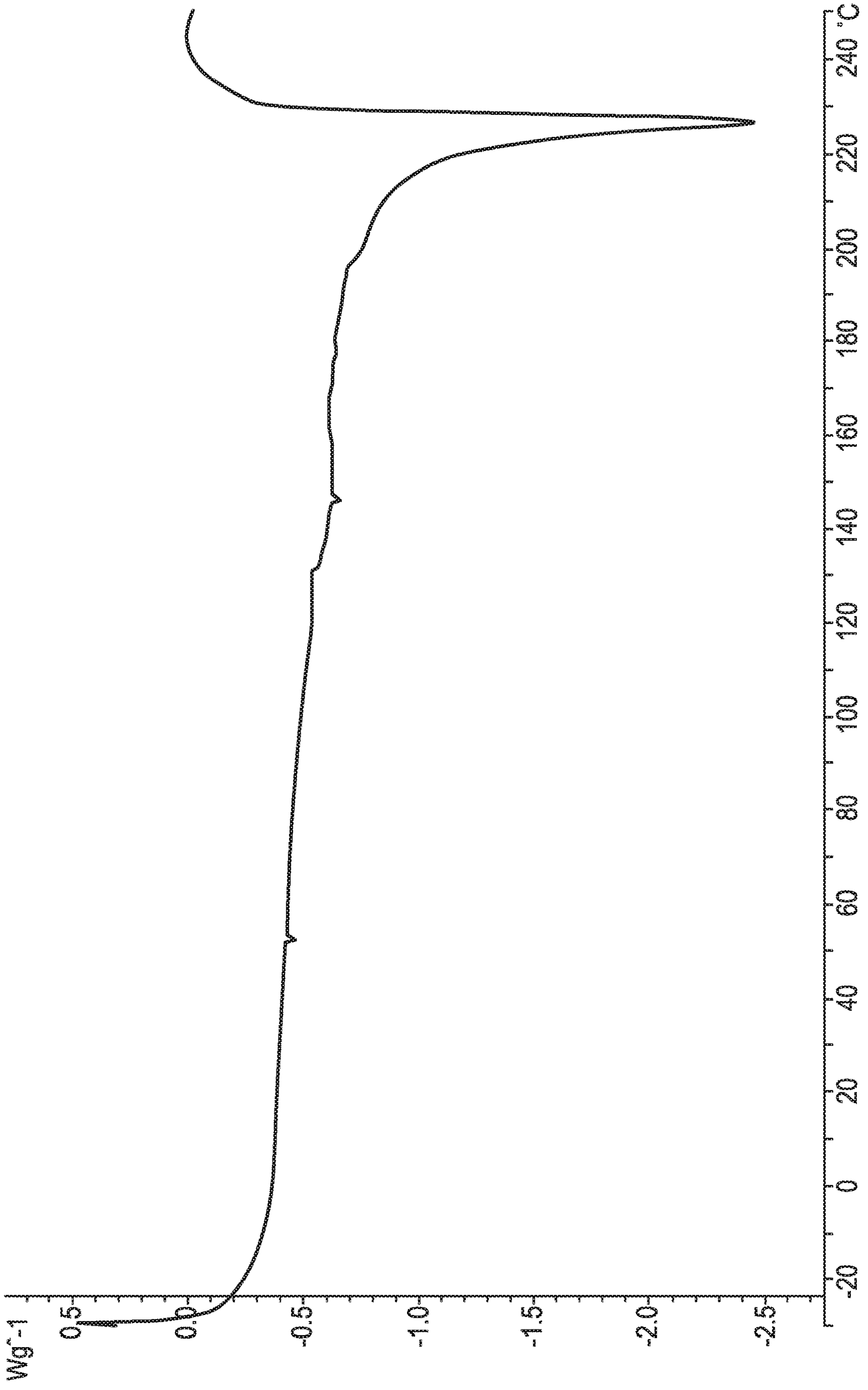
FIG. 20 is a DSC thermogram of Compound 1 Form K.
Figure 21:
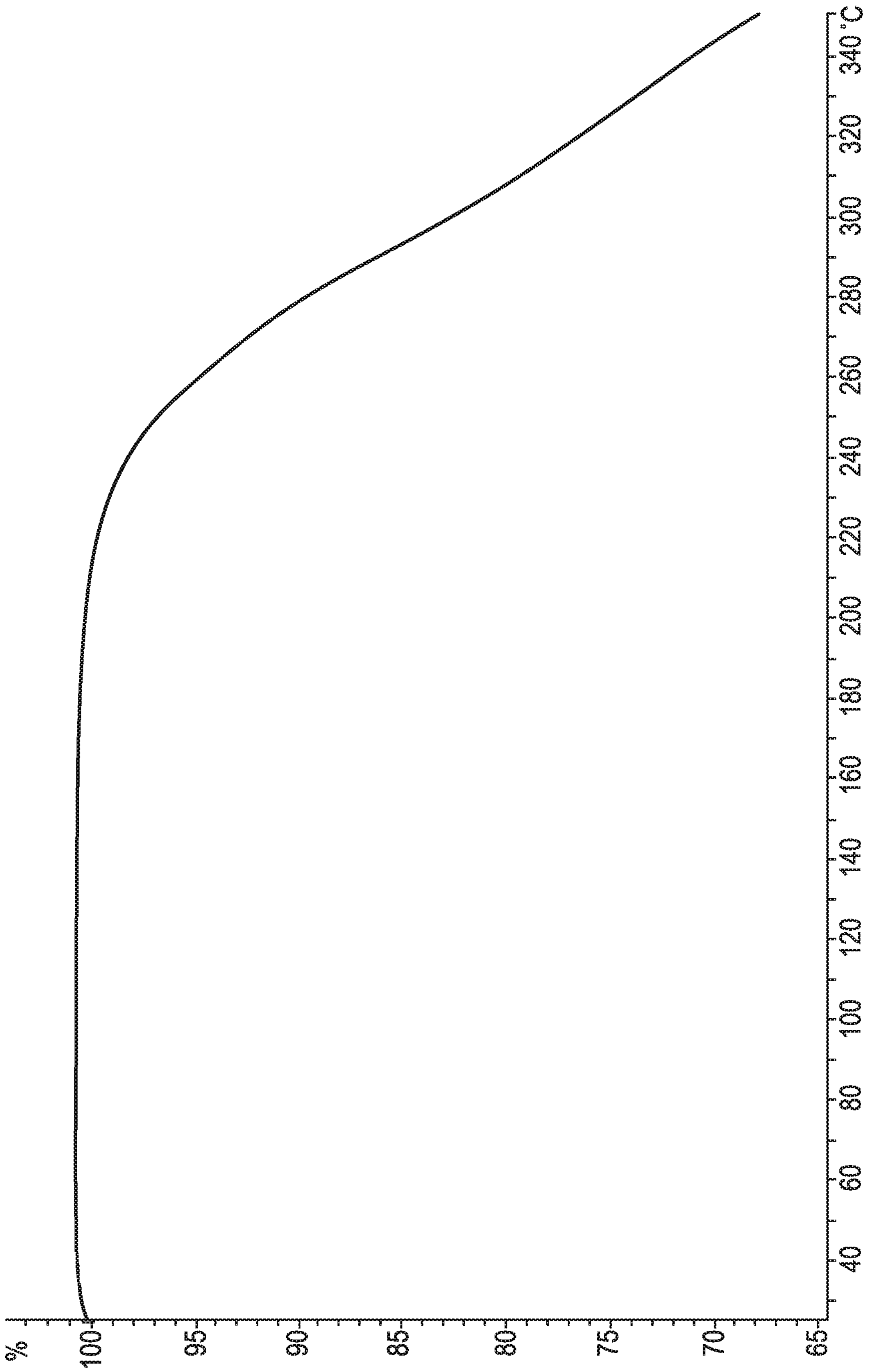
FIG. 21 is a TGA thermogram of Compound 1 Form K.

DSC and TGA thermograms for Compound 1 Form K are presented in FIGS. 20 and 21, respectively. Negligible weight loss was observed by TGA up to 180° C., consistent with an anhydrous/non-solvated material. An endotherm at ~220° C. (onset) by DSC likely corresponds with simultaneous melting and decomposition.

Compound 1 Form O

Compound 1 Form O is a likely TFE solvate of Compound 1 that resulted from one or more salt screen experiments in TFE-containing solvent systems.

The XRPD pattern for Compound 1 Form O is provided in FIG. 22, and a list of peaks from the pattern is provided in Table 10 below.

TABLE 10

| XRPD peaks of Compound 1 Form O | | |
|---|---|---|
| 2θ (°) | d-spacing (Å) | Intensity (%) |
| 6.10 ± 0.20 | 14.467 ± 0.474 | 24 |
| 9.01 ± 0.20 | 9.809 ± 0.217 | 16 |
| 9.83 ± 0.20 | 8.991 ± 0.182 | 8 |
| 10.68 ± 0.20 | 8.277 ± 0.155 | 20 |
| 11.12 ± 0.20 | 7.953 ± 0.143 | 20 |
| 11.33 ± 0.20 | 7.806 ± 0.137 | 37 |
| 12.25 ± 0.20 | 7.221 ± 0.117 | 33 |
| 12.99 ± 0.20 | 6.810 ± 0.104 | 18 |
| 13.93 ± 0.20 | 6.351 ± 0.091 | 38 |
| 14.51 ± 0.20 | 6.099 ± 0.084 | 44 |
| 14.92 ± 0.20 | 5.932 ± 0.079 | 41 |
| 15.55 ± 0.20 | 5.694 ± 0.073 | 8 |
| 15.79 ± 0.20 | 5.607 ± 0.071 | 10 |
| 17.14 ± 0.20 | 5.170 ± 0.060 | 12 |
| 17.43 ± 0.20 | 5.083 ± 0.058 | 74 |
| 17.58 ± 0.20 | 5.042 ± 0.057 | 41 |
| 18.15 ± 0.20 | 4.885 ± 0.053 | 11 |
| 18.42 ± 0.20 | 4.812 ± 0.052 | 7 |
| 19.35 ± 0.20 | 4.583 ± 0.047 | 100 |
| 19.77 ± 0.20 | 4.486 ± 0.045 | 34 |
| 20.24 ± 0.20 | 4.385 ± 0.043 | 57 |
| 20.71 ± 0.20 | 4.286 ± 0.041 | 22 |
| 20.90 ± 0.20 | 4.246 ± 0.040 | 25 |
| 21.49 ± 0.20 | 4.131 ± 0.038 | 25 |

TABLE 10-continued

XRPD peaks of Compound 1 Form O

| 2θ (°) | d-spacing (Å) | Intensity (%) |
|---|---|---|
| 21.68 ± 0.20 | 4.096 ± 0.037 | 25 |
| 22.04 ± 0.20 | 4.030 ± 0.036 | 17 |
| 22.36 ± 0.20 | 3.973 ± 0.035 | 56 |
| 22.78 ± 0.20 | 3.900 ± 0.034 | 23 |
| 23.37 ± 0.20 | 3.803 ± 0.032 | 27 |
| 23.96 ± 0.20 | 3.711 ± 0.031 | 92 |
| 24.39 ± 0.20 | 3.647 ± 0.029 | 54 |
| 24.92 ± 0.20 | 3.570 ± 0.028 | 11 |
| 25.62 ± 0.20 | 3.474 ± 0.027 | 9 |
| 26.20 ± 0.20 | 3.398 ± 0.025 | 16 |
| 26.64 ± 0.20 | 3.343 ± 0.025 | 8 |
| 26.93 ± 0.20 | 3.308 ± 0.024 | 6 |
| 27.32 ± 0.20 | 3.262 ± 0.023 | 9 |
| 27.68 ± 0.20 | 3.221 ± 0.023 | 35 |
| 27.96 ± 0.20 | 3.189 ± 0.022 | 12 |
| 28.26 ± 0.20 | 3.156 ± 0.022 | 11 |
| 28.60 ± 0.20 | 3.118 ± 0.021 | 22 |
| 28.81 ± 0.20 | 3.096 ± 0.021 | 11 |

The XRPD pattern was successfully indexed, and the unit cell volume could accommodate Compound 1 with up to 1 mole of TFE. The material was not further characterized.

Unit Cell Data for Compound 1 Form O

| Bravais Type | Triclinic |
|---|---|
| a [Å] | 10.079 |
| b [Å] | 10.592 |
| c [Å] | 14.589 |
| α [deg] | 98.17 |
| β [deg] | 90.51 |
| γ [deg] | 103.21 |
| Volume [$Å^3$/cell] | 1,499.5 |
| Chiral Contents? | Not Specified |
| Extinction Symbol | P~ |
| Space Group(s) | P1 (1), P$\bar{1}$ (2) |

Compound 1 Form P

Compound 1 Form P is a likely hydrate of Compound 1 that was observed only as a mixture with minor Compound 1 Form A.

The XRPD pattern for Compound 1 Form P is provided in FIG. 22, and a list of peaks from the pattern is provided in Table 11 below.

TABLE 11

XRPD peaks of Compound 1 Form P

| 2θ (°) | d-spacing (Å) | Intensity (%) |
|---|---|---|
| 5.99 ± 0.20 | 14.745 ± 0.492 | 8 |
| 8.78 ± 0.20 | 10.063 ± 0.229 | 5 |
| 9.40 ± 0.20 | 9.404 ± 0.200 | 5 |
| 10.12 ± 0.20 | 8.738 ± 0.172 | 8 |
| 11.99 ± 0.20 | 7.376 ± 0.123 | 64 |
| 14.61 ± 0.20 | 6.058 ± 0.082 | 30 |
| 14.87 ± 0.20 | 5.953 ± 0.080 | 41 |
| 15.61 ± 0.20 | 5.674 ± 0.072 | 7 |
| 15.98 ± 0.20 | 5.542 ± 0.069 | 10 |
| 16.32 ± 0.20 | 5.428 ± 0.066 | 22 |
| 16.62 ± 0.20 | 5.330 ± 0.064 | 4 |
| 17.56 ± 0.20 | 5.047 ± 0.057 | 10 |
| 17.62 ± 0.20 | 5.030 ± 0.057 | 10 |
| 17.84 ± 0.20 | 4.967 ± 0.055 | 4 |
| 18.05 ± 0.20 | 4.910 ± 0.054 | 4 |
| 18.43 ± 0.20 | 4.810 ± 0.052 | 10 |
| 18.88 ± 0.20 | 4.695 ± 0.049 | 12 |
| 19.22 ± 0.20 | 4.614 ± 0.048 | 12 |
| 19.72 ± 0.20 | 4.499 ± 0.045 | 15 |

TABLE 11-continued

XRPD peaks of Compound 1 Form P

| 2θ (°) | d-spacing (Å) | Intensity (%) |
|---|---|---|
| 19.85 ± 0.20 | 4.469 ± 0.045 | 22 |
| 20.32 ± 0.20 | 4.367 ± 0.043 | 6 |
| 20.91 ± 0.20 | 4.246 ± 0.040 | 100 |
| 21.67 ± 0.20 | 4.097 ± 0.037 | 30 |
| 22.04 ± 0.20 | 4.029 ± 0.036 | 47 |
| 22.39 ± 0.20 | 3.967 ± 0.035 | 11 |
| 22.93 ± 0.20 | 3.875 ± 0.033 | 38 |
| 23.46 ± 0.20 | 3.789 ± 0.032 | 8 |
| 23.71 ± 0.20 | 3.749 ± 0.031 | 8 |
| 23.98 ± 0.20 | 3.708 ± 0.030 | 7 |
| 24.11 ± 0.20 | 3.688 ± 0.030 | 10 |
| 24.43 ± 0.20 | 3.640 ± 0.029 | 15 |
| 24.84 ± 0.20 | 3.581 ± 0.028 | 6 |
| 25.74 ± 0.20 | 3.459 ± 0.026 | 6 |
| 26.39 ± 0.20 | 3.374 ± 0.025 | 15 |
| 26.64 ± 0.20 | 3.344 ± 0.025 | 18 |
| 26.85 ± 0.20 | 3.318 ± 0.024 | 39 |
| 27.77 ± 0.20 | 3.210 ± 0.023 | 17 |
| 28.74 ± 0.20 | 3.104 ± 0.021 | 5 |
| 29.26 ± 0.20 | 3.049 ± 0.020 | 7 |
| 29.55 ± 0.20 | 3.020 ± 0.020 | 15 |
| 30.07 ± 0.20 | 2.970 ± 0.019 | 17 |

Despite existing as a mixture, the XRPD pattern for Compound 1 Form P was successfully indexed. The peaks at 11.36°, 14.35°, and 28.18° are not consistent with the indexing solution and are due to Compound 1 Form A. The unit cell volume per molecule is larger than that of Compound 1 Form A, and can potentially also accommodate up to 2 mol/mol of water.

Unit Cell Data for Compound 1 Form P

| Bravais Type | Primitive Monoclinic |
|---|---|
| a [Å] | 6.152 |
| b [Å] | 23.805 |
| c [Å] | 18.961 |
| α [deg] | 90 |
| β [deg] | 97.82 |
| γ [deg] | 90 |
| Volume [$Å^3$/cell] | 2,751.0 |
| Chiral Contents? | Achiral |
| Extinction Symbol | P 1 $2_1$/n 1 |
| Space Group(s) | P$2_1$/n (14) |

The proton NMR spectrum of the mixture is consistent with the chemical structure of Compound 1 with negligible THF present.

Figure 24:
FIG. 24 is a DSC thermogram of Compound 1 Form P.

A DSC thermogram is shown in FIG. 24. Small, overlapping, broad endotherms are observed at 90° C. and 109° C., consistent with dehydration. No other thermal events, such as recrystallization or melting, are observed following these events, suggesting a loss of crystallinity following dehydration.

Compound 1 Form Q

Compound 1 Form Q was characterized by XRPD, DSC, TGA, and SEM (Not shown in the figures).

The XRPD pattern for Compound 1 Form Q is provided in FIG. 25, and a list of peaks from the pattern is provided in Table 12 below.

TABLE 12

| XRPD peaks of Compound 1 Form Q | | |
|---|---|---|
| 2θ (°) | d-spacing (Å) | Intensity (%) |
| 6.11 ± 0.20 | 14.454 ± 0.473 | 18 |
| 8.61 ± 0.20 | 10.266 ± 0.238 | 15 |
| 9.06 ± 0.20 | 9.755 ± 0.215 | 48 |
| 9.74 ± 0.20 | 9.071 ± 0.186 | 21 |
| 10.64 ± 0.20 | 8.305 ± 0.156 | 45 |
| 10.89 ± 0.20 | 8.117 ± 0.149 | 15 |
| 11.24 ± 0.20 | 7.869 ± 0.140 | 25 |
| 11.33 ± 0.20 | 7.803 ± 0.137 | 25 |
| 12.06 ± 0.20 | 7.331 ± 0.121 | 8 |
| 12.24 ± 0.20 | 7.223 ± 0.118 | 10 |
| 12.91 ± 0.20 | 6.852 ± 0.106 | 12 |
| 13.82 ± 0.20 | 6.401 ± 0.092 | 21 |
| 14.46 ± 0.20 | 6.120 ± 0.084 | 42 |
| 14.83 ± 0.20 | 5.969 ± 0.080 | 23 |
| 15.69 ± 0.20 | 5.645 ± 0.072 | 8 |
| 15.76 ± 0.20 | 5.619 ± 0.071 | 8 |
| 16.07 ± 0.20 | 5.510 ± 0.068 | 7 |
| 17.05 ± 0.20 | 5.195 ± 0.060 | 10 |
| 17.31 ± 0.20 | 5.118 ± 0.059 | 62 |
| 17.40 ± 0.20 | 5.092 ± 0.058 | 69 |
| 17.78 ± 0.20 | 4.985 ± 0.056 | 8 |
| 18.16 ± 0.20 | 4.881 ± 0.053 | 18 |
| 18.42 ± 0.20 | 4.813 ± 0.052 | 6 |
| 18.88 ± 0.20 | 4.697 ± 0.049 | 8 |
| 19.08 ± 0.20 | 4.647 ± 0.048 | 20 |
| 19.28 ± 0.20 | 4.601 ± 0.047 | 100 |
| 19.56 ± 0.20 | 4.535 ± 0.046 | 69 |
| 19.84 ± 0.20 | 4.471 ± 0.045 | 8 |
| 20.07 ± 0.20 | 4.420 ± 0.044 | 58 |
| 20.70 ± 0.20 | 4.287 ± 0.041 | 10 |
| 21.04 ± 0.20 | 4.220 ± 0.040 | 14 |
| 21.38 ± 0.20 | 4.153 ± 0.038 | 30 |
| 21.59 ± 0.20 | 4.112 ± 0.038 | 8 |
| 21.91 ± 0.20 | 4.054 ± 0.037 | 29 |
| 22.18 ± 0.20 | 4.004 ± 0.036 | 17 |
| 22.30 ± 0.20 | 3.984 ± 0.035 | 20 |
| 22.58 ± 0.20 | 3.934 ± 0.034 | 50 |
| 22.78 ± 0.20 | 3.900 ± 0.034 | 11 |
| 23.04 ± 0.20 | 3.856 ± 0.033 | 11 |
| 23.23 ± 0.20 | 3.826 ± 0.032 | 34 |
| 23.50 ± 0.20 | 3.783 ± 0.032 | 7 |
| 23.81 ± 0.20 | 3.734 ± 0.031 | 55 |
| 24.01 ± 0.20 | 3.703 ± 0.030 | 13 |
| 24.32 ± 0.20 | 3.657 ± 0.030 | 87 |
| 24.86 ± 0.20 | 3.579 ± 0.028 | 10 |
| 25.43 ± 0.20 | 3.500 ± 0.027 | 8 |
| 25.80 ± 0.20 | 3.450 ± 0.026 | 5 |
| 26.05 ± 0.20 | 3.417 ± 0.026 | 10 |
| 26.20 ± 0.20 | 3.398 ± 0.025 | 10 |
| 26.69 ± 0.20 | 3.337 ± 0.025 | 16 |
| 27.02 ± 0.20 | 3.297 ± 0.024 | 8 |
| 27.44 ± 0.20 | 3.247 ± 0.023 | 10 |
| 27.63 ± 0.20 | 3.225 ± 0.023 | 38 |
| 27.99 ± 0.20 | 3.185 ± 0.022 | 22 |
| 28.48 ± 0.20 | 3.131 ± 0.022 | 14 |
| 28.75 ± 0.20 | 3.103 ± 0.021 | 16 |
| 29.17 ± 0.20 | 3.059 ± 0.021 | 17 |
| 29.36 ± 0.20 | 3.040 ± 0.020 | 20 |

The XRPD pattern for Compound 1 Form Q was successfully indexed with a unit cell that is isostructural with the 2,2,2-trifluoroethanol (TFE) solvate, Compound 1 Form O.

Unit Cell Data for Compound 1 Form Q

| Bravais Type | Triclinic |
|---|---|
| a [Å] | 10.044 |
| b [Å] | 10.691 |
| c [Å] | 14.626 |
| α [deg] | 98.58 |
| β [deg] | 91.18 |
| γ [deg] | 103.65 |
| Volume [$Å^3$/cell] | 1,506.5 |
| Chiral Contents? | Not Specified |
| Extinction Symbol | P~ |
| Space Group(s) | P1 (1), P$\bar{1}$ (2) |

Figure 26:
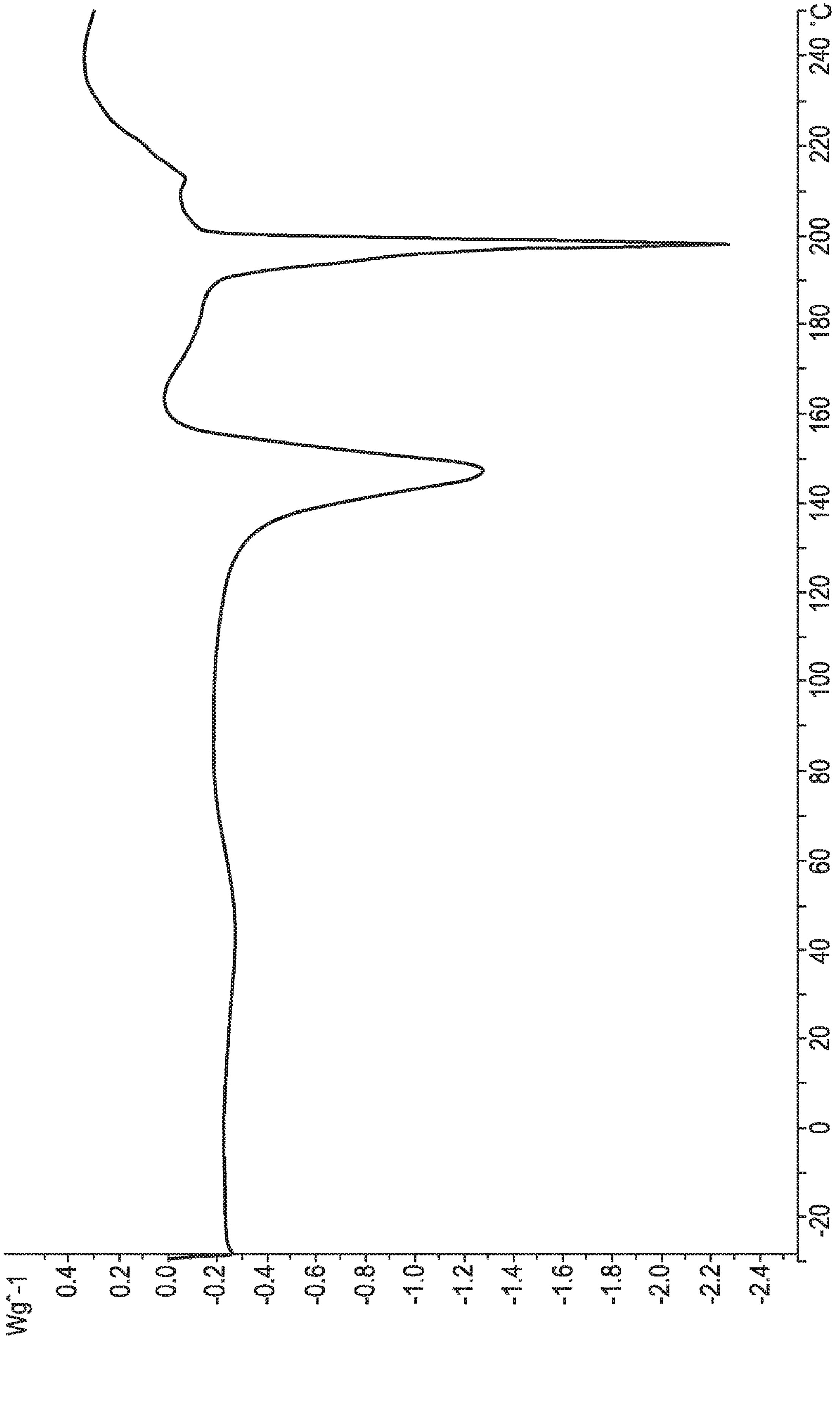
FIG. 26 is a DSC thermogram of Compound 1 Form Q.

DSC (FIG. 26) showed a small shallow peak followed by a broad peak that coincides with weight loss in thermogravimetric analysis, and a final sharp endotherm with an onset of ~194-195° C.

Figure 27:
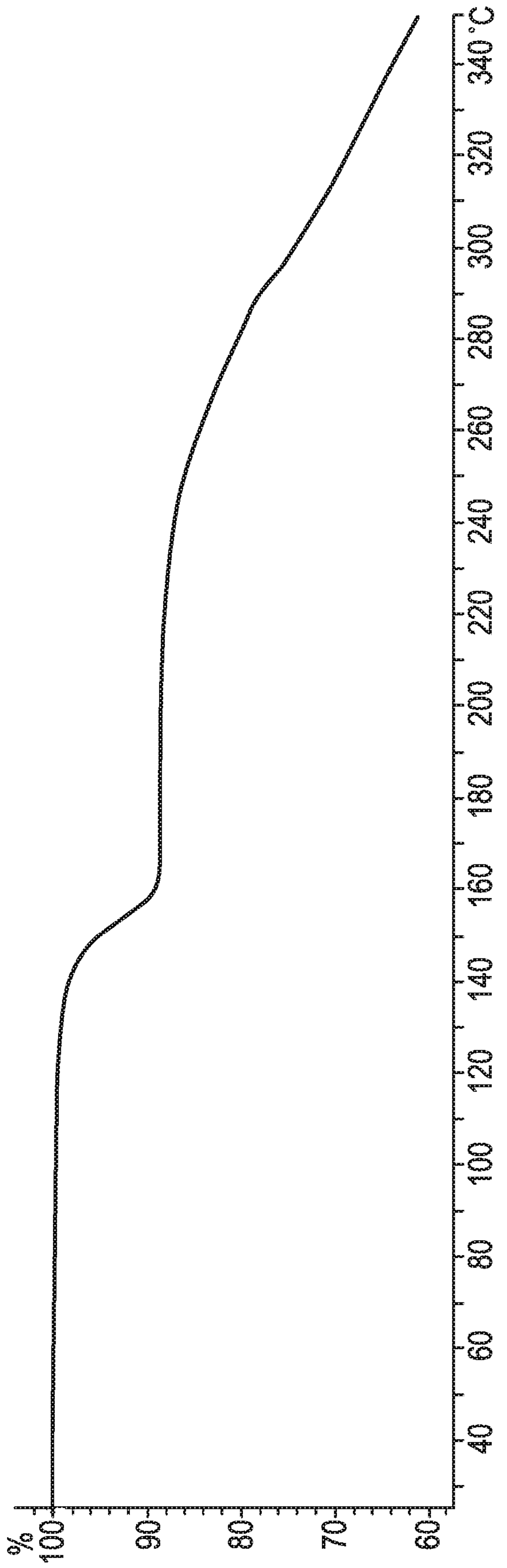
FIG. 27 is a TGA thermogram of Compound 1 Form Q.

The TGA weight loss that was consistent with the broad endotherm in the DSC was approximately ~11-12% (FIG. 27).

Scanning electron microscopy images were obtained for two samples of Compound 1 Form Q over 100×-5000× magnification. The first sample contained agglomerates larger than 200 μm that are composed of flakes smaller than 20 μm. The second sample was composed of blades at least 50 μm long and not more than 5 μm wide.

Compound 1 Fumarate Form A

Compound 1 Fumarate Form A was made from a slurry at elevated temperature consisting of acetone, fumaric acid, and the free base of Compound 1. The elevated temperature slurry was stirred for 4 days, and then was followed by a RT slurry for an additional day.

The XRPD pattern for Compound 1 Fumarate Form A is provided in FIG. 28.

Compound 1 Hemifumarate Form B

Compound 1 Hemifumarate Form B is an anhydrous salt of Compound 1. The form is physically stable at 40° C. and 75% RH over 15 days, and disproportionation was not evident in either acetone or water. In addition, the form is not hygroscopic by DVS analysis. By DSC and hot stage microscopy, Compound 1 Hemifumarate Form B exhibits a melt onset near 225° C., which is higher relative to other crystalline salts identified within this study.

Compound 1 Hemifumarate Form B was prepared by the method described below.

Compound 1 (199.0 mg) was combined with 2 molar equivalents of fumaric acid (88.8 mg). The mixture was slurried in 10 mL of acetone at ~50° C. A spatula full of Compound 1 Hemifumarate Form B seeds was added to the slurry. After 6 days at ~50° C., pale pink solids were collected by vacuum filtration and dried on filter paper, exposed to air, under reduced pressure for approximately 5 minutes.

The XRPD pattern for Compound 1 Hemifumarate Form B is provided in FIG. 29, and a list of peaks from the pattern is provided in Table 13 below.

TABLE 13

| XRPD peaks of Compound 1 Hemifumarate Form B | | |
|---|---|---|
| 2θ (°) | d-spacing (Å) | Intensity (%) |
| 7.55 ± 0.20 | 11.702 ± 0.310 | 14 |
| 7.92 ± 0.20 | 11.158 ± 0.281 | 5 |
| 9.08 ± 0.20 | 9.732 ± 0.214 | 84 |
| 9.40 ± 0.20 | 9.397 ± 0.199 | 11 |
| 10.81 ± 0.20 | 8.179 ± 0.151 | 38 |
| 11.18 ± 0.20 | 7.909 ± 0.141 | 8 |
| 13.24 ± 0.20 | 6.681 ± 0.100 | 12 |
| 13.35 ± 0.20 | 6.627 ± 0.099 | 8 |
| 14.47 ± 0.20 | 6.114 ± 0.084 | 4 |

TABLE 13-continued

XRPD peaks of Compound 1 Hemifumarate Form B

| 2θ (°) | d-spacing (Å) | Intensity (%) |
|---|---|---|
| 14.90 ± 0.20 | 5.942 ± 0.079 | 5 |
| 15.14 ± 0.20 | 5.846 ± 0.077 | 6 |
| 15.89 ± 0.20 | 5.573 ± 0.070 | 13 |
| 16.64 ± 0.20 | 5.325 ± 0.064 | 4 |
| 16.95 ± 0.20 | 5.227 ± 0.061 | 63 |
| 17.14 ± 0.20 | 5.168 ± 0.060 | 20 |
| 17.29 ± 0.20 | 5.124 ± 0.059 | 21 |
| 17.44 ± 0.20 | 5.080 ± 0.058 | 35 |
| 17.79 ± 0.20 | 4.982 ± 0.056 | 5 |
| 18.24 ± 0.20 | 4.860 ± 0.053 | 20 |
| 18.34 ± 0.20 | 4.834 ± 0.052 | 17 |
| 19.16 ± 0.20 | 4.629 ± 0.048 | 74 |
| 19.91 ± 0.20 | 4.456 ± 0.044 | 10 |
| 20.19 ± 0.20 | 4.395 ± 0.043 | 11 |
| 20.42 ± 0.20 | 4.346 ± 0.042 | 9 |
| 20.70 ± 0.20 | 4.287 ± 0.041 | 20 |
| 21.16 ± 0.20 | 4.196 ± 0.039 | 8 |
| 21.74 ± 0.20 | 4.085 ± 0.037 | 10 |
| 22.29 ± 0.20 | 3.986 ± 0.035 | 28 |
| 22.48 ± 0.20 | 3.952 ± 0.035 | 26 |
| 22.75 ± 0.20 | 3.905 ± 0.034 | 16 |
| 23.82 ± 0.20 | 3.733 ± 0.031 | 25 |
| 24.37 ± 0.20 | 3.650 ± 0.030 | 48 |
| 24.97 ± 0.20 | 3.563 ± 0.028 | 4 |
| 25.17 ± 0.20 | 3.535 ± 0.028 | 7 |
| 25.69 ± 0.20 | 3.465 ± 0.027 | 6 |
| 26.34 ± 0.20 | 3.380 ± 0.025 | 100 |
| 26.75 ± 0.20 | 3.330 ± 0.024 | 7 |
| 27.05 ± 0.20 | 3.294 ± 0.024 | 49 |
| 27.35 ± 0.20 | 3.258 ± 0.023 | 8 |
| 27.50 ± 0.20 | 3.241 ± 0.023 | 6 |
| 27.88 ± 0.20 | 3.198 ± 0.022 | 16 |

The XRPD pattern of Compound 1 Hemifumarate Form B was successfully indexed, which indicates the material is composed of a single crystalline phase. It has a triclinic unit cell containing two molecules of Compound 1 and one molecule of fumaric acid. The formula unit volume calculated from the indexing solution is consistent with an anhydrous form.

Unit Cell Data for Compound 1 Hemifumarate Form B

| Bravais Type | Triclinic |
|---|---|
| a [Å] | 10.711 |
| b [Å] | 11.401 |
| c [Å] | 12.626 |
| α [deg] | 86.78 |
| β [deg] | 67.95 |
| γ [deg] | 77.89 |
| Volume [$Å^3$/cell] | 1,396.8 |
| Chiral Contents? | Not Specified |
| Extinction Symbol | P~ |
| Space Group(s) | P1 (1), P$\bar{1}$ (2) |

The $^1H$ NMR spectra are consistent with the chemical structure of Compound 1. Based on peak integrations, approximately 0.5 mole of fumaric acid per mole of Compound 1 is present, consistent with a Compound 1 Hemifumarate salt. A negligible amount of residual acetone is also evident.

Figure 30:
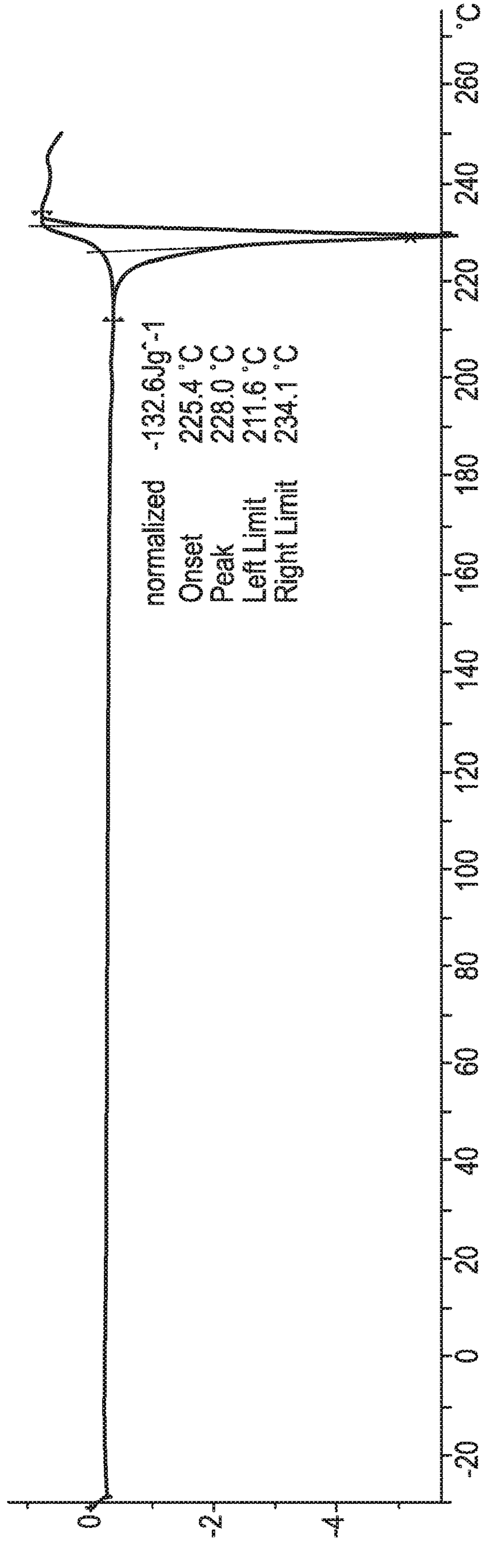
FIG. 30 is a DSC thermogram of Compound 1 Hemifumarate Form B.
Figure 31:
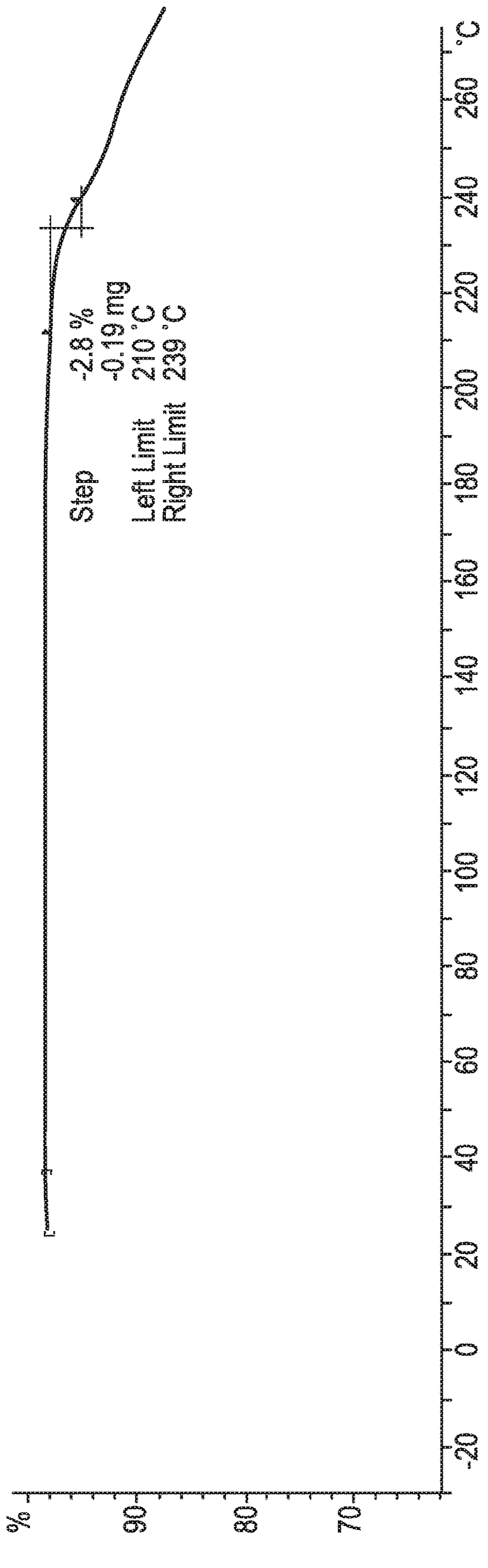
FIG. 31 is a TGA thermogram of Compound 1 Hemifumarate Form B.

The curve of the TGA thermogram (FIG. 31) shows negligible weight loss until decomposition. The curve of the DSC thermogram (FIG. 30) exhibits a single endotherm with an onset of ~225° C. (132.6 J/g).

Hot stage photomicrographs (FIGS. 33A-33D) for Compound 1 Hemifumarate Form B confirm the event as the melt with concurrent decomposition.

Figure 32:
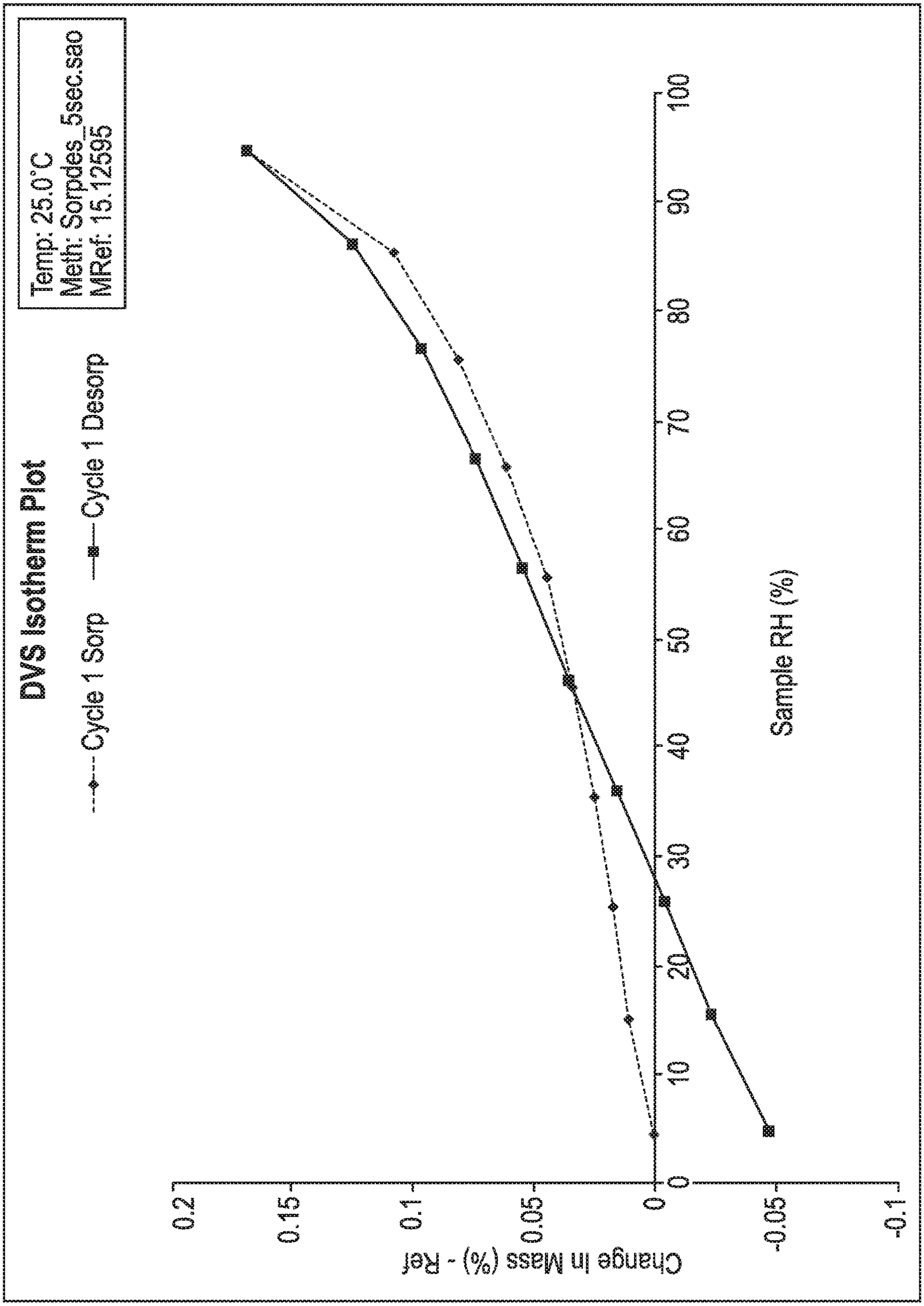
FIG. 32 is a DVS isotherm plot of Compound 1 Hemifumarate Form B.
Figure 33A:
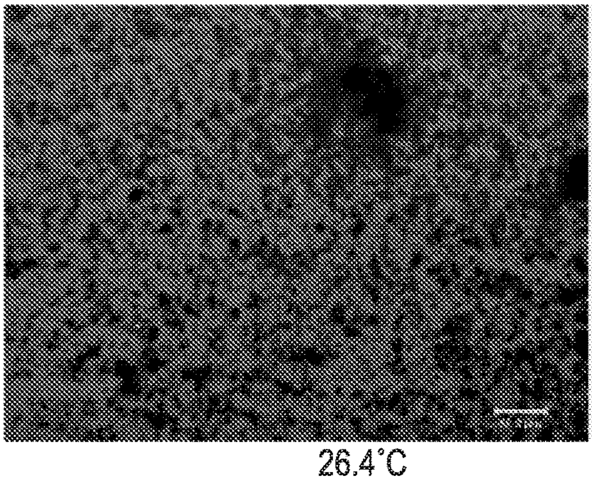
FIG. 33A-FIG. 33D are hot stage photomicrographs showing Compound 1 Hemifumarate Form B at (A) 26.4° C. with no change in crystalline form, (B) 209.6° C. with no change in crystalline form, (C) 222.1° C. with some melting, and (D) 223.1° C. with complete melting and some darkening indicating decomposition.
Figure 33B:
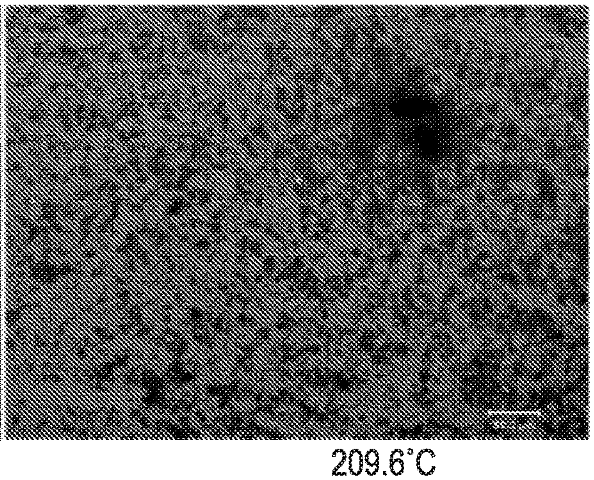
Figure 33C:
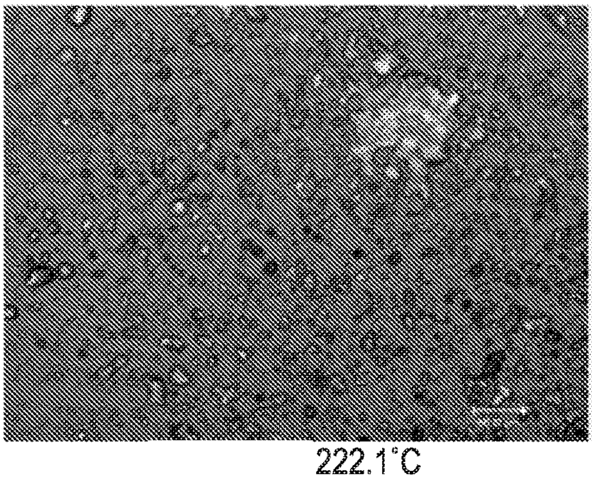
Figure 33D:
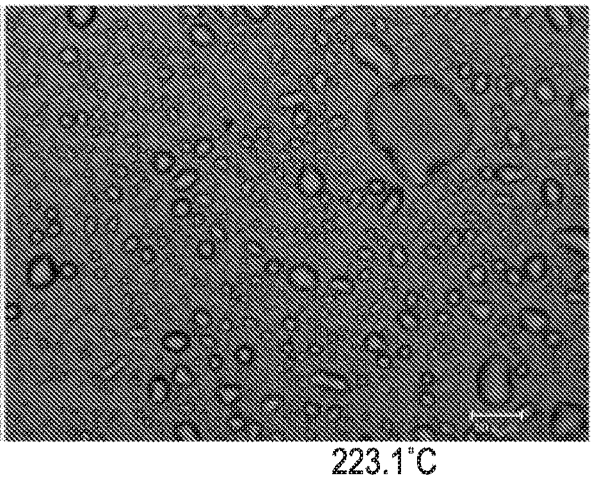

The DVS isotherm (FIG. 32) indicates the form is not hygroscopic. Compound 1 Hemifumarate Form B gains/losses less than 0.2% weight through the sorption/desorption experiment without hysteresis.

The material recovered from the experiment remained unchanged and identified as Compound 1 Hemifumarate Form B by XRPD.

The physical stability of Hemifumarate Form B was investigated. Compound 1 Hemifumarate Form B was slurried in water at ambient conditions for approximately 24 hours. In a separate experiment, the material was repeatedly washed with acetone. Both recovered materials were identified by XRPD analysis as Compound 1 Hemifumarate Form B, indicating that these conditions did not cause disproportionation of the salt. In addition, material exposed to 75% RH/40° C. for approximately 2 weeks did not change by XRPD.

Compound 1 Hemifumarate Form B was successfully reproduced on a 200 and 1-g laboratory scale. This suggests that Compound 1 Hemifumarate Form B can be generated relatively easily and reproducibly.

Compound 1 HCl Form A

Compound 1 HCl Form A was produced by slurrying Compound 1 and HCl in TGF at room temperature.

The XRPD pattern for Compound 1 HCl Form A is provided in FIG. 34, and a list of peaks from the pattern is provided in Table 14 below.

TABLE 14

XRPD peaks of Compound 1 HCl Form A

| 2θ (°) | d-spacing (Å) | Intensity (%) |
|---|---|---|
| 5.19 ± 0.20 | 17.007 ± 0.655 | 55 |
| 8.17 ± 0.20 | 10.809 ± 0.264 | 26 |
| 9.84 ± 0.20 | 8.980 ± 0.182 | 27 |
| 10.10 ± 0.20 | 8.749 ± 0.173 | 8 |
| 10.42 ± 0.20 | 8.480 ± 0.162 | 22 |
| 11.07 ± 0.20 | 7.986 ± 0.144 | 9 |
| 12.52 ± 0.20 | 7.064 ± 0.112 | 12 |
| 12.76 ± 0.20 | 6.934 ± 0.108 | 17 |
| 12.98 ± 0.20 | 6.817 ± 0.105 | 25 |
| 13.49 ± 0.20 | 6.560 ± 0.097 | 10 |
| 13.69 ± 0.20 | 6.463 ± 0.094 | 13 |
| 13.89 ± 0.20 | 6.372 ± 0.091 | 21 |
| 14.31 ± 0.20 | 6.185 ± 0.086 | 25 |
| 14.84 ± 0.20 | 5.966 ± 0.080 | 10 |
| 15.12 ± 0.20 | 5.856 ± 0.077 | 6 |
| 15.68 ± 0.20 | 5.647 ± 0.072 | 11 |
| 16.34 ± 0.20 | 5.420 ± 0.066 | 7 |
| 16.68 ± 0.20 | 5.310 ± 0.063 | 10 |
| 17.08 ± 0.20 | 5.188 ± 0.060 | 5 |
| 17.47 ± 0.20 | 5.072 ± 0.058 | 24 |
| 17.96 ± 0.20 | 4.936 ± 0.055 | 26 |
| 18.49 ± 0.20 | 4.794 ± 0.051 | 10 |
| 19.23 ± 0.20 | 4.613 ± 0.048 | 31 |
| 19.78 ± 0.20 | 4.484 ± 0.045 | 28 |
| 20.31 ± 0.20 | 4.369 ± 0.043 | 14 |
| 20.91 ± 0.20 | 4.244 ± 0.040 | 18 |
| 21.16 ± 0.20 | 4.196 ± 0.039 | 22 |
| 21.42 ± 0.20 | 4.145 ± 0.038 | 44 |
| 22.10 ± 0.20 | 4.019 ± 0.036 | 45 |
| 22.81 ± 0.20 | 3.896 ± 0.034 | 100 |
| 23.18 ± 0.20 | 3.835 ± 0.033 | 38 |
| 23.89 ± 0.20 | 3.722 ± 0.031 | 11 |
| 24.39 ± 0.20 | 3.646 ± 0.029 | 36 |
| 25.20 ± 0.20 | 3.532 ± 0.028 | 7 |
| 25.87 ± 0.20 | 3.441 ± 0.026 | 8 |
| 26.34 ± 0.20 | 3.380 ± 0.025 | 48 |
| 27.06 ± 0.20 | 3.293 ± 0.024 | 14 |
| 27.59 ± 0.20 | 3.230 ± 0.023 | 9 |
| 28.07 ± 0.20 | 3.176 ± 0.022 | 10 |

The XRPD pattern of Compound 1 HCl Form A was successfully indexed.

Unit Cell Data for Compound 1 Form A

| Bravais Type | Primitive Monoclinic |
|---|---|
| a [Å] | 10.803 |
| b [Å] | 9.043 |
| c [Å] | 33.901 |
| α [deg] | 90 |
| β [deg] | 91.90 |
| γ [deg] | 90 |
| Volume [$Å^3$/cell] | 3,310.0 |
| Chiral Contents? | Achiral |
| Extinction Symbol | P 1 $2_1$/c 1 |
| Space Group(s) | $P2_1$/c (14) |

Compound 1 HCl Form B

Compound 1 HCl Form B was produced by slurrying Compound 1 and HCl in chloroform at elevated temperature.

The XRPD pattern for Compound 1 HCl Form B is provided in FIG. 35, and a list of peaks from the pattern is provided in Table 15 below.

TABLE 15

XRPD peaks of Compound 1 HC1 Form B

| 2θ (°) | d-spacing (Å) | Intensity (%) |
|---|---|---|
| 8.20 ± 0.20 | 10.772 ± 0.262 | 9 |
| 9.72 ± 0.20 | 9.094 ± 0.187 | 15 |
| 9.81 ± 0.20 | 9.006 ± 0.183 | 18 |
| 10.04 ± 0.20 | 8.804 ± 0.175 | 5 |
| 10.56 ± 0.20 | 8.374 ± 0.158 | 9 |
| 12.52 ± 0.20 | 7.065 ± 0.112 | 9 |
| 12.97 ± 0.20 | 6.823 ± 0.105 | 20 |
| 13.32 ± 0.20 | 6.640 ± 0.099 | 11 |
| 13.48 ± 0.20 | 6.565 ± 0.097 | 6 |
| 13.81 ± 0.20 | 6.408 ± 0.092 | 42 |
| 14.35 ± 0.20 | 6.166 ± 0.085 | 5 |
| 14.95 ± 0.20 | 5.922 ± 0.079 | 10 |
| 15.89 ± 0.20 | 5.573 ± 0.070 | 5 |
| 16.63 ± 0.20 | 5.328 ± 0.064 | 13 |
| 17.37 ± 0.20 | 5.101 ± 0.058 | 5 |
| 17.83 ± 0.20 | 4.970 ± 0.055 | 15 |
| 17.99 ± 0.20 | 4.926 ± 0.054 | 20 |
| 18.32 ± 0.20 | 4.839 ± 0.052 | 11 |
| 19.15 ± 0.20 | 4.630 ± 0.048 | 13 |
| 19.31 ± 0.20 | 4.592 ± 0.047 | 15 |
| 19.51 ± 0.20 | 4.546 ± 0.046 | 17 |
| 19.72 ± 0.20 | 4.498 ± 0.045 | 18 |
| 20.17 ± 0.20 | 4.399 ± 0.043 | 17 |
| 20.84 ± 0.20 | 4.260 ± 0.040 | 9 |
| 21.04 ± 0.20 | 4.219 ± 0.040 | 19 |
| 21.15 ± 0.20 | 4.198 ± 0.039 | 17 |
| 21.30 ± 0.20 | 4.168 ± 0.039 | 26 |
| 21.81 ± 0.20 | 4.071 ± 0.037 | 28 |
| 22.02 ± 0.20 | 4.034 ± 0.036 | 25 |
| 22.65 ± 0.20 | 3.922 ± 0.034 | 100 |
| 23.11 ± 0.20 | 3.846 ± 0.033 | 8 |
| 23.40 ± 0.20 | 3.799 ± 0.032 | 24 |
| 23.75 ± 0.20 | 3.744 ± 0.031 | 16 |
| 24.76 ± 0.20 | 3.593 ± 0.029 | 26 |
| 25.34 ± 0.20 | 3.511 ± 0.027 | 5 |
| 25.74 ± 0.20 | 3.458 ± 0.026 | 13 |
| 26.20 ± 0.20 | 3.399 ± 0.025 | 56 |
| 26.90 ± 0.20 | 3.311 ± 0.024 | 21 |
| 27.71 ± 0.20 | 3.217 ± 0.023 | 6 |
| 27.98 ± 0.20 | 3.186 ± 0.022 | 8 |
| 28.34 ± 0.20 | 3.146 ± 0.022 | 5 |
| 28.98 ± 0.20 | 3.079 ± 0.021 | 10 |

Compound 1 HCl Form C

Compound 1 HCl Form C was produced by a procedure including crystallization from methanol with MTBE as an anti-solvent.

The XRPD pattern for Compound 1 HCl Form C is provided in FIG. 36.

The XRPD pattern of Compound 1 HCl Form C includes the following peaks in degrees on a 2-theta scale, +0.2: 2.5, 3.0, 4.3, 5.1, 6.2, 6.8, 7.3, 7.8, 8.8, 10.6, 11.6, 12.5, 13.3, 13.8, 15.3, 15.7, 17.1, 17.8, 19.0, 19.4, 20.0, 20.5, 20.8, 21.5, 22.2, 22.6, 23.0, 23.5, 23.9, 25.2, 26.2, 26.8, 27.2, 28.0, 28.9, and 29.5.

Compound 1 HCl Form D

Compound 1 HCl Form D was produced by first slurrying Compound 1 in acetone at ~50° C., and adding 2 molar equivalents of acid, and stirring the resulting acidic slurry at ~50° C. for 5 days. The product was collected by positive pressure filtration.

The XRPD pattern for Compound 1 HCl Form D is provided in FIG. 37, and a list of peaks from the pattern is provided in Table 16 below.

TABLE 16

XRPD peaks of Compound 1 HCl Form D

| 2θ (°) | d-spacing (Å) | Intensity (%) |
|---|---|---|
| 3.47 ± 0.20 | 25.471 ± 1.469 | 100 |
| 5.27 ± 0.20 | 16.748 ± 0.635 | 40 |
| 6.93 ± 0.20 | 12.745 ± 0.367 | 11 |
| 8.21 ± 0.20 | 10.758 ± 0.262 | 30 |
| 8.97 ± 0.20 | 9.856 ± 0.219 | 24 |
| 9.86 ± 0.20 | 8.964 ± 0.181 | 18 |
| 10.16 ± 0.20 | 8.700 ± 0.171 | 87 |
| 10.44 ± 0.20 | 8.469 ± 0.162 | 31 |
| 10.69 ± 0.20 | 8.271 ± 0.154 | 65 |
| 11.28 ± 0.20 | 7.838 ± 0.139 | 18 |
| 12.26 ± 0.20 | 7.215 ± 0.117 | 46 |
| 12.75 ± 0.20 | 6.939 ± 0.108 | 22 |
| 13.27 ± 0.20 | 6.668 ± 0.100 | 19 |
| 13.92 ± 0.20 | 6.357 ± 0.091 | 17 |
| 14.23 ± 0.20 | 6.220 ± 0.087 | 31 |
| 14.54 ± 0.20 | 6.085 ± 0.083 | 52 |
| 14.95 ± 0.20 | 5.921 ± 0.079 | 65 |
| 15.44 ± 0.20 | 5.734 ± 0.074 | 11 |
| 15.58 ± 0.20 | 5.682 ± 0.072 | 11 |
| 15.80 ± 0.20 | 5.603 ± 0.070 | 12 |
| 16.08 ± 0.20 | 5.508 ± 0.068 | 16 |
| 16.25 ± 0.20 | 5.451 ± 0.067 | 13 |
| 17.84 ± 0.20 | 4.967 ± 0.055 | 45 |
| 18.44 ± 0.20 | 4.807 ± 0.052 | 20 |
| 18.65 ± 0.20 | 4.755 ± 0.051 | 33 |
| 19.34 ± 0.20 | 4.586 ± 0.047 | 19 |
| 19.75 ± 0.20 | 4.492 ± 0.045 | 23 |
| 20.13 ± 0.20 | 4.408 ± 0.043 | 23 |
| 20.93 ± 0.20 | 4.241 ± 0.040 | 75 |
| 21.29 ± 0.20 | 4.171 ± 0.039 | 45 |
| 22.05 ± 0.20 | 4.028 ± 0.036 | 52 |
| 22.69 ± 0.20 | 3.916 ± 0.034 | 51 |
| 22.90 ± 0.20 | 3.880 ± 0.033 | 49 |
| 23.69 ± 0.20 | 3.753 ± 0.031 | 63 |
| 24.15 ± 0.20 | 3.682 ± 0.030 | 21 |
| 24.39 ± 0.20 | 3.647 ± 0.029 | 33 |
| 24.60 ± 0.20 | 3.616 ± 0.029 | 38 |
| 24.91 ± 0.20 | 3.571 ± 0.028 | 67 |
| 25.16 ± 0.20 | 3.536 ± 0.028 | 52 |
| 26.27 ± 0.20 | 3.389 ± 0.025 | 39 |
| 27.03 ± 0.20 | 3.296 ± 0.024 | 47 |
| 27.61 ± 0.20 | 3.228 ± 0.023 | 36 |
| 28.37 ± 0.20 | 3.144 ± 0.022 | 28 |

Compound 1 Phosphate Form A

Compound 1 Phosphate Form A was prepared by adding 1 molar equivalent of phosphoric acid to a slurry of Compound 1 in chloroform, and slurrying at elevated temperature for 3 days.

The XRPD pattern of Compound 1 Phosphate Form A is provided in FIG. 48, and a list of peaks from the pattern is provided below.

The XRPD pattern of Compound 1 Phosphate Form A includes the following peaks in degrees on a 2-theta scale, +0.2: 6.3, 6.8, 10.3, 10.5, 11.4, 12.7, 13.8, 14.7, 15.7, 16.1, 17.3, 17.5, 18.1, 18.8, 19.4, 20.3, 20.9, 21.2, 22.1, 22.7, 23.2, 23.6, 24.7, 25.5, 27.4, 27.8, 28.5, 29.1, and 29.3.

General Administration

Administration of the crystalline forms or crystalline salt forms of the present invention, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracistemally, or rectally, in the form of solid, semi-solid, lyophilized powder, or liquid dosage forms, such as, for example, tablets, suppositories, pills, soft elastic and hard gelatin capsules, powders, solutions, suspensions, aerosols, and the like, preferably in unit dosage forms suitable for simple administration of precise dosages.

The compositions will include a conventional pharmaceutical excipient and a crystalline form or crystalline salt form of the present invention as the/an active agent, and, in addition, may include other medicinal agents, pharmaceutical agents, excipients, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate, and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan, monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous excipients, diluents, solvents, or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate, and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., crystalline forms or crystalline salt forms of Compound 1, and optional pharmaceutical adjuvants in an excipient, such as, for example, water, saline, aqueous dextrose, glycerol, ethanol, and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, and dimethylformamide; oils, in particular, cottonseed oil, groundnut oil, corn germ oil, olive oil, castor oil, and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol, and sorbitan esters, microcrystalline cellulose, aluminum metahydroxide, bentonite, agar-agar, and tragacanth, or mixtures of these substances, and the like.

Compositions for rectal administrations are, for example, suppositories that can be prepared by mixing the crystalline forms or crystalline salt forms of Compound 1 with for example suitable non-irritating excipients such as cocoa butter, polyethyleneglycol, or a suppository wax, which are solid at ordinary temperatures but liquid at body temperature and therefore melt while in a suitable body cavity and release the active component therein.

Dosage forms for topical administration of a compound of this invention include ointments, powders, sprays, and inhalants. The active component is admixed under sterile conditions with a physiologically acceptable excipient and any preservatives, buffers, or propellants as may be required.

Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a crystalline form or crystalline salt form of Compound 1, and 99% to 1% by weight of a suitable pharmaceutical excipient. In one example, the composition will be between about 5% and about 75% by weight of a crystalline form or crystalline salt form of Compound 1, with the rest being suitable pharmaceutical excipients.

Actual methods of preparing such dosage forms are known, or will be apparent, to those skilled in this art; for example, see Remington's Pharmaceutical Sciences, $21^{st}$ Ed., (Lippincott, Williams and Wilkins Philadelphia, P A, 2006). The composition to be administered will, in any event, contain a therapeutically effective amount of a crystalline form or crystalline salt form of Compound 1, or a pharmaceutically acceptable salt thereof, for treatment of a disease-state in accordance with the teachings of this invention.

The crystalline forms or crystalline salt forms of Compound 1, are administered in a therapeutically effective amount which will vary depending upon a variety of factors including the activity of Compound 1, the metabolic stability and length of action of Compound 1, the age, body weight, general health, sex, diet, mode, and time of administration, rate of excretion, drug combination, the severity of the particular disease-states, and the host undergoing therapy. The crystalline forms or crystalline salt forms of Compound 1 can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

Combination Therapy

A crystalline form or crystalline salt form of compound 1 as disclosed herein can be administered as a single therapy or in combination ("co-administered") with one or more additional therapies for the treatment of a disease or disorder, for instance a disease or disorder associated with hyper-proliferation such as cancer. Therapies that may be used in combination with a compound disclosed herein include: (i) surgery; (ii) radiotherapy (for example, gamma radiation, neutron beam radiotherapy, electron beam radiotherapy, proton therapy, brachytherapy, and systemic radioactive isotopes); (iii) endocrine therapy; (iv) adjuvant therapy, immunotherapy, CAR T-cell therapy; and (v) other chemotherapeutic agents.

The term "co-administered" ("co-administering") refers to either simultaneous administration, or any manner of separate sequential administration, of a crystalline form or crystalline salt form of compound 1 as disclosed herein, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Typically, any agent that has activity against a disease or condition being treated may be co-administered. Examples of such agents for cancer treatment can be found, for instance, at https://www.cancer.gov/about-cancer/treatment/drugs (last visited Jan. 22, 2019) and in publically available sources such as Cancer Principles and Practice of Oncology by V. T. Devita and S. Hellman (editors), $11^{th}$ edition (2018), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a crystalline form or crystalline salt form of compound 1 as disclosed herein, and at least one immunotherapy. Immunotherapy (also called biological response modifier therapy, biologic therapy, biotherapy, immune therapy, or biological therapy) is a treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include, but are not limited to vaccines including cancer vaccines, tumor cell vaccines (autologous or allogeneic), dendritic cell vaccines, antigen vaccines, anti-idiotype vaccines, DNA vaccines, viral vaccines, or Tumor-Infiltrating Lymphocyte (TIL) Vaccine with Interleukin-2 (IL-2) or Lymphokine-Activated Killer (LAK) Cell Therapy.

Examples of passive immunotherapies include but are not limited to monoclonal antibodies and targeted therapies containing toxins. Monoclonal antibodies include naked antibodies and conjugated monoclonal antibodies (also called tagged, labeled, or loaded antibodies). Naked monoclonal antibodies do not have a drug or radioactive material attached whereas conjugated monoclonal antibodies are joined to, for example, a chemotherapy drug (chemolabeled), a radioactive particle (radiolabeled), or a toxin (immunotoxin). Examples of these naked monoclonal antibody drugs include, but are not limited to Rituximab (Rituxan), an antibody against the CD20 antigen used to treat, for example, B cell non-Hodgkin lymphoma; Trastuzumab (Herceptin), an antibody against the HER2 protein used to treat, for example, advanced breast cancer; Alemtuzumab (Campath), an antibody against the CD52 antigen used to treat, for example, B cell chronic lymphocytic leukemia (B-CLL); Cetuximab (Erbitux), an antibody against the EGFR protein used, for example, in combination with irnnotecan to treat, for example, advanced colorectal cancer and head and neck cancers; and Bevacizumab (Avastin) which is an antiangiogenesis therapy that works against the VEGF protein and is used, for example, in combination with chemotherapy to treat, for example, metastatic colorectal cancer. Examples of the conjugated monoclonal antibodies include, but are not limited to Radiolabeled antibody Ibritumomab tiuxetan (Zevalin) which delivers radioactivity directly to cancerous B lymphocytes and is used to treat, for example, B cell non-Hodgkin lymphoma; radiolabeled antibody Tositumomab (Bexxar) which is used to treat, for example, certain types of non-Hodgkin lymphoma; and immunotoxin Gemtuzumab ozogamicin (Mylotarg) which contains calicheamicin and is used to treat, for example, acute myelogenous leukemia (AML). BL22 is a conjugated monoclonal antibody for treating, for example, hairy cell leukemia, immunotoxins for treating, for example, leukemias, lymphomas, and brain tumors, and radiolabeled antibodies such as OncoScint for example, for colorectal and ovarian cancers and ProstaScint for example, for prostate cancers.

Further examples of therapeutic antibodies that can be used include, but are not limited to, HERCEPTIN™ (Trastuzumab) (Genentech, Calif) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX™ (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3epitope) IgG antibody (ImClone System); IMC-C225 which is a chimeric anti-EGFR IgG antibody (ImClone System); VITAXIN™ which is a humanized anti-alpha V beta 3 integrin antibody (Applied Molecular Evolution/Medlmmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-alpha antibody (CAT/BASF); CDP870 is a humanized anti-TNF-alpha. Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CD20-sreptdavidin (+biotin-yttrium 90; NeoRx); CDP571 is a humanized anti-TNF-alpha. IgG4 antibody (Celltech); LDP-02 is a humanized anti-alpha4 beta7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-beta2 antibody (Cambridge Ab Tech). Others are provided in later paragraphs.

Immunotherapies that can be used in combination with a crystalline form or crystalline salt form of compound 1 as disclosed herein include adjuvant immunotherapies. Examples include cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as combinations of interleukins, for example IL-2 with other cytokines, such as IFN-alpha.

In various embodiments, a crystalline form or crystalline salt form of compound 1 can be combined with an immunological therapy and/or an immunological therapeutic agent. In various embodiments, an immunological therapy and/or an immunological therapeutic agent can include, one or more of the following: an adoptive cell transfer, an angiogenesis inhibitor, *Bacillus* Calmette-Guerin therapy, biochemotherapy, a cancer vaccine, a chimeric antigen receptor (CAR) T-cell therapy, a cytokine therapy, gene therapy, an immune checkpoint modulator, an immunoconjugate, a radioconjugate, an oncolytic virus therapy, or a targeted drug therapy. The immunological therapy or immunological therapeutic agent, is collectively referred to herein as an "immunotherapeutic agent".

The present disclosure provides a method for preventing, treating, reducing, inhibiting or controlling a neoplasia, a tumor or a cancer in a subject in need thereof, involving administering a therapeutically effective amount of a crystalline form or crystalline salt form of compound 1 in combination with an immunotherapeutic agent. In one non-limiting embodiment, the method comprises administering a therapeutically effective amount of a combination comprising a crystalline form or crystalline salt form of compound 1 in combination with an immunotherapeutic agent. In various embodiments, the combination provides a cooperative effect, an additive effect, or a synergistic effect in reducing the number of cancer cells when treated with the combination as compared to each treatment alone. In some embodiments, administration of a therapeutically effective amount of a combination comprising a crystalline form or crystalline salt form of compound 1 and an immunotherapeutic agent, results in synergistic anti-tumor activity and/or antitumor activity that is more potent than the additive effect of administration of a crystalline form or crystalline salt form of compound 1 or immunotherapeutic agent alone.

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities.

The present disclosure provides a combination of a crystalline form or crystalline salt form of compound 1 and an immunotherapeutic agent. These exemplified combinations can be used to treat a subject with a cancer. In various embodiments, immunotherapeutic agents that find utility in the present compositions, formulations, and methods can include one or more agents or therapies, including: an adoptive cell transfer, an angiogenesis inhibitor, *Bacillus* Calmette-Guerin therapy, biochemotherapy, a cancer vaccine, a chimeric antigen receptor (CAR) T-cell therapy, a cytokine therapy, gene therapy, an immune checkpoint modulator, for example an immune checkpoint inhibitor, an immunoconjugate, a radioconjugate, an oncolytic virus therapy, or a targeted drug therapy.

In certain embodiments of the present disclosure, a therapeutically effective combination comprises a crystalline form or crystalline salt form of compound 1 and an immunotherapeutic agent. In various related embodiments, the crystalline form or crystalline salt form of compound 1 enhances the activity of the immunotherapeutic agent.

In certain embodiments of each of the aforementioned aspects, as well as other aspects and embodiments described elsewhere herein, the immunotherapeutic agent enhances the activity of the crystalline form or crystalline salt form of compound 1 of the present invention.

In certain embodiments of each of the aforementioned aspects, as well as other aspects and embodiments described elsewhere herein, the crystalline form or crystalline salt form of compound 1 and the immunotherapeutic agent act synergistically. In various embodiments described herein, an exemplary immunotherapeutic agent is an immune cell (e.g. T-cell, dendritic cell, a natural killer cell and the like) modulator chosen from an agonist or an activator of a costimulatory molecule, wherein the modulator is a monoclonal antibody, a bispecific antibody comprising one or more immune checkpoint antigen binding moieties, a trispecific antibody, or an immune cell-engaging multivalent antibody/fusion protein/construct known in the art. In some embodiments, the immunotherapeutic agent can be an antibody that modulates a costimulatory molecule, bind to an antigen on the surface of an immune cell, or a cancer cell. In each of these different embodiments, the antibody modulator can be a monoclonal antibody, a polyclonal antibody, a bispecific antibody, a trispecific or multispecific format antibody, a fusion protein, or a fragment thereof, for example, a Diabody, a Single-chain (sc)-diabody (scFv)2, a Miniantibody, a Minibody, a Barnase-barstar, a scFv-Fc, a sc(Fab)2, a Trimeric antibody construct, a Triabody antibody construct, a Trimerbody antibody construct, a Tribody antibody construct, a Collabody antibody construct, a (scFv-TNFa)3, or a F(ab)3/DNL antibody construct.

In certain embodiments of each of the aforementioned aspects, as well as other aspects and embodiments described elsewhere herein, the immunotherapeutic agent is an agent that modulates immune responses, for example, a checkpoint inhibitor or a checkpoint agonist. In some embodiments, the immunotherapeutic agent is an agent that enhances anti-tumor immune responses. In some embodiments, the immunotherapeutic agent is an agent that increases cell-mediated immunity. In some embodiments, the immunotherapeutic agent is an agent that increases T-cell activity. In some embodiments, the immunotherapeutic agent is an agent that increases cytolytic T-cell (CTL) activity.

In some embodiments, the present methods of treatment may include administering a crystalline form or crystalline salt form of compound 1 together in combination with a molecule, for example, a binding agent, for example, an antibody or functional fragment thereof that modulates (activates or inhibits) a checkpoint protein. A checkpoint inhibitor can be any molecule, agent, treatment and/or method of inhibiting an immune checkpoint, and/or promoting an inhibitor of an immune checkpoint, e.g., by promoting an intrinsic immune checkpoint inhibitor; inhibiting a transcription factor involved in the expression of an immune checkpoint; and/or by acting in concert with some additional extrinsic factor. For example, a checkpoint inhibitor could include a treatment that inhibits transcription factors involved in the expression of immune checkpoint genes, or promotes the expression of transcription factors for tumor-suppressor genes, e.g., BACH2 (Luan et al., (2016). Transcription Factors and Checkpoint Inhibitor Expression with Age: Markers of Immunosenescence. Blood, 128(22), 5983). Moreover, a checkpoint inhibitor can inhibit the transcription of immune checkpoint genes; the modification and/or processing of immune checkpoint mRNA; the translation of immune checkpoint proteins; and/or molecules involved in immunity or the immune checkpoint pathway, e.g., PD-1 transcription factors such as HIF-1, STAT3, NF-κB, and AP-1, or the activation of common oncogenic pathways such as JAK/STAT, RAS/ERK, or PI3K/AKT/mTOR (Zerdes et al., Genetic, transcriptional and post-translational regulation of the programmed death protein ligand 1 in cancer: biology and clinical correlations, Oncogene volume 37, pages 4639-4661 (2018), the disclosure of which is incorporated herein by reference in its entirety).

Checkpoint inhibitors can include treatments, molecules, agents, and/or methods that regulate immune checkpoints at the transcriptional level, e.g., using the RNA-interference pathway co-suppression, and/or post-transcriptional gene silencing (PTGS) (e.g., microRNAs, miRNA; silencing-RNA, small-interfering-RNA, or short-interfering-RNA (siRNA). Transcriptional regulation of checkpoint molecules has been shown to involve mir-16, which has been shown to target the 3'UTR of the checkpoint mRNAs CD80, CD274 (PD-L1) and CD40 (Leibowitz et al., Post-transcriptional regulation of immune checkpoint genes by mir-16 in melanoma, Annals of Oncology (2017) 28; v428-v448). Mir-33a has also been shown to be involved in regulating the expression of PD-1 in cases of lung adenocarcinoma (Boldini et al., Role of microRNA-33a in regulating the expression of PD-1 in lung adenocarcinoma, Cancer Cell Int. 2017; 17: 105, the disclosure of which is incorporated herein by reference in its entirety).

T-cell-specific aptamer-siRNA chimeras have been suggested as a highly specific method of inhibiting molecules in the immune checkpoint pathway (Hossain et al., The aptamer-siRNA conjugates: reprogramming T cells for cancer therapy, Ther. Deliv. 2015 January; 6(1): 1-4, the disclosure of which is incorporated herein by reference in its entirety).

Alternatively, members of the immune checkpoint pathway can be inhibited using treatments that affect associated pathways, e.g., metabolism. For example, oversupplying the glycolytic intermediate pyruvate in mitochondria from CAD macrophages promoted expression of PD-L1 via induction of the bone morphogenetic protein 4/phosphorylated SMAD1/5/IFN regulatory factor 1 (BMP4/p-SMAD1/5/IRF1) signaling pathway. Accordingly, implementing treatments that modulate the metabolic pathway can result in subsequent modulation of the immunoinhibitory PD-1/PD-L1 checkpoint pathway (Watanabe et al., Pyruvate controls the checkpoint inhibitor PD-L1 and suppresses T cell immunity, J Clin Invest. 2017 Jun. 30; 127(7): 2725-2738).

Checkpoint immunity can be regulated via oncolytic viruses that selectively replicate within tumor cells and induce acute immune responses in the tumor-micro-environment, i.e., by acting as genetic vectors that carry specific agents (e.g., antibodies, miRNA, siRNA, and the like) to cancer cells and effecting their oncolysis and secretion of cytokines and chemokines to synergize with immune checkpoint inhibition (Shi et al., Cancer Immunotherapy: A Focus on the Regulation of Immune Checkpoints, Int J Mol Sci. 2018 May; 19(5): 1389). Currently, there are clinical trials underway that utilize the following viruses as checkpoint inhibitors: poliovirus, measles virus, adenoviruses, poxviruses, herpes simplex virus (HSV), coxsackieviruses, reovirus, Newcastle disease virus (NDV), T-VEC (a herpes virus encoded with GM-CSF (granulocyte-macrophage colony stimulating factor)), and H101 (Shi et al., supra).

Checkpoint inhibitors can operate at the translational level of checkpoint immunity. The translation of mRNA into protein represents a key event in the regulation of gene expression, thus inhibition of immune checkpoint translation is a method in which the immune checkpoint pathway can be inhibited.

Inhibition of the immune checkpoint pathway can occur at any stage of the immune checkpoint translational process. For example, drugs, molecules, agents, treatments, and/or methods can inhibit the initiation process (whereby the 40S ribosomal subunit is recruited to the 5' end of the mRNA and scans the 5'UTR of the mRNA toward its 3' end. Inhibition can occur by targeting the anticodon of the initiator methionyl-transfer RNA (tRNA) (Met-tRNAi), its base-pairing with the start codon, or the recruitment of the 60S subunit to begin elongation and sequential addition of amino acids in the translation of immune-checkpoint-specific genes. Alternatively, a checkpoint inhibitor can inhibit checkpoints at the translational level by preventing the formation of the ternary complex (TC), i.e., eukaryotic initiation factor (eIF)2 (or one or more of its α, β, and γ subunits); GTP; and Met-tRNAi.

Checkpoint inhibition can occur via destabilization of eIF2α by precluding its phosphorylation via protein kinase R (PKR), PERK, GCN2, or HRI, or by precluding TCs from associating with the 40S ribosome and/or other initiation factors, thus preventing the preinitiation complex (PIC) from forming; inhibiting the eIF4F complex and/or its cap-binding protein eIF4E, the scaffolding protein eIF4G, or eIF4A helicase. Methods discussing the translational control of cancer are discussed in Truitt et al., New frontiers in translational control of the cancer genome, Nat Rev Cancer. 2016 Apr. 26; 16(5): 288-304, the disclosure of which is incorporated herein by reference in its entirety.

Checkpoint inhibitors can also include treatments, molecules, agents, and/or methods that regulate immune checkpoints at the cellular and/or protein level, e.g., by inhibiting an immune checkpoint receptor. Inhibition of checkpoints can occur via the use of antibodies, antibody fragments, antigen-binding fragments, small-molecules, and/or other drugs, agents, treatments, and/or methods.

Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response ('block' the immune response) against tumor tissues. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a cytokine, a chemokine, an interferon, an interleukin, a lymphokine, a member of the tumor necrosis factor (TNF) family, or an immunostimulatory oligonucleotide. In some embodiments, the immune checkpoint modulator, i.e. is an inhibitor or antagonist, or is an activator or agonist, for example, a CD28 modulator, a 4-1BB modulator, an OX40 modulator, a CD27 modulator, a CD80 modulator, a CD86 modulator, a CD40 modulator, or a GITR modulator, a Lag-3 modulator, a 41BB modulator, a LIGHT modulator, a CD40 modulator, a GITR modulator, a TGF-beta modulator, a TIM-3 modulator, a SIRP-alpha modulator, a TIGIT modulator, a VSIG8 modulator, a BTLA modulator, a SIGLEC7 modulator, a SIGLEC9 modulator, a ICOS modulator, a B7H3 modulator, a B7H4 modulator, a FAS modulator, and/or a BTNL2 modulator. In some embodiments, the immunotherapeutic agent is an immune checkpoint modulator as described above (e.g., an immune checkpoint modulator antibody, which can be in the form of a monoclonal antibody, a bispecific antibody comprising one or more immune checkpoint antigen binding moieties, a trispecific antibody, or an immune cell-engaging multivalent antibody/fusion protein/construct known in the art).

In some embodiments, the immunotherapeutic agent is an agent that inhibits the activity of PD-1. In some embodiments, the immunotherapeutic agent is an agent that inhibits the activity of PD-L1 and/or PD-L2. In some embodiments, the immunotherapeutic agent is an agent that inhibits the activity of CTLA-4. In some embodiments, the immunotherapeutic agent is an agent that inhibits the activity of CD80 and/or CD86. In some embodiments, the immunotherapeutic agent is an agent that inhibits the activity of TIGIT. In some embodiments, the immunotherapeutic agent is an agent that inhibits the activity of KIR. In some embodiments, the immunotherapeutic agent is an agent that enhances or stimulates the activity of activating immune checkpoint receptors.

PD-1 (also known as Programmed Death 1, CD279, PDCD1) is a cell surface receptor with a critical role in regulating the balance between stimulatory and inhibitory signals in the immune system and maintaining peripheral tolerance (Ishida, Y et al. 1992 EMBO J. 11 3887; Kier, Mary E et al. 2008 Annu Rev Immunol 26 677-704; Okazaki, Taku et al. 2007 International Immunology 19 813-824). PD-1 is an inhibitory member of the immunoglobulin super-family with homology to CD28. The structure of PD-1 is a monomeric type 1 transmembrane protein, consisting of one immunoglobulin variable-like extracellular domain and a cytoplasmic domain containing an immunoreceptor tyrosine-based inhibitory motif (ITIM) and an immunoreceptor tyrosine-based switch motif (ITSM). Expression of PD-1 is inducible on T cells, B cells, natural killer (NK) cells and monocytes, for example upon lymphocyte activation via T cell receptor (TCR) or B cell receptor (BCR) signalling (Kier, Mary E et al. 2008 Annu Rev Immunol 26 677-704; Agata, Y et al 1996 Int Immunol 8 765-72). PD-1 is a receptor for the ligands CD80, CD86, PD-L1 (B7-H1, CD274) and PD-L2 (B7-DC, CD273), which are cell surface expressed members of the B7 family (Freeman, Gordon et al. 2000 J Exp Med 192 1027; Latchman, Y et al. 2001 Nat Immunol 2: 261). Upon ligand engagement, PD-1 recruits phosphatases such as SHP-1 and SHP-2 to its intracellular tyrosine motifs which subsequently dephosphorylate effector molecules activated by TCR or BCR signalling (Chemnitz, J et al. 2004 J Immunol 173: 945-954; Riley, James L 2009 Immunological Reviews 229: 114-125) In this way, PD-1 transduces inhibitory signals into T and B cells only when it is engaged simultaneously with the TCR or BCR.

PD-1 has been demonstrated to down-regulate effector T cell responses via both cell-intrinsic and cell-extrinsic functional mechanisms. Inhibitory signaling through PD-1 induces a state of unresponsiveness in T cells, resulting in the cells being unable to clonally expand or produce optimal levels of effector cytokines. PD-1 may also induce apoptosis in T cells via its ability to inhibit survival signals from co-stimulation, which leads to reduced expression of key anti-apoptotic molecules such as Bcl-XL (Kier, Mary E et al. 2008 Annu Rev Immunol 26: 677-704). In addition to these direct effects, recent publications have implicated PD-1 as being involved in the suppression of effector cells by promoting the induction and maintenance of regulatory T cells (TREG). For example, PD-L1 expressed on dendritic cells was shown to act in synergy with TGF-β to promote the induction of CD4+ FoxP3+TREG with enhanced suppressor function (Francisco, Loise M et al. 2009 J Exp Med 206: 3015-3029).

TIM-3 (also known as T-cell immunoglobulin and mucin-domain containing-3, TIM-3, Hepatitis A virus cellular receptor 2, HAVCR2, HAVcr-2, KIM-3, TIMD-3, TIMD3, Tim-3, and CD366) is a ~33.4-kDa single-pass type I membrane protein involved in immune responses (Sanchez-Fueyo et al., Tim-3 inhibits T helper type 1-mediated auto- and alloimmune responses and promotes immunological tolerance, Nat. Immunol. 4: 1093-1101(2003)).

TIM-3 is selectively expressed on Th1-cells, and phagocytic cells (e.g., macrophages and dendritic cells). The use of siRNA or a blocking antibody to reduce the expression of human TIM-3 resulted in increased secretion of interferon γ (IFN-γ) from CD4 positive T-cells, implicating the inhibitory role of TIM-3 in human T cells. Analysis of clinical samples from autoimmune disease patients showed no expression of TIM-3 in CD4 positive cells. In particular, expression level of TIM-3 is lower and secretion of IFN-γ is higher in T cell clones derived from the cerebrospinal fluid of patients with multiple sclerosis than those in clones derived from normal healthy persons (Koguchi K et al., J Exp Med. 203: 1413-8. (2006)).

TIM-3 is the receptor for the ligand Galectin-9, which is a member of galectin family, molecules ubiquitously expressed on a variety of cell types and which binds 0-galactoside; Phospatidyl serine (PtdSer) (DeKryff et al., T cell/transmembrane, Ig, and mucin-3 allelic variants differentially recognize phosphatidylserine and mediate phagocytosis of apoptotic cells, J Immunol. 2010 Feb. 15; 184(4): 1918-30); High Mobility Group Protein 1 (also known as HMGB1, HMG1, HMG3, SBP-1, HMG-1, and high mobility group box 1) Chiba et al., Tumor-infiltrating DCs suppress nucleic acid-mediated innate immune responses through interactions between the receptor TIM-3 and the alarmin HMGB1, Nat Immunol. 2012 September; 13(9): 832-42); and Carcinoembryonic Antigen Related Cell Adhesion Molecule 1 (also known as CEACAM1, BGP, BGP1, BGP1, carcinoembryonic antigen related cell adhesion molecule 1) (Huang et al., CEACAM1 regulates TIM-3-mediated tolerance and exhaustion, Nature. 2015 Jan. 15; 517 (7534): 386-90).

BTLA (also known as B- and T-lymphocyte attenuator, BTLA1, CD272, and B and T lymphocyte associated) is a ~27.3-kDa single-pass type I membrane protein involved in lymphocyte inhibition during immune response. BTLA is constitutively expressed in both B and T cells. BTLA interacts with HVEM (herpes virus-entry mediator), a member of the tumor-necrosis factor receptor (TNFR) family (Gonzalez et al., Proc. Natl. Acad. Sci. USA, 2005, 102: 1116-21). The interaction of BTLA, which belongs to the CD28 family of the immunoglobulin superfamily, and HVEM, a costimulatory tumor-necrosis factor (TNF) receptor (TNFR), is unique in that it defines a cross talk between these two families of receptors. BTLA contains a membrane proximal immunoreceptor tyrosine-based inhibitory motif (ITIM) and membrane distal immunoreceptor tyrosine-based switch motif (ITSM). Disruption of either the ITIM or ITSM abrogated the ability of BTLA to recruit either SHP1 or SHP2, suggesting that BTLA recruits SHP1 and SHP2 in a manner distinct from PD-1 and both tyrosine motifs are required to block T cell activation. The BTLA cytoplasmic tail also contains a third conserved tyrosine-containing motif within the cytoplasmic domain, similar in sequence to a Grb-2 recruitment site (YXN). Also, a phosphorylated peptide containing this BTLA N-terminal tyrosine motif can interact with GRB2 and the p85 subunit of PI3K in vitro, although the functional effects of this interaction remain unexplored in vivo (Gavrieli et al., Bioochem. Biophysi Res Commun, 2003, 312, 1236-43). BTLA is the receptor for the ligands PTPN6/SHP-1; PTPN11/SHP-2; TNFRSF14/HVEM; and B7H4.

VISTA (also known as V-domain Ig suppressor of T cell activation VSIR, B7-H5, B7H5, GI24, PP2135, SISP1, DD1alpha, VISTA, C10orf54, chromosome 10 open reading frame 54, PD-1H, and V-set immunoregulatory receptor) is a ~33.9-kDa single-pass type I membrane protein involved in T-cell inhibitory response, embryonic stem cells differentiation via BMP4 signaling inhibition, and MMP14-mediated MMP2 activation (Yoon et al., Control of signaling-mediated clearance of apoptotic cells by the tumor suppressor p53, Science. 2015 Jul. 31; 349(6247): 1261669). VISTA interacts with the ligand VSIG-3 (Wang et al., VSIG-3 as a ligand of VISTA inhibits human T-cell function, Immunology. 2019 January; 156(1): 74-85)

LAG-3 (also known as Lymphocyte-activation gene 3, LAG3, CD223, and lymphocyte activating 3) is a ~57.4-kDa single-pass type I membrane protein involved in lymphocyte activation that also binds to HLA class-II antigens. LAG-3 is a member of the immunoglobulin supergene family, and is expressed on activated T cells (Huard et al., 1994, Immunogenetics 39: 213), NK cells (Triebel et al., 1990, J. Exp. Med. 171: 1393-1405), regulatory T cells (Huang et al., 2004, Immunity 21: 503-513; Camisaschi et al., 2010, J Immunol. 184: 6545-6551; Gagliani et al., 2013, Nat Med 19: 739-746), and plasmacytoid dendritic cells (DCs) (Workman et al., 2009, J Immunol 182: 1885-1891). LAG-3 is a membrane protein encoded by a gene located on chromosome 12, and is structurally and genetically related to CD4. Similar to CD4, LAG-3 can interact with MHC class II molecules on the cell surface (Baixeras et al., 1992, J. Exp. Med. 176: 327-337; Huard et al., 1996, Eur. J. Immunol. 26: 1180-1186). It has been suggested that the direct binding of LAG-3 to MHC class II plays a role in down-regulating antigen-dependent stimulation of CD4+ T lymphocytes (Huard et al., 1994, Eur. J. Immunol. 24: 3216-3221) and LAG-3 blockade has also been shown to reinvigorate CD8+ lymphocytes in both tumor or self-antigen (Gross et al., 2007, J Clin Invest. 117: 3383-3392) and viral models (Blackburn et al., 2009, Nat. Immunol. 10: 29-37). Further, the intra-cytoplasmic region of LAG-3 can interact with LAP (LAG-3-associated protein), which is a signal transduction molecule involved in the downregulation of the CD3/TCR activation pathway (Iouzalen et al., 2001, Eur. J. Immunol. 31: 2885-2891). Moreover, CD4+CD25+ regulatory T cells (Treg) have been shown to express LAG-3 upon activation, which contributes to the suppressor activity of Treg cells (Huang, C. et al., 2004, Immunity 21: 503-513). LAG-3 can also negatively regulate T cell homeostasis by Treg cells in both T cell-dependent and independent mechanisms (Workman, C. J. and Vignali, D. A., 2005, J. Immunol. 174: 688-695).

LAG-3 has been shown to interact with MHC class II molecules (Huard et al., CD4/major histocompatibility complex class II interaction analyzed with CD4− and lymphocyte activation gene-3 (LAG-3)-Ig fusion proteins, Eur J Immunol. 1995 September; 25(9): 2718-21).

Additionally, several kinases are known to be checkpoint inhibitors. For example, CHEK-1, CHEK-2, and A2aR.

CHEK-1 (also known as CHK 1 kinase, CHK1, and checkpoint kinase 1) is a ~54.4-kDa serine/threonine-protein kinase that is involved with checkpoint-mediated cell cycle arrest, and the activation of DNA repair in response to the DNA damage and/or unreplicated DNA.

CHEK-2 (also known as CHK2 kinase, CDS1, CHK2, HuCds1, LFS2, PP1425, RAD53, hCds1, and checkpoint kinase 2) is a ~60.9-kDa. serine/threonine-protein kinase involved in checkpoint-mediated cell cycle arrest, DNA-repair activation, and double-strand break-mediated apoptosis.

A2aR (also known as adenosine A2A receptor, ADORA2A, adenosine A2a receptor, A2aR, ADORA2, and RDC8) is a ~44.7-kDa multi-pass membrane receptor for adenosine and other ligands.

In some embodiments, illustrative immunotherapeutic agents can include one or more antibody modulators that target PD-1, PD-L1, PD-L2, CEACAM (e.g., CEACAM-1, -3 and/or -5), CTLA-4, TIM-3, LAG-3, VISTA, BTLA, TIGIT, LAIR1, CD160, 2B4, TGF beta, OX40, 41BB, LIGHT, CD40, GITR, TGF-beta, TIM-3, SIRP-alpha, VSIG8, BTLA, SIGLEC7, SIGLEC9, ICOS, B7H3, B7H4, FAS, and/or BTNL2 among others known in the art. In some embodiments, the immunotherapeutic agent is an agent that increases natural killer (NK) cell activity. In some embodiments, the immunotherapeutic agent is an agent that inhibits suppression of an immune response. In some embodiments, the immunotherapeutic agent is an agent that inhibits suppressor cells or suppressor cell activity. In some embodiments, the immunotherapeutic agent is an agent or therapy that inhibits Treg activity. In some embodiments, the immunotherapeutic agent is an agent that inhibits the activity of inhibitory immune checkpoint receptors.

In some embodiments, the combination of the present disclosure comprises a crystalline form or crystalline salt form of compound 1 and an immunotherapeutic agent, wherein the immunotherapeutic agent includes a T cell modulator chosen from an agonist or an activator of a costimulatory molecule. In one embodiment, the agonist of the costimulatory molecule is chosen from an agonist (e.g., an agonistic antibody or antigen-binding fragment thereof, or a soluble fusion) of GITR, OX40, SLAM (e.g., SLAMF7), HVEM, LIGHT, CD2, CD27, CD28, CDS, ICAM-1, LFA-1 (CD11a/CD18), ICOS (CD278), 4-1BB (CD137), CD30, CD40, BAFFR, CD7, NKG2C, NKp80, CD160, B7-H3, or CD83 ligand. In other embodiments, the effector cell combination includes a bispecific T cell engager (e.g., a bispecific antibody molecule that binds to CD3 and a tumor antigen (e.g., EGFR, PSCA, PSMA, EpCAM, HER2 among others).

In some embodiments, the immunotherapeutic agent is a modulator of PD-1 activity, a modulator of PD-L1 activity, a modulator of PD-L2 activity, a modulator of CTLA-4 activity, a modulator of CD28 activity, a modulator of CD80 activity, a modulator of CD86 activity, a modulator of 4-1BB activity, an modulator of OX40 activity, a modulator of KIR activity, a modulator of Tim-3 activity, a modulator of LAG3 activity, a modulator of CD27 activity, a modulator of CD40 activity, a modulator of GITR activity, a modulator of TIGIT activity, a modulator of CD20 activity, a modulator of CD96 activity, a modulator of IDO1 activity, a modulator of SIRP-alpha activity, a modulator of TIGIT activity, a modulator of VSIG8 activity, a modulator of BTLA activity, a modulator of SIGLEC7 activity, a modulator of SIGLEC9 activity, a modulator of ICOS activity, a modulator of B7H3 activity, a modulator of B7H4 activity, a modulator of FAS activity, a modulator of BTNL2 activity, a cytokine, a chemokine, an interferon, an interleukin, a lymphokine, a member of the tumor necrosis factor (TNF) family, or an immunostimulatory oligonucleotide.

In some embodiments, the immunotherapeutic agent is an immune checkpoint modulator (e.g., an immune checkpoint inhibitor e.g. an inhibitor of PD-1 activity, a modulator of PD-L1 activity, a modulator of PD-L2 activity, a modulator of CTLA-4, or a CD40 agonist (e.g., an anti-CD40 antibody molecule), (xi) an OX40 agonist (e.g., an anti-OX40 antibody molecule), or (xii) a CD27 agonist (e.g., an anti-CD27 antibody molecule). In one embodiment, the immunotherapeutic agent is an inhibitor of: PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta, Galectin 9, CD69, Galectin-1, CD113, GPR56, CD48, GARP, PD1H, LAIR1, TIM-1, and TIM-4. In one embodiment, the inhibitor of an immune checkpoint molecule inhibits PD-1, PD-L1, LAG-3, TIM-3, CEACAM (e.g., CEACAM-1, -3 and/or -5), CTLA-4, or any combination thereof.

In one embodiment, the immunotherapeutic agent is an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, the immunotherapeutic agent used in the combinations disclosed herein (e.g., in combination with a crystalline form or crystalline salt form of compound 1 of the present invention) is an activator or agonist of a costimulatory molecule. In one embodiment, the agonist of the costimulatory molecule is chosen from an agonist (e.g., an agonistic antibody or antigen-binding fragment thereof, or a soluble fusion) of CD2, CD28, CDS, ICAM-1, LFA-1 (CD11a/CD18), ICOS (CD278), 4-1BB (CD137), GITR, CD30, BAFFR, HVEM, CD7, LIGHT, NKG2C, SLAMF7, NKp80, CD160, B7-H3, or CD83 ligand.

Inhibition of an inhibitory molecule can be performed at the DNA, RNA or protein level. In embodiments, an inhibitory nucleic acid (e.g., a dsRNA, siRNA or shRNA), can be used to inhibit expression of an inhibitory molecule. In other embodiments, the inhibitor of an inhibitory signal is, a polypeptide e.g., a soluble ligand (e.g., PD-1-Ig or CTLA-4 Ig), or an antibody or antigen-binding fragment thereof, for example, a monoclonal antibody, a bispecific antibody comprising one or more immune checkpoint antigen binding moieties, a trispecific antibody, or an immune cell-engaging multivalent antibody/fusion protein/construct known in the art that binds to the inhibitory molecule; e.g., an antibody or fragment thereof (also referred to herein as "an antibody molecule") that binds to PD-1, PD-L1, PD-L2, CTLA-4, TIM-3, LAG-3, CEACAM (e.g., CEACAM-1, -3 and/or -5), VISTA, BTLA, TIGIT, LAIR1, CD160, 2B4 and/or TGF beta, Galectin 9, CD69, Galectin-1, CD113, GPR56, CD48, GARP, PD1H, LAIR1, TIM-1, TIM-4, or a combination thereof.

In some embodiments, where the combination comprises a crystalline form or crystalline salt form of compound 1 and an immunotherapeutic agent, wherein the immunotherapeutic agent is a monoclonal antibody or a bispecific antibody. For example, the monoclonal or bispecific antibody may specifically bind a member of the c-Met pathway and/or an immune checkpoint modulator (e.g., the bispecific antibody binds to both a hepatocyte growth factor receptor (HGFR) and an immune checkpoint modulator described herein, such as an antibody that binds PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2 or CD27). In particular embodiments, the bispecific antibody specifically binds a human HGFR protein and one of PD-1, PD-L1, and CTLA-4.

In some of the embodiments of the methods described herein, the immunotherapeutic agent is a PD-1 antagonist, a PD-L1 antagonist, a PD-L2 antagonist, a CTLA-4 antagonist, a CD80 antagonist, a CD86 antagonist, a KIR antagonist, a Tim-3 antagonist, a LAG3 antagonist, a TIGIT antagonist, a CD20 antagonist, a CD96 antagonist, or an IDO1 antagonist.

In some embodiments, the PD-1 antagonist is an antibody that specifically binds PD-1. In some embodiments, the antibody that binds PD-1 is pembrolizumab (KEYTRUDA®, MK-3475; Merck), pidilizumab (CT-011; Curetech Ltd.), nivolumab (OPDIVO®, BMS-936558, MDX-1106; Bristol Myer Squibb), MEDI0680 (AMP-514; AstraZenenca/MedImmune), REGN2810 (Regeneron Pharmaceuticals), BGB-A317 (BeiGene Ltd.), PDR-001 (Novartis), or STI-A1110 (Sorrento Therapeutics). In some embodiments, the antibody that binds PD-1 is described in PCT Publication WO 2014/179664, for example, an antibody identified as APE2058, APE1922, APE1923, APE1924, APE 1950, or APE1963 (Anaptysbio), or an antibody containing the CDR regions of any of these antibodies. In other embodiments, the PD-1 antagonist is a fusion protein that includes the extracellular domain of PD-L1 or PD-L2, for example, AMP-224 (AstraZeneca/Medlmmune). In other embodiments, the PD-1 antagonist is a peptide inhibitor, for example, AUNP-12 (Aurigene).

In some embodiments, the PD-L1 antagonist is an antibody that specifically binds PD-L1. In some embodiments, the antibody that binds PD-L1 is atezolizumab (RG7446, MPDL3280A; Genentech), MED14736 (AstraZeneca/Medlmmune), BMS-936559 (MDX-1105; Bristol Myers Squibb), avelumab (MSB0010718C; Merck KGaA), KD033 (Kadmon), the antibody portion of KD033, or STI-A1014 (Sorrento Therapeutics). In some embodiments, the antibody that binds PD-L1 is described in PCT Publication WO 2014/055897, for example, Ab-14, Ab-16, Ab-30, Ab-31, Ab-42, Ab-50, Ab-52, or Ab-55, or an antibody that contains the CDR regions of any of these antibodies, the disclosure of which is incorporated herein by reference in its entirety.

In some embodiments, the CTLA-4 antagonist is an antibody that specifically binds CTLA-4. In some embodiments, the antibody that binds CTLA-4 is ipilimumab (YERVOY®; Bristol Myer Squibb) or tremelimumab (CP-675, 206; Pfizer). In some embodiments, the CTLA-4 antagonist a CTLA-4 fusion protein or soluble CTLA-4 receptor, for example, KARR-102 (Kahr Medical Ltd.).

In some embodiments, the LAG3 antagonist is an antibody that specifically binds LAG3. In some embodiments, the antibody that binds LAG3 is IMP701 (Prima BioMed), IMP731 (Prima BioMed/GlaxoSmithKline), BMS-986016 (Bristol Myer Squibb), LAG525 (Novartis), and GSK2831781 (GlaxoSmithKline). In some embodiments, the LAG3 antagonist includes a soluble LAG3 receptor, for example, IMP321 (Prima BioMed).

In some embodiments, the KIR antagonist is an antibody that specifically binds KIR. In some embodiments, the antibody that binds KIR is lirilumab (Bristol Myer Squibb/Innate Pharma).

In some embodiments, the immunotherapeutic agent is a cytokine, for example, a chemokine, an interferon, an interleukin, lymphokine, or a member of the tumor necrosis factor family. In some embodiments, the cytokine is IL-2, IL15, or interferon-gamma.

In some embodiments of any of the above aspects or those described elsewhere herein, the cancer is selected from the group consisting of lung cancer (e.g., a non-small cell lung cancer (NSCLC)), a kidney cancer (e.g., a kidney urothelial carcinoma), a bladder cancer (e.g., a bladder urothelial (transitional cell) carcinoma), a breast cancer, a colorectal cancer (e.g., a colon adenocarcinoma), an ovarian cancer, a pancreatic cancer, a gastric carcinoma, an esophageal cancer, a mesothelioma, a melanoma (e.g., a skin melanoma), a head and neck cancer (e.g., a head and neck squamous cell carcinoma (HNSCC)), a thyroid cancer, a sarcoma (e.g., a soft-tissue sarcoma, a fibrosarcoma, a myxosarcoma, a liposarcoma, an osteogenic sarcoma, an osteosarcoma, a chondrosarcoma, an angiosarcoma, an endotheliosarcoma, a lymphangiosarcoma, a lymphangioendotheliosarcoma, a leiomyosarcoma, or a rhabdomyosarcoma), a prostate cancer, a glioblastoma, a cervical cancer, a thymic carcinoma, a leukemia (e.g., an acute lymphocytic leukemia (ALL), an acute myelocytic leukemia (AML), a chronic myelocytic leukemia (CML), a chronic eosinophilic leukemia, or a chronic lymphocytic leukemia (CLL)), a lymphoma (e.g., a Hodgkin lymphoma or a non-Hodgkin lymphoma (NHL)), a myeloma (e.g., a multiple myeloma (MM)), a mycoses fungoides, a merkel cell cancer, a hematologic malignancy, a cancer of hematological tissues, a B cell cancer, a bronchus cancer, a stomach cancer, a brain or central nervous system cancer, a peripheral nervous system cancer, a uterine or endometrial cancer, a cancer of the oral cavity or pharynx, a liver cancer, a testicular cancer, a biliary tract cancer, a small bowel or appendix cancer, a salivary gland cancer, an adrenal gland cancer, adrenal cortex carcinoma, an adenocarcinoma, an inflammatory myofibroblastic tumor, a gastrointestinal stromal tumor (GIST), a colon cancer, a myelodysplastic syndrome (MDS), a myeloproliferative disorder (MPD), a polycythemia Vera, a chordoma, a synovioma, an Ewing's tumor, a squamous cell carcinoma, a basal cell carcinoma, an adenocarcinoma, a sweat gland carcinoma, a sebaceous gland carcinoma, a papillary carcinoma, a papillary adenocarcinoma, a medullary carcinoma, a bronchogenic carcinoma, a renal cell carcinoma, a hepatoma, a bile duct carcinoma, a choriocarcinoma, a seminoma, an embryonal carcinoma, a Wilms' tumor, a bladder carcinoma, an epithelial carcinoma, a glioma, anaplastic astrocytoma, an astrocytoma, a medulloblastoma, a craniopharyngioma, an ependymoma, a pinealoma, a hemangioblastoma, an acoustic neuroma, an oligodendroglioma, a meningioma, a neuroblastoma, a retinoblastoma, a follicular lymphoma, a diffuse large B-cell lymphoma, a mantle cell lymphoma, a hepatocellular carcinoma, a thyroid cancer, a small cell cancer, an essential thrombocythemia, an agnogenic myeloid metaplasia, a hypereosinophilic syndrome, a systemic mastocytosis, a familiar hypereosinophilia, a neuroendocrine cancer, or a carcinoid tumor.

In some embodiments of any of the above aspects or those described elsewhere herein, the subject's cancer or tumor does not respond to immune checkpoint inhibition (e.g., to any immune checkpoint inhibitor described herein, such as a PD-1 antagonist or PD-L1 antagonist) or the subject's cancer or tumor has progressed following an initial response to immune checkpoint inhibition (e.g., to any immune checkpoint inhibitor described herein, such as a PD-1 antagonist or PD-L1 antagonist).

In various embodiments, the immunotherapeutic agent can comprise an antibody or an antigen binding fragment thereof. Within this definition, immune checkpoint inhibitors include bispecific antibodies and immune cell-engaging multivalent antibody/fusion protein/constructs known in the art. In some embodiments, immunotherapeutic agents which comprise bispecific antibodies may include bispecific antibodies that are bivalent and bind either the same epitope of the immune checkpoint molecule, two different epitopes of the same immune checkpoint molecule or different epitopes of two different immune checkpoints.

Persons of ordinary skill in the art can implement several bispecific antibody formats known in the field to target one or more of CTLA4, PD1, PD-L1 TIM-3, LAG-3, various B-7 ligands, B7H3, B7H4, CHK 1 and CHK2 kinases, BTLA, A2aR, OX40, 41BB, LIGHT, CD40, GITR, TGF-beta, SIRP-alpha, TIGIT, VSIG8, SIGLEC7, SIGLEC9, ICOS, FAS, BTNL2 and other for use in the combination described herein.

In various embodiments, the immunotherapeutic agent can include am immune cell-engaging multivalent antibody/fusion protein/construct.

In an embodiment of the disclosure, the checkpoint inhibitor, in combination with a crystalline form or crystalline salt form of compound 1, is used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression.

In a further embodiment of the disclosure, provided herein is a combination therapy for treating cancer, which comprises a crystalline form or crystalline salt form of compound 1 and a checkpoint inhibitor with the potential to elicit potent and durable immune responses with enhanced therapeutic benefit and more manageable toxicity.

In a further embodiment of the disclosure, provided herein is a combination therapy for treating cancer, which comprises a crystalline form or crystalline salt form of compound 1 and an immune checkpoint inhibitor. In an embodiment of the disclosure provided herein is a method for treating cancer and/or preventing the establishment of metastases by employing a crystalline form or crystalline salt form of compound 1 of the present invention, which acts synergistically with a checkpoint inhibitor.

In further embodiments, the disclosure provides methods for one or more of the following: 1) reducing or inhibiting growth, proliferation, mobility or invasiveness of tumor or cancer cells that potentially or do develop metastases, 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established, 4) reducing or inhibiting formation or establishment of additional metastasis after the metastasis has been formed or established, 5) prolonged overall survival, 6) prolonged progression free survival, or 7) disease stabilization. The methods include administering to a subject in need thereof a crystalline form or crystalline salt form of compound 1 of the present invention, in combination with a check point inhibitor as described herein.

In an embodiment of the disclosure, administration of a crystalline form or crystalline salt form of compound 1 in combination with the immunotherapeutic agent, provides a detectable or measurable improvement in a condition of a given subject, such as alleviating or ameliorating one or more adverse (physical) symptoms or consequences associated with the presence of a cell proliferative or cellular hyperproliferative disorder, neoplasia, tumor or cancer, or metastasis, i.e., a therapeutic benefit or a beneficial effect.

A therapeutic benefit or beneficial effect is any objective or subjective, transient, temporary, or long-term improvement in the condition or pathology, or a reduction in onset, severity, duration or frequency of adverse symptom associated with or caused by cell proliferation or a cellular hyperproliferative disorder such as a neoplasia, tumor or cancer, or metastasis. It may lead to improved survival. A satisfactory clinical endpoint of a treatment method in accordance with the disclosure is achieved, for example, when there is an incremental or a partial reduction in severity, duration or frequency of one or more associated pathologies, adverse symptoms or complications, or inhibition or reversal of one or more of the physiological, biochemical or cellular manifestations or characteristics of cell proliferation or a cellular hyperproliferative disorder such as a neoplasia, tumor or cancer, or metastasis. A therapeutic benefit or improvement therefore may be, but is not limited to destruction of target proliferating cells (e.g., neoplasia, tumor or cancer, or metastasis) or ablation of one or more, most or all pathologies, adverse symptoms or complications associated with or caused by cell proliferation or the cellular hyperproliferative disorder such as a neoplasia, tumor or cancer, or metastasis. However, a therapeutic benefit or improvement need not be a cure or complete destruction of all target proliferating cells (e.g., neoplasia, tumor or cancer, or metastasis) or ablation of all pathologies, adverse symptoms or complications associated with or caused by cell proliferation or the cellular hyperproliferative disorder such as a neoplasia, tumor or cancer, or metastasis. For example, partial destruction of a tumor or cancer cell mass, or a stabilization of the tumor or cancer mass, size or cell numbers by inhibiting progression or worsening of the tumor or cancer, can reduce mortality and prolong lifespan even if only for a few days, weeks or months, even though a portion or the bulk of the tumor or cancer mass, size or cells remain.

Specific non-limiting examples of therapeutic benefit include a reduction in neoplasia, tumor or cancer, or metastasis volume (size or cell mass) or numbers of cells; inhibiting or preventing an increase in neoplasia, tumor or cancer volume (e.g., stabilizing); slowing or inhibiting neoplasia, tumor or cancer progression, worsening or metastasis; or inhibiting neoplasia, tumor or cancer proliferation, growth or metastasis.

In an embodiment of the disclosure, administration of the immunotherapeutic agent, in combination therapy with a crystalline form or crystalline salt form of compound 1, provides a detectable or measurable improvement or overall response according to the irRC (as derived from time-point response assessments and based on tumor burden), including one of more of the following: (i) irCR-complete disappearance of all lesions, whether measurable or not, and no new lesions (confirmation by a repeat, consecutive assessment no less than 4 weeks from the date first documented), (ii)

irPR-decrease in tumor burden ≥50% relative to baseline (confirmed by a consecutive assessment at least 4 weeks after first documentation).

Optionally, any method described herein may not take effect immediately. For example, treatment may be followed by an increase in the neoplasia, tumor or cancer cell numbers or mass, but over time eventual stabilization or reduction in tumor cell mass, size or numbers of cells in a given subject may subsequently occur.

Additional adverse symptoms and complications associated with neoplasia, tumor, cancer and metastasis that can be inhibited, reduced, decreased, delayed or prevented include, for example, nausea, lack of appetite, lethargy, pain and discomfort. Thus, a partial or complete decrease or reduction in the severity, duration or frequency of adverse symptom or complication associated with or caused by a cellular hyperproliferative disorder, an improvement in the subject's quality of life and/or well-being, such as increased energy, appetite, psychological well-being, are all particular non-limiting examples of therapeutic benefit.

A therapeutic benefit or improvement therefore can also include a subjective improvement in the quality of life of a treated subject. In an additional embodiment, a method prolongs or extends lifespan (survival) of the subject. In a further embodiment, a method improves the quality of life of the subject.

In one embodiment, administration of the immunotherapeutic agent, in combination therapy with a crystalline form or crystalline salt form of compound 1, results in a clinically relevant improvement in one or more markers of disease status and progression selected from one or more of the following: (i) overall survival, (ii) progression-free survival, (iii) overall response rate, (iv) reduction in metastatic disease, (v) circulating levels of tumor antigens such as carbohydrate antigen 19.9 (CAT9.9) and carcinoembryonic antigen (CEA) or others depending on tumor, (vii) nutritional status (weight, appetite, serum albumin), (viii) pain control or analgesic use, and (ix) CRP/albumin ratio.

Treatment with a crystalline form or crystalline salt form of compound 1 in combination with an immunotherapeutic agent gives rise to more complex immunity including not only the development of innate immunity and type-1 immunity, but also immunoregulation which more efficiently restores appropriate immune functions.

In various exemplary methods, a checkpoint inhibitor antibody (monoclonal or polyclonal, bispecific, trispecific, or an immune cell-engaging multivalent antibody/fusion protein/construct) directed to a checkpoint molecule of interest (e.g., PD-1) may be sequenced and the polynucleotide sequence may then be cloned into a vector for expression or propagation. The sequence encoding the antibody or antigen-binding fragment thereof of interest may be maintained in vector in a host cell and the host cell can then be expanded and frozen for future use. Production of recombinant monoclonal antibodies in cell culture can be carried out through cloning of antibody genes from B cells by means known in the art. See, e.g. Tiller et al., 2008, J. Immunol. Methods 329: 112; U.S. Pat. No. 7,314,622.

Pharmaceutical compositions containing a crystalline form or crystalline salt form of compound 1 according to the present disclosure will comprise an effective amount of a crystalline form or crystalline salt form of compound 1, an immunotherapeutic agent, and/or both, typically dispersed in a pharmaceutically acceptable excipient. The phrases "pharmaceutically or pharmacologically acceptable" refers to molecular entities and compositions that do not produce adverse, allergic or other untoward reaction when administered to animal, such as, for example, a human, as appropriate. The preparation of an pharmaceutical composition that contains a crystalline form or crystalline salt form of compound 1 will be known to those of skill in the art in light of the present disclosure, as exemplified by Remington's Pharmaceutical Sciences, 21$^{st}$ Ed., (Lippincott, Williams and Wilkins Philadelphia, P A, 2006). Moreover, for animal (e.g., human) administration, it will be understood that preparations should meet sterility, pyrogenicity, general safety and purity standards. A specific example of a pharmacologically acceptable excipient for a combination composition, containing a crystalline form or crystalline salt form of compound 1 in admixture with an immunotherapeutic agent as described herein is borate buffer or sterile saline solution (0.9% NaCl).

Formulations of the an immunotherapeutic agent, for example an immune checkpoint modulator antibody used in accordance with the present disclosure can be prepared for storage by mixing an antibody having the desired degree of purity with optional pharmaceutically acceptable excipients or stabilizers as amply described and illustrated in Remington's Pharmaceutical Sciences 21$^{st}$ Ed., (Lippincott, Williams and Wilkins Philadelphia, P A, 2006), in the form of lyophilized formulations or aqueous solutions and/or suspensions. Acceptable excipients, buffers or stabilizers are nontoxic to recipients at the dosages and concentrations employed, and include suitable aqueous and/or non-aqueous excipients that may be employed in the pharmaceutical compositions of the disclosure, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants, buffers such as phosphate, citrate, and other organic acids. Antioxidants may be included, for example, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like; preservatives (such as octade-cyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues). Other exemplary pharmaceutically acceptable excipients may include polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In one illustrative embodiment, the pharmaceutical compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. In some embodiments, the checkpoint inhibitor antibodies or antigen-binding fragments thereof of the present disclosure are formulated for and can be lyophilized for storage and reconstituted in a suitable excipient prior to use according to art-known lyophilization and reconstitution techniques. In one exemplary pharmaceutical composition containing one or more checkpoint inhibitor antibodies or antigen-binding fragment thereof, the composition is formulated as a sterile, preservative-free solution of one or more checkpoint inhibitor antibodies or antigen-binding fragment thereof for intravenous or subcutaneous administration. The formulation can be supplied as either a single-use, prefilled pen, as a single-use, for example containing about 1 mL prefilled glass syringe, or as a single-use institutional use vial. Preferably, the pharmaceutical composition containing the checkpoint inhibitor antibody or antigen-binding fragment thereof is clear and colorless, with a pH of about 6.9-5.0, preferably a pH of 6.5-5.0, and even more preferably a pH ranging from about 6.0 to about 5.0. In various embodiments, the formulations comprising the pharmaceutical compositions can contain from about 500 mg to about 10 mg, or from about 400 mg to about 20 mg, or from about 300 mg to about 30 mg or from about 200 mg to about 50 mg of the checkpoint inhibitor antibody or antigen-binding fragment thereof per mL of solution when reconstituted and administered to the subject. Exemplary injection or infusion excipients can include mannitol, citric acid monohydrate, dibasic sodium phosphate dihydrate, monobasic sodium phosphate dihydrate, polysorbate 80, sodium chloride, sodium citrate and water for parenteral administration, for example, intravenously, intramuscularly, intraperitoneally, or subcutaneous administration.

In another exemplary embodiment, one or more immunotherapeutic agents, or an antigen-binding fragment thereof is formulated for intravenous or subcutaneous administration as a sterile aqueous solution containing 1-75 mg/mL, or more preferably, about 5-60 mg/mL, or yet more preferably, about 10-50 mg/mL, or even more preferably, about 10-40 mg/mL of antibody, with sodium acetate, polysorbate 80, and sodium chloride at a pH ranging from about 5 to 6. Preferably, the intravenous or subcutaneous formulation is a sterile aqueous solution containing 5, 10, 15, 20, 25, 30, 35, 40, 45, or 50 mg/mL of the immunotherapeutic agent, for example, an immune checkpoint inhibitor antibody or an antigen-binding fragment thereof, with 20 mM sodium acetate, 0.2 mg/mL polysorbate 80, and 140 mM sodium chloride at pH 5.5. Further, a solution comprising a checkpoint inhibitor antibody or an antigen-binding fragment thereof, can comprise, among many other compounds, histidine, mannitol, sucrose, trehalose, glycine, poly(ethylene) glycol, EDTA, methionine, and any combination thereof, and many other compounds known in the relevant art.

In one embodiment, a pharmaceutical composition of the present disclosure comprises the following components: 5-500 mg of an immunotherapeutic agent or antigen-binding fragment thereof of the present disclosure, 10 mM histidine, 5% sucrose, and 0.01% polysorbate 80 at pH 5.8, with a crystalline form or crystalline salt form of compound 1. This composition may be provided as a lyophilized powder. When the powder is reconstituted at full volume, the composition retains the same formulation. Alternatively, the powder may be reconstituted at half volume, in which case the composition comprises 10-500 mg of an immunotherapeutic agent or antigen-binding fragment thereof of the present disclosure, 20 mM histidine, 10% sucrose, and 0.02% polysorbate 80 at pH 5.8.

In one embodiment, part of the dose is administered by an intravenous bolus and the rest by infusion of the immunotherapeutic agent formulation. For example, from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof, may be given as a bolus, and the rest of the antibody dose may be administered by intravenous injection. A predetermined dose of the immunotherapeutic agent, or antigen-binding fragment thereof, may be administered, for example, over a period of an hour to two hours to five hours.

In a further embodiment, part of the dose is administered by a subcutaneous injection and/or infusion in the form of a bolus and the rest by infusion of the immunotherapeutic agent formulation. In some exemplary doses, the immunotherapeutic agent formulation can be administered subcutaneously in a dose ranging from about 0.001 to about 200 mg/kg, for example, from about 0.001 mg/kg to about 100 mg/kg, or from about 0.001 mg/kg to about 50 mg/kg, or from about 0.001 mg/kg to about 10 mg/kg intravenous injection of the immunotherapeutic agent, or antigen-binding fragment thereof. In some embodiments the dose may be given as a bolus, and the rest of the immunotherapeutic agent dose may be administered by subcutaneous or intravenous injection. A predetermined dose of the immunotherapeutic agent, or antigen-binding fragment thereof, may be administered, for example, over a period of an hour to two hours to five hours.

The formulation herein may also contain more than one active compound as necessary for the particular indication being treated, preferably those with complementary activities that do not adversely affect each other. For example, it may be desirable to provide one or more immunotherapeutic agents with other specificities. Alternatively, or in addition, the composition may comprise an anti-inflammatory agent, a chemotherapeutic agent, a cytotoxic agent, a cytokine, a growth inhibitory agent and/or a small molecule antagonist. Such molecules are suitably present in combination in amounts that are effective for the purpose intended.

The formulations to be used for in vivo administration should be sterile, or nearly so. This is readily accomplished by filtration through sterile filtration membranes.

In various embodiments, illustrative formulations of the pharmaceutical compositions described herein can be prepared using methods widely known in the field of pharmaceutical formulations. In general, such preparatory methods can include the step of bringing the active ingredient into association with a excipient or one or more other accessory ingredients, and then, if desirable, packaging the product into a desired single- or multi-dose unit.

In some embodiments, the composition comprising a crystalline form or crystalline salt form of compound 1 can be also delivered in a vesicle, and the immunotherapeutic agent can be delivered in the same liposome formulation, or in a separate formulation that is compatible with the liposomal formulation containing the crystalline form or crystalline salt form of compound 1. In some illustrative examples, a liposome containing one or more liposomal surface moieties for example, polyethylene glycol, antibodies and antibody fragments thereof that target a desired tumor surface antigen, receptor, growth factor, glycoprotein, glycolipid or neoantigen, which are selectively transported into specific cells or organs, thus enhance targeted drug delivery.

In another embodiment, a crystalline form or crystalline salt form of compound 1 can be delivered in a vesicle, in particular a liposome (see Langer, Science 249: 1527-1533 (1990); Treat et al., in LIPOSOMES IN THE THERAPY OF INFECTIOUS DISEASE AND CANCER, Lopez-Berestein and Fidler (eds.), Liss, N.Y., pp. 353-365 (1989); Lopez-Berestein, ibid., pp. 317-327; see generally ibid.).

In yet another embodiment, a crystalline form or crystalline salt form of compound 1, or the composition containing the combination, or a composition containing the immunotherapeutic agent, can be delivered in a controlled release system. In one embodiment, a pump can be used (see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989)). In another embodiment, controlled release of the crystalline form or crystalline salt form of compound 1 can comprise polymeric materials to provide sustained, intermediate, pulsatile, or alternate release (see MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Ranger and Peppas, J. Macromol. Sci. Rev. Macromol. Chem. 23: 61 (1983); see also Levy et al., Science 228: 190 (1985); During et al., Ann. Neurol. 25: 351 (1989); Howard et al., J. Neurosurg. 71: 105 (1989)). Other controlled-release systems discussed in the review by Langer (Science 249: 1527-1533 (1990)) can be used.

The optimum concentration of the active ingredient(s) in the chosen medium can be determined empirically, according to procedures well known to the skilled artisan, and will depend on the ultimate pharmaceutical formulation desired and the use to be employed.

The present disclosure also provides a pharmaceutical pack or kit comprising one or more containers filled with one or more of the ingredients of the pharmaceutical compositions of the disclosure, which at minimum will include a crystalline form or crystalline salt form of compound 1 and one or more checkpoint inhibitor antibodies or antigen-binding fragment thereof as described herein. In other embodiments, the kit may contain one or more further containers providing a pharmaceutically acceptable excipient, for example a diluent. In one embodiment a kit may comprise at least one container, wherein the container can include a crystalline form or crystalline salt form of compound 1, a checkpoint inhibitor antibody or an antigen-binding fragment thereof of the present disclosure. The kit may also include a set of instructions for preparing and administering the final pharmaceutical composition to the subject in need thereof, for the treatment of a checkpoint molecule-mediated disease or disorder.

In some embodiments of the present disclosure, the immunotherapeutic agent is a population of immune cells, which can be administered in combination with a crystalline form or crystalline salt form of compound 1 to treat a subject with cancer. In some embodiments, the immunotherapeutic agent is a population of immune cells, such as leukocytes (nucleated white blood cells), comprising (e.g., expressing) a receptor that binds to an antigen of interest. A leukocyte of the present disclosure may be, for example, a neutrophil, eosinophil, basophil, lymphocyte or a monocyte. In some embodiments, a leukocyte is a lymphocyte. Examples of lymphocytes include T cells, B cells, Natural Killer (NK) cells or NKT cells. In some embodiments, a T-cell is a CD4+ Th (T helper) cell, a CD8+θcytotoxic T cell, a γδT cell or a regulatory (suppressor) T cell. In some embodiments, an immune cell is a dendritic cell.

Immune cells of the present disclosure, in some embodiments, are genetically engineered to express an antigen-binding receptor. A cell is considered "engineered" if it contains an engineered (exogenous) nucleic acid. Engineered nucleic acids of the present disclosure may be introduced into a cell by any known (e.g., conventional) method. For example, an engineered nucleic acid may be introduced into a cell by electroporation (see, e.g., Heiser W. C. Transcription Factor Protocols: Methods in Molecular Biology™ 2000; 130: 117-134), chemical (e.g., calcium phosphate or lipid), transfection (see, e.g., Lewis W. H., et al., Somatic Cell Genet. 1980 May; 6(3): 333-47; Chen C., et al., Mol Cell Biol. 1987 August; 7(8): 2745-2752), fusion with bacterial protoplasts containing recombinant plasmids (see, e.g., Schaffner W. Proc Natl Acad Sci USA. 1980 April; 77(4): 2163-7), microinjection of purified DNA directly into the nucleus of the cell (see, e.g., Capecchi M. R. Cell. 1980 November; 22(2 Pt 2): 479-88), or retrovirus transduction.

Some aspects of the present disclosure provide an "adoptive cell" approach, which involves isolating immune cells (e.g., T-cells) from a subject with cancer, genetically engineering the immune cells (e.g., to express an antigen-binding receptor, such as a chimeric antigen receptor), expanding the cells ex vivo, and then re-introducing the immune cells into the subject. This method results in a greater number of engineered immune cells in the subject relative to what could be achieved by conventional gene delivery and vaccination methods. In some embodiments, immune cells are isolated from a subject, expanded ex vivo without genetic modification, and then re-introduced into the subject.

Immune cells of the present disclosure comprise receptors that bind to antigens, such as an antigen encoded by an exogenously delivered nucleic acid, as provided herein. In some embodiments, a leukocyte is modified (e.g., genetically modified) to express a receptor that binds to an antigen. The receptor may be, in some embodiments, a naturally-occurring antigen receptor (normally expressed on the immune cell), recombinant antigen receptor (not normally expressed on the immune cell) or a chimeric antigen receptor (CAR). Naturally-occurring and recombinant antigen receptors encompassed by the present disclosure include T cell receptors, B cell receptors, NK cell receptors, NKT cell receptors and dendritic cell receptors. A "chimeric antigen receptor" refers to an artificial immune cell receptor that is engineered to recognize and bind to an antigen expressed by tumor cells. Generally, a CAR is designed for a T cell and is a chimera of a signaling domain of the T-cell receptor (TcR) complex and an antigen-recognizing domain (e.g., a single chain fragment (scFv) of an antibody) (Enblad et al., Human Gene Therapy. 2015; 26(8): 498-505), the disclosure of which is incorporated herein by reference in its entirety.

In some embodiments, an antigen binding receptor is a chimeric antigen receptor (CAR). A T cell that expresses a CAR is referred to as a "CAR T cell." A CAR T cell receptor, in some embodiments, comprises a signaling domain of the T-cell receptor (TcR) complex and an antigen-recognizing domain (e.g., a single chain fragment (scFv) of an antibody) (Enblad et al., Human Gene Therapy. 2015; 26(8): 498-505) the disclosure of which is incorporated herein by reference in its entirety.

There are four generations of CARs, each of which contains different components. First generation CARs join an antibody-derived scFv to the CD3zeta (zeta. or z) intracellular signaling domain of the T-cell receptor through hinge and transmembrane domains. Second generation CARs incorporate an additional domain, e.g., CD28, 4-1BB (41BB), or ICOS, to supply a costimulatory signal. Third-generation CARs contain two costimulatory domains fused with the TcR CD3-zeta chain. Third-generation costimulatory domains may include, e.g., a combination of CD3z, CD27, CD28, 4-1BB, ICOS, or OX40. CARs, in some embodiments, contain an ectodomain (e.g., CD3), commonly derived from a single chain variable fragment (scFv), a hinge, a transmembrane domain, and an endodomain with one (first generation), two (second generation), or three (third generation) signaling domains derived from CD3Z and/or co-stimulatory molecules (Maude et al., Blood. 2015; 125(26): 4017-4023; Kakarla and Gottschalk, Cancer J. 2014; 20(2): 151-155) the disclosure of which is incorporated herein by reference in its entirety.

In some embodiments, the chimeric antigen receptor (CAR) is a T-cell redirected for universal cytokine killing (TRUCK), also known as a fourth generation CAR. TRUCKs are CAR-redirected T-cells used as vehicles to produce and release a transgenic cytokine that accumulates in the targeted tissue, e.g., a targeted tumor tissue. The transgenic cytokine is released upon CAR engagement of the target. TRUCK cells may deposit a variety of therapeutic cytokines in the target. This may result in therapeutic concentrations at the targeted site and avoid systemic toxicity.

CARs typically differ in their functional properties. The CD3zeta signaling domain of the T-cell receptor, when engaged, will activate and induce proliferation of T-cells but can lead to anergy (a lack of reaction by the body's defense mechanisms, resulting in direct induction of peripheral lymphocyte tolerance). Lymphocytes are considered anergic when they fail to respond to a specific antigen. The addition of a costimulatory domain in second-generation CARs improved replicative capacity and persistence of modified T-cells. Similar antitumor effects are observed in vitro with CD28 or 4-1BB CARs, but preclinical in vivo studies suggest that 4-1BB CARs may produce superior proliferation and/or persistence. Clinical trials suggest that both of these second-generation CARs are capable of inducing substantial T-cell proliferation in vivo, but CARs containing the 4-1BB costimulatory domain appear to persist longer. Third generation CARs combine multiple signaling domains (costimulatory) to augment potency. Fourth generation CARs are additionally modified with a constitutive or inducible expression cassette for a transgenic cytokine, which is released by the CAR T-cell to modulate the T-cell response. See, for example, Enblad et al., Human Gene Therapy. 2015; 26(8): 498-505; Chmielewski and Hinrich, Expert Opinion on Biological Therapy. 2015; 15(8): 1145-1154 the disclosures of which are incorporated herein by reference in their entireties.

In some embodiments, an illustrative immunotherapeutic agent is a first generation chimeric antigen receptor CAR. In some embodiments, a chimeric antigen receptor is a second generation CAR. In some embodiments, a chimeric antigen receptor is a third generation CAR. In some embodiments, the chimeric antigen receptor is a fourth generation CAR or a T-cell redirected for universal cytokine killing (TRUCK).

In some embodiments, a chimeric antigen receptor (CAR) comprises an extracellular domain comprising an antigen binding domain, a transmembrane domain, and a cytoplasmic domain. In some embodiments, a CAR is fully human. In some embodiments, the antigen binding domain of a CAR is specific for one or more antigens. In some embodiments, a "spacer" domain or "hinge" domain is located between an extracellular domain (comprising the antigen binding domain) and a transmembrane domain of a CAR, or between a cytoplasmic domain and a transmembrane domain of the CAR. A "spacer domain" refers to any oligopeptide or polypeptide that functions to link the transmembrane domain to the extracellular domain and/or the cytoplasmic domain in the polypeptide chain. A "hinge domain" refers to any oligopeptide or polypeptide that functions to provide flexibility to the CAR, or domains thereof, or to prevent steric hindrance of the CAR, or domains thereof. In some embodiments, a spacer domain or hinge domain may comprise up to 300 amino acids (e.g., 10 to 100 amino acids, or 5 to 20 amino acids). In some embodiments, one or more spacer domain(s) may be included in other regions of a CAR.

In some embodiments, a CAR of the disclosure comprises an antigen binding domain, such as a single chain Fv (scFv) specific for a tumor antigen. The choice of binding domain depends upon the type and number of ligands that define the surface of a target cell. For example, the antigen binding domain may be chosen to recognize a ligand that acts as a cell surface marker on target cells associated with a particular disease state, such as cancer or an autoimmune disease. Thus, examples of cell surface markers that may act as ligands for the antigen binding domain in the CAR of the present disclosure include those associated with cancer cells and/or other forms of diseased cells. In some embodiments, a CAR is engineered to target a tumor antigen of interest by way of engineering a desired antigen binding domain that specifically binds to an antigen on a tumor cell encoded by an engineered nucleic acid, as provided herein.

An antigen binding domain (e.g., an scFv) that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antigen binding domain (e.g., an scFv) that specifically binds to a first target antigen may or may not specifically bind to a second target antigen. As such, "specific binding" does not necessarily require (although it can include) exclusive binding.

In some embodiments, immune cells expressing a CAR are genetically modified to recognize multiple targets or antigens, which permits the recognition of unique target or antigen expression patterns on tumor cells. Examples of CARs that can bind multiple targets include: "split signal CARs," which limit complete immune cell activation to tumors expressing multiple antigens; "tandem CARs" (TanCARs), which contain ectodomains having two scFvs; and "universal ectodomain CARs," which incorporate avidin or a fluorescein isothiocyanate (FITC)-specific scFv to recognize tumor cells that have been incubated with tagged monoclonal antibodies (Mabs).

A CAR is considered "bispecific" if it recognizes two distinct antigens (has two distinct antigen recognition domains). In some embodiments, a bispecific CAR is comprised of two distinct antigen recognition domains present in tandem on a single transgenic receptor (referred to as a TanCAR; see, e.g., Grada Z et al. Molecular Therapy Nucleic Acids 2013; 2: e105, incorporated herein by reference in its entirety). Thus, methods, in some embodiments, comprise delivering to a tumor a combination comprising a crystalline form or crystalline salt form of compound 1 and an immunotherapeutic agent, wherein the immunotherapeutic agent is an engineered nucleic acid that encodes an antigen, or delivering to a tumor an engineered nucleic acid that induces expression of a self-antigen, and delivering to the tumor an immune cell expressing a bispecific CAR that binds to two antigens, one of which is encoded by the engineered nucleic acid.

In some embodiments, a CAR is an antigen-specific inhibitory CAR (iCAR), which may be used, for example, to avoid off-tumor toxicity (Fedorov, V D et al. Sci. Transl. Med. published online Dec. 11, 2013, incorporated herein by reference in its entirety). iCARs contain an antigen-specific inhibitory receptor, for example, to block nonspecific immunosuppression, which may result from extra tumor target expression. iCARs may be based, for example, on inhibitory molecules CTLA-4 or PD-1. In some embodiments, these iCARs block T cell responses from T cells activated by either their endogenous T cell receptor or an activating CAR. In some embodiments, this inhibiting effect is temporary.

In some embodiments, CARs may be used in adoptive cell transfer, wherein immune cells are removed from a subject and modified so that they express receptors specific to an antigen, e.g., a tumor-specific antigen. The modified immune cells, which may then recognize and kill the cancer cells, are reintroduced into the subject (Pule, et al., Cytotherapy. 2003; 5(3): 211-226; Maude et al., Blood. 2015; 125(26): 4017-4023, each of which is incorporated herein by reference in their entireties).

According to other aspects of the disclosure, the tumor antigenic component in the vaccine of the invention is any natural or synthetic tumor-associated protein or peptide or combination of tumor-associated proteins and/or peptides or glycoproteins or glycopeptides. In still yet other aspects, the antigenic component can be patient-specific or common to many or most patients with a particular type of cancer. According to one aspect, the antigenic component consists of a cell lysate derived from tumor tissue removed from the patient being treated. In another aspect, the lysate can be engineered or synthesized from exosomes derived from tumor tissue. In yet another aspect, the antigenic component consists of a cell lysate derived from tumor tissue extracted from one or more unrelated individuals or from tumor-cell lines.

In various embodiments, an illustrative immunotherapeutic agent comprises one or more cancer vaccines, for use in combination with a crystalline form or crystalline salt form of compound 1. The tumor-associated antigen component of the vaccine may be manufactured by any of a variety of well-known techniques. For individual protein components, the antigenic protein is isolated from tumor tissue or a tumor-cell line by standard chromatographic means such as high-pressure liquid chromatography or affinity chromatography or, alternatively, it is synthesized by standard recombinant DNA technology in a suitable expression system, such as *E. coli*, yeast or plants. The tumor-associated antigenic protein is then purified from the expression system by standard chromatographic means. In the case of peptide antigenic components, these are generally prepared by standard automated synthesis. Proteins and peptides can be modified by addition of amino acids, lipids and other agents to improve their incorporation into the delivery system of the vaccine (such as a multilamellar liposome). For a tumor-associated antigenic component derived from the patient's own tumor, or tumors from other individuals, or cell lines, the tumor tissue, or a single cell suspension derived from the tumor tissue, is typically homogenized in a suitable buffer. The homogenate can also be fractionated, such as by centrifugation, to isolate particular cellular components such as cell membranes or soluble material. The tumor material can be used directly or tumor-associated antigens can be extracted for incorporation in the vaccine using a buffer containing a low concentration of a suitable agent such as a detergent. An example of a suitable detergent for extracting antigenic proteins from tumor tissue, tumor cells, and tumor-cell membranes is diheptanoyl phosphatidylcholine. Exosomes derived from tumor tissue or tumor cells, whether autologous or heterologous to the patient, can be used for the antigenic component for incorporation in the vaccine or as a starting material for extraction of tumor-associated antigens.

In some embodiments of the present disclosure, a combination therapy comprises a crystalline form or crystalline salt form of compound 1 in combination with a cancer vaccine immunotherapeutic agent. In various examples, the cancer vaccine includes at least one tumor-associated antigen, at least one immunostimulant, and optionally, at least one cell-based immunotherapeutic agent. In some embodiments, the immunostimulant component in the cancer vaccine of the disclosure is any Biological Response Modifier (BRM) with the ability to enhance the therapeutic cancer vaccine's effectiveness to induce humoral and cellular immune responses against cancer cells in a patient. According to one aspect, the immunostimulant is a cytokine or combination of cytokines. Examples of such cytokines include the interferons, such as IFN-gamma, the interleukins, such as IL-2, IL-15 and IL-23, the colony stimulating factors, such as M-CSF and GM-CSF, and tumor necrosis factor. According to another aspect, the immunostimulant component of the disclosed cancer vaccine includes one or more adjuvant-type immunostimulatory agents such as APC Toll-like Receptor agonists or costimulatory/cell adhesion membrane proteins, with or without immunostimulatory cytokines. Examples of Toll-like Receptor agonists include lipid A and CpG, and costimulatory/adhesion proteins such as CD80, CD86, and ICAM-1.

In some embodiments, the immunostimulant is selected from the group consisting of IFN-gamma (IFN-γ), IL-2, IL-15, IL-23, M-CSF, GM-CSF, tumor necrosis factor, lipid A, CpG, CD80, CD86, and ICAM-1, or combinations thereof. According to other aspects, the cell-based immunotherapeutic agent is selected from the group consisting of dendritic cells, tumor-infiltrating T lymphocytes, chimeric antigen receptor-modified T effector cells directed to the patient's tumor type, B lymphocytes, natural killer cells, bone marrow cells, and any other cell of a patient's immune system, or combinations thereof. In one aspect, the cancer vaccine immunostimulant includes one or more cytokines, such as interleukin 2 (IL-2), GM-CSF, M-CSF, and interferon-gamma (IFN-γ), one or more Toll-like Receptor agonists and/or adjuvants, such as monophosphoryl lipid A, lipid A, muramyl dipeptide (MDP) lipid conjugate and double stranded RNA, or one or more costimulatory membrane proteins and/or cell adhesion proteins, such CD80, CD86 and ICAM-1, or any combination of the above. In one aspect, the cancer vaccine includes an immunostimulant that is a cytokine selected from the group consisting of interleukin 2 (IL-2), GM-CSF, M-CSF, and interferon-gamma (IFN-γ). In another aspect, the cancer vaccine includes an immunostimulant that is a Toll-like Receptor agonist and/or adjuvant selected from the group consisting of monophosphoryl lipid A, lipid A, and muramyl dipeptide (MDP) lipid conjugate and double stranded RNA. In yet another aspect, the cancer vaccine includes an immunostimulant that is a costimulatory membrane protein and/or cell adhesion protein selected from the group consisting of CD80, CD86, and ICAM-1.

In various embodiments, an immunotherapeutic agent can include a cancer vaccine, wherein the cancer vaccine incorporates any tumor antigen that can be potentially used to construct a fusion protein according to the invention and particularly the following: (a) cancer-testis antigens including NY-ESO-1, SSX2, SCP1 as well as RAGE, BAGE, GAGE and MAGE family polypeptides, for example, GAGE-1, GAGE-2, MAGE-1 MAGE-2, MAGE-3, MAGE-4, MAGE-5, MAGE-6, and MAGE-12, which can be used, for example, to address melanoma, lung, head and neck, NSCLC, breast, gastrointestinal, and bladder tumors; (b) mutated antigens, including p53, associated with various solid tumors, e.g., colorectal, lung, head and neck cancer; p21/Ras associated with, e.g., melanoma, pancreatic cancer and colorectal cancer; CDK4, associated with, e.g., melanoma; MUM1 associated with, e.g., melanoma; caspase-8 associated with, e.g., head and neck cancer; CIA 0205 associated with, e.g., bladder cancer; HLA-A2-R1701, beta catenin associated with, e.g., melanoma; TCR associated with, e.g., T-cell non-Hodgkin lymphoma; BCR-abl associated with, e.g., chronic myelogenous leukemia; triosephosphate isomerase; KIA 0205; CDC-27, and LDLR-FUT; (c) over-expressed antigens, including, Galectin 4 associated with, e.g., colorectal cancer; Galectin 9 associated with, e.g., Hodgkin's disease; proteinase 3 associated with, e.g., chronic myelogenous leukemia; WT 1 associated with, e.g., various leukemias; carbonic anhydrase associated with, e.g., renal cancer; aldolase A associated with, e.g., lung cancer; PRAME associated with, e.g., melanoma; HER-2/neu associated with, e.g., breast, colon, lung and ovarian cancer; mammaglobin, alpha-fetoprotein associated with, e.g., hepatoma; KSA associated with, e.g., colorectal cancer; gastrin associated with, e.g., pancreatic and gastric cancer; telomerase catalytic protein, MUC-1 associated with, e.g., breast and ovarian cancer; G-250 associated with, e.g., renal cell carcinoma; p53 associated with, e.g., breast, colon cancer; and carcinoembryonic antigen associated with, e.g., breast cancer, lung cancer, and cancers of the gastrointestinal tract such as colorectal cancer; (d) shared antigens, including melanoma-melanocyte differentiation antigens such as MART-1/Melan A; gpl00; MC1R; melanocyte-stimulating hormone receptor; tyrosinase; tyrosinase related protein-1/TRP1 and tyrosinase related protein-2/TRP2 associated with, e.g., melanoma; (e) prostate associated antigens including PAP, PSA, PSMA, PSH-P1, PSM-P1, PSM-P2, associated with e.g., prostate cancer; (f) immunoglobulin idiotypes associated with myeloma and B cell lymphomas. In certain embodiments, the one or more TAA can be selected from pi 5, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, pl85erbB2, pl 80erbB-3, c-met, mn-23H1, TAG-72-4, CA 19-9, CA 72-4, CAM 17.1, NuMa, K-ras, pi 6, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS or any combinations thereof.

In some embodiments, the present disclosure provides a crystalline form or crystalline salt form of compound 1 for use in combination with a cancer vaccine which can include a tumor antigen comprising the entire amino acid sequence, a portion of it, or specific immunogenic epitopes of a human protein.

In various embodiments, an illustrative immunotherapeutic agent may include an mRNA operable to encode any one or more of the aforementioned cancer antigens useful for synthesizing a cancer vaccine. In some illustrative embodiments, the mRNA based cancer vaccine may have one or more of the following properties: a) the mRNA encoding each cancer antigen is interspersed by cleavage sensitive sites; b) the mRNA encoding each cancer antigen is linked directly to one another without a linker; c) the mRNA encoding each cancer antigen is linked to one another with a single nucleotide linker; d) each cancer antigen comprises a 20-40 amino acids and includes a centrally located SNP mutation; e) at least 40% of the cancer antigens have a highest affinity for class I MHC molecules from the subject; f) at least 40% of the cancer antigens have a highest affinity for class II MHC molecules from the subject; g) at least 40% of the cancer antigens have a predicted binding affinity of IC>500 nM for HLA-A, HLA-B and/or DRB1; h) the mRNA encodes 1 to 15 cancer antigens; i) 10-60% of the cancer antigens have a binding affinity for class I MHC and 10-60% of the cancer antigens have a binding affinity for class II MHC; and/or j) the mRNA encoding the cancer antigens is arranged such that the cancer antigens are ordered to minimize pseudo-epitopes.

In various embodiments, the combination comprising a crystalline form or crystalline salt form of compound 1 and a cancer vaccine immunotherapeutic agent as disclosed herein can be used to illicit an immune response in a subject against a cancer antigen. The method involves administering to the subject a RNA vaccine comprising at least one RNA polynucleotide having an open reading frame encoding at least one antigenic polypeptide or an immunogenic fragment thereof, thereby inducing in the subject an immune response specific to the antigenic polypeptide or an immunogenic fragment thereof, in combination with administering a crystalline form or crystalline salt form of compound 1 either in the same composition or a separate composition, administered at the same time, or sequentially dosed, wherein the anti-antigenic polypeptide antibody titer in the subject is increased following vaccination relative to anti-antigenic polypeptide antibody titer in a subject vaccinated with a prophylactically effective dose of a traditional vaccine against the cancer. An "anti-antigenic polypeptide antibody" is a serum antibody the binds specifically to the antigenic polypeptide.

A prophylactically effective dose is a therapeutically effective dose that prevents advancement of cancer at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, and the like. In exemplary embodiments, a traditional vaccine is a vaccine that has achieved regulatory approval and/or is registered by a national drug regulatory body, for example the Food and Drug Administration (FDA) in the United States or the European Medicines Agency (EMA.)

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the cancer. In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the cancer.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for sero-protection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

In preferred aspects, RNA vaccine immunotherapeutic agents of the present disclosure (e.g., mRNA vaccines) produce prophylactically- and/or therapeutically-efficacious levels, concentrations and/or titers of antigen-specific antibodies in the blood or serum of a vaccinated subject. As defined herein, the term antibody titer refers to the amount of antigen-specific antibody produced in a subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, and the like.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of g/ml or are measured in units of IU/L (International Units per liter) or mIU/ml (milli International Units per ml).

In exemplary embodiments of the invention, an efficacious vaccine produces >0.5 μg/mL, >0.1 μg/mL, >0.2 μg/mL, >0.35 μg/mL, >0.5 μg/mL, >1 μg/mL, >2 μg/mL, >5 μg/mL or >10 μg/mL. In exemplary embodiments of the invention, an efficacious vaccine produces >10 mIU/mL, >20 mIU/mL, >50 mIU/mL, >100 mIU/mL, >200 mIU/mL, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay. Also provided are nucleic acid vaccines comprising one or more RNA polynucleotides having an open reading frame encoding a first antigenic polypeptide or a concatemeric polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce neutralizing antibodies within one week of a single administration. In some embodiments, the adjuvant is selected from a cationic peptide and an immunostimulatory nucleic acid. In some embodiments, the cationic peptide is protamine.

Immunotherapeutic agents comprising a nucleic acid vaccine comprising one or more RNA polynucleotides having an open reading frame comprising at least one chemical modification or optionally no nucleotide modification, the open reading frame encoding a first antigenic polypeptide or a concatemeric polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Aspects of the invention also provide a unit of use vaccine, comprising between 10 μg and 400 μg of one or more RNA polynucleotides having an open reading frame comprising at least one chemical modification or optionally no nucleotide modification, the open reading frame encoding a first antigenic polypeptide or a concatemeric polypeptide, and a pharmaceutically acceptable excipient, formulated for delivery to a human subject. In some embodiments, the vaccine further comprises a cationic lipid nanoparticle.

Aspects of the invention provide methods of creating, maintaining or restoring antigenic memory to a tumor in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 μg/kg and 400 μg/kg of a nucleic acid vaccine comprising one or more RNA polynucleotides having an open reading frame encoding a first antigenic polypeptide or a concatemeric polypeptide in an effective amount to vaccinate the subject.

Other aspects provide nucleic acid vaccines comprising one or more RNA polynucleotides having an open reading frame comprising at least one chemical modification, the open reading frame encoding a first antigenic polypeptide or a concatemeric polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

In some embodiments, a crystalline form or crystalline salt form of compound 1 can be used in combination with a bispecific antibody immunotherapeutic agent. The bispecific antibody can include a protein construct having a first antigen binding moiety and a second antigen binding site that binds to a cytotoxic immune cell. The first antigen binding site can bind to a tumor antigen that is specifically being treated with the combination of the present invention. For example, the first antigen binding moiety may bind to a non-limiting example of tumor antigens selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin αVβ3, Integrin α5β1, MUC1, ERBB2, ERBB3, MET, IGF1R, EPHA3, TRAILR1, TRAILR2, RANKL, FAP and Tenascin among others. In some embodiments, the first antigen binding moiety has specificity to a protein or a peptide that is overexpressed on a tumor cell as compared to a corresponding non-tumor cell. In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor.

The second antigen-binding moiety is any molecule that specifically binds to an antigen or protein or polypeptide expressed on the surface of a cytotoxic immune cell (a CIK cell). Exemplary non-limiting antigens expressed on the surface of the cytotoxic immune cells suitable for use with the present disclosure may include CD2, CD3, CD4, CD5, CD8, CD11a, CD11b, CD14, CD16a, CD27, CD28, CD45, CD45RA, CD56, CD62L, the Fc receptor, LFA, LFA-1, TCRαβ, CCR7, macrophage inflammatory protein 1a, perforin, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell. In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for modulation with the present disclosure may include CD2, CD3, CD4, CD5, CD8, CD11a, CD11b, CD14, CD16a, CD27, CD28, CD45, CD45RA, CD56, CD62L, the Fc receptor, LFA, LFA-1, TCRαβ, CCR7, macrophage inflammatory protein 1a, perform, PD-1, PD-L1, PD-L2, or CTLA-4, LAG-3, OX40, 41BB, LIGHT, CD40, GITR, TGF-beta, TIM-3, SIRP-alpha, TIGIT, VSIG8, BTLA, SIGLEC7, SIGLEC9, ICOS, B7H3, B7H4, FAS, BTNL2, CD27 and Fas ligand. In other embodiments, the bispecific antibody modulator is an activator of a costimulatory molecule (e.g., an OX40 agonist). In one embodiment, the OX40 agonist is a bispecific antibody molecule to OX40 and another tumor antigen or a costimulatory antigen. The OX40 agonist can be administered alone, or in combination with other immunomodulators, e.g., in combination with an inhibitor (for example an antibody construct) of PD-1, PD-L1, CTLA-4, CEACAM (e.g., CEACAM-1, -3 and/or -5), TIM-3 or LAG-3. In some embodiments, the anti-OX40 antibody molecule is a bispecific antibody that binds to GITR and PD-1, PD-L1, CTLA-4, CEACAM (e.g., CEACAM-1, -3 and/or -5), TIM-3 or LAG-3. In one exemplary embodiment, an OX40 antibody molecule is administered in combination with an anti-PD-1 antibody molecule (e.g., an anti-PD-1 molecule as described herein). The OX40 antibody molecule and the anti-PD-1 antibody molecule may be in the form of separate antibody composition, or as a bispecific antibody molecule. In other embodiments, the OX40 agonist can be administered in combination with other costimulatory molecule, e.g., an agonist of GITR, CD2, CD27, CD28, CDS, ICAM-1, LFA-1 (CD11a/CD18), ICOS (CD278), 4-1BB (CD137), CD30, CD40, BAFFR, HVEM, CD7, LIGHT, NKG2C, SLAMF7, NKp80, CD160, B7-H3, or CD83 ligand. In some embodiments, the second antigen binding moiety binds to the Fc receptor on the cytotoxic immune cell, e.g., CIK cell.

In some embodiments, the bispecific antibody immunotherapeutic agent has specificities for a tumor antigen and a CIK cell, which brings the tumor antigen expressing tumor cell in close proximity of the CIK cell, leading to the elimination of the tumor cell through anti-tumor cytotoxicity of CIK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, a crystalline form or crystalline salt form of compound 1 can be used in combination with an immune cell-engaging multivalent antibody/fusion protein/construct immunotherapeutic agent. In various embodiments, an exemplary immunotherapeutic agent can include immune cell-engaging multivalent antibody/fusion protein/construct which may comprise a recombinant structure, for example, all engineered antibodies that do not imitate the original IgG structure. Here, different strategies to multimerize antibody fragments are utilized. For example, shortening the peptide linker between the V domains forces the scFv to self-associate into a dimer (diabody; 55 kDa). Bispecific diabodies are formed by the noncovalent association of two VHA-VLB and VHB-VLA fragments expressed in the same cell. This leads to the formation of heterodimers with two different binding sites. Single-chain diabodies (sc-diabodies) are bispecific molecules where the VHA-VLB and VHB-VLA fragments are linked together by an additional third linker. Tandem-diabodies (Tandabs) are tetravalent bispecific antibodies generated by two scDiabodies.

Also included are the di-diabodies known in the art. This 130-kDa molecule is formed by the fusion of a diabody to the N-terminus of the CH3 domain of an IgG, resulting in an IgG-like structure. Further diabody derivatives are the triabody and the tetra-body, which fold into trimeric and tetrameric fragments by shortening the linker to <5 or 0-2 residues. Also exemplified are (scFv)2 constructs known as 'bispecific T cell engager' (BITE). BITEs are bispecific single-chain antibodies consisting of two scFv antibody fragments, joined via a flexible linker, that are directed against a surface antigen on target cells and CD3 on T cells. Also exemplified are bivalent (Fab)2 and trivalent (Fab)3 antibody formats. Also exemplified are minibodies and trimerbodies generated from scFvs. Exemplary constructs useful to target tumor antigens as can include one or more of: Diabody, Single-chain (sc)-diabody (scFv)2, Minianti-body, Minibody, Barnase-barstar, scFv-Fc, sc(Fab)2, Trimeric antibody constructs, Triabody antibody constructs, Trimerbody antibody constructs, Tribody antibody constructs, Collabody antibody constructs, (scFv-TNFa)3, F(ab)3/DNL. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, a crystalline form or crystalline salt form of compound 1 can be used in combination with a radioconjugate immunotherapeutic agent.

In various embodiments, a radioconjugate is a small molecule or large molecule (herein referred to as a "cell targeting agent"), for example and polypeptide, an antibody or an antibody fragment thereof, that is coupled to or otherwise affixed to a radionuclide, or a plurality of radionuclides, such that the binding of the radioconjugate to its target (a protein or molecule on or in a cancer cell), will lead to the death or morbidity of said cancer cell. In various embodiments, the radioconjugate can be a cell targeting agent labelled with a radionuclide, or the cell targeting agent may be coupled or otherwise affixed to a particle, or microparticle, or nanoparticle containing a plurality of radionuclides, wherein the radionuclides are the same or different. Methods for synthesizing radioconjugates are known in the art, and may include the class of immunoglobulin or antigen binding parts thereof, that are conjugated to a toxic radionuclide.

In some embodiments, the molecule that binds to the cancer cell can be known as a "cell targeting agent". As used herein, an exemplary cell targeting agent can allow the drug-containing nanoparticles or radionuclide to target the specific types of cells of interest. Examples of cell targeting agents include, but are not limited to, small molecules (e.g., folate, adenosine, purine) and large molecule (e.g., peptide or antibody) that bind to or target a tumor associated antigen. Examples of tumor associated antigens include, but are not limited to, adenosine receptors, alpha v beta 3, aminopeptidase P, alpha fetoprotein, cancer antigen 125, carcinoembryonic antigen, cCaveolin-1, chemokine receptors, clusterin, oncofetal antigens, CD20, epithelial tumor antigen, melanoma associated antigen, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyosinase, and tyrosine kinases. In some embodiments, the cell targeting agent is folate or a folate derivative that binds specifically to folate receptors (FRs). In some embodiments, the cell targeting agent is an antibody, a bispecific antibody, a trispecific antibody or an antigen binding construct thereof, that specifically binds to a cancer antigen selected from: EGFR, HGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin $\alpha V\beta 3$, Integrin $\alpha 5\beta 1$, MUC1, ERBB2, ERBB3, MET, IGF1R, EPHA3, TRAILR1, TRAILR2, RANKL, FAP and Tenascin among others.

The use of folate as a targeting agent in the radioconjugate also allow both tumor cells and regulatory T (Treg) cells to be targeted for destruction. It is well accepted that high numbers of Treg cells suppress tumor immunity. Specifically, Treg cells suppress (foreign and self) reactive T cells without killing them through contact-dependent or cytokine (e.g., IL-10, TGF-beta., and the like) secretion. FR4 is selectively upregulated on Treg cells. It has been shown that antibody blockade of FR4 depleted Treg cells and provoked tumor immunity in tumor-bearing mice. Thus, folate-coated PBM nanoparticles carrying a cytotoxic agent would take FR-expressing cells for their destruction, which would both directly (i.e., BrCa cell) and indirectly (i.e., breast tumor associated and peripheral Treg cells) inhibit tumor progression.

In another further embodiment, the targeting agent is an antibody or peptide, or immune cell-engaging multivalent antibody/fusion protein/constructs capable of binding tumor associated antigens consisting of but not limited to: adenosine receptors, alpha v beta 3, aminopeptidase P, alpha fetoprotein, cancer antigen 125, carcinoembryonic antigen, caveolin-1, chemokine receptors, clusterin, oncofetal antigens, CD20, Human Growth Factor Receptor (HGFR), epithelial tumor antigen, melanoma associated antigen, MUC1, Ras, p53, Her2/Neu, ErbB2, ErbB3, ErbB4, folate receptor, prostate-specific membrane antigen, prostate specific antigen, purine receptors, radiation-induced cell surface receptor, serpin B3, serpin B4, squamous cell carcinoma antigens, thrombospondin, tumor antigen 4, tumor-associated glycoprotein 72, tyrosinase, tyrosine kinases, and the like.

In some embodiments, a crystalline form or crystalline salt form of compound 1 as described herein can be used in combination with a vaccination protocol for the treatment of cancer. In some embodiments, a crystalline form or crystalline salt form of compound 1 as described herein can be used in combination with an immunotherapeutic agent such as a vaccine. In various embodiments, exemplary vaccines include those used to stimulate the immune response to cancer antigens.

The amount of both the crystalline form or crystalline salt form of compound 1 as disclosed herein and the additional one or more additional therapeutic agents (in those compositions which comprise an additional therapeutic agent as described above) that may be combined with excipient materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the crystalline form or crystalline salt form of compound 1 as disclosed herein may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-10,000 μg/kg body weight/day of the additional therapeutic agent can be administered.

In some embodiments, the crystalline forms or crystalline salt forms of compound 1 as disclosed herein can be combined with one or more inhibitors of the following kinases for the treatment of a disease disclosed herein such as cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, 1NS-R, IGF-1R, IR-R, PDGFαR, PDGFβ/R, CSFIR, KIT, FLK-II, KDR/FLK-1, FLK-4, fit-1, FGFR1, FGFR2, FGFR3, FGFR4, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYR, FRK, JAK, ABL, ALK, CDK7, CDK12, CDK13, KRAS, and B-Raf. In some embodiments, the crystalline forms or salt forms of compound 1 as disclosed herein can be combined with one or more inhibitors of CD47 and MALT1 proteins for the treatment of cancer.

In some embodiments, the crystalline forms or crystalline salt forms of compound 1 as disclosed herein can be used in combination with one or more Poly ADP ribose polymerase (PARP) inhibitors for the treatment of a disease disclosed herein such as cancer. Exemplary PARP inhibitors include, but are not limited to, olaparib (Lynparza®), rucaprib (Rubraca®) niraparib (Zejula®), talzoparib (Talzenna®) and TPST-1120.

In some embodiments, the crystalline forms or crystalline salt forms of compound 1 as disclosed herein can be used in combination therapy with any of the kinase inhibitors disclosed herein for the treatment of diseases such as cancer. Exemplary kinase inhibitors include imatinib, baricitinib gefitinib, erlotinib, sorafenib, dasatinib, sunitinib, lapatinib, nilotinib, pirfenidone, zanubrutinib, updacitinib, fedratinib, entrectinib, alpelisib, pazopanib, crizotinib, vemurafenib, vandetanib, ruxolitinib, axitinib, bosutinib, regorafenib, tofacitinib, cabozantinib, ponatinib, trametinib, dabrafenib, afatinib, ibrutinib, ceritinib, idelalisib, nintedanib, palbociclib, lenvatinib, cobimetinib, abemaciclib, acalabrutinib, alectinib, binimetinib, brigatinib, encorafenib, erdafitinib, everolimus, fostamatinib, gilter, larotrectinib, lorlatinib, netarsudil, osimertinib, pexidartinib, ribociclib, temsirolimus, XL-147, XL-765, XL-499, and XL-880. In some embodiments, a compound as described herein can be used in combination with a HSP90 inhibitor (e.g., XL888), liver X receptor (LXR) modulators, retinoid-related orphan receptor gamma (RORy) modulators, a CK1 inhibitor, a CK1-a inhibitor, a Wnt pathway inhibitor (e.g., SST-215), or a mineralocorticoid receptor inhibitor, (e.g., esaxerenone or XL-550) for the treatment of a disease disclosed herein such as cancer.

In some embodiments, the crystalline forms or crystalline salt forms of compound 1 as disclosed herein can be used in combination with polatuzumab vedotin for the treatment of a disease disclosed herein such as cancer.

Labeled Compounds and Assay Methods

Another aspect relates to labeled crystalline forms or crystalline salt forms of the present invention (radio-labeled, fluorescent-labeled, etc.) that would be useful not only in imaging techniques but also in assays, both in vitro and in vivo, for localizing and quantitating TAM kinases in tissue samples, including human, and for identifying TAM kinase ligands by inhibition binding of a labeled compound. Accordingly, the present invention includes TAM kinase assays that contain such labeled compounds.

The present invention further includes isotopically-labeled crystalline forms or crystalline salt forms of the present invention. An "isotopically" or "radio-labeled" compound is a crystalline form or crystalline salt form of the present invention where one or more atoms are replaced or substituted by an atom having an atomic mass or mass number different from the atomic mass or mass number typically found in nature (i.e., naturally occurring). Suitable radionuclides that may be incorporated in crystalline forms or crystalline salt forms of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. The radionuclide that is incorporated in the instant radio-labeled compounds will depend on the specific application of that radio-labeled compound. For example, for in vitro metalloprotease labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$, or $^{77}Br$ will generally be most useful. In some embodiments, the crystalline forms or crystalline salt forms described herein in which one or more hydrogens is/are replaced by deuterium, such as hydrogen bonded to a carbon atom. Such compounds exhibit increased resistance to metabolism and are thus useful for increasing the half-life of any compound when administered to a mammal, particularly a human.

It is understood that a "radio-labeled" or "labeled compound" is a compound that has incorporated at least one radionuclide. In some embodiments, the radionuclide is selected from the group consisting of $^{3}H$, $^{14}C$, $^{125}I$, $^{35}S$, and $^{82}Br$.

The present invention can further include synthetic methods for incorporating radio-isotopes into crystalline forms or crystalline salt forms of the present invention. Synthetic methods for incorporating radio-isotopes into organic compounds are well known in the art, and a person of ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a TAM by monitoring its concentration variation when contacting with the TAM kinases, through tracking of the labeling. For example, a test compound (labeled) can be evaluated for its ability to reduce binding of another compound which is known to bind to a TAM kinase (i.e., standard compound). Accordingly, the ability of a test compound to compete with the standard compound for binding to the TAM kinase directly correlates to its binding affinity. Conversely, in some other screening assays, the standard compound is labeled, and test compounds are unlabeled. Accordingly, the concentration of the labeled standard compound is monitored in order to evaluate the competition between the standard compound and the test compound, and the relative binding affinity of the test compound is thus ascertained.

PREPARATIONS AND EXAMPLES

General Experimental Techniques

Aqueous Slurry Experiments: Salts of Compound 1 that were determined to have aqueous solubility less than 1 mg/mL were slurried in 20 mL of water at ambient temperature for 1 day. Solids were then collected by vacuum filtration and analyzed by XRPD.

Crash Cooling (CC): Concentrated solutions of Compound 1 and various counterions were prepared in MeOH at elevated temperature with stirring. Capped vials containing hot solutions were transferred to the freezer (~-20° C.) and rapidly cooled. Solids that were formed were collected. If no solids were present, additional crystallization techniques were employed.

Crash Precipitation (CP): Clear solutions of Compound 1 and coformer were prepared in various solvents at RT. Aliquots of various anti-solvents were added to the solution, slowly, with gentle stirring until solids crashed out of solution. Mixtures were allowed to stir for a specified period of time. Solids that formed were collected by positive-pressure filtration.

Fast Cooling (FC): Concentrated solutions of Compound 1 and various counterions were prepared in acetone or MeOH at elevated temperature with stirring. Capped vials containing hot solutions were transferred to the bench top at ambient temperature. Solids that were formed were collected. If no solids were present, additional crystallization techniques were employed.

Fast Evaporation (FE): Clear solutions of Compound 1 and coformer were prepared in various solvents. Vials were left uncapped and solvent evaporated at ambient conditions.

Interconversion Slurry: A slurry of Compound 1 Form A was prepared by adding enough solids to a given solvent system at ambient conditions so that undissolved solids were present. The mixture was then agitated for an extended period of time to ensure saturation. Solids of the forms of interest were then added to an aliquot of the saturated solution (filtered through a 0.2-μm nylon filter) so that undissolved solids were present. The mixture was then agitated at ambient temperature for an extended period of time, and the solids were isolated.

Isolation Techniques: In general, isolation was done quickly after removing non-ambient samples from their respective temperature control devices to minimize equilibration to ambient temperature prior to isolation of the solids.

Decanting LiquidPhase: Some of the solids isolated from solution-based crystallization techniques were collected by centrifuging the suspension (if needed) and discarding the liquid phase, leaving behind damp solids. Solids were dried briefly (e.g., air dried or dried under nitrogen) unless specified as "analyzed damp" herein.

Positive-Pressure Filtration: Solids were collected on 0.2-μm nylon or PTFE filters by pressing a slurry through a syringe and Swinnex filter holder assembly. In general, solids were dried briefly by blowing a 20-mL syringe of air over the filter. If designated as "analyzed damp" herein, solids were left damp with mother liquor. Some samples were additionally dried briefly under a gentle stream of nitrogen gas prior to analysis.

Vacuum Filtration: Solids were collected on paper or nylon filters by vacuum filtration and air dried on the filters under reduced pressure briefly before transferring to a vial.

Reaction Crystallization (RC): A mixture of Compound 1 and various coformers were combined in an elevated temperature, acetone slurry, such that the molarity of coformer was 2-fold greater than the API. The solution stirred for a given period of time. Additional crystallization techniques were employed when clear solutions were observed.

Stability Testing: Various Compound 1 salts were placed in open vials within a 75% RH chamber (saturated sodium chloride solution). The RH chamber was placed in a 40° C. oven for 15-16 days. Samples were analyzed by PLM and XRPD upon the end of the duration.

Slow Cooling (SC): Concentrated solutions of Compound 1 and various coformers were prepared in a variety of solvents at elevated temperatures with stirring. Vials were capped in the heated sample block and the hot plate was turned off, allowing the vials to gradually cool to ambient temperature in the heated vial block. Clear solutions, upon cooling to ambient, were further cooled in the refrigerator (5 to 7° C.) and/or the freezer (~-20° C.). If no solids were present, additional crystallization techniques were employed.

Slow Evaporation: Solutions were prepared in various solvents with agitation and, typically, filtered through a 0.2-μm nylon or PTFE filter. Each solution was allowed to evaporate from a covered vial (such as loosely capped or covered with perforated aluminum foil) at ambient conditions, unless otherwise stated. Solutions were allowed to evaporate to dryness unless designated as partial evaporations (solid present with a small amount of solvent remaining), in which case solids were isolated as described herein.

Solubility Estimation: Aliquots of various solvents were added to measured amounts of Compound 1 with agitation (typically sonication) at stated temperatures until complete dissolution was achieved, as judged by visual observation. If dissolution occurred after the addition of the first aliquot, values are reported as ">." If dissolution did not occur, values are reported as "<."

Aqueous Solubility Estimation: Aliquots of water were added to measured amounts of various Compound 1 salts with sonication.

Slurry Experiments: Saturated solutions of Compound 1 and various coformers were prepared in a variety of solvents and solvent mixtures. Mixtures were stirred at ambient and elevated temperatures for the noted duration of time. Solids were collected by the stated technique and additional crystallization techniques were employed where appropriate.

Vacuum Oven Desolvation: Salts of Compound 1 that were determined to be solvates by various analytical methods underwent an attempted desolvation. Samples were placed in a vacuum oven at temperatures ranging from ambient to 80° C. for a given period of time. Samples were analyzed by XRPD and/or TGA for determination of desolvation success.

Vapor Diffusion: Concentrated solutions were prepared in various solvents and, typically, filtered through a 0.2-μm nylon or PTFE filter. The filtered solution was dispensed into a small vial, which was then placed inside a larger vial containing anti-solvent. The small vial was left uncapped and the larger vial was capped to allow vapor diffusion to occur. Any solids present were isolated as described herein.

Vapor Stressing: Select solids were transferred to a small vial, which was then placed inside a larger vial containing solvent. The small vial was left uncapped and the larger vial was capped to allow vapor stressing to occur at the stated temperature.

Coformer means one or more pharmaceutically acceptable bases and/or pharmaceutically acceptable acids disclosed herein in association with Compound 1. Exemplary coformers as used herein include fumaric acid, HCl, and phosphoric acid.

Instrumental Techniques

Differential Scanning Calorimetry (DSC): DSC was performed using a Mettler-Toledo DSC3+ differential scanning calorimeter. Temperature calibration was performed using adamantane, phenyl salicylate, indium, tin, and zinc. The sample was placed into a hermetically sealed or an open aluminum DSC pan, and the weight was accurately recorded. A weighed aluminum pan configured as the sample pan was placed on the reference side of the cell. The samples were analyzed from −30 to 250° C. at a ramp rate of 10° C./min. Although thermograms are plotted by reference temperature (x-axis), results are reported according to sample temperatures.

Dynamic Vapor Sorption (DVS)

a. VTI: Automated vapor sorption (VS) data were collected on a VTI SGA-100 Vapor Sorption Analyzer. NaCl and PVP were used as calibration standards. Samples were dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

b. Intrinsic: Automated vapor sorption (VS) data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Hot stage Microscopy (HSM): Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 20× objective with crossed polarizers and a first order red compensator. Images were captured using SPOT software (v. 4.5.9).

Optical Microscopy: Samples were observed under a Motic or Wolfe optical microscope with crossed polarizers or under a Leica stereomicroscope with a first order red compensator with crossed polarizers.

pKa and log P Determination: pKa and log P determination were performed by Pion Inc./Sirius Analytical Instruments Ltd. in East Sussex, United Kingdom.

Solution Proton Nuclear Magnetic Resonance Spectroscopy ($^1$HNMR): The solution $^1$H NMR spectra were acquired by Spectral Data Services of Champaign, IL. The samples were prepared by dissolving approximately 5-10 mg of sample in DMSO-$d_6$. The data acquisition parameters are displayed on the first page of each spectrum in the Data section of this report.

Thermogravimetric Analysis (TGA): Thermogravimetric analyses were performed using a Mettler Toledo TGA/DSC3+ analyzer. Temperature calibration was performed using phenyl salicylate, indium, tin, and zinc. The sample was placed in an aluminum pan. The open pan was inserted into the TG furnace. The furnace was heated under nitrogen. Each sample was heated from ambient temperature to 350° C., at ramp rates of 2, 5, or 10° C./min. Although thermograms are plotted by reference temperature (x-axis), results are reported according to sample temperatures.

X-Ray Powder Diffraction (XRPD)

a. Reflection: XRPD patterns were collected with a PANalytical X'Pert PRO MPD diffractometer using an incident beam of Cu Kα radiation produced using a long, fine-focus source and a nickel filter at room temperature (298 Kelvin). The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was packed in a well. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are displayed above the image in the Data section of this report including the divergence slit (DS) and the incident-beam SS.

b. Transmission: XRPD patterns were collected with a PANalytical X'Pert PRO MPD diffractometer using an incident beam of Cu radiation produced using an Optix long, fine-focus source at room temperature (298 Kelvin). An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

XRPD Indexing

Indexing and structure refinement are computational studies. Within the figure referenced for a given indexed XRPD pattern, agreement between the allowed peak positions, marked with bars, and the observed peaks indicates a consistent unit cell determination. Successful indexing of a pattern indicates that the sample is composed primarily of a single crystalline phase unless otherwise stated. Space groups consistent with the assigned extinction symbol, unit cell parameters, and derived quantities are tabulated.

EXAMPLES

Preparative Example 1: Synthesis of Compound 1

Step 1: N-(4-Fluorophenyl)-N-(4-hydroxyphenyl) cyclopropane-1,1-dicarboxamide (4)

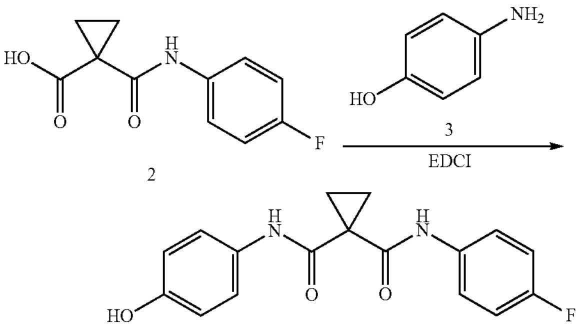

4

To a solution of Compound 2 (10 g, 44.80 mmol, 1 eq.) and Compound 3 (5.87 g, 53.8 mmol, 1.2 eq.) in dimethyl acetamide (DMA) (60 mL) was added 3-(ethyliminomethyleneamino)-N,N-dimethyl-propan-1-amine hydrochloride (EDCI) (10.31 g, 53.8 mmol, 1.2 eq.). The mixture was stirred vigorously at 20° C. until the reaction was complete. The mixture was poured into aqueous (aq) saturated $NaHCO_3$ (400 mL) and extracted with EtOAc (4×100 mL). The combined organic phases were washed with aqueous saturated NaCl (100 mL), dried over anhydrous (anhyd) $Na_2SO_4$, and concentrated. Compound 4 (21 g, crude) (50% purity) was obtained. $^1H$ NMR (400 MHz, DMSO-$d_6$) δ 10.16 (br s, 1H), 9.72 (br s, 1H), 7.61 (dd, 2H), 7.34 (d, 2H), 7.13 (t, 2H) 6.68 (d, 2H), 1.42 (s, 4H); MS (EI) for $C_{17}H_{15}FN_2O_3$, found 314.9 (MH+).

Step 2: Methyl 4-[4-[[1-[(4-fluorophenyl)carbamoyl]cyclopropane-carbonyl]amino]phenoxy]-7-methoxyquinoline-6-carboxylate (6)

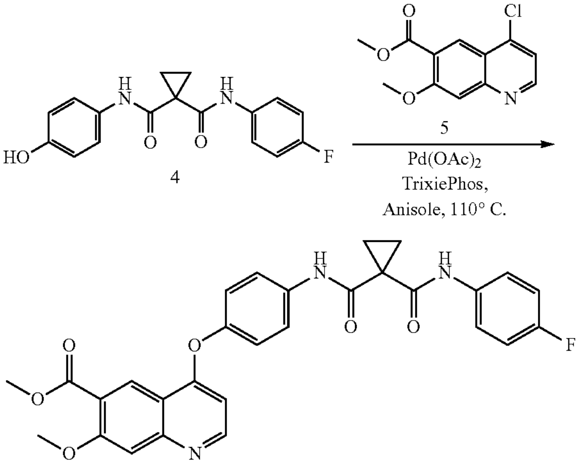

6

A mixture of Compound 4 (5.99 g, 9.5 mmol, 1.2 eq.), Compound 5 (2 g, 8.0 mmol, 1.0 eq.), $Pd(OAc)_2$ (89 mg, 397.4 μmol, 0.05 eq.), rac-2-(Di-tert-butylphosphino)-1,1'-binaphthyl (TrixiePhos, 316.71 mg, 794.7 μmol, 0.1 eq.) and $K_3PO_4$ (2.53 g, 11.9 mmol, 1.5 eq.) in anisole (50 mL) was stirred at 110° C. for 2 hours (h) under an atmosphere of nitrogen. The mixture was filtered, and the filtrate was concentrated. The residue was purified by flash silica gel chromatography (1:1 petroleum ether:EtOAc to 20:1 EtOAc:MeOH). Compound 6 was obtained (2.6 g, 61.8% yield). $^1H$ NMR (400 MHz, $CDCl_3$) δ 9.38 (s, 1H), 8.80 (s, 1H), 8.63 (d, 2H), 7.64 (d, 2H), 7.54-7.41 (m, 3H), 7.18 (d, 2H), 7.09-7.01 (m, 2H), 6.43 (d, 1H), 4.05 (s, 3H), 3.97 (s, 3H), 1.78-1.72 (m, 2H), 1.69-1.63 (m, 2H); MS (EI) for $C_{29}H_{24}FN_3O_6$, found 530.0 (MH+).

Step 3: 4-[4-[[1-[(4-Fluorophenyl)carbamoyl]cyclopropane-carbonyl]amino]phenoxy]-7-methoxyquinoline-6-carboxylic acid (7)

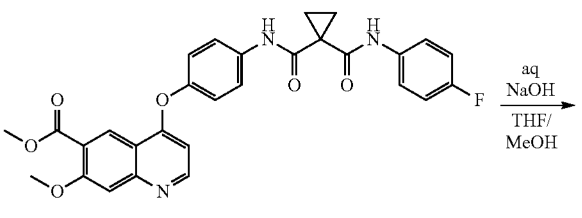

6

-continued

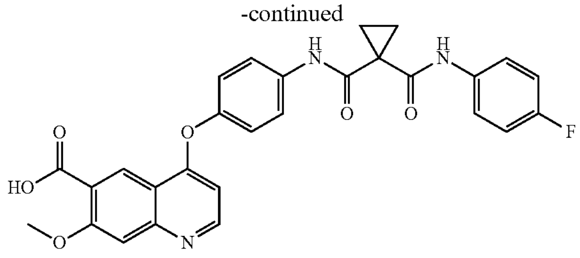

7

To a solution of Compound 6 (1.8 g, 3.4 mmol, 1 eq.) in tetrahydrofuran (THF) (15 mL) and MeOH (15 mL) was added 2 M aqueous NaOH (7 mL, 4.1 eq.). The mixture was stirred at 6-13° C. for 4 hours. The mixture was adjusted to a pH of approximately 8 with 1 M aqueous HCl and concentrated to remove solvent. Water (50 mL) was added, and the mixture was adjusted to a pH of approximately 6 with 1 M aqueous HCl. The resulting precipitate was filtered, washed with water (2×10 mL), and dried under vacuum. Compound 7 was obtained (1.7 g, 97.0% yield). $^1$H NMR (400 MHz, DMSO-$d_6$) δ 10.22 (s, 1H), 10.08 (s, 1H), 8.65 (d, 1H), 8.48 (s, 1H), 7.77 (d, 2H), 7.64 (dd, 2H) 7.47 (s, 1H), 7.25 (d, 2H), 7.15 (t, 2H), 6.45 (d, 1H), 3.96 (s, 3H), 1.47 (s, 4H); MS (EI) for $C_{28}H_{22}FN_3O_6$, found 516.1 (MH+).

Step 4: 1-N'-(4-Fluorophenyl)-1-N-[4-[7-methoxy-6-(methylcarbamoyl)quinolin-4-yl]oxyphenyl]cyclopropane-1.1-dicarboxamide (1)

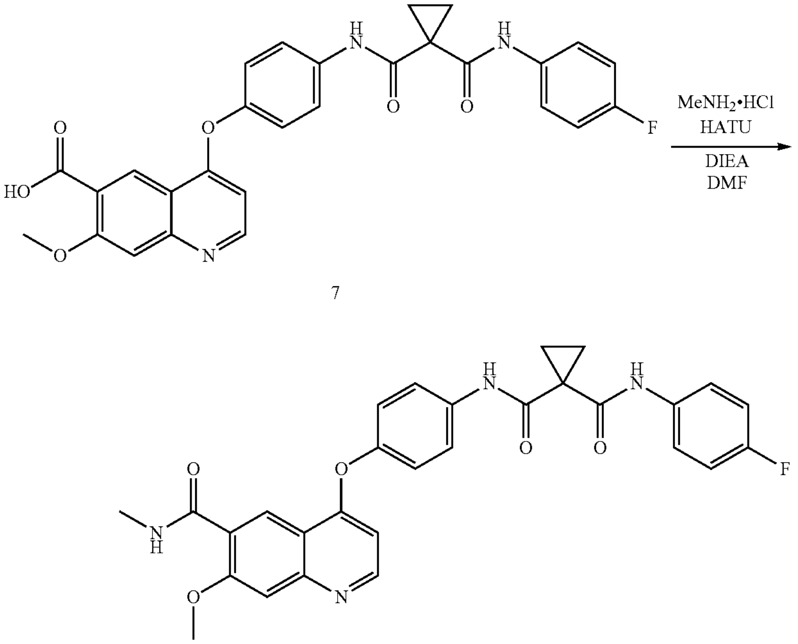

7

1

A solution of Compound 7 (300 mg, 582.0 μmol, 1 eq.), HATU (332 mg, 873.2 μmol, 1.5 eq.), and DIEA (301 mg, 2.3 mmol, 406 μL, 4 eq.) in DMF (10 mL) was stirred at 6-10° C. for 1 hour. Methanamine hydrochloride (79 mg, 1.2 mmol, 2.0 eq.) was added, and the mixture was stirred at 6-10° C. for 17 hours. The mixture was filtered, and the resulting filtrate purified by prep HPLC (Column: Waters Xbridge 150 mm*25 mm*5 μm, gradient: 33-63% of acetonitrile in 10 mM aqueous $NH_4HCO_3$, flow rate: 25 mL/min). Compound 1 was obtained (105.4 mg, 34.3% yield). $^1$H NMR (400 MHz, DMSO-$d_6$) δ 10.20 (s, 1H), 10.06 (s, 1H), 8.65 (d, 1H), 8.61 (s, 1H), 8.42-8.33 (m, 1H), 7.77 (d, 2H), 7.68-7.61 (m, 2H), 7.51 (s, 1H), 7.25 (d, 2H), 7.19-7.11 (m, 2H), 6.46 (d, 1H), 4.02 (s, 3H), 2.84 (d, 3H) 1.47 (s, 4H); MS (EI) for $C_{29}H_{25}FN_4O_5$, found 529.1 (MH+).

Example 1: Preparation of Compound 1 Fumarate Form A

Fumaric acid (1 eq.) in acetone was added to the free base of Compound 1 (1 eq.) and the resulting reddish slurry was stirred at about 50° C. for 4 days. The slurry was then SC to RT and stirred for an addition 1 day to provide a pink slurry. The solids were then removed by positive pressure filtration to provide a mixture of Fumarate Form A and free base Form A.

Example 2: Preparation of Compound 1 Hemifumarate Form B

Fumaric acid (2 eq.) in acetone was added to the free base of Compound 1 (1 eq.) and the resulting reddish slurry was stirred at about 50° C. for 6 days to provide a resulting off-white slurry. The solids were then removed by positive pressure filtration of the hot solution to provide Hemifumarate Form B.

Example 3: Preparation of Compound 1 HCl Form A 1 eq. of HCl was added to the free base of Compound 1 in THF and the resulting dark reddish slurry was stirred at RT for 3 days to provide a resulting thick off-white slurry. The solids were then removed by positive pressure filtration to provide HCl Form A.

Example 4: Preparation of Compound 1 HCl Form B 1 eq. of HCl was added to the free base of Compound 1 in chloroform and the resulting reddish slurry was stirred at about 50° C. for 3 days to provide a resulting pale pink slurry. The solids were then removed by positive pressure filtration to provide HCl Form B.

Example 5: Preparation of Compound 1 HCl Form C 1 eq. of HCl was added to the free base of Compound 1 in methanol at a temperature of about 60° C. resulting in a yellowish slurry. The solution was then CC to about −20° C. and kept cold for about 2 days to provide a clear orange solution. Partial FE provided a clear red solution and then four volumes of the anti-solvent MTBE was added and the solution was stirred for 1 day at RT to provide off-white solid Compound 1 HCl Form C that was separated by positive pressure filtration.

Example 6: Preparation of Compound 1 HCl Form D 2 eq. HCl was added to the free base of Compound 1 at about 50° C., and the resulting pink slurry was stirred at 50° C. for 5 days. The solid Compound 1 HCl Form D was separated by positive pressure filtration.

Example 7: Preparation of Compound 1 Form A

Compound 1 Form A is likely the most thermodynamically stable crystalline form of the free base of Compound 1. Accordingly, multiple procedures lead to the formation of this form. A list of some of the possible procedures to obtain Compound 1 Form A are listed in Table 17. This list in Table 17 is not meant to be exclusive, indeed there are likely many more procedures that will produce this form.

TABLE 17

Selected procedures for producing Compound 1 Form A

| Solvent | Conditions |
|---|---|
| ACN/water 80:20 | 1) Slurry at 2-8° C. for 14 d; or<br>2) Slurry at room temperature for 14 d |
| Chloroform | Slurry at 57° C. for 2 days |
| DCM | Slurry at room temperature for 14 days |
| Ethyl Acetate | Slurry at 76° C. for 3 days |
| Ethanol | 1) Slurry at room temperature for 14 days; or<br>2) Slurry at 76° C. for 3 days |
| Ethanol/water 90:10 | Slurry at room temperature for 14 days |
| Isopropyl alcohol | 1) Slurry at room temperature for 14 days; or<br>2) Slurry at 76° C. for 3 days |
| Methanol | 1) Slurry at room temperature for 14 days;<br>2) Slurry at 57-58° C. for 4 days; or<br>3) Fast evaporation |
| Methanol/Ethyl Acetate 3:2 | Slurry at room temperature for 14 days |
| 2,2,2-Trifluoroethanol | 1) Slow evaporation;<br>2) Fast evaporation; or<br>3) Crash precipitation using diethyl ether as the anti-solvent, then slurry for 1 day. |

TABLE 17-continued

Selected procedures for producing Compound 1 Form A

| Solvent | Conditions |
|---|---|
| Tetrahydrofuran | 1) Slurry at room temperature for 14 days; or<br>2) Slurry at 57-58° C. for 4 days |
| Tetrahydrofuran/water 50:50 | Slurry at room temperature for 14 days |

Example 8: Preparation of Compound 1 Form B

Compound 1 was dissolved in AcOH, and crystallized by VD with diethyl ether as the anti-solvent.

Example 9: Preparation of Compound 1 Form C

Compound 1 was dissolved in HFIPA, and crystallized by CP with MTBE as the anti-solvent.

Example 10: Preparation of Compound 1 Form D

Compound 1 was dissolved in methanol, and crystallized by CC. The mixture was then slurried at 2-8° C. to provide Form D.

Example 11: Preparation of Compound 1 Form E

Method A: Compound 1 was dissolved in THF, and crystallized by CC.

Method B: Compound 1 was dissolved in 90:10 THF:Water, and precipitated by CP.

Example 12: Preparation of Compound 1 Form F

Method A: Compound 1 was dissolved in chloroform, and crystallized by SE.

Method B: Compound 1 was slurried in chloroform.

Example 13: Preparation of Compound 1 Form G

Compound 1 was dissolved in chloroform, and crystallized by placing the mixture in the freezer.

Example 14: Preparation of Compound 1 Form H

Form H was obtained by VS of Amorphous Compound 1 with DCM.

Example 15: Preparation of Compound 1 Form K

Compound 1 Form K was made by desolvation of Form F or Form G, which are chloroform solvates.

Example 16: Preparation of Compound 1 Form O

Compound 1 Form O was discovered during salt attempts with various counterions in TFE-containing solvent systems, and is likely a TFE solvate.

Example 17: Preparation of Compound 1 Phosphate Form A 1 molar equivalent of phosphoric acid was added to a slurry of Compound 1 in chloroform, and then the resulting mixture was slurried for 3 days at about ~50° C. The product was isolated by positive pressure filtration.

Example 18: Preparation of Compound 1 Form I

Compound 1 in a 90:10 THF/water mixture was crash precipitated with heptane and then stirred at freezing temperatures for 7 days.

Example 19: Preparation of Compound 1 Form J

Compound 1 was slurried in acetone for 14 days.

Example 20: Preparation of Compound 1 Form L

Compound 1 was slurried in chloroform for 14 days.

Example 21: Preparation of Compound 1 Form M

Dehydration of Compound 1 Form E in a vacuum oven at −77° C. for 1 day.

Example 22: Preparation of Compound 1 Form N

Compound 1 was slurried in a 70:30 mixture of TFE/MTBE for 7 days at room temperature.

OTHER EMBODIMENTS

The foregoing disclosure has been described in some detail by way of illustration and example, for purposes of clarity and understanding. The invention has been described with reference to various specific and preferred embodiments and techniques. However, it should be understood that many variations and modifications can be made while remaining within the spirit and scope of the invention. It will be obvious to one of skill in the art that changes and modifications can be practiced within the scope of the appended claims. Therefore, it is to be understood that the above description is intended to be illustrative and not restrictive.

The scope of the invention should, therefore, be determined not with reference to the above description, but should instead be determined with reference to the following appended claims, along with the full scope of equivalents to which such claims are entitled.

The invention claimed is:

1. A crystalline hemifumarate Form B of Compound 1 having the structure

Compound 1

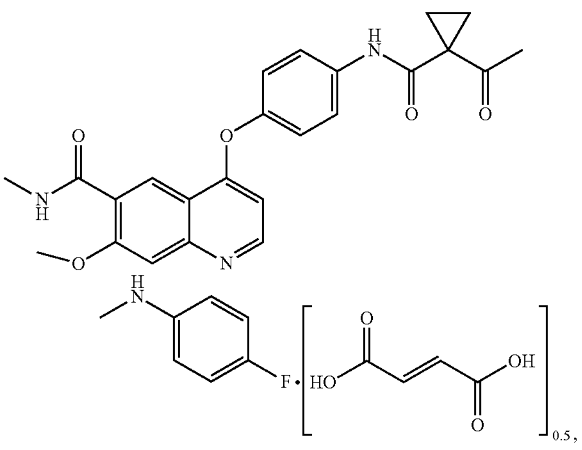

Hemifumarate

2. The crystalline hemifumarate Form B of Compound 1 according to claim 1, characterized by an X-ray powder diffraction pattern comprising peaks at 16.95, 19.16, and 26.34 degrees 2θ (±0.20 degrees).

3. The crystalline hemifumarate Form B of Compound 1 according to claim 2, characterized by an X-ray powder diffraction pattern further comprising peaks at 9.08, 24.37, and 27.05 degrees 2θ (±0.20 degrees).

4. The crystalline hemifumarate Form B of Compound 1 according to claim 1, characterized by an endotherm with an onset temperature of about 226° C. in a differential scanning calorimetry thermogram.

5. The crystalline hemifumarate salt Form B of Compound 1 according to claim 1, characterized by negligible weight loss under a temperature of about 220° C. in a thermogravimetric analysis thermogram.

6. The crystalline hemifumarate Form B of Compound 1 according to claim 1, characterized by an increase in weight of about 0.2 wt %, as measured by dynamic vapor sorption, in an environment that is taken from 5% relative humidity to 95% relative humidity.

7. A Compound 1 hemifumarate having the structure

Compound 1

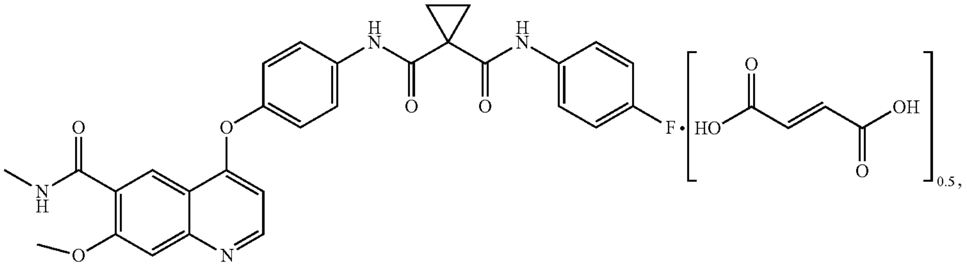

Hemifumarate wherein said Compound 1 hemifumarate is in crystalline Form B and said Form B is characterized by an X-ray powder diffraction pattern comprising peaks at 9.08, 16.95, 19.16, and 26.34 degrees 2θ (±0.20 degrees).

8. A Compound 1 hemifumarate having the structure

Compound 1

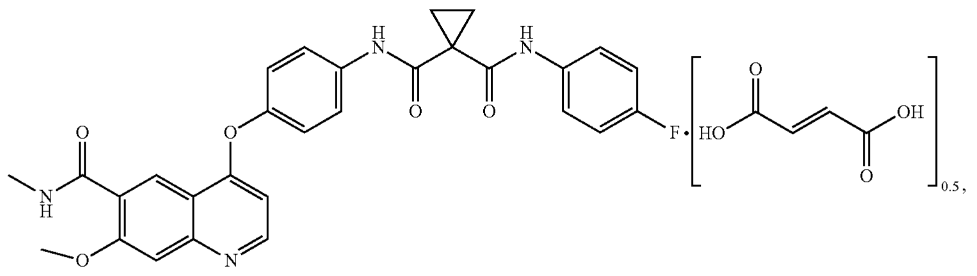

Hemifumarate wherein said Compound 1 hemifumarate is in crystalline Form B and said Form B is characterized by an X-ray powder diffraction pattern substantially as depicted in FIG. 29.

9. The Compound 1 hemifumarate in crystalline Form B according to claim 7, characterized by an endotherm with an onset temperature of about 226° C. in a differential scanning calorimetry thermogram.

10. The Compound 1 hemifumarate in crystalline Form B according to claim 7, characterized by negligible weight loss under a temperature of about 220° C. in a thermogravimetric analysis thermogram.

11. The Compound 1 hemifumarate in crystalline Form B according to claim 7, characterized by an increase in weight of about 0.2 wt %, as measured by dynamic vapor sorption, in an environment that is taken from 5% relative humidity to 95% relative humidity.

* * * * *